(12) United States Patent
Maxwell et al.

(10) Patent No.: US 9,844,546 B2
(45) Date of Patent: Dec. 19, 2017

(54) ANTIBODY AGAINST HUMAN HIF HYDROXYLASE

(71) Applicant: OXFORD UNIVERSITY INNOVATION LIMITED, Oxford (GB)

(72) Inventors: Patrick Henry Maxwell, Oxford (GB); Christopher William Pugh, Oxford (GB); Peter John Ratcliffe, Oxford (GB); Christopher Joseph Schofield, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 0 days.

(21) Appl. No.: 14/713,085

(22) Filed: May 15, 2015

(65) Prior Publication Data
US 2015/0353646 A1    Dec. 10, 2015

Related U.S. Application Data

(60) Division of application No. 14/028,167, filed on Sep. 16, 2013, now abandoned, which is a continuation of
(Continued)

(30) Foreign Application Priority Data

Mar. 21, 2001 (GB) .................................. 0107123.2
Aug. 2, 2001 (GB) .................................. 0118952.1

(51) Int. Cl.
| C07K 16/18 | (2006.01) |
|---|---|
| C07K 16/40 | (2006.01) |
| C07K 14/47 | (2006.01) |
| A61K 31/455 | (2006.01) |
| G01N 33/573 | (2006.01) |
| C12N 9/02 | (2006.01) |
| C12Q 1/26 | (2006.01) |
| C07C 235/80 | (2006.01) |
| C07C 323/60 | (2006.01) |
| C07C 327/32 | (2006.01) |
| C07D 213/80 | (2006.01) |
| C07D 213/81 | (2006.01) |
| C07D 213/82 | (2006.01) |
| A61K 31/137 | (2006.01) |
| A61K 31/166 | (2006.01) |
| A61K 31/185 | (2006.01) |
| A61K 31/198 | (2006.01) |

(Continued)

(52) U.S. Cl.
CPC .......... *A61K 31/455* (2013.01); *A61K 31/137* (2013.01); *A61K 31/14* (2013.01); *A61K 31/166* (2013.01); *A61K 31/185* (2013.01); *A61K 31/192* (2013.01); *A61K 31/194* (2013.01); *A61K 31/195* (2013.01); *A61K 31/197* (2013.01); *A61K 31/198* (2013.01); *A61K 31/21* (2013.01); *A61K 31/221* (2013.01); *A61K 31/225* (2013.01); *A61K 31/24* (2013.01); *A61K 31/327* (2013.01); *A61K 31/44* (2013.01); *A61K 31/4412* (2013.01); *C07C 235/80* (2013.01); *C07C 323/60* (2013.01); *C07C 327/32* (2013.01); *C07D 213/80* (2013.01); *C07D 213/81* (2013.01); *C07D 213/82* (2013.01); *C07K 14/4702* (2013.01); *C07K 16/40* (2013.01); *C12N 9/0071* (2013.01); *C12Q 1/26* (2013.01); *G01N 33/573* (2013.01); *A01K 2217/05* (2013.01); *A61K 38/00* (2013.01); *A61K 39/3955* (2013.01); *C07K 2317/30* (2013.01); *G01N 2333/90245* (2013.01); *G01N 2500/04* (2013.01); *G01N 2500/20* (2013.01)

(58) Field of Classification Search
CPC ............ A61K 2300/00; A61K 39/3955; A61K 2039/505; C07K 16/40; C07K 16/18; C12N 9/0071
See application file for complete search history.

(56) References Cited

U.S. PATENT DOCUMENTS

| 5,719,164 A | 2/1998 | Weidmann et al. |
|---|---|---|
| 6,566,088 B1 | 5/2003 | McKnight et al. |

(Continued)

FOREIGN PATENT DOCUMENTS

| DE | 19909503 A1 | 9/2000 |
|---|---|---|
| WO | WO 9741103 | 11/1997 |

(Continued)

OTHER PUBLICATIONS

Fernandez-Botran et al. Cellular Immunology (2001) Boca Raton: CRC Press, pp. 181-211.*

(Continued)

Primary Examiner — Bridget E Bunner
(74) Attorney, Agent, or Firm — Finnegan, Henderson, Farabow, Garrett & Dunner, LLP

(57) ABSTRACT

A novel class of hydroxylases is described having the amino acid sequence of SEQ ID NO: 2, 4, 6 and 8, and variants and fragments thereof having HIF hydroxylation activity. The polypeptides of the invention have in particular prolyl hydroxylase activity. An assay method monitors the interaction of the HIF hydroxylase with a substrate. Modulators of HIF hydroxylase are provided for use in the treatment of a condition associated with increased or decreased HIF levels or activity or for the treatment of a condition where it is desirable to modulate HIF levels or activity.

6 Claims, 23 Drawing Sheets

Related U.S. Application Data application No. 12/654,993, filed on Jan. 12, 2010, now Pat. No. 8,535,899, which is a continuation of application No. 10/472,595, filed as application No. PCT/GB02/01381 on Mar. 21, 2002, now abandoned.

(51) Int. Cl.

| | |
|---|---|
| A61K 31/21 | (2006.01) |
| A61K 31/225 | (2006.01) |
| A61K 31/44 | (2006.01) |
| A61K 31/192 | (2006.01) |
| A61K 31/195 | (2006.01) |
| A61K 31/197 | (2006.01) |
| A61K 31/24 | (2006.01) |
| A61K 31/327 | (2006.01) |
| A61K 31/4412 | (2006.01) |
| A61K 31/14 | (2006.01) |
| A61K 31/194 | (2006.01) |
| A61K 31/221 | (2006.01) |
| C07K 14/435 | (2006.01) |
| C12N 9/00 | (2006.01) |
| A61K 39/395 | (2006.01) |
| A61K 38/00 | (2006.01) |

(56) References Cited

U.S. PATENT DOCUMENTS

| | | |
|---|---|---|
| 6,855,510 B2 | 2/2005 | Kaelin, Jr. et al. |
| 7,470,675 B2 | 12/2008 | Horton et al. |

FOREIGN PATENT DOCUMENTS

| | | |
|---|---|---|
| WO | WO 00/69908 | 11/2000 |
| WO | WO 01/75067 A2 | 11/2001 |
| WO | WO 01/90304 A2 | 11/2001 |

OTHER PUBLICATIONS

Taylor, M.S. UniProt Accession No. Q9H6Z9; Mar. 1, 2001.*
Taylor, M.S. Genbank Accession No. CAC42510 (gi14547148); Mar. 1, 2001.*
Yarmush et al. ("Monoclonal Antibodies and Their Engineered Fragments". The Biomedical Engineering Handbook: Second Edition (2000) Boca Raton: CRC Press, sections 102-102.6 (21 total pages).*
CAC42510.1 protein NCBI Genbank revision history. Printed Jun. 21, 2017, 2 pages.*
Q9H6Z9 protein UniProt entry from Mar. 1, 2001 (original), 1 page.*
Examination Report for Application No. 02-706-994.7-2404 dated Apr. 10, 2008.
Taylor, Martin S. "Characterization and Comparative Analysis of the EGLN Gene Family". Medical Genetics Section, University of Edinburgh, Western General Hospital, Jul. 25, 2001, pp. 125-132.
Dupuy, Denis Mapping, Characterization, and Expression Analysis of the SM-20 Human Homologue, C1orf12, and Identification of a Novel Related Gene, SCAND2, Genomics 69, pp. 348-354, 2000.
Cunliffe, C.J., et al., "Inhibition of Prolyl 4-Hydroxylase by Hydroxylanthraquinones", Biochem. J., 239(2):311-315 (1986).
Bruick Richard, et al., "A Conserved Family of Prolyl-4-Hydroxylases that Modify HIF", Science, vol. 294, Nov. 9, 2001, pp. 1337-1340.
Wax, S.D., et al., "Sm-20 Is a Novel 40-kd Protein Whose Expression in the Arterial Wall Is Restricted to Smooth Muscle", Laboratory Investigation, vol. 74. No. 4, p. 797, 1996, pp. 797-808.
Examination Report for Japanese Patent Application No. 2002-574370, dated Mar. 3, 2009.
Examination Report for Japanese Patent Application No. 2008-202010, dated Dec. 1, 2009.
Darby, Creg, et al., "Lethal Paralysis of Caenorhabditis elegans by Pseudomas Aeuruginosa", PNAS, vol. 96, No. 26, Dec. 21, 1999, pp. 15202-15207.
Ivan, et al., "HIFα Targeted for VHL-Mediated Destruction by Proline Hydroxylation: Implications for $O_2$ Sensing", www.sciencemag.org, vol. 292, Apr. 20, 2001, p. 464-467.
Wang, G.L. Desferrioxamine Induces Erythropoietin Gene Expression and Hypoxia-inducible Factor 1 DNA-binding Activity: Implication for Models of Hypoxia Signal Transduction, Blood, vol. 82, No. 12, Dec. 15, 1993: pp. 3610-3615.
Takahashi, et al., "Accelerated Collagen Deposition by Hypoxic Stress", Department of Life Science, Tokyo Pharmaceutical University, Japan, Lung Perspectives, 2001, vol. 9, No. 3, pp. 323-328.
Takahashi, et al., "Accelerated Collagen Deposition by Hypoxic Stress", Chemical Abstracts, 2002, vol. 136, No. 5, Abstract No. 67250b, p. 496-.
Jaakkola, P., et al., "Targeting of HIF-α to the von Hippel-Lindau Ubiquitylation Complex By $O_2$-Regulated Prolyl Hydroxylation", Science, 292:468-472. (Apr. 5, 2001).
Shibasaki, T., et al., "Substrate Selectives of Proline Hydroxylases", Tetrahedron Letters, Elsevier Science Publishers, Amsterdam, NL, 40 (28):5227-5230, (Jul. 9, 1999).
Millhorn, D.E., et al., "Regulation of Gene Expression of Tyroisine Hydroxylase in Oxygen Sensitive Cells by Hypoxia", Kidney International, 51:527-535 (1997).
Cunliffe et al., "Novel Inhibitors of Prolyl 4-Hydroxylase. 3. Inhibition by the Substrate Analogue N-Oxaloglycine and its Derivatives", J. Med. Chem., vol. 35, pp. 2652-2658 (1992).
Epstein, A.C.R., "C. elegans EGL-9 and Mammalian Homologs Define a Family of Dioxygenases that Regulate HIF by Prolyl Hydroxylation", Cell, 107:43-54 (Oct. 5, 2001).
Maxwell, P.H., et al., "The Tumor Suppressor Protein VHL Targets Hypoxia-Inducible Factors for Oxygen-Dependent Proteolysis", Nature, 399:271-275 (May 20, 1999).
Lando, E., et al., "Asparagine Hydroxylation of the HIF Transactivation Domain: A Hypoxic Switch", Science, 295:858-861 (Feb. 1, 2002).
Aravind, L., et al., "The DNA-Repair Protein AlkB, EGL-9, and leprecan Define New Families of 2-Oxoglutarate- and Iron-Dependent Dioxygenases", Genome Biology, 2(3):1-8 (2001).
Clifton, I.J., "Structure of Proline 3-Hydroxylase Evolution of the Family of 2-Oxoglutarate Dependent Oxygenases", Eur. J. Biochem., 268:6625-6636 (2001).
Franklin, T.J., et al, "Inhibition of Prolyl 4-Hydroxylase in vitro and in vivo by Members of a Novel Series of Phenanthrolinones", Biochem., J., 353:333-338 (2001).
Franklin, T.J., et al., "Inhibition of Collagen Hydroxylation by 2,7,8-trihydroxyanthraquinone in Embryonic-Chick Tendon Cells", Biochem. J., 261(1):127-130 (1989).
Database Uniprot (Online) Retrieved from EMBL Database accession No. Q9GZT9, Jun. 16, 2003.
Database Uniprot (Online) Retrieved from EMBL Database accession No. Q9NTU9, Oct. 1, 2000.
Database Uniprot (Online) Retrieved from EMBL Database accession No. Q9H6Z9, Jun. 16, 2003.
Database Uniprot (Online) Retrieved from EMBL Database accession No. AX035284, May 31, 2006.
Database Uniprot (Online) Retrieved from EMBL Database accession No. AAB37420, Feb. 20, 2001.
Database Uniprot (Online) D1 Mar. 2001 Retrieved from EMBL Database accession No. 045915.
English language Abstract of DE 199 09 503 A1, Sep. 7, 2000.
Chopp et al., "Postischemic Administration of Anti-Mac-1 Antibody Reduces Ischemic Cell Damage After Transient Middle Cerebral Artery Occlusion in Rats," Stroke, vol. 25 (1994), pp. 869-876.
Palmer et al. "Deferoxamine Posttreatment Reduces Ischemic Brain Injury in Neonatal Rats," Stroke, vol. 25 (1994), pp. 1039-1045.
Uchida et al. "Prevention of Ischemia-Induced Death of Hippocampal Neurons by Pituitary Adenylare Cyclase Activating Polypeptide," Brain Research, vol. 736 (1996), pp. 280-286.

(56) References Cited

OTHER PUBLICATIONS

Yang et al., "Overexpression of Interleukin-1 Receptor Antagonist in the Mouse Brain Reduces Ischemic Brain Injury," Brain Research, vol. 751 (1997), pp. 181-188.

* cited by examiner

HIF-1α (556-574)   DLDLEMLAPYIPMD-DDFQL (SEQ ID NO: 23)
HIF-2α             ELDLETLAPYIPMDGEDFQL (SEQ ID NO: 24)
X.laevis           DLDLEMLAPYIPMD-DDFQL (SEQ ID NO: 25)
D.melanogaster     FEAFAMRAPYIPID-DDNPL (SEQ ID NO: 26)
C.elegans          EPDLSCLAPFVDTY-DMMQM (SEQ ID NO: 27)

FIG. 1A

| POLYPEPTIDE | INHIBITION | INHIBITION WITH EXTRACT |
|---|---|---|
| PFSTQDTDLDLEMLAPYIPMDDDFQLRSFDQLSP | - | ++ (SEQ ID NO: 28) |
| DLDLEMLAPYIPMDDDFQL | - | ++ (SEQ ID NO: 29) |
| LEMLAPYIPMDDDFQL | - | + (SEQ ID NO: 30) |
| LAPYIPMDDDFQL | - | - (SEQ ID NO: 31) |
| DLDLEMLAPYIPMD | - | - (SEQ ID NO: 32) |
| DLDLEMLAGYIPMDDDFQL | - | - (SEQ ID NO: 33) |
| DLDLEMLAPY*IPMDDDFQL | - | ++ (SEQ ID NO: 34) |

HIF-1α  380  SEDTSSLFDKLKKEPDALTLLAPAAGDTIISLDFGSND  417  (SEQ ID NO: 37)

HIF-2α  383  SEKSNFLFTKLKEEPEELAQLAPTPGDAIISLDFGNQN  420  (SEQ ID NO: 38)

HIF-1α  556  DLDLEMLAPYIPMDDDFQL  574  (SEQ ID NO: 39)

FIG. 3A

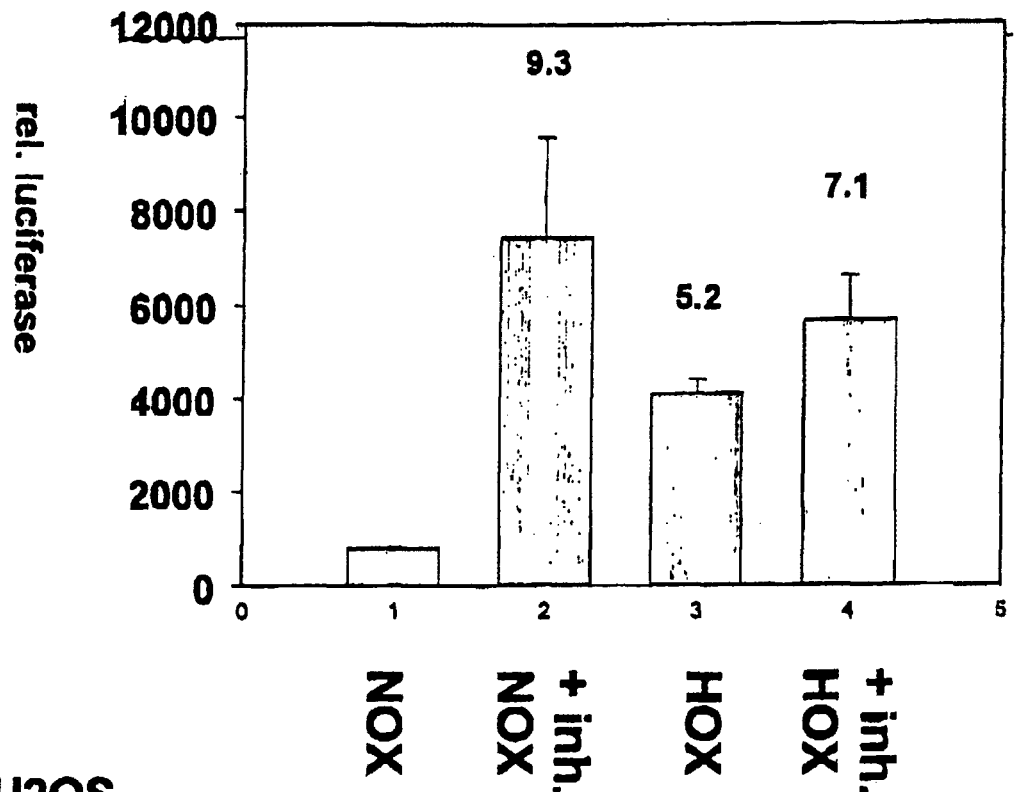
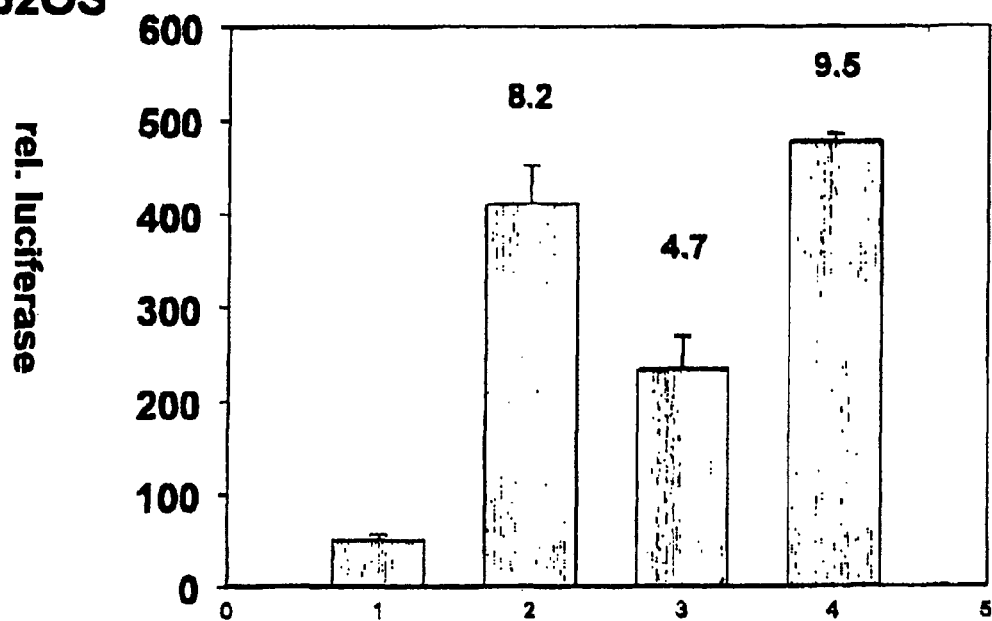
Figure 6

CAS.Fe(II).2-OG    DAOCS.Fe(II).2-OG

```
EGL9     IDHDIGGRSRAMLAIYPGNGTRYVKHVDNPVK  (SEQ ID NO: 40)
EGLN1    GSYKINGRTKAMVACYPGNGTGYVRHVDNPNG  (SEQ ID NO: 41)
EGLN2    GSYVINGRTKAMVACYPGNGLGYVRHVDNPHG  (SEQ ID NO: 42)
EGLN3      KYYVKERSKAMVACYPGNGTGYVRHVDNPNG (SEQ ID NO: 43)
Rat SM20 GKYYVKERSKAMVACYPGNGTGYVRHVDNPNG  (SEQ ID NO: 44)
P3OH           FDGTHLQMARSRNLKNAIVIPHRDFVEL (SEQ ID NO: 45)
                   ─────       ──
                     1          2
```

```
EGL9     DGRCITTIYYCNENWDMA
EGLN1    DGRCVTCIYYLNKDWDAK
EGLN2    DGRCITCIYYLNQNWDVK
EGLN3    DGRCITCIYYLNKNWDAK
Rat SM20 DGRCITCIYYLNKNWDAK
P3OH     DREVDR  YFRTF   MV
         ──────
            3
```

```
EGL9     TDGGTLRLYPETSMTPMDIDPRADRLVFFWSDRRNPHE
EGLN1    VSQGILRIFPEGKAQFADIEPKFDRLLFFWSDRRNPHE
EGLN2    VHGGLLQIFPEGRPVVANIEPLFDRLLIFWSDRRNPHE
EGLN3    LHGGILRIFPEGKSFIADVEPIFDRLLFFWSDRRNPHE
Rat SM20 LHGGVLRIFPEGKSFVADVEPIFDRLLFSWSDRRNPHE
P3OH     LEDSPLA FHSNEDTVIHMRP GEIWFL  DAATVHS
         ───────  ──────────  ─────    ──────
            4          5         6        7
```

```
EGL9     VMPVFRHRFAITIWYMDKSERDKALAKGKES
EGLN1    VQPAYATRYAITVWYFDADER   ARAKVKY
EGLN2    VKPAYATRYAITVWYFDAKER   AAAKDKY
EGLN3    VQPSYATRYAMTVWYFDAEER   AEAKKRF
Rat SM20 VQPSYATRYAMTVWYFDAEER   AEAKKRF
P3OH     AVNFSEISRQSLCVDFAP
         ──                ──
          7                 8
```

Figure 9

N-ODD:
hHIF1α 390 LKKEPDALTLLAPAAGDTIISLDFGSND 417 (SEQ ID NO: 50)
mHIF1α 378 LKKEPDALTLLAPAAGDTIISLDFGSDD 395 (SEQ ID NO: 51)

C-ODD:
hHIF1α 556 _____ DLDLEMLAPYIPMDDDFQL 574 (SEQ ID NO: 39)
mHIF1α 543 _____ DLDLEMLAPYIPMDDDFQL 561 (SEQ ID NO: 52)

motif _____ LxxLAP (SEQ ID NO: 53)

SEQUENCE LISTING

<160> NUMBER OF SEQ ID NOS: 53

<210> SEQ ID NO 1
<211> LENGTH: 2110
<212> TYPE: DNA
<213> ORGANISM: Homo sapiens
<220> FEATURE:
<221> NAME/KEY: CDS
<222> LOCATION: (297)..(1517)

<400> SEQUENCE: 1

```
gctttcccct gcctgcctgt ctctagtttc tctcacatcc cttttttttt tcctttctct    60
agccaccctg aagggtccct tcccaagccc ttagggaccg cagaggactt ggggaccagc   120
aagcaacccc cagggcacga gaagagctct tgctgtctgc cctgcctcac cctgccccac   180
accaggcccg gtggccccca gctgcatcaa gtggaggcg aggaggaggc ggaggaggt    240 ggcaccatgg gcccgggcgg tgccctccat gcccggggga tgaagacact gctgcc atg   299
```

-continued

|  |  |
|---|---|
| | Met<br>1 |
| gac agc ccg tgc cag ccg cag ccc cta agt cag gct ctc cct cag tta<br>Asp Ser Pro Cys Gln Pro Gln Pro Leu Ser Gln Ala Leu Pro Gln Leu<br>              5                              10                        15 | 347 |
| cca ggg tct tcg tca gag ccc ttg gag cct gag cct ggc cgg gcc agg<br>Pro Gly Ser Ser Ser Glu Pro Leu Glu Pro Glu Pro Gly Arg Ala Arg<br>                     20                           25                          30 | 395 |
| atg gga gtg gag agt tac ctg ccc tgt ccc ctg ctc ccc tcc tac cac<br>Met Gly Val Glu Ser Tyr Leu Pro Cys Pro Leu Leu Pro Ser Tyr His<br> 35                            40                          45 | 443 |
| tgt cca gga gtg cct agt gag gcc tcg gca ggg agt ggg acc ccc aga<br>Cys Pro Gly Val Pro Ser Glu Ala Ser Ala Gly Ser Gly Thr Pro Arg<br>50                          55                          60                         65 | 491 |
| gcc aca gcc acc tct acc act gcc agc cct ctt cgg gac ggt ttt ggc<br>Ala Thr Ala Thr Ser Thr Thr Ala Ser Pro Leu Arg Asp Gly Phe Gly<br>                   70                           75                          80 | 539 |
| ggg cag gat ggt ggt gag ctg cgg ccg ctg cag agt gaa ggc gct gca<br>Gly Gln Asp Gly Gly Glu Leu Arg Pro Leu Gln Ser Glu Gly Ala Ala<br>                  85                           90                          95 | 587 |
| gcg ctg gtc acc aag ggg tgc cag cga ttg gca gcc cag ggc gca cgg<br>Ala Leu Val Thr Lys Gly Cys Gln Arg Leu Ala Ala Gln Gly Ala Arg<br>                   100                       105                       110 | 635 |
| cct gag gcc ccc aaa cgg aaa tgg gcc gag gat ggt ggg gat gcc cct<br>Pro Glu Ala Pro Lys Arg Lys Trp Ala Glu Asp Gly Gly Asp Ala Pro<br>115                        120                       125 | 683 |
| tca ccc agc aaa cgg ccc tgg gcc agg caa gag aac cag gag gca gag<br>Ser Pro Ser Lys Arg Pro Trp Ala Arg Gln Glu Asn Gln Glu Ala Glu<br>130                        135                       140                       145 | 731 |
| cgg gag ggt ggc atg agc tgc agc tgc agc agt ggc agt ggt gag gcc<br>Arg Glu Gly Gly Met Ser Cys Ser Cys Ser Ser Gly Ser Gly Glu Ala<br>                   150                       155                       160 | 779 |
| agt gct ggg ctg atg gag gag gcg ctg ccc tct gcg ccc gag cgc ctg<br>Ser Ala Gly Leu Met Glu Glu Ala Leu Pro Ser Ala Pro Glu Arg Leu<br>                   165                       170                       175 | 827 |
| gcc ctg gac tat atc gtg ccc tgc atg cgg tac tac ggc atc tgc gtc<br>Ala Leu Asp Tyr Ile Val Pro Cys Met Arg Tyr Tyr Gly Ile Cys Val<br>                   180                       185                       190 | 875 |
| aag gac agc ttc ctg ggg gca gca ctg ggc ggt cgc gtg ctg gcc gag<br>Lys Asp Ser Phe Leu Gly Ala Ala Leu Gly Gly Arg Val Leu Ala Glu<br>195                        200                       205 | 923 |
| gtg gag gcc ctc aaa cgg ggt ggg cgc ctg cga gac ggg cag cta gtg<br>Val Glu Ala Leu Lys Arg Gly Gly Arg Leu Arg Asp Gly Gln Leu Val<br>210                        215                       220                       225 | 971 |
| agc cag agg gcg atc ccg ccg cgc agc atc cgt ggg gac cag att gcc<br>Ser Gln Arg Ala Ile Pro Pro Arg Ser Ile Arg Gly Asp Gln Ile Ala<br>                   230                       235                       240 | 1019 |
| tgg gtg gaa ggc cat gaa cca ggc tgt cga agc att ggt gcc ctc atg<br>Trp Val Glu Gly His Glu Pro Gly Cys Arg Ser Ile Gly Ala Leu Met<br>                   245                       250                       255 | 1067 |
| gcc cat gtg gac gcc gtc atc cgc cac tgc gca ggg cgg ctg ggc agc<br>Ala His Val Asp Ala Val Ile Arg His Cys Ala Gly Arg Leu Gly Ser<br>                   260                       265                       270 | 1115 |
| tat gtc atc aac ggg cgc acc aag gcc atg gtg gcg tgt tac cca ggc<br>Tyr Val Ile Asn Gly Arg Thr Lys Ala Met Val Ala Cys Tyr Pro Gly<br>275                        280                       285 | 1163 |
| aac ggg ctc ggg tac gta agg cac gtt gac aat ccc cac ggc gat ggg<br>Asn Gly Leu Gly Tyr Val Arg His Val Asp Asn Pro His Gly Asp Gly<br>290                        295                       300                       305 | 1211 |

-continued

```
cgc tgc atc acc tgt atc tat tac ctg aat cag aac tgg gac gtt aag     1259
Arg Cys Ile Thr Cys Ile Tyr Tyr Leu Asn Gln Asn Trp Asp Val Lys
            310                 315                 320 gtg cat ggc ggc ctg ctg cag atc ttc cct gag ggc cgg ccc gtg gta     1307
Val His Gly Gly Leu Leu Gln Ile Phe Pro Glu Gly Arg Pro Val Val
        325                 330                 335 gcc aac atc gag cca ctc ttt gac cgg ttg ctc att ttc tgg tct gac     1355
Ala Asn Ile Glu Pro Leu Phe Asp Arg Leu Leu Ile Phe Trp Ser Asp
    340                 345                 350 cgg cgg aac ccc cac gag gtg aag cca gcc tat gcc acc agg tac gcc     1403
Arg Arg Asn Pro His Glu Val Lys Pro Ala Tyr Ala Thr Arg Tyr Ala
355                 360                 365 atc act gtc tgg tat ttt gat gcc aag gag cgg gca gca gcc aaa gac     1451
Ile Thr Val Trp Tyr Phe Asp Ala Lys Glu Arg Ala Ala Ala Lys Asp
370                 375                 380                 385 aag tat cag cta gca tca gga cag aaa ggt gtc caa gta cct gta tca     1499
Lys Tyr Gln Leu Ala Ser Gly Gln Lys Gly Val Gln Val Pro Val Ser
                390                 395                 400 cag ccg cct acg ccc acc tagtggccag tcccagagcc gcatggcaga             1547
Gln Pro Pro Thr Pro Thr
                405 cagcttaaat gacttcagga gagccctggg cctgtgctgg ctgctccttc cctgccaccg    1607 ctgctgcttc tgactttgcc tctgtcctgc ctggtgtgga gggctctgtc tgttgctgag    1667 gaccaaggag gagaagagac ctttgctgcc ccatcatggg ggctggggtt gtcacctgga    1727 caggggggcag ccgtggaggc caccgttacc aactgaagct gggggcctgg gtcctaccct   1787 gtctggtcat gacccccatta ggtatggaga gctgggagga gcattgtca cttcccacca   1847 ggatgcagga cttggggttg aggtgagtca tggcctcttg ctggcaatgg ggtgggagga   1907 gtaccccccaa gtcctctcac tcctccagcc tggaatgtga agtgactccc caacccctt   1967 ggccatggca ggcacctttt ggactgggct gccactgctt gggcagagta aaaggtgcca   2027 ggaggagcat gggtgtggaa gtcctgtcag ccaagaaata aagtttacc tcagagctgc    2087 aaaaaaaaaa aaaaaaaaa aaa                                            2110

<210> SEQ ID NO 2
<211> LENGTH: 407
<212> TYPE: PRT
<213> ORGANISM: Homo sapiens

<400> SEQUENCE: 2

Met Asp Ser Pro Cys Gln Pro Gln Pro Leu Ser Gln Ala Leu Pro Gln
1               5                   10                  15

Leu Pro Gly Ser Ser Glu Pro Leu Glu Pro Glu Pro Gly Arg Ala
            20                  25                  30

Arg Met Gly Val Glu Ser Tyr Leu Pro Cys Pro Leu Pro Ser Tyr
        35                  40                  45

His Cys Pro Gly Val Pro Ser Glu Ala Ser Ala Gly Ser Gly Thr Pro
    50                  55                  60

Arg Ala Thr Ala Thr Ser Thr Ala Ser Pro Leu Arg Asp Gly Phe
65                  70                  75                  80

Gly Gly Gln Asp Gly Gly Glu Leu Arg Pro Leu Gln Ser Glu Gly Ala
                85                  90                  95

Ala Ala Leu Val Thr Lys Gly Cys Gln Arg Leu Ala Ala Gln Gly Ala
            100                 105                 110

Arg Pro Glu Ala Pro Lys Arg Lys Trp Ala Glu Asp Gly Gly Asp Ala
        115                 120                 125
```

```
Pro Ser Pro Ser Lys Arg Pro Trp Ala Arg Gln Glu Asn Gln Glu Ala
            130                 135                 140

Glu Arg Glu Gly Gly Met Ser Cys Ser Cys Ser Ser Gly Ser Gly Glu
145                 150                 155                 160

Ala Ser Ala Gly Leu Met Glu Glu Ala Leu Pro Ser Ala Pro Glu Arg
                165                 170                 175

Leu Ala Leu Asp Tyr Ile Val Pro Cys Met Arg Tyr Tyr Gly Ile Cys
            180                 185                 190

Val Lys Asp Ser Phe Leu Gly Ala Ala Leu Gly Gly Arg Val Leu Ala
        195                 200                 205

Glu Val Glu Ala Leu Lys Arg Gly Gly Arg Leu Arg Asp Gly Gln Leu
210                 215                 220

Val Ser Gln Arg Ala Ile Pro Pro Arg Ser Ile Arg Gly Asp Gln Ile
225                 230                 235                 240

Ala Trp Val Glu Gly His Glu Pro Gly Cys Arg Ser Ile Gly Ala Leu
                245                 250                 255

Met Ala His Val Asp Ala Val Ile Arg His Cys Ala Gly Arg Leu Gly
            260                 265                 270

Ser Tyr Val Ile Asn Gly Arg Thr Lys Ala Met Val Ala Cys Tyr Pro
        275                 280                 285

Gly Asn Gly Leu Gly Tyr Val Arg His Val Asp Asn Pro His Gly Asp
290                 295                 300

Gly Arg Cys Ile Thr Cys Ile Tyr Tyr Leu Asn Gln Asn Trp Asp Val
305                 310                 315                 320

Lys Val His Gly Gly Leu Leu Gln Ile Phe Pro Glu Gly Arg Pro Val
                325                 330                 335

Val Ala Asn Ile Glu Pro Leu Phe Asp Arg Leu Leu Ile Phe Trp Ser
            340                 345                 350

Asp Arg Arg Asn Pro His Glu Val Lys Pro Ala Tyr Ala Thr Arg Tyr
        355                 360                 365

Ala Ile Thr Val Trp Tyr Phe Asp Ala Lys Glu Arg Ala Ala Ala Lys
370                 375                 380

Asp Lys Tyr Gln Leu Ala Ser Gly Gln Lys Gly Val Gly Val Pro Val
385                 390                 395                 400

Ser Gln Pro Pro Thr Pro Thr
                405

<210> SEQ ID NO 3
<211> LENGTH: 5163
<212> TYPE: DNA
<213> ORGANISM: Homo sapiens
<220> FEATURE:
<221> NAME/KEY: CDS
<222> LOCATION: (3157)..(4434)

<400> SEQUENCE: 3
ttaggggcag aaaaacattt gtaataatta atggctttga gagacacaag gctttgtttg      60
ccccagagta ttagttaacc cacctagtgc tcctaatcat acaatattaa ggattgggag     120
ggacattcat tgcctcactc tctatttgtt tcaccttctg taaaattggt agaataatag     180
tacccacttc atagcattgt atgatgatta aattggttaa tatttttaaa atgcttagaa     240
cacagattgg gcacataaca gcaagcacca catgtgttta agataaat tcctttgtgt      300 tgccttccgt taagtttaa ataagtaaat aaataaataa atacttgcat gacatttga      360 agtctctcta taacatctga gtaagtggcg gctgcgacaa tgctactgga gttccagaat     420
```

|  |  |  |  | |
|---|---|---|---|---|
| cgtgttggtg | acaagattgt | tcaccagcat | atggtgtggt | gaaaactcac | taatttggaa | 480 |
| ttagttcaga | ttattaagcc | tgaataggtg | aaaatcctga | aatcaaggat | ctttggaact | 540 |
| atttgaaatc | agtatttat | attttcctgt | tgtattcatt | aaagtgttgc | aagtgttcta | 600 |
| tttgatggat | taagtatatt | taggatatac | atgttcaatt | tgtgattttg | tatacttaat | 660 |
| tggaacaaga | aagctaataa | aggttttgat | atggacatct | attcttttaa | gtaaacttca | 720 |
| atgaaaatat | atgagtagag | catatagaga | tgtaaataat | ttgtggacac | accacagact | 780 |
| gaaatagcaa | atttaaaaga | aattgttgga | agaatcaagt | gtttgtggaa | tgagtcctcc | 840 |
| tagtaaagtt | cctgctcttg | tgaataatta | agcctcatgt | ataattacta | tagcaaaagg | 900 |
| aagcctaaga | agtattagac | tctacttgta | tttaaattac | attttacata | atttatgtgt | 960 |
| atgaaaaatg | ttttaaatgc | ttattttcgt | aagccatgag | atagctcctt | tatattttaa | 1020 |
| gaatttctga | attaatttgc | ttggatttta | ttagtgcaaa | tggcagagct | agcaattcct | 1080 |
| ttttctgtgt | tcccattcca | tcctattcat | ccctctttta | ggaaactctg | aactctggat | 1140 |
| tgtccttgtt | tacatacctg | cctcctgcat | tggactatgt | gtctctgagt | gtagtatgac | 1200 |
| taattcattt | gtttgtcaag | gactctcaat | gcatttgttg | aacagcctaa | ttagtaatgt | 1260 |
| ctgcaacaat | gacattttac | tgtatttaat | aaagctctgg | gaaagtagga | tacacataag | 1320 |
| acaggtctag | gtctaaattc | tttacagaaa | cttggatttt | tagttcggtt | tgaaatttga | 1380 |
| agatgtgagt | atatttatct | cagtttccca | aaggacaagc | taattggaat | tatcatcctc | 1440 |
| tttcacttga | ttggatcccc | agaatgccat | ttacgcatgc | agcaggattt | tataacagtt | 1500 |
| ttaaattctg | tatatttgat | gaagaggttt | tatattttg | gattcaagcc | tctttttaaa | 1560 |
| cttctacaat | atggtttaca | ataattcctt | atatcctgct | tttgaaatac | atattacaac | 1620 |
| tttttaagtt | tggaaggcta | tatttcaagg | actgaagtta | cagtatactc | aagtgataca | 1680 |
| caagcctagc | accccacttt | ccacatagtg | ttcgataaag | attgataaac | tcgaaatcac | 1740 |
| agacctttta | attcttaaga | caaatagcag | cagaaagaaa | catctttggc | ttatttctgg | 1800 |
| taaggttttt | atgctctgta | aaacaaagaa | ttgtattcat | ccgcgcagca | cagattctat | 1860 |
| taaaaataaa | tgtgagagtc | gttaatgtag | tactgctcat | ttaccatcaa | aattcacttt | 1920 |
| tcaggaataa | tcccatcagt | ttaaattgga | tattggaatg | agcattgatt | acatttaact | 1980 |
| tggtagccca | aaatttcttc | atggggtttt | gaactcggcg | ggatttcaaa | ggttttaaaa | 2040 |
| atgagttttt | gatttttttt | aaaaccctca | aatttcatta | cctttaaact | aggtcgaaac | 2100 |
| ggggcgcaag | agattggatt | aacaccatag | taatacttat | tttgttctta | accatttcag | 2160 |
| ggcttcttga | aatagaggct | gtatggtgta | atggaaaaaa | cagccttgga | atctgggagc | 2220 |
| ctgattcctg | gattcagtcc | cagttttgcg | tgaccttggg | caagttactt | tacttctctg | 2280 |
| aatttccgtt | tcctcctctg | caaaatgagg | atcgcaatag | ccaccttgca | accttgactg | 2340 |
| gagcgagcct | cgcacacccc | gcgccggcct | ggaggaagag | cagccatgat | tacgccgcct | 2400 |
| tcgctccgct | acccgcttgc | ggctggcgcc | ctcctccagc | aggtgtaggc | gctgccgcgc | 2460 |
| tgccccacgc | ctttccgccg | ctcgcgggcc | tgcgcctcgg | cgtccccgag | gaggccgctg | 2520 |
| cgggctgagg | tagcgcaccg | gcctctcggc | gtccagtccg | gtcccgggc | ggagggaaag | 2580 |
| cgggcgaccc | acctccgagg | cagaagccga | ggcccggccc | cgccgagtgc | ggaggagcgc | 2640 |
| aggcagcccc | cgcccctcgg | ccctcccccc | ggccctcccg | gccctccctc | cgccccctcc | 2700 |
| gccctcgcgc | gccgcccgcc | cgggtcgccg | cggggccgtg | gtgtacgtgc | agagcgcgca | 2760 |

| | |
|---|---|
| gagcgagtgg cgcccgtatg ccctgcgctc ctccacagcc tgggccgggc cgcccgggac | 2820 |
| gctgaggcgg cggcggcggc cgaggggggcc ggtcttgcgc tccccaggcc cgcgcgcctg | 2880 |
| agcccaggtt gccattcgcc gcacaggccc tattctctca gccctcggcg gcgatgaggc | 2940 |
| gctgaggcgg ctgccggcgc tgcgccggag cttaggactc ggaagcggcc gggccgaggg | 3000 |
| cgtggggtgc cggcctccct gaggcgaggg tagcgggtgc atggcgcagt aacggcccct | 3060 |
| atctctctcc ccgctcccca gcctcggcg aggccgtccg gccgctaccc ctcctgctcg | 3120 |

```
gccgccgcag tcgccgtcgc cgccgccgcc gccgcc atg gcc aat gac agc ggc     3174
                                        Met Ala Asn Asp Ser Gly
                                        1               5 ggg ccc ggc ggg ccg agc ccg agc gag cga gac cgg cag tac tgc gag     3222
Gly Pro Gly Gly Pro Ser Pro Ser Glu Arg Asp Arg Gln Tyr Cys Glu
         10                  15                  20 ctg tgc ggg aag atg gag aac ctg ctg cgc tgc agc cgc tgc cgc agc     3270
Leu Cys Gly Lys Met Glu Asn Leu Leu Arg Cys Ser Arg Cys Arg Ser
 25                  30                  35 tcc ttc tac tgc tgc aag gag cac cag cgt cag gac tgg aag aag cac     3318
Ser Phe Tyr Cys Cys Lys Glu His Gln Arg Gln Asp Trp Lys Lys His
     40                  45                  50 aag ctc gtg tgc cag ggc agc gag ggc gcc ctc ggc cac gga gtg ggc     3366
Lys Leu Val Cys Gln Gly Ser Glu Gly Ala Leu Gly His Gly Val Gly
55                  60                  65                  70 cca cac cag cat tcc ggc ccc gcg ccg ccg gct gca gtg ccg ccg ccc     3414
Pro His Gln His Ser Gly Pro Ala Pro Pro Ala Ala Val Pro Pro Pro
                 75                  80                  85 agg gcc ggg gcc cgg gag ccc agg aag gca gcg gcg cgc cgg gac aac     3462
Arg Ala Gly Ala Arg Glu Pro Arg Lys Ala Ala Ala Arg Arg Asp Asn
         90                  95                 100 gcc tcc ggg gac gcg gcc aag gga aaa gta aag gcc aag ccc ccg gcc     3510
Ala Ser Gly Asp Ala Ala Lys Gly Lys Val Lys Ala Lys Pro Pro Ala
    105                 110                 115 gac cca gcg gcg gcc gcg tcg ccg tgt cgt gcg gcc gcc ggc ggc cag     3558
Asp Pro Ala Ala Ala Ala Ser Pro Cys Arg Ala Ala Ala Gly Gly Gln
120                 125                 130 ggc tcg gcg gtg gct gcc gaa gcc gag ccc ggc aag gag gag ccg ccg     3606
Gly Ser Ala Val Ala Ala Glu Ala Glu Pro Gly Lys Glu Glu Pro Pro
135                 140                 145                 150 gcc cgc tca tcg ctg ttc cag gag aag gcg aac ctg tac ccc cca agc     3654
Ala Arg Ser Ser Leu Phe Gln Glu Lys Ala Asn Leu Tyr Pro Pro Ser
                155                 160                 165 aac acg ccc ggg gat gcg ctg agc ccc ggc ggc ggc ctg cgg ccc aac     3702
Asn Thr Pro Gly Asp Ala Leu Ser Pro Gly Gly Gly Leu Arg Pro Asn
            170                 175                 180 ggg cag acg aag ccc ctg ccg gcg ctg aag ctg gcg ctc gag tac atc     3750
Gly Gln Thr Lys Pro Leu Pro Ala Leu Lys Leu Ala Leu Glu Tyr Ile
        185                 190                 195 gtg ccg tgc atg aac aag cac ggc atc tgt gtg gtg gac gac ttc ctc     3798
Val Pro Cys Met Asn Lys His Gly Ile Cys Val Val Asp Asp Phe Leu
200                 205                 210 ggc aag gag acc gga cag cag atc ggc gac gag gtg cgc gcc ctg cac     3846
Gly Lys Glu Thr Gly Gln Gln Ile Gly Asp Glu Val Arg Ala Leu His
215                 220                 225                 230 gac acc ggg aag ttc acg gac ggg cag ctg gtc agc cag aag agt gac     3894
Asp Thr Gly Lys Phe Thr Asp Gly Gln Leu Val Ser Gln Lys Ser Asp
                235                 240                 245 tcg tcc aag gac atc cga ggc gat aag atc acc tgg atc gag ggc aag     3942
Ser Ser Lys Asp Ile Arg Gly Asp Lys Ile Thr Trp Ile Glu Gly Lys
            250                 255                 260
```

```
gag ccc ggc tgc gaa acc att ggg ctg ctc atg agc agc atg gac gac        3990
Glu Pro Gly Cys Glu Thr Ile Gly Leu Leu Met Ser Ser Met Asp Asp
            265                 270                 275 ctg ata cgc cac tgt aac ggg aag ctg ggc agc tac aaa atc aat ggc        4038
Leu Ile Arg His Cys Asn Gly Lys Leu Gly Ser Tyr Lys Ile Asn Gly
        280                 285                 290 cgg acg aaa gcc atg gtt gct tgt tat ccg ggc aat gga acg ggt tat        4086
Arg Thr Lys Ala Met Val Ala Cys Tyr Pro Gly Asn Gly Thr Gly Tyr
295                 300                 305                 310 gta cgt cat gtt gat aat cca aat gga gat gga aga tgt gtg aca tgt        4134
Val Arg His Val Asp Asn Pro Asn Gly Asp Gly Arg Cys Val Thr Cys
                315                 320                 325 ata tat tat ctt aat aaa gac tgg gat gcc aag gta agt gga ggt ata        4182
Ile Tyr Tyr Leu Asn Lys Asp Trp Asp Ala Lys Val Ser Gly Gly Ile
            330                 335                 340 ctt cga att ttt cca gaa ggc aaa gcc cag ttt gct gac att gaa ccc        4230
Leu Arg Ile Phe Pro Glu Gly Lys Ala Gln Phe Ala Asp Ile Glu Pro
        345                 350                 355 aaa ttt gat aga ctg ctg ttt ttc tgg tct gac cgt cgc aac cct cat        4278
Lys Phe Asp Arg Leu Leu Phe Phe Trp Ser Asp Arg Arg Asn Pro His
360                 365                 370 gaa gta caa cca gca tat gct aca agg tac gca ata act gtt tgg tat        4326
Glu Val Gln Pro Ala Tyr Ala Thr Arg Tyr Ala Ile Thr Val Trp Tyr
375                 380                 385                 390 ttt gat gca gat gag aga gca cga gct aaa gta aaa tat cta aca ggt        4374
Phe Asp Ala Asp Glu Arg Ala Arg Ala Lys Val Lys Tyr Leu Thr Gly
                395                 400                 405 gaa aaa ggt gtg agg gtt gaa ctc aat aaa cct tca gat tcg gtc ggt        4422
Glu Lys Gly Val Arg Val Glu Leu Asn Lys Pro Ser Asp Ser Val Gly
            410                 415                 420 aaa gac gtc ttc tagagccttt gatccagcaa taccccactt cacctacaat          4474
Lys Asp Val Phe
            425 attgttaact atttgttaac ttgtgaatac gaataaatgg gataaagaaa aatagacaac     4534 cagttcgcat tttaataagg aaacagaaac aacttttttgt gttgcatcaa acagaagatt    4594 ttgactgctg tgactttgta ctgcatgatc aacttcaaat ctgtgattgc ttacaggagg    4654 aagataagct actaattgaa aatggttttt acatctggat atgaaataag tgccctgtgt    4714 agaatttttt tcattcttat attttgccag atctgttatc tagctgagtt catttcatct    4774 ctcccttttt tatatcaagt ttgaatttgg gataatttttt ctatattagg tacaatttat   4834 ctaaactgaa ttgagaaaaa attacagtat tattcctcaa ataacatca atctattttt     4894 gtaaacctgt tcatactatt aaattttgcc ctaaaagacc tcttaataat gattgttgcc    4954 agtgactgat gattaatttt attttactta aataagaaaa aggagcactt taattacaac    5014 tgaaaaatca gattgttttg cagtccttcc ttacactaat ttgaactctt aaagattgct    5074 gctttttttt tgacattgtc aataacgaaa cctaattgta aaacagtcac catttactac   5134 caataacttt tagttaatgt tttacaagg                                      5163

<210> SEQ ID NO 4
<211> LENGTH: 426
<212> TYPE: PRT
<213> ORGANISM: Homo sapiens

<400> SEQUENCE: 4

Met Ala Asn Asp Ser Gly Gly Pro Gly Gly Pro Ser Pro Ser Glu Arg
1               5                   10                  15
```

```
Asp Arg Gln Tyr Cys Glu Leu Cys Gly Lys Met Glu Asn Leu Leu Arg
             20                  25                  30

Cys Ser Arg Cys Arg Ser Ser Phe Tyr Cys Cys Lys Glu His Gln Arg
         35                  40                  45

Gln Asp Trp Lys Lys His Lys Leu Val Cys Gln Gly Ser Glu Gly Ala
     50                  55                  60

Leu Gly His Gly Val Gly Pro His Gln His Ser Gly Pro Ala Pro Pro
 65                  70                  75                  80

Ala Ala Val Pro Pro Arg Ala Gly Ala Arg Glu Pro Arg Lys Ala
                 85                  90                  95

Ala Ala Arg Arg Asp Asn Ala Ser Gly Asp Ala Ala Lys Gly Lys Val
             100                 105                 110

Lys Ala Lys Pro Pro Ala Asp Pro Ala Ala Ala Ser Pro Cys Arg
         115                 120                 125

Ala Ala Ala Gly Gly Gln Gly Ser Ala Val Ala Ala Glu Ala Glu Pro
 130                 135                 140

Gly Lys Glu Glu Pro Pro Ala Arg Ser Ser Leu Phe Gln Glu Lys Ala
145                 150                 155                 160

Asn Leu Tyr Pro Pro Ser Asn Thr Pro Gly Asp Ala Leu Ser Pro Gly
             165                 170                 175

Gly Gly Leu Arg Pro Asn Gly Gln Thr Lys Pro Leu Pro Ala Leu Lys
             180                 185                 190

Leu Ala Leu Glu Tyr Ile Val Pro Cys Met Asn Lys His Gly Ile Cys
         195                 200                 205

Val Val Asp Asp Phe Leu Gly Lys Glu Thr Gly Gln Gln Ile Gly Asp
     210                 215                 220

Glu Val Arg Ala Leu His Asp Thr Gly Lys Phe Thr Asp Gly Gln Leu
225                 230                 235                 240

Val Ser Gln Lys Ser Asp Ser Ser Lys Asp Ile Arg Gly Asp Lys Ile
             245                 250                 255

Thr Trp Ile Glu Gly Lys Glu Pro Gly Cys Glu Thr Ile Gly Leu Leu
             260                 265                 270

Met Ser Ser Met Asp Asp Leu Ile Arg His Cys Asn Gly Lys Leu Gly
         275                 280                 285

Ser Tyr Lys Ile Asn Gly Arg Thr Lys Ala Met Val Ala Cys Tyr Pro
     290                 295                 300

Gly Asn Gly Thr Gly Tyr Val Arg His Val Asp Asn Pro Asn Gly Asp
305                 310                 315                 320

Gly Arg Cys Val Thr Cys Ile Tyr Tyr Leu Asn Lys Asp Trp Asp Ala
             325                 330                 335

Lys Val Ser Gly Gly Ile Leu Arg Ile Phe Pro Glu Gly Lys Ala Gln
             340                 345                 350

Phe Ala Asp Ile Glu Pro Lys Phe Asp Arg Leu Leu Phe Phe Trp Ser
         355                 360                 365

Asp Arg Arg Asn Pro His Glu Val Gln Pro Ala Tyr Ala Thr Arg Tyr
         370                 375                 380

Ala Ile Thr Val Trp Tyr Phe Asp Ala Asp Glu Arg Ala Arg Ala Lys
385                 390                 395                 400

Val Lys Tyr Leu Thr Gly Glu Lys Gly Val Arg Val Glu Leu Asn Lys
             405                 410                 415

Pro Ser Asp Ser Val Gly Lys Asp Val Phe
             420                 425
```

```
<210> SEQ ID NO 5
<211> LENGTH: 2770
<212> TYPE: DNA
<213> ORGANISM: Homo sapiens
<220> FEATURE:
<221> NAME/KEY: CDS
<222> LOCATION: (327)..(1043)

<400> SEQUENCE: 5
```

| | | |
|---|---|---|
| gagtctggcc gcagtcgcgg cagtggtggc ttcccatccc caaaaggcgc cctccgactc | 60 | |
| cttgcgccgc actgctcgcc gggccagtcc ggaaacgggt cgtggagctc cgcaccactc | 120 | |
| ccgctggttc ccgaaggcag atcccttctc ccgagagttg cgagaaactt tcccttgtcc | 180 | |
| ccgacgctgc agcggctcgg gtaccgtggc agccgcaggt ttctgaaccc cgggccacgc | 240 | |
| tccccgcgcc tcggcttcgc gctcgtgtag atcgttccct ctctggttgc acgctgggga | 300 | |

```
tccccggacct cgattctgcg ggcgag atg ccc ctg gga cac atc atg agg ctg     353
                              Met Pro Leu Gly His Ile Met Arg Leu
                                1               5 gac ctg gag aaa att gcc ctg gag tac atc gtg ccc tgt ctg cac gag      401
Asp Leu Glu Lys Ile Ala Leu Glu Tyr Ile Val Pro Cys Leu His Glu
 10              15                  20                  25 gtg ggc ttc tgc tac ctg gac aac ttc ctg ggc gag gtg gtg ggc gac      449
Val Gly Phe Cys Tyr Leu Asp Asn Phe Leu Gly Glu Val Val Gly Asp
             30                  35                  40 tgc gtc ctg gag cgc gtc aag cag ctg cac tgc acc ggg gcc ctg cgg      497
Cys Val Leu Glu Arg Val Lys Gln Leu His Cys Thr Gly Ala Leu Arg
         45                  50                  55 gac ggc cag ctg gcg ggg ccg cgc gcc ggc gtc tcc aag cga cac ctg      545
Asp Gly Gln Leu Ala Gly Pro Arg Ala Gly Val Ser Lys Arg His Leu
     60                  65                  70 cgg ggc gac cag atc acg tgg atc ggg ggc aac gag gag ggc tgc gag      593
Arg Gly Asp Gln Ile Thr Trp Ile Gly Gly Asn Glu Glu Gly Cys Glu
 75                  80                  85 gcc atc agc ttc ctc ctg tcc ctc atc gac agg ctg gtc ctc tac tgc      641
Ala Ile Ser Phe Leu Leu Ser Leu Ile Asp Arg Leu Val Leu Tyr Cys
 90                  95                 100                 105 ggg agc cgg ctg ggc aaa tac tac gtc aag gag agg tct aag gca atg      689
Gly Ser Arg Leu Gly Lys Tyr Tyr Val Lys Glu Arg Ser Lys Ala Met
                110                 115                 120 gtg gct tgc tat ccg gga aat gga aca ggt tat gtt cgc cac gtg gac      737
Val Ala Cys Tyr Pro Gly Asn Gly Thr Gly Tyr Val Arg His Val Asp
            125                 130                 135 aac ccc aac ggt gat ggt cgc tgc atc acc tgc atc tac tat ctg aac      785
Asn Pro Asn Gly Asp Gly Arg Cys Ile Thr Cys Ile Tyr Tyr Leu Asn
        140                 145                 150 aag aat tgg gat gcc aag cta cat ggt ggg atc ctg cgg ata ttt cca      833
Lys Asn Trp Asp Ala Lys Leu His Gly Gly Ile Leu Arg Ile Phe Pro
    155                 160                 165 gag ggg aaa tca ttc ata gca gat gtg gag ccc att ttt gac aga ctc      881
Glu Gly Lys Ser Phe Ile Ala Asp Val Glu Pro Ile Phe Asp Arg Leu
170                 175                 180                 185 ctg ttc ttc tgg tca gat cgt agg aac cca cac gaa gtg cag ccc tct      929
Leu Phe Phe Trp Ser Asp Arg Arg Asn Pro His Glu Val Gln Pro Ser
                190                 195                 200 tac gca acc aga tat gct atg act gtc tgg tac ttt gat gct gaa gaa      977
Tyr Ala Thr Arg Tyr Ala Met Thr Val Trp Tyr Phe Asp Ala Glu Glu
            205                 210                 215 agg gca gaa gcc aaa aag aaa ttc agg aat tta act agg aaa act gaa     1025
Arg Ala Glu Ala Lys Lys Lys Phe Arg Asn Leu Thr Arg Lys Thr Glu
```

```
           220              225              230
tct gcc ctc act gaa gac tgaccgtgct ctgaaatctg ctggccttgt         1073
Ser Ala Leu Thr Glu Asp
    235 tcatttttagt aacggttcct gaattctctt aaattctttg agatccaaag atggcctctt  1133
cagtgacaac aatctccctg ctacttcttg catccttcac atccctgtct tgtgtgtggt  1193
acttcatgtt ttcttgccaa gactgtgttg atcttcagat actctctttg ccagatgaag  1253
ttatttgcta actccagaaa ttcctgcaga catcctactc ggccagcggt ttacctgata  1313
gattcggtaa tactatcaag agaagagcct aggagcacag cgagggaatg aaccttactt  1373
gcactttatg tatacttcct gatttgaaag gaggaggttt gaaaagaaaa aaatggaggt  1433
ggtagatgcc acagagaggc atcacggaag ccttaacagc aggaaacaga gaaatttgtg  1493
tcatctgaac aatttccaga tgttcttaat ccagggctgt tggggtttct ggagaattat  1553
cacaacctaa tgacattaat acctctagaa agggctgctg tcatagtgaa caatttataa  1613
gtgtcccatg gggcagacac tcctttttc ccagtcctgc aacctggatt ttctgcctca  1673
gctccatttt gctgaaaata atgactttct gaataaagat ggcaacacaa ttttttctcc  1733
attttcagtt cttacctggg aacctaattc cccagaagct aaaaaactag acattagttg  1793
ttttggttgc tttgttggaa tggaatttaa atttaaatga aggaaaaat atatccctgg  1853
tagttttgtg ttaaccactg ataactgtgg aaagagctag gtctactgat atacaataaa  1913
catgtgtgca tcttgaacaa tttgagaggg gaggtggagt tggaaatgtg ggtgttcctg  1973
tttttttttt tttttttttt tttttttagt tttcctttt aatgagctca ccctttaaca  2033
caaaaaagc agggtgatgt attttaaaaa aggaagtgga ataaaaaaa tctcaaagct  2093
atttgagttc tcgtctgtcc ctagcagtct ttcttcagct cacttggctc tctagatcca  2153
ctgtggttgg cagtatgacc agaatcatgg aacttgctag aactgtggaa gcttctactc  2213
ctgcagtaag cacagatcgc actgcctcaa taacttggta ttgagcacgt attttgcaaa  2273
agctactttt cctagttttc agtattactt tcatgtttta aaaatcccct taatttcttg  2333
cttgaaaatc ccatgaacat taaagagcca gaaatatttt cctttgttat gtacggatat  2393
atatatatat atagtcttcc aagatagaag tttacttttt cctcttctgg ttttggaaaa  2453
tttccagata agacatgtca ccattaattc tcaacgactg ctctattttg ttgtacggta  2513
atagttatca ccttctaaat tactatgtaa tttactcact tattatgttt attgtcttgt  2573
atcctttctc tggagtgtaa gcacaatgaa gacaggaatt ttgtatattt ttaaccaatg  2633
caacatactc tcagcaccta aaatagtgcc gggaacatag taagggctca gtaaatactt  2693
gttgaataaa ctcagtctcc tacattagca ttctaaaaaa aaaaaaaaaa aaaaaaaaa  2753
aaaaaaaaaa aaaaaag                                               2770
```

<210> SEQ ID NO 6
<211> LENGTH: 239
<212> TYPE: PRT
<213> ORGANISM: Homo sapiens

<400> SEQUENCE: 6

Met Pro Leu Gly His Ile Met Arg Leu Asp Leu Glu Lys Ile Ala Leu
1               5                   10                  15

Glu Tyr Ile Val Pro Cys Leu His Glu Val Gly Phe Cys Tyr Leu Asp
            20                  25                  30

Asn Phe Leu Gly Glu Val Val Gly Asp Cys Val Leu Glu Arg Val Lys

```
                35                  40                  45
Gln Leu His Cys Thr Gly Ala Leu Arg Asp Gly Gln Leu Ala Gly Pro
 50                  55                  60

Arg Ala Gly Val Ser Lys Arg His Leu Arg Gly Asp Gln Ile Thr Trp
 65                  70                  75                  80

Ile Gly Gly Asn Glu Glu Gly Cys Glu Ala Ile Ser Phe Leu Leu Ser
                 85                  90                  95

Leu Ile Asp Arg Leu Val Leu Tyr Cys Gly Ser Arg Leu Gly Lys Tyr
            100                 105                 110

Tyr Val Lys Glu Arg Ser Lys Ala Met Val Ala Cys Tyr Pro Gly Asn
        115                 120                 125

Gly Thr Gly Tyr Val Arg His Val Asp Asn Pro Asn Gly Asp Gly Arg
    130                 135                 140

Cys Ile Thr Cys Ile Tyr Tyr Leu Asn Lys Asn Trp Asp Ala Lys Leu
145                 150                 155                 160

His Gly Gly Ile Leu Arg Ile Phe Pro Glu Gly Lys Ser Phe Ile Ala
                165                 170                 175

Asp Val Glu Pro Ile Phe Asp Arg Leu Leu Phe Phe Trp Ser Asp Arg
            180                 185                 190

Arg Asn Pro His Glu Val Gln Pro Ser Tyr Ala Thr Arg Tyr Ala Met
        195                 200                 205

Thr Val Trp Tyr Phe Asp Ala Glu Glu Arg Ala Glu Ala Lys Lys Lys
    210                 215                 220

Phe Arg Asn Leu Thr Arg Lys Thr Glu Ser Ala Leu Thr Glu Asp
225                 230                 235

<210> SEQ ID NO 7
<211> LENGTH: 2369
<212> TYPE: DNA
<213> ORGANISM: Caenorhabditis elegans
<220> FEATURE:
<221> NAME/KEY: CDS
<222> LOCATION: (11)..(2179)

<400> SEQUENCE: 7
agcacatgac atg agc agt gcc cca aat gat gac tgt gag atc gac aag       49
            Met Ser Ser Ala Pro Asn Asp Asp Cys Glu Ile Asp Lys
              1               5                  10 gga aca cct tct acc gct tca ctt ttt aca acg ctg atg ctc agt caa      97
Gly Thr Pro Ser Thr Ala Ser Leu Phe Thr Thr Leu Met Leu Ser Gln
 15                  20                  25 cca tct tct tct aca gct gtt tta cag tgt aca tat tgt gga agc tcg     145
Pro Ser Ser Ser Thr Ala Val Leu Gln Cys Thr Tyr Cys Gly Ser Ser
 30                  35                  40                  45 tgc aca tct tcc caa ttg caa aca tgt tta ttc tgt gga aca gtg gct     193
Cys Thr Ser Ser Gln Leu Gln Thr Cys Leu Phe Cys Gly Thr Val Ala
                 50                  55                  60 tat tgt tcc aag gag cac cag caa ctc gat tgg cta aca cat aaa atg     241
Tyr Cys Ser Lys Glu His Gln Gln Leu Asp Trp Leu Thr His Lys Met
             65                  70                  75 ata tgc aag tca ctt caa aca agt ggc atg gtg cca agt aat ttg atg     289
Ile Cys Lys Ser Leu Gln Thr Ser Gly Met Val Pro Ser Asn Leu Met
         80                  85                  90 cct cag gca gca cct gct gtt atg gct cca att cca cct act gtt tcg     337
Pro Gln Ala Ala Pro Ala Val Met Ala Pro Ile Pro Pro Thr Val Ser
     95                 100                 105 ttt gat gat cct gca ctt acc acg tca ctt ctt cta tct ctt caa aat     385
Phe Asp Asp Pro Ala Leu Thr Thr Ser Leu Leu Leu Ser Leu Gln Asn
```

-continued

| | | | | |
|---|---|---|---|---|
| 110 | 115 | 120 | 125 | |
| aat cca att ctg aat caa act att tca aat ttt ccg cca aca ttt tcg<br>Asn Pro Ile Leu Asn Gln Thr Ile Ser Asn Phe Pro Pro Thr Phe Ser<br>130 135 140 | | | | 433 |
| atc aca tcg aag acc gaa cca gag cca tcg att cca atc caa att cca<br>Ile Thr Ser Lys Thr Glu Pro Glu Pro Ser Ile Pro Ile Gln Ile Pro<br>145 150 155 | | | | 481 |
| caa agg ata tca tca aca agt aca gta ccg ttc agt agt gaa gga agt<br>Gln Arg Ile Ser Ser Thr Ser Thr Val Pro Phe Ser Ser Glu Gly Ser<br>160 165 170 | | | | 529 |
| gca ttc aaa cca tac aga aat acg cat gtg ttt aat tca att tct tct<br>Ala Phe Lys Pro Tyr Arg Asn Thr His Val Phe Asn Ser Ile Ser Ser<br>175 180 185 | | | | 577 |
| gaa tca atg tct tcc atg tgc aca tca cat gaa gca tca ctt gaa cac<br>Glu Ser Met Ser Ser Met Cys Thr Ser His Glu Ala Ser Leu Glu His<br>190 195 200 205 | | | | 625 |
| atg tca tca gct tcc ctt gca atg ttc cca aca agt agt act gct caa<br>Met Ser Ser Ala Ser Leu Ala Met Phe Pro Thr Ser Ser Thr Ala Gln<br>210 215 220 | | | | 673 |
| agt gat atc agt aga ctc gct caa gtt ttg agt ctt gct gga gat tca<br>Ser Asp Ile Ser Arg Leu Ala Gln Val Leu Ser Leu Ala Gly Asp Ser<br>225 230 235 | | | | 721 |
| cca gct tcg ttg gct ctt gtc aca act tcg gta ccg tca act gct tcc<br>Pro Ala Ser Leu Ala Leu Val Thr Thr Ser Val Pro Ser Thr Ala Ser<br>240 245 250 | | | | 769 |
| aca gca act att cca cct cca gcg aca acg aca agt tca gct aca agt<br>Thr Ala Thr Ile Pro Pro Pro Ala Thr Thr Thr Ser Ser Ala Thr Ser<br>255 260 265 | | | | 817 |
| tca ggc aaa agc gag aca ata act gtt gga aaa gaa aag ata att caa<br>Ser Gly Lys Ser Glu Thr Ile Thr Val Gly Lys Glu Lys Ile Ile Gln<br>270 275 280 285 | | | | 865 |
| act gat gat ccg gat att cag atc atc gaa aca gaa ggt gga tca aaa<br>Thr Asp Asp Pro Asp Ile Gln Ile Ile Glu Thr Glu Gly Gly Ser Lys<br>290 295 300 | | | | 913 |
| cca acg gta tcc aga aca cgg aaa cga cca act cct tct aac tcc gct<br>Pro Thr Val Ser Arg Thr Arg Lys Arg Pro Thr Pro Ser Asn Ser Ala<br>305 310 315 | | | | 961 |
| gac cca aaa att aat tac aag gat cac aat aag aat gtc gtt tac tcg<br>Asp Pro Lys Ile Asn Tyr Lys Asp His Asn Lys Asn Val Val Tyr Ser<br>320 325 330 | | | | 1009 |
| aca acc ctc caa gaa cat cag aag cat ctt cag aat cgt ggt ctc gca<br>Thr Thr Leu Gln Glu His Gln Lys His Leu Gln Asn Arg Gly Leu Ala<br>335 340 345 | | | | 1057 |
| cta agc att cac caa gca atg gtt cta cgg tta aga tac att gcc gag<br>Leu Ser Ile His Gln Ala Met Val Leu Arg Leu Arg Tyr Ile Ala Glu<br>350 355 360 365 | | | | 1105 |
| cat gtg atc aga agc ctg aat gag ttt gga tgg gcc gtt gtt gac aat<br>His Val Ile Arg Ser Leu Asn Glu Phe Gly Trp Ala Val Val Asp Asn<br>370 375 380 | | | | 1153 |
| ttt ctg ggc tcg gat cac tac aaa ttt acc gcg aaa gaa att gag cga<br>Phe Leu Gly Ser Asp His Tyr Lys Phe Thr Ala Lys Glu Ile Glu Arg<br>385 390 395 | | | | 1201 |
| ctc tat gaa cgg gga ctc ttc agc cct ggt cag ttg atg gaa gca aaa<br>Leu Tyr Glu Arg Gly Leu Phe Ser Pro Gly Gln Leu Met Glu Ala Lys<br>400 405 410 | | | | 1249 |
| cac aaa gac gaa ttt cac atc aaa gat att cga tct gac cac att tac<br>His Lys Asp Glu Phe His Ile Lys Asp Ile Arg Ser Asp His Ile Tyr<br>415 420 425 | | | | 1297 |
| tgg tat gat ggt tat gat gga cgt gcc aag gat gct gca act gtt cgt | | | | 1345 |

```
Trp Tyr Asp Gly Tyr Asp Gly Arg Ala Lys Asp Ala Ala Thr Val Arg
430                 435                 440                 445 cta ttg att tca atg att gat tct gta att caa cat ttc aaa aaa cga      1393
Leu Leu Ile Ser Met Ile Asp Ser Val Ile Gln His Phe Lys Lys Arg
                450                 455                 460 att gat cat gat att gga gga cgt tct cgt gca atg ctt gcc atc tat      1441
Ile Asp His Asp Ile Gly Gly Arg Ser Arg Ala Met Leu Ala Ile Tyr
                465                 470                 475 cct gga aat gga act cgt tat gtg aag cat gta gat aat ccg gta aaa      1489
Pro Gly Asn Gly Thr Arg Tyr Val Lys His Val Asp Asn Pro Val Lys
            480                 485                 490 gat gga aga tgt ata acc act att tat tac tgt aat gaa aat tgg gat      1537
Asp Gly Arg Cys Ile Thr Thr Ile Tyr Tyr Cys Asn Glu Asn Trp Asp
        495                 500                 505 atg gca act gat ggt ggt act ctc aga tta tat cca gag act tca atg      1585
Met Ala Thr Asp Gly Gly Thr Leu Arg Leu Tyr Pro Glu Thr Ser Met
510                 515                 520                 525 act cca atg gat att gat cca agg gct gat cgt ctg gta ttc ttc tgg      1633
Thr Pro Met Asp Ile Asp Pro Arg Ala Asp Arg Leu Val Phe Phe Trp
                530                 535                 540 tcc gat cgt cgc aat cct cat gaa gtc atg cca gtc ttc cgt cat cgt      1681
Ser Asp Arg Arg Asn Pro His Glu Val Met Pro Val Phe Arg His Arg
                545                 550                 555 ttc gca att act att tgg tat atg gat aaa tcc gaa aga gat aag gct      1729
Phe Ala Ile Thr Ile Trp Tyr Met Asp Lys Ser Glu Arg Asp Lys Ala
            560                 565                 570 ttg gca aaa gga aaa gag tca gat gcg gca tgt gct tca aag aaa gag      1777
Leu Ala Lys Gly Lys Glu Ser Asp Ala Ala Cys Ala Ser Lys Lys Glu
        575                 580                 585 aat gat cca aca agc tct tca cta aat tcc ctt att gga tca ctt ttg      1825
Asn Asp Pro Thr Ser Ser Ser Leu Asn Ser Leu Ile Gly Ser Leu Leu
590                 595                 600                 605 aga cca cgg aaa aat cca agt act cac gat tta tca aaa ctt gac ctt      1873
Arg Pro Arg Lys Asn Pro Ser Thr His Asp Leu Ser Lys Leu Asp Leu
                610                 615                 620 cga ctc ttc ccg tcc aca tca tcc gat cca gct ctg gta tct gca gca      1921
Arg Leu Phe Pro Ser Thr Ser Ser Asp Pro Ala Leu Val Ser Ala Ala
                625                 630                 635 gat gaa gat aga gtt gac atc tct gcc gac ttt caa tcc act tca agt      1969
Asp Glu Asp Arg Val Asp Ile Ser Ala Asp Phe Gln Ser Thr Ser Ser
            640                 645                 650 ctg gct cat ccg gaa tct act gac tcg gga gta tct ctc tcc acc ttc      2017
Leu Ala His Pro Glu Ser Thr Asp Ser Gly Val Ser Leu Ser Thr Phe
        655                 660                 665 aat gtc gct cat aat cac atg gaa cgt act acc agt ctc cag tcg atc      2065
Asn Val Ala His Asn His Met Glu Arg Thr Thr Ser Leu Gln Ser Ile
670                 675                 680                 685 tcc gat cat ttc cgt tcc gaa aga tca cac gaa cgt cgc agc tca aca      2113
Ser Asp His Phe Arg Ser Glu Arg Ser His Glu Arg Arg Ser Ser Thr
                690                 695                 700 agc agc gat caa gat cta gac gaa ggg ctc cca cca cct cct tcc aca      2161
Ser Ser Asp Gln Asp Leu Asp Glu Gly Leu Pro Pro Pro Pro Ser Thr
            705                 710                 715 aac cca gag tat tac atc tgaagttttt ctggttttg ttactttcta              2209
Asn Pro Glu Tyr Tyr Ile
            720 tatatatata tgtcaccttc attcaatacg ggtaaagtca atcttgaaat tccgattccc    2269 gagaaaatca ttgtcattcg agttttttta tgtatggact ctacaaatta ttatctcgac   2329
``` tttttccatgt gagatagagt accaattcaa catggttttt 2369

<210> SEQ ID NO 8
<211> LENGTH: 723
<212> TYPE: PRT
<213> ORGANISM: Caenorhabditis elegans
<400> SEQUENCE: 8

```
Met Ser Ser Ala Pro Asn Asp Asp Cys Glu Ile Asp Lys Gly Thr Pro
1               5                   10                  15

Ser Thr Ala Ser Leu Phe Thr Thr Leu Met Leu Ser Gln Pro Ser Ser
            20                  25                  30

Ser Thr Ala Val Leu Gln Cys Thr Tyr Cys Gly Ser Ser Cys Thr Ser
        35                  40                  45

Ser Gln Leu Gln Thr Cys Leu Phe Cys Gly Thr Val Ala Tyr Cys Ser
    50                  55                  60

Lys Glu His Gln Gln Leu Asp Trp Leu Thr His Lys Met Ile Cys Lys
65                  70                  75                  80

Ser Leu Gln Thr Ser Gly Met Val Pro Ser Asn Leu Met Pro Gln Ala
                85                  90                  95

Ala Pro Ala Val Met Ala Pro Ile Pro Pro Thr Val Ser Phe Asp Asp
            100                 105                 110

Pro Ala Leu Thr Thr Ser Leu Leu Leu Ser Leu Gln Asn Asn Pro Ile
        115                 120                 125

Leu Asn Gln Thr Ile Ser Asn Phe Pro Pro Thr Phe Ser Ile Thr Ser
    130                 135                 140

Lys Thr Glu Pro Glu Pro Ser Ile Pro Ile Gln Ile Pro Gln Arg Ile
145                 150                 155                 160

Ser Ser Thr Ser Thr Val Pro Phe Ser Ser Glu Gly Ser Ala Phe Lys
                165                 170                 175

Pro Tyr Arg Asn Thr His Val Phe Asn Ser Ile Ser Ser Glu Ser Met
            180                 185                 190

Ser Ser Met Cys Thr Ser His Glu Ala Ser Leu Glu His Met Ser Ser
        195                 200                 205

Ala Ser Leu Ala Met Phe Pro Thr Ser Ser Thr Ala Gln Ser Asp Ile
    210                 215                 220

Ser Arg Leu Ala Gln Val Leu Ser Leu Ala Gly Asp Ser Pro Ala Ser
225                 230                 235                 240

Leu Ala Leu Val Thr Thr Ser Val Pro Ser Thr Ala Ser Thr Ala Thr
                245                 250                 255

Ile Pro Pro Pro Ala Thr Thr Thr Ser Ser Ala Thr Ser Ser Gly Lys
            260                 265                 270

Ser Glu Thr Ile Thr Val Gly Lys Glu Lys Ile Ile Gln Thr Asp Asp
        275                 280                 285

Pro Asp Ile Gln Ile Ile Glu Thr Gly Gly Ser Lys Pro Thr Val
    290                 295                 300

Ser Arg Thr Arg Lys Arg Pro Thr Pro Ser Asn Ser Ala Asp Pro Lys
305                 310                 315                 320

Ile Asn Tyr Lys Asp His Asn Lys Asn Val Val Tyr Ser Thr Thr Leu
                325                 330                 335

Gln Glu His Gln Lys His Leu Gln Asn Arg Gly Leu Ala Leu Ser Ile
            340                 345                 350

His Gln Ala Met Val Leu Arg Leu Arg Tyr Ile Ala Glu His Val Ile
        355                 360                 365
```

```
Arg Ser Leu Asn Glu Phe Gly Trp Ala Val Val Asp Asn Phe Leu Gly
370                 375                 380

Ser Asp His Tyr Lys Phe Thr Ala Lys Glu Ile Glu Arg Leu Tyr Glu
385                 390                 395                 400

Arg Gly Leu Phe Ser Pro Gly Gln Leu Met Glu Ala Lys His Lys Asp
                405                 410                 415

Glu Phe His Ile Lys Asp Ile Arg Ser Asp His Ile Tyr Trp Tyr Asp
                420                 425                 430

Gly Tyr Asp Gly Arg Ala Lys Asp Ala Thr Val Arg Leu Leu Ile
                435                 440                 445

Ser Met Ile Asp Ser Val Ile Gln His Phe Lys Lys Arg Ile Asp His
450                 455                 460

Asp Ile Gly Gly Arg Ser Arg Ala Met Leu Ala Ile Tyr Pro Gly Asn
465                 470                 475                 480

Gly Thr Arg Tyr Val Lys His Val Asp Asn Pro Val Lys Asp Gly Arg
                485                 490                 495

Cys Ile Thr Thr Ile Tyr Tyr Cys Asn Glu Asn Trp Asp Met Ala Thr
                500                 505                 510

Asp Gly Gly Thr Leu Arg Leu Tyr Pro Glu Thr Ser Met Thr Pro Met
                515                 520                 525

Asp Ile Asp Pro Arg Ala Asp Arg Leu Val Phe Phe Trp Ser Asp Arg
530                 535                 540

Arg Asn Pro His Glu Val Met Pro Val Phe Arg His Arg Phe Ala Ile
545                 550                 555                 560

Thr Ile Trp Tyr Met Asp Lys Ser Glu Arg Asp Lys Ala Leu Ala Lys
                565                 570                 575

Gly Lys Glu Ser Asp Ala Ala Cys Ala Ser Lys Lys Glu Asn Asp Pro
                580                 585                 590

Thr Ser Ser Ser Leu Asn Ser Leu Ile Gly Ser Leu Leu Arg Pro Arg
                595                 600                 605

Lys Asn Pro Ser Thr His Asp Leu Ser Lys Leu Asp Leu Arg Leu Phe
610                 615                 620

Pro Ser Thr Ser Ser Asp Pro Ala Leu Val Ser Ala Ala Asp Glu Asp
625                 630                 635                 640

Arg Val Asp Ile Ser Ala Asp Phe Gln Ser Thr Ser Ser Leu Ala His
                645                 650                 655

Pro Glu Ser Thr Asp Ser Gly Val Ser Leu Ser Thr Phe Asn Val Ala
                660                 665                 670

His Asn His Met Glu Arg Thr Thr Ser Leu Gln Ser Ile Ser Asp His
                675                 680                 685

Phe Arg Ser Glu Arg Ser His Glu Arg Arg Ser Ser Thr Ser Ser Asp
690                 695                 700

Gln Asp Leu Asp Glu Gly Leu Pro Pro Pro Ser Thr Asn Pro Glu
705                 710                 715                 720

Tyr Tyr Ile

<210> SEQ ID NO 9
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
```

```
<223> OTHER INFORMATION: 4-hydroxy proline

<400> SEQUENCE: 9

Asp Leu Asp Leu Glu Met Leu Ala Pro Tyr Ile Pro Met Asp Asp Asp
1               5                   10                  15

Phe Gln Leu

<210> SEQ ID NO 10
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: 4-hydroxy proline

<400> SEQUENCE: 10

Asp Leu Asp Leu Glu Met Leu Ala Pro Tyr Ile Ser Met Asp Asp Asp
1               5                   10                  15

Phe Gln Leu

<210> SEQ ID NO 11
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: 4-hydroxy proline

<400> SEQUENCE: 11

Asp Leu Asp Leu Glu Met Leu Leu Pro Tyr Ile Pro Met Asp Asp Asp
1               5                   10                  15

Phe Gln Leu

<210> SEQ ID NO 12
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: 4-hydroxy proline

<400> SEQUENCE: 12

Asp Leu Asp Leu Glu Met Leu Val Pro Tyr Ile Pro Met Asp Asp Asp
1               5                   10                  15

Phe Gln Leu

<210> SEQ ID NO 13
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (9)..(9)
<223> OTHER INFORMATION: 4-hydroxy proline

<400> SEQUENCE: 13

Asp Leu Asp Leu Glu Met Ile Ala Pro Tyr Ile Pro Met Asp Asp
1               5                   10                  15

Phe Gln Leu

<210> SEQ ID NO 14
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: 4-hydroxy proline

<400> SEQUENCE: 14

Asp Leu Asp Leu Glu Met Ile Ala Pro Tyr Ile Pro Met Glu Asp
1               5                   10                  15

Phe Gln Leu

<210> SEQ ID NO 15
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: 4-hydroxy proline

<400> SEQUENCE: 15

Asp Leu Asp Leu Glu Met Leu Val Pro Tyr Ile Ser Met Asp Asp
1               5                   10                  15

Phe Gln Leu

<210> SEQ ID NO 16
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Pro Phe Ser Thr Gln Asp Thr Asp Leu Asp Leu Glu Met Leu Ala Pro
1               5                   10                  15

Tyr Ile Pro Met Asp Asp Asp Phe Gln Leu Arg Ser Phe Asp Gln Leu
                20                  25                  30

Ser Pro

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (2)..(3)
<223> OTHER INFORMATION: Any amino acid
<220> FEATURE:
<221> NAME/KEY: MOD_RES
<222> LOCATION: (6)..(6)
<223> OTHER INFORMATION: 4-hydroxy proline

<400> SEQUENCE: 17

Leu Xaa Xaa Leu Ala Pro
1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid

<400> SEQUENCE: 18

His Xaa Asp Xaa His
1               5

<210> SEQ ID NO 19
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(61)
<223> OTHER INFORMATION: Any amino acid

<400> SEQUENCE: 19

His Xaa Asp Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa His
    50                  55                  60

<210> SEQ ID NO 20
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(14)
<223> OTHER INFORMATION: Any amino acid
<220> FEATURE:
<221> NAME/KEY: MOD_RES
```

```
<222> LOCATION: (16)..(16)
<223> OTHER INFORMATION: Any amino acid
<220> FEATURE:
<221> NAME/KEY: MOD_RES
<222> LOCATION: (18)..(21)
<223> OTHER INFORMATION: Any amino acid
<220> FEATURE:
<221> NAME/KEY: MOD_RES
<222> LOCATION: (23)..(29)
<223> OTHER INFORMATION: Any amino acid
<220> FEATURE:
<221> NAME/KEY: MOD_RES
<222> LOCATION: (31)..(44)
<223> OTHER INFORMATION: Any amino acid
<220> FEATURE:
<221> NAME/KEY: MOD_RES
<222> LOCATION: (46)..(59)
<223> OTHER INFORMATION: Any amino acid
<220> FEATURE:
<221> NAME/KEY: MOD_RES
<222> LOCATION: (61)..(70)
<223> OTHER INFORMATION: Any amino acid
<220> FEATURE:
<221> NAME/KEY: MOD_RES
<222> LOCATION: (72)..(75)
<223> OTHER INFORMATION: Any amino acid
<220> FEATURE:
<221> NAME/KEY: MOD_RES
<222> LOCATION: (77)..(77)
<223> OTHER INFORMATION: Any amino acid
<220> FEATURE:
<221> NAME/KEY: MOD_RES
<222> LOCATION: (79)..(84)
<223> OTHER INFORMATION: Any amino acid

<400> SEQUENCE: 20

Met Xaa Xaa Xaa Xaa Xaa Xaa Xaa Xaa Xaa Xaa Xaa Xaa His Xaa
1               5                   10                  15

Asp Xaa Xaa Xaa Xaa Asp Xaa Xaa Xaa Xaa Xaa Xaa Xaa Tyr Xaa Xaa
            20                  25                  30

Xaa Xaa Xaa Xaa Xaa Xaa Xaa Xaa Xaa Xaa Xaa Leu Xaa Xaa Xaa
        35                  40                  45

Xaa Xaa Xaa Xaa Xaa Xaa Xaa Xaa Xaa Xaa Xaa Pro Xaa Xaa Xaa Xaa
    50                  55                  60

Xaa Xaa Xaa Xaa Xaa Xaa Asp Xaa Xaa Xaa Xaa His Xaa Val Xaa Xaa
65                  70                  75                  80

Xaa Xaa Xaa Xaa Arg
            85

<210> SEQ ID NO 21
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(4)
<223> OTHER INFORMATION: Any amino acid
<220> FEATURE:
<221> NAME/KEY: MOD_RES
<222> LOCATION: (6)..(8)
<223> OTHER INFORMATION: Any amino acid
<220> FEATURE:
<221> NAME/KEY: MOD_RES
<222> LOCATION: (14)..(15)
<223> OTHER INFORMATION: Any amino acid
<220> FEATURE:
<221> NAME/KEY: MOD_RES
<222> LOCATION: (18)..(18)
<223> OTHER INFORMATION: Any amino acid
```

-continued

```
<220> FEATURE:
<221> NAME/KEY: MOD_RES
<222> LOCATION: (24)..(25)
<223> OTHER INFORMATION: Any amino acid
<220> FEATURE:
<221> NAME/KEY: MOD_RES
<222> LOCATION: (30)..(30)
<223> OTHER INFORMATION: Any amino acid
<220> FEATURE:
<221> NAME/KEY: MOD_RES
<222> LOCATION: (32)..(32)
<223> OTHER INFORMATION: Any amino acid
<220> FEATURE:
<221> NAME/KEY: MOD_RES
<222> LOCATION: (36)..(36)
<223> OTHER INFORMATION: Any amino acid
<220> FEATURE:
<221> NAME/KEY: MOD_RES
<222> LOCATION: (38)..(39)
<223> OTHER INFORMATION: Any amino acid
<220> FEATURE:
<221> NAME/KEY: MOD_RES
<222> LOCATION: (42)..(45)
<223> OTHER INFORMATION: Any amino acid
<220> FEATURE:
<221> NAME/KEY: MOD_RES
<222> LOCATION: (48)..(48)
<223> OTHER INFORMATION: Any amino acid
<220> FEATURE:
<221> NAME/KEY: MOD_RES
<222> LOCATION: (50)..(51)
<223> OTHER INFORMATION: Any amino acid
<220> FEATURE:
<221> NAME/KEY: MOD_RES
<222> LOCATION: (55)..(63)
<223> OTHER INFORMATION: Any amino acid
<220> FEATURE:
<221> NAME/KEY: MOD_RES
<222> LOCATION: (65)..(66)
<223> OTHER INFORMATION: Any amino acid
<220> FEATURE:
<221> NAME/KEY: MOD_RES
<222> LOCATION: (70)..(70)
<223> OTHER INFORMATION: Any amino acid
<220> FEATURE:
<221> NAME/KEY: MOD_RES
<222> LOCATION: (72)..(72)
<223> OTHER INFORMATION: Any amino acid
<220> FEATURE:
<221> NAME/KEY: MOD_RES
<222> LOCATION: (83)..(83)
<223> OTHER INFORMATION: Any amino acid
<220> FEATURE:
<221> NAME/KEY: MOD_RES
<222> LOCATION: (85)..(88)
<223> OTHER INFORMATION: Any amino acid
<220> FEATURE:
<221> NAME/KEY: MOD_RES
<222> LOCATION: (90)..(90)
<223> OTHER INFORMATION: Any amino acid
<220> FEATURE:
<221> NAME/KEY: MOD_RES
<222> LOCATION: (92)..(92)
<223> OTHER INFORMATION: Any amino acid
<220> FEATURE:
<221> NAME/KEY: MOD_RES
<222> LOCATION: (97)..(97)
<223> OTHER INFORMATION: Any amino acid
<220> FEATURE:
<221> NAME/KEY: MOD_RES
<222> LOCATION: (99)..(100)
<223> OTHER INFORMATION: Any amino acid
<220> FEATURE:
<221> NAME/KEY: MOD_RES
<222> LOCATION: (103)..(104)
<223> OTHER INFORMATION: Any amino acid
<220> FEATURE:
<221> NAME/KEY: MOD_RES
<222> LOCATION: (106)..(106)
```

```
<223> OTHER INFORMATION: Any amino acid
<220> FEATURE:
<221> NAME/KEY: MOD_RES
<222> LOCATION: (109)..(109)
<223> OTHER INFORMATION: Any amino acid

<400> SEQUENCE: 21

Arg Xaa Xaa Xaa Met Xaa Xaa Xaa Tyr Pro Gly Asn Gly Xaa Xaa Tyr
1               5                   10                  15

Val Xaa His Val Asp Asn Pro Xaa Asp Gly Arg Cys Xaa Thr Xaa
            20                  25                  30

Ile Tyr Tyr Xaa Asn Xaa Xaa Trp Asp Xaa Xaa Xaa Gly Gly Xaa
            35                  40                  45

Leu Xaa Xaa Phe Pro Glu Xaa Xaa Xaa Xaa Xaa Xaa Xaa Xaa Pro
        50                  55                  60

Xaa Xaa Asp Arg Leu Xaa Phe Xaa Trp Ser Asp Arg Arg Asn Pro His
65                  70                  75                  80

Glu Val Xaa Pro Xaa Xaa Xaa Xaa Arg Xaa Ala Xaa Thr Val Trp Tyr
                85                  90                  95

Xaa Asp Xaa Xaa Glu Arg Xaa Xaa Ala Xaa Ala Lys Xaa Lys
            100                 105                 110

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: 4-hydroxy proline or any amino acid
<220> FEATURE:
<221> NAME/KEY: MOD_RES
<222> LOCATION: (5)..(6)
<223> OTHER INFORMATION: 4-hydroxy proline or any amino acid

<400> SEQUENCE: 22

Leu Xaa Xaa Leu Xaa Xaa
1               5

<210> SEQ ID NO 23
<211> LENGTH: 19
<212> TYPE: PRT
<213> ORGANISM: Homo sapiens

<400> SEQUENCE: 23

Asp Leu Asp Leu Glu Met Leu Ala Pro Tyr Ile Pro Met Asp Asp
1               5                   10                  15

Phe Gln Leu

<210> SEQ ID NO 24
<211> LENGTH: 20
<212> TYPE: PRT
<213> ORGANISM: Homo sapiens

<400> SEQUENCE: 24

Glu Leu Asp Leu Glu Thr Leu Ala Pro Tyr Ile Pro Met Asp Gly Glu
1               5                   10                  15

Asp Phe Gln Leu
            20
```

```
<210> SEQ ID NO 25
<211> LENGTH: 19
<212> TYPE: PRT
<213> ORGANISM: Xenopus laevis

<400> SEQUENCE: 25

Asp Leu Asp Leu Glu Met Leu Ala Pro Tyr Ile Pro Met Asp Asp
1               5                   10                  15

Phe Gln Leu

<210> SEQ ID NO 26
<211> LENGTH: 19
<212> TYPE: PRT
<213> ORGANISM: Drosophila melanogaster

<400> SEQUENCE: 26

Phe Glu Ala Phe Ala Met Arg Ala Pro Tyr Ile Pro Ile Asp Asp
1               5                   10                  15

Met Pro Leu

<210> SEQ ID NO 27
<211> LENGTH: 19
<212> TYPE: PRT
<213> ORGANISM: Caenorhabditis elegans

<400> SEQUENCE: 27

Glu Pro Asp Leu Ser Cys Leu Ala Pro Phe Val Asp Thr Tyr Asp Met
1               5                   10                  15

Met Gln Met

<210> SEQ ID NO 28
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Pro Phe Ser Thr Gln Asp Thr Asp Leu Asp Leu Glu Met Leu Ala Pro
1               5                   10                  15

Tyr Ile Pro Met Asp Asp Asp Phe Gln Leu Arg Ser Phe Asp Gln Leu
                20                  25                  30

Ser Pro

<210> SEQ ID NO 29
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Asp Leu Asp Leu Glu Met Leu Ala Pro Tyr Ile Pro Met Asp Asp
1               5                   10                  15

Phe Gln Leu

<210> SEQ ID NO 30
<211> LENGTH: 16
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 30

Leu Glu Met Leu Ala Pro Tyr Ile Pro Met Asp Asp Asp Phe Gln Leu
1               5                   10                  15

<210> SEQ ID NO 31
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Leu Ala Pro Tyr Ile Pro Met Asp Asp Asp Phe Gln Leu
1               5                   10

<210> SEQ ID NO 32
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Asp Leu Asp Leu Glu Met Leu Ala Pro Tyr Ile Pro Met Asp
1               5                   10

<210> SEQ ID NO 33
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Asp Leu Asp Leu Glu Met Leu Ala Gly Tyr Ile Pro Met Asp Asp
1               5                   10                  15

Phe Gln Leu

<210> SEQ ID NO 34
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Asp Leu Asp Leu Glu Met Leu Ala Pro Tyr Ile Pro Met Asp Asp Asp
1               5                   10                  15

Phe Gln Leu

<210> SEQ ID NO 35
<211> LENGTH: 826
<212> TYPE: PRT
<213> ORGANISM: Homo sapiens

<400> SEQUENCE: 35

Met Glu Gly Ala Gly Gly Ala Asn Asp Lys Lys Lys Ile Ser Ser Glu
1               5                   10                  15

Arg Arg Lys Glu Lys Ser Arg Asp Ala Ala Arg Ser Arg Arg Ser Lys
            20                  25                  30

Glu Ser Glu Val Phe Tyr Glu Leu Ala His Gln Leu Pro Leu Pro His
            35                  40                  45

Asn Val Ser Ser His Leu Asp Lys Ala Ser Val Met Arg Leu Thr Ile
            50                  55                  60

Ser Tyr Leu Arg Val Arg Lys Leu Leu Asp Ala Gly Asp Leu Asp Ile
65                  70                  75                  80

Glu Asp Asp Met Lys Ala Gln Met Asn Cys Phe Tyr Leu Lys Ala Leu
                85                  90                  95

Asp Gly Phe Val Met Val Leu Thr Asp Asp Gly Asp Met Ile Tyr Ile
            100                 105                 110

Ser Asp Asn Val Asn Lys Tyr Met Gly Leu Thr Gln Phe Glu Leu Thr
            115                 120                 125

Gly His Ser Val Phe Asp Phe Thr His Pro Cys Asp His Glu Glu Met
130                 135                 140

Arg Glu Met Leu Thr His Arg Asn Gly Leu Val Lys Lys Gly Lys Glu
145                 150                 155                 160

Gln Asn Thr Gln Arg Ser Phe Phe Leu Arg Met Lys Cys Thr Leu Thr
                165                 170                 175

Ser Arg Gly Arg Thr Met Asn Ile Lys Ser Ala Thr Trp Lys Val Leu
            180                 185                 190

His Cys Thr Gly His Ile His Val Tyr Asp Thr Asn Ser Asn Gln Pro
            195                 200                 205

Gln Cys Gly Tyr Lys Lys Pro Pro Met Thr Cys Leu Val Leu Ile Cys
210                 215                 220

Glu Pro Ile Pro His Pro Ser Asn Ile Glu Ile Pro Leu Asp Ser Lys
225                 230                 235                 240

Thr Phe Leu Ser Arg His Ser Leu Asp Met Lys Phe Ser Tyr Cys Asp
                245                 250                 255

Glu Arg Ile Thr Glu Leu Met Gly Tyr Glu Pro Glu Glu Leu Leu Gly
            260                 265                 270

Arg Ser Ile Tyr Glu Tyr Tyr His Ala Leu Asp Ser Asp His Leu Thr
            275                 280                 285

Lys Thr His His Asp Met Phe Thr Lys Gly Gln Val Thr Thr Gly Gln
290                 295                 300

Tyr Arg Met Leu Ala Lys Arg Gly Gly Tyr Val Trp Val Glu Thr Gln
305                 310                 315                 320

Ala Thr Val Ile Tyr Asn Thr Lys Asn Ser Gln Pro Gln Cys Ile Val
                325                 330                 335

Cys Val Asn Tyr Val Val Ser Gly Ile Ile Gln His Asp Leu Ile Phe
            340                 345                 350

Ser Leu Gln Gln Thr Glu Cys Val Leu Lys Pro Val Glu Ser Ser Asp
            355                 360                 365

Met Lys Met Thr Gln Leu Phe Thr Lys Val Glu Ser Glu Asp Thr Ser
370                 375                 380

Ser Leu Phe Asp Lys Leu Lys Lys Glu Pro Asp Ala Leu Thr Leu Leu
385                 390                 395                 400

Ala Pro Ala Ala Gly Asp Thr Ile Ile Ser Leu Asp Phe Gly Ser Asn
                405                 410                 415

Asp Thr Glu Thr Asp Asp Gln Gln Leu Glu Glu Val Pro Leu Tyr Asn
            420                 425                 430

Asp Val Met Leu Pro Ser Pro Asn Glu Lys Leu Gln Asn Ile Asn Leu

```
                    435                 440                 445
Ala Met Ser Pro Leu Pro Thr Ala Glu Thr Pro Lys Pro Leu Arg Ser
    450                 455                 460

Ser Ala Asp Pro Ala Leu Asn Gln Glu Val Ala Leu Lys Leu Glu Pro
465                 470                 475                 480

Asn Pro Glu Ser Leu Glu Leu Ser Phe Thr Met Pro Gln Ile Gln Asp
                485                 490                 495

Gln Thr Pro Ser Pro Ser Asp Gly Ser Thr Arg Gln Ser Ser Pro Glu
            500                 505                 510

Pro Asn Ser Pro Ser Glu Tyr Cys Phe Tyr Val Asp Ser Asp Met Val
        515                 520                 525

Asn Glu Phe Lys Leu Glu Leu Val Glu Lys Leu Phe Ala Glu Asp Thr
    530                 535                 540

Glu Ala Lys Asn Pro Phe Ser Thr Gln Asp Thr Asp Leu Asp Leu Glu
545                 550                 555                 560

Met Leu Ala Pro Tyr Ile Pro Met Asp Asp Phe Gln Leu Arg Ser
                565                 570                 575

Phe Asp Gln Leu Ser Pro Leu Glu Ser Ser Ala Ser Pro Glu Ser
            580                 585                 590

Ala Ser Pro Gln Ser Thr Val Thr Val Phe Gln Gln Thr Gln Ile Gln
        595                 600                 605

Glu Pro Thr Ala Asn Ala Thr Thr Thr Thr Ala Thr Thr Asp Glu Leu
    610                 615                 620

Lys Thr Val Thr Lys Asp Arg Met Glu Asp Ile Lys Ile Leu Ile Ala
625                 630                 635                 640

Ser Pro Ser Pro Thr His Ile His Lys Glu Thr Thr Ser Ala Thr Ser
                645                 650                 655

Ser Pro Tyr Arg Asp Thr Gln Ser Arg Thr Ala Ser Pro Asn Arg Ala
            660                 665                 670

Gly Lys Gly Val Ile Glu Gln Thr Glu Lys Ser His Pro Arg Ser Pro
        675                 680                 685

Asn Val Leu Ser Val Ala Leu Ser Gln Arg Thr Thr Val Pro Glu Glu
    690                 695                 700

Glu Leu Asn Pro Lys Ile Leu Ala Leu Gln Asn Ala Gln Arg Lys Arg
705                 710                 715                 720

Lys Met Glu His Asp Gly Ser Leu Phe Gln Ala Val Gly Ile Gly Thr
                725                 730                 735

Leu Leu Gln Gln Pro Asp Asp His Ala Ala Thr Thr Ser Leu Ser Trp
            740                 745                 750

Lys Arg Val Lys Gly Cys Lys Ser Ser Glu Gln Asn Gly Met Glu Gln
        755                 760                 765

Lys Thr Ile Ile Leu Ile Pro Ser Asp Leu Ala Cys Arg Leu Leu Gly
    770                 775                 780

Gln Ser Met Asp Glu Ser Gly Leu Pro Gln Leu Thr Ser Tyr Asp Cys
785                 790                 795                 800

Glu Val Asn Ala Pro Ile Gln Gly Ser Arg Asn Leu Leu Gln Gly Glu
                805                 810                 815

Glu Leu Leu Arg Ala Leu Asp Gln Val Asn
            820                 825

<210> SEQ ID NO 36
<211> LENGTH: 719
<212> TYPE: PRT
<213> ORGANISM: Caenorhabditis elegans
```

<400> SEQUENCE: 36

```
Met Glu Asp Asn Arg Lys Arg Asn Met Glu Arg Arg Glu Thr Ser
1               5                   10                  15

Arg His Ala Ala Arg Asp Arg Arg Ser Lys Glu Ser Asp Ile Phe Asp
                20                  25                  30

Asp Leu Lys Met Cys Val Pro Ile Val Glu Glu Gly Thr Val Thr His
            35                  40                  45

Leu Asp Arg Ile Ala Leu Leu Arg Val Ala Ala Thr Ile Cys Arg Leu
    50                  55                  60

Arg Lys Thr Ala Gly Asn Val Leu Glu Asn Asn Leu Asp Asn Glu Ile
65                  70                  75                  80

Thr Asn Glu Val Trp Thr Glu Asp Thr Ile Ala Glu Cys Leu Asp Gly
                85                  90                  95

Phe Val Met Ile Val Asp Ser Asp Ser Ser Ile Leu Tyr Val Thr Glu
            100                 105                 110

Ser Val Ala Met Tyr Leu Gly Leu Thr Gln Thr Asp Leu Thr Gly Arg
        115                 120                 125

Ala Leu Arg Asp Phe Leu His Pro Ser Asp Tyr Asp Glu Phe Asp Lys
    130                 135                 140

Gln Ser Lys Met Leu His Lys Pro Arg Gly Glu Asp Thr Asp Thr Thr
145                 150                 155                 160

Gly Ile Asn Met Val Leu Arg Met Lys Thr Val Ile Ser Pro Arg Gly
                165                 170                 175

Arg Cys Leu Asn Leu Lys Ser Ala Leu Tyr Lys Ser Val Ser Phe Leu
            180                 185                 190

Val His Ser Lys Val Ser Thr Gly Gly His Val Ser Phe Met Gln Gly
        195                 200                 205

Ile Thr Ile Pro Ala Gly Gln Gly Thr Thr Asn Ala Asn Ala Ser Ala
    210                 215                 220

Met Thr Lys Tyr Thr Glu Ser Pro Met Gly Ala Phe Thr Thr Arg His
225                 230                 235                 240

Thr Cys Asp Met Arg Ile Thr Phe Val Ser Asp Lys Phe Asn Tyr Ile
                245                 250                 255

Leu Lys Ser Glu Leu Lys Thr Leu Met Gly Thr Ser Phe Tyr Glu Leu
            260                 265                 270

Val His Pro Ala Asp Met Met Ile Val Ser Lys Ser Met Lys Glu Leu
        275                 280                 285

Phe Ala Lys Gly His Ile Arg Thr Pro Tyr Tyr Arg Leu Ile Ala Ala
    290                 295                 300

Asn Asp Thr Leu Ala Trp Ile Gln Thr Glu Ala Thr Thr Ile Thr His
305                 310                 315                 320

Thr Thr Lys Gly Gln Lys Gly Gln Tyr Val Ile Cys Val His Tyr Val
                325                 330                 335

Leu Gly Ile Gln Gly Ala Glu Glu Ser Leu Val Val Cys Thr Asp Ser
            340                 345                 350

Met Pro Ala Gly Met Gln Val Asp Ile Lys Lys Glu Val Asp Asp Thr
        355                 360                 365

Arg Asp Tyr Ile Gly Arg Gln Pro Glu Ile Val Glu Cys Val Asp Phe
    370                 375                 380

Thr Pro Leu Ile Glu Pro Glu Asp Pro Phe Asp Thr Val Ile Glu Pro
385                 390                 395                 400

Val Val Gly Gly Glu Glu Pro Val Lys Gln Ala Asp Met Gly Ala Arg
```

405                 410                 415
Lys Asn Ser Tyr Asp Asp Val Leu Gln Trp Leu Phe Arg Asp Gln Pro
                420                 425                 430

Ser Ser Pro Pro Pro Ala Arg Tyr Arg Ser Ala Asp Arg Phe Arg Thr
            435                 440                 445

Thr Glu Pro Ser Asn Phe Gly Ser Ala Leu Ala Ser Pro Asp Phe Met
        450                 455                 460

Asp Ser Ser Ser Arg Thr Ser Arg Pro Lys Thr Ser Tyr Gly Arg Arg
465                 470                 475                 480

Ala Gln Ser Gln Gly Ser Arg Thr Thr Gly Ser Ser Ser Thr Ser Ala
                485                 490                 495

Ser Ala Thr Leu Pro His Ser Ala Asn Tyr Ser Pro Leu Ala Glu Gly
            500                 505                 510

Ile Ser Gln Cys Gly Leu Asn Ser Pro Pro Ser Ile Lys Ser Gly Gln
        515                 520                 525

Val Val Tyr Gly Asp Ala Arg Ser Met Gly Arg Ser Cys Asp Pro Ser
    530                 535                 540

Asp Ser Ser Arg Arg Phe Ser Ala Leu Ser Pro Ser Asp Thr Leu Asn
545                 550                 555                 560

Val Ser Ser Thr Arg Gly Ile Asn Pro Val Ile Gly Ser Asn Asp Val
                565                 570                 575

Phe Ser Thr Met Pro Phe Ala Asp Ser Ile Ala Ile Ala Glu Arg Ile
            580                 585                 590

Asp Ser Ser Pro Thr Leu Thr Ser Gly Glu Pro Ile Leu Cys Asp Asp
        595                 600                 605

Leu Gln Trp Glu Glu Pro Asp Leu Ser Cys Leu Ala Pro Phe Val Asp
610                 615                 620

Thr Tyr Asp Met Met Gln Met Asp Glu Gly Leu Pro Pro Glu Leu Gln
                625                 630                 635                 640

Ala Leu Tyr Asp Leu Pro Asp Phe Thr Pro Ala Val Pro Gln Ala Pro
            645                 650                 655

Ala Ala Arg Pro Val His Ile Asp Arg Ser Pro Pro Ala Lys Arg Met
        660                 665                 670

His Gln Ser Gly Pro Ser Asp Leu Asp Phe Met Tyr Thr Gln His Tyr
    675                 680                 685

Gln Pro Phe Gln Gln Asp Glu Thr Tyr Trp Gln Gly Gln Gln Gln Gln
                690                 695                 700

Asn Glu Gln Gln Pro Ser Ser Tyr Ser Pro Phe Pro Met Leu Ser
705                 710                 715

<210> SEQ ID NO 37
<211> LENGTH: 38
<212> TYPE: PRT
<213> ORGANISM: Homo sapiens

<400> SEQUENCE: 37

Ser Glu Asp Thr Ser Ser Leu Phe Asp Lys Leu Lys Lys Glu Pro Asp
1               5                   10                  15

Ala Leu Thr Leu Leu Ala Pro Ala Ala Gly Asp Thr Ile Ile Ser Leu
            20                  25                  30

Asp Phe Gly Ser Asn Asp
        35

<210> SEQ ID NO 38
<211> LENGTH: 38

```
<212> TYPE: PRT
<213> ORGANISM: Homo sapiens

<400> SEQUENCE: 38

Ser Glu Lys Ser Asn Phe Leu Phe Thr Lys Leu Lys Glu Glu Pro Glu
1               5                   10                  15

Glu Leu Ala Gln Leu Ala Pro Thr Pro Gly Asp Ala Ile Ile Ser Leu
            20                  25                  30

Asp Phe Gly Asn Gln Asn
        35

<210> SEQ ID NO 39
<211> LENGTH: 19
<212> TYPE: PRT
<213> ORGANISM: Homo sapiens

<400> SEQUENCE: 39

Asp Leu Asp Leu Glu Met Leu Ala Pro Tyr Ile Pro Met Asp Asp Asp
1               5                   10                  15

Phe Gln Leu

<210> SEQ ID NO 40
<211> LENGTH: 119
<212> TYPE: PRT
<213> ORGANISM: Caenorhabditis elegans

<400> SEQUENCE: 40

Ile Asp His Asp Ile Gly Gly Arg Ser Arg Ala Met Leu Ala Ile Tyr
1               5                   10                  15

Pro Gly Asn Gly Thr Arg Tyr Val Lys His Val Asp Asn Pro Val Lys
            20                  25                  30

Asp Gly Arg Cys Ile Thr Thr Ile Tyr Tyr Cys Asn Glu Asn Trp Asp
        35                  40                  45

Met Ala Thr Asp Gly Gly Thr Leu Arg Leu Tyr Pro Glu Thr Ser Met
    50                  55                  60

Thr Pro Met Asp Ile Asp Pro Arg Ala Asp Arg Leu Val Phe Phe Trp
65                  70                  75                  80

Ser Asp Arg Arg Asn Pro His Glu Val Met Pro Val Phe Arg His Arg
                85                  90                  95

Phe Ala Ile Thr Ile Trp Tyr Met Asp Lys Ser Glu Arg Asp Lys Ala
            100                 105                 110

Leu Ala Lys Gly Lys Glu Ser
        115

<210> SEQ ID NO 41
<211> LENGTH: 116
<212> TYPE: PRT
<213> ORGANISM: Homo sapiens

<400> SEQUENCE: 41

Gly Ser Tyr Lys Ile Asn Gly Arg Thr Lys Ala Met Val Ala Cys Tyr
1               5                   10                  15

Pro Gly Asn Gly Thr Gly Tyr Val Arg His Val Asp Asn Pro Asn Gly
            20                  25                  30

Asp Gly Arg Cys Val Thr Cys Ile Tyr Tyr Leu Asn Lys Asp Trp Asp
        35                  40                  45

Ala Lys Val Ser Gly Gly Ile Leu Arg Ile Phe Pro Glu Gly Lys Ala
    50                  55                  60
```

```
Gln Phe Ala Asp Ile Glu Pro Lys Phe Asp Arg Leu Leu Phe Phe Trp
 65                  70                  75                  80

Ser Asp Arg Arg Asn Pro His Glu Val Gln Pro Ala Tyr Ala Thr Arg
                 85                  90                  95

Tyr Ala Ile Thr Val Trp Tyr Phe Asp Ala Asp Glu Arg Ala Arg Ala
            100                 105                 110

Lys Val Lys Tyr
        115

<210> SEQ ID NO 42
<211> LENGTH: 116
<212> TYPE: PRT
<213> ORGANISM: Homo sapiens

<400> SEQUENCE: 42

Gly Ser Tyr Val Ile Asn Gly Arg Thr Lys Ala Met Val Ala Cys Tyr
 1               5                  10                  15

Pro Gly Asn Gly Leu Gly Tyr Val Arg His Val Asp Asn Pro His Gly
                 20                  25                  30

Asp Gly Arg Cys Ile Thr Cys Ile Tyr Tyr Leu Asn Gln Asn Trp Asp
             35                  40                  45

Val Lys Val His Gly Gly Leu Leu Gln Ile Phe Pro Glu Gly Arg Pro
 50                  55                  60

Val Val Ala Asn Ile Glu Pro Leu Phe Asp Arg Leu Leu Ile Phe Trp
 65                  70                  75                  80

Ser Asp Arg Arg Asn Pro His Glu Val Lys Pro Ala Tyr Ala Thr Arg
                 85                  90                  95

Tyr Ala Ile Thr Val Trp Tyr Phe Asp Ala Lys Glu Arg Ala Ala Ala
            100                 105                 110

Lys Asp Lys Tyr
        115

<210> SEQ ID NO 43
<211> LENGTH: 115
<212> TYPE: PRT
<213> ORGANISM: Homo sapiens

<400> SEQUENCE: 43

Lys Tyr Tyr Val Lys Glu Arg Ser Lys Ala Met Val Ala Cys Tyr Pro
 1               5                  10                  15

Gly Asn Gly Thr Gly Tyr Val Arg His Val Asp Asn Pro Asn Gly Asp
                 20                  25                  30

Gly Arg Cys Ile Thr Cys Ile Tyr Tyr Leu Asn Lys Asn Trp Asp Ala
             35                  40                  45

Lys Leu His Gly Gly Ile Leu Arg Ile Phe Pro Glu Gly Lys Ser Phe
 50                  55                  60

Ile Ala Asp Val Glu Pro Ile Phe Asp Arg Leu Leu Phe Phe Trp Ser
 65                  70                  75                  80

Asp Arg Arg Asn Pro His Glu Val Gln Pro Ser Tyr Ala Thr Arg Tyr
                 85                  90                  95

Ala Met Thr Val Trp Tyr Phe Asp Ala Glu Glu Arg Ala Glu Ala Lys
            100                 105                 110

Lys Lys Phe
        115

<210> SEQ ID NO 44
<211> LENGTH: 116
```

<212> TYPE: PRT
<213> ORGANISM: Rattus sp.

<400> SEQUENCE: 44

Gly Lys Tyr Tyr Val Lys Glu Arg Ser Lys Ala Met Val Ala Cys Tyr
1               5                   10                  15

Pro Gly Asn Gly Thr Gly Tyr Val Arg His Val Asp Asn Pro Asn Gly
            20                  25                  30

Asp Gly Arg Cys Ile Thr Cys Ile Tyr Tyr Leu Asn Lys Asn Trp Asp
        35                  40                  45

Ala Lys Leu His Gly Gly Val Leu Arg Ile Phe Pro Glu Gly Lys Ser
    50                  55                  60

Phe Val Ala Asp Val Glu Pro Ile Phe Asp Arg Leu Leu Phe Ser Trp
65                  70                  75                  80

Ser Asp Arg Arg Asn Pro His Glu Val Gln Pro Ser Tyr Ala Thr Arg
                85                  90                  95

Tyr Ala Met Thr Val Trp Tyr Phe Asp Ala Glu Glu Arg Ala Glu Ala
                100                 105                 110

Lys Lys Lys Phe
            115

<210> SEQ ID NO 45
<211> LENGTH: 92
<212> TYPE: PRT
<213> ORGANISM: Streptomyces sp.

<400> SEQUENCE: 45

Phe Asp Gly Thr His Leu Gln Met Ala Arg Ser Arg Asn Leu Lys Asn
1               5                   10                  15

Ala Ile Val Ile Pro His Arg Asp Phe Val Glu Leu Ser Arg Glu Val
            20                  25                  30

Asp Arg Tyr Phe Arg Thr Phe Met Val Leu Glu Asp Ser Pro Leu Ala
        35                  40                  45

Phe His Ser Asn Glu Asp Thr Val Ile His Met Arg Pro Gly Glu Ile
    50                  55                  60

Trp Phe Leu Asp Ala Ala Thr Val His Ser Ala Val Asn Phe Ser Glu
65                  70                  75                  80

Ile Ser Arg Gln Ser Leu Cys Val Asp Phe Ala Phe
                85                  90

<210> SEQ ID NO 46
<211> LENGTH: 37
<212> TYPE: DNA
<213> ORGANISM: Artificial Sequence
<220> FEATURE:
<223> OTHER INFORMATION: Description of Artificial Sequence: Synthetic
      forward primer

<400> SEQUENCE: 46
gatttatcgt gcttggcagg attcgttgac acttatg                           37

<210> SEQ ID NO 47
<211> LENGTH: 36
<212> TYPE: DNA
<213> ORGANISM: Artificial Sequence
<220> FEATURE:
<223> OTHER INFORMATION: Description of Artificial Sequence: Synthetic
      reverse primer

<400> SEQUENCE: 47
gtgtcaacga atcctgccaa gcacgataaa tcaggc                                  36

<210> SEQ ID NO 48
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: 4-hydroxy proline or any amino acid
<220> FEATURE:
<221> NAME/KEY: MOD_RES
<222> LOCATION: (6)..(6)
<223> OTHER INFORMATION: 4-hydroxy proline or any amino acid

<400> SEQUENCE: 48

Leu Xaa Xaa Leu Ala Xaa
1               5

<210> SEQ ID NO 49
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
      peptide
<220> FEATURE:
<221> NAME/KEY: MOD_RES
<222> LOCATION: (3)..(3)
<223> OTHER INFORMATION: 4-hydroxy proline

<400> SEQUENCE: 49

Leu Ala Pro Tyr Ile Pro
1               5

<210> SEQ ID NO 50
<211> LENGTH: 28
<212> TYPE: PRT
<213> ORGANISM: Homo sapiens

<400> SEQUENCE: 50

Leu Lys Lys Glu Pro Asp Ala Leu Thr Leu Leu Ala Pro Ala Ala Gly
1               5                   10                  15

Asp Thr Ile Ile Ser Leu Asp Phe Gly Ser Asn Asp
            20                  25

<210> SEQ ID NO 51
<211> LENGTH: 28
<212> TYPE: PRT
<213> ORGANISM: Mus sp.

<400> SEQUENCE: 51

Leu Lys Lys Glu Pro Asp Ala Leu Thr Leu Leu Ala Pro Ala Ala Gly
1               5                   10                  15

Asp Thr Ile Ile Ser Leu Asp Phe Gly Ser Asp Asp
            20                  25

<210> SEQ ID NO 52
<211> LENGTH: 19
<212> TYPE: PRT
<213> ORGANISM: Mus sp.

<400> SEQUENCE: 52

```
Asp Leu Asp Leu Glu Met Leu Ala Pro Tyr Ile Pro Met Asp Asp Asp
1               5                   10                  15

Phe Gln Leu

<210> SEQ ID NO 53
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Thr or Glu
<220> FEATURE:
<221> NAME/KEY: MOD_RES
<222> LOCATION: (3)..(3)
<223> OTHER INFORMATION: Leu or Met

<400> SEQUENCE: 53

Leu Xaa Xaa Leu Ala Pro
1               5
```

ANTIBODY AGAINST HUMAN HIF HYDROXYLASE

This is a divisional of application Ser. No. 14/028,167, filed Sep. 16, 2013, which is a continuation of application Ser. No. 12/654,993, filed Jan. 12, 2010, which issued as U.S. Pat. No. 8,535,899 on Sep. 17, 2013, which is a continuation of application Ser. No. 10/472,595, filed Jan. 20, 2004 (abandoned), which is the U.S. National Phase of International Application No. PCT/GB02/01381, filed Mar. 21, 2002, published in English, which claims priority under 35 U.S.C. §371 to GB 0107123.2, filed Mar. 21, 2001, and GB 0118952.1, filed Aug. 2, 2001, all of which are incorporated herein by reference.

FIELD OF INVENTION

The present invention relates to hydroxylases which act on hypoxia inducible factor alpha (HIF-α) and which are involved in the regulation of the cellular turnover of HIF. Compounds, methods and means for the modulation of the activity of these enzymes are provided.

BACKGROUND OF INVENTION

The transcription factor HIF (hypoxia inducible factor) system is a key regulator of responses to hypoxia, occupying a central position in oxygen homeostasis in a wide range of organisms (1). A large number of transcriptional targets have been identified, with critical roles in angiogenesis, erythropoiesis, energy metabolism, inflammation, vasomotor function, and apoptotic/proliferative responses (1). The system is essential for normal development (2, 3), and plays a key role in pathophysiological responses to ischaemia/hypoxia (1). HIF is also important in cancer, in which it is commonly upregulated, and has major effects on tumour growth and angiogenesis (1). The HIF DNA binding complex consists of a heterodimer of α and β subunits (4). Regulation by oxygen occurs through hydroxylation of the α-subunits, which are rapidly destroyed by the proteasome in oxygenated cells (5, 6, 7). This involves binding of HIF-α subunits by the von Hippel-Lindau tumour suppressor protein (pVHL) (8), with pVHL acting as the, or part of the, recognition component for a ubiquitin ligase that promotes ubiquitin dependent proteolysis through interaction with a specific sequence or sequences in HIF-α-subunits (11, 12, 13, 14). In hypoxia, this process is suppressed, so stabilizing HIF-α and permitting transcription activation via the HIFα-β.

DISCLOSURE OF THE INVENTION

Investigations by the present inventors have revealed that the interaction between HIF-α and VHL is controlled by oxidation of critical proline residues in the HIF-α protein. In the human HIF-1α protein these are Pro402 and Pro564, though the equivalent residue(s) exists in other HIF-α forms and are conserved in *C. elegans*, indicating that these are critical components which have been conserved through evolution.

The data herein demonstrates that hydroxylation of proline residues such as Pro564 in HIF-1α is mediated by a family of specific prolyl-hydroxylases, referred to here as the HIF hydroxylases, which include the *C. elegans* protein EGL-9 and the human proteins PHD1-3. These enzymes recognise a conserved core LXXLAP motif for prolyl hydroxylation. Different members of the family act differentially on hydroxylation sites within HIF-α and the activity of the recombinant enzymes is directly modulated by oxygen tension, iron availability and cobaltous ions.

The activity of HIF hydroxylases represents a novel target for the control of HIFα. By blocking activity, hydroxylation of HIFα will be reduced, leading to the accumulation of HIF-α in cells. This, in turn, will lead to the promotion or modulation of angiogenesis, erythropoiesis, energy metabolism, inflammation, vasomotor function, and will also affect apoptotic/proliferative responses. Thus, mechanisms which either block, inhibit, reduce or decrease the activity of the HIF hydroxylase, and in particular its prolyl-hydroxylase activity, have therapeutic applications in certain target cells.

Conversely, in hypoxic conditions such as those commonly found in tumours, the lack of hydroxylation may lead to the accumulation of HIFα and the concomitant promotion of angiogenesis and other growth promoting events. Thus mechanisms which either rescue, stimulate, enhance or increase the activity of the HIF hydroxylase, and in particular the prolyl-hydroxylase activity of the enzyme, have different therapeutic applications with respect to certain target cells.

One aspect of the present invention therefore provides an assay method for identifying an agent which modulates the interaction of a HIF hydroxylase with a substrate of the hydroxylase, the method including contacting a HIF hydroxylase and a substrate of the hydroxylase in the presence of a test substance; and, determining the interaction or lack of interaction of the HIF hydroxylase and the substrate.

The HIF hydroxylase and the test substance may be contacted under conditions in which the HIF hydroxylase normally interacts with the substrate of the hydroxylase.

Interaction, or lack of interaction, between the HIF hydroxylase and the substrate may be determined in the presence and/or absence of the test substance. A change, i.e. an increase or decrease in interaction in the presence relative to the absence of test substance being indicative of the test substance being a modulator of said interaction.

Interaction may be determined according to any one of a range of conventional techniques and may include determining the prolyl hydroxylation of the substrate as described below. Interaction in such assays may be any functional interrelation.

Accordingly, the present invention provides an assay method for identifying an agent which modulates the interaction of a hypoxia inducible factor (HIF) hydroxylase with a substrate of the hydroxylase, the method comprising:
  contacting a HIF hydroxylase and a test substance in the presence of a substrate of the hydroxylase under conditions in which the hydroxylase interacts with the substrate in the absence of the test substance; and
  determining the interaction, or lack of interaction, of the hydroxylase and the substrate.

The present invention also provides the HIF hydroxylases themselves. Thus in accordance with the present invention, there is provided a polypeptide comprising:
  (a) the amino acid sequence of SEQ ID NO: 2, 4, 6 or 8;
  (b) a variant thereof having at least 60% identity to the amino acid sequence of SEQ ID NO: 2, 4, 6 or 8 and having HIF hydroxylase activity; or
  (c) a fragment of either thereof having HIF hydroxylase activity.

Preferably, a polypeptide of the invention has prolyl hydroxylase activity.

The present invention also relates to polynucleotides which encode a polypeptide of the invention. Thus, in accordance with another aspect of the invention, a polynucleotide comprises:

(i) SEQ ID NO: 1, 3, 5 or 7 or a complementary sequence thereto;

(ii) a sequence which hybridises under stringent conditions to the sequence defined in (i);

(iii) a sequence which is degenerate as a result of the genetic code to a sequence as defined in (i) or (ii);

(iv) a sequence having at least 60% identity to a sequence as defined in (i); or (v) a fragment of any of the sequences (i), (ii), (iii) or (iv), and which encodes a polypeptide having hydroxylase activity or capable of generating antibodies specific for a HIF hydroxylase.

The invention also relates to expression vectors comprising a polynucleotide of the invention and antibodies capable of specifically binding a polypeptide of the invention.

The invention also relates to the use of the substances identified in accordance with the assays of the present invention and to the use of inhibitors of the activity of the peptides of the invention in the treatment of a condition or disease associated with altered HIF levels with respect to healthy (or normal) levels, or a condition in which it is desirable to alter HIF activity.

DETAILED DESCRIPTION OF THE INVENTION

SEQ ID NO: 1 comprises the nucleotide and amino acid sequence for PHD1.

SEQ ID NO: 2 comprises the amino acid sequence for PHD1.

SEQ ID NO: 3 comprises the nucleotide and amino acid sequence for PHD2.

SEQ ID NO: 4 comprises the amino acid sequence alone for PHD2

SEQ ID NO: 5 comprises the nucleotide and amino acid sequence for PHD3.

SEQ ID NO: 6 comprises the amino acid sequence alone for PHD3.

SEQ ID NO: 7 comprises the nucleotide and amino acid sequence for EGL-9.

SEQ ID NO: 8 comprises the amino acid sequence alone for EGL-9.

SEQ ID NOs: 9 to 16 represent a number of polypeptides which antagonize the interaction of a HIFα subunit with VHL.

SEQ ID NOs: 17 to 22 represent a number of HIF hydroxylase sequence motifs.

SEQ ID NO: 23 provides the amino acid sequence of pVHL minimal binding domain of HIF-1α.

SEQ ID NO: 24 provides the amino acid sequence of pVHL minimal binding domain of HIF-2α.

SEQ ID NO: 25 provides the amino acid sequence of pVHL minimal binding domain of HIF-α from *X. laevis*.

SEQ ID NO: 26 provides the amino acid sequence of pVHL minimal binding domain of HIF-α from *D. melanogaster*.

SEQ ID NO: 27 provides the amino acid sequence of pVHL minimal binding domain of HIF-α from *C. elegans*.

SEQ ID NOs: 28 to 34 represent the amino acid sequence of a number of synthetic peptides assessed for their ability to block HIF-1α/pVHL interaction.

SEQ ID NO: 35 comprises the amino acid sequence alone for human HIF-α.

SEQ ID NO: 36 comprises the amino acid sequence alone for *C. elegans* HW-α.

SEQ ID NO: 37 comprises the amino acid sequence of a portion of HIF-1α which is involved in VHL dependent ubiquitylation and contains an LxxLAP motif.

SEQ ID NO: 38 comprises the amino acid sequence of a portion of HIF-2α which is involved in VHL dependent ubiquitylation and contains an LxxLAP motif.

SEQ ID NO: 39 comprises the amino acid sequence of a second portion of HIF-1α which is involved in VHL dependent ubiquitylation and contains an LxxLAP motif:

SEQ ID NO: 40 comprises the amino acid sequence of the predicted jelly roll core of the *C. elegans* HIF hydroxylase EGL-9.

SEQ ID NO: 41 comprises the amino acid sequence of the predicted jelly roll core of PHD 1.

SEQ ID NO: 42 comprises the amino acid sequence of the predicted jelly roll core of PHD 2.

SEQ ID NO: 43 comprises the amino acid sequence of the predicted jelly roll core of PHD 3.

SEQ ID NO: 44 comprises the amino acid sequence of the predicted jelly roll core of rat SM20.

SEQ ID NO: 45 comprises the amino acid sequence of the prolyl-3-hydroylase from *Streptomyces*.

SEQ ID NOs: 46 and 47 provide the nucleotide sequences of two primers used to generate a mutagenized ceHIF.

SEQ ID No: 48 provides the amino acid sequence of a possible HIF hydroxylase motif.

HIF Hydroxylases

The present invention relates to a family of novel hydroxylases, referred to herein as HIF hydroxylases, functional variants thereof and functional fragments of HIF hydroxylases or of variants thereof. Sequence information for three human HIF hydroxylases termed PHD polypeptides (PHD 1, 2 and 3) are provided in SEQ ID NOS: 1, 3 and 5 (nucleotide and amino acid) and in SEQ ID NOS: 2, 4 and 6 comprising the corresponding amino acid sequence. Sequence information for a *C. elegans* HIF hydroxylase, EGL-9, is provided in SEQ ID NO: 7 (nucleotide and amino acid) and in SEQ ID NO: 8 comprising the corresponding amino acid sequence. A polypeptide of the invention thus consists essentially of the amino acid sequence of SEQ ID NO: 2, 4, 6 or 8 or a variant of any one of these sequences or of a fragment of any one of these sequences or variants of the fragments.

PHD1, 2 and 3 are 2-oxoglutarate dependent non-haem iron-dependent dioxygenases. These dioxygenases have hydroxylase activity, and in particular they mediate hydroxylation HIF 1α. They are related by sequence to non-haem oxygenases for which crystal structures are known such as proline-3-hydroxylase (Clifton et al., Eur. J. Biochem., 2001, 268, 6625-6636). PHD 1, 2 and 3 are related to EGL9 of *C. elegans* and may also be referred to herein as EGLN 2, 1 and 3 respectively. The PHD 1, 2 and 3 and EGL9 hydroxylases are all considered to be HIF hydroxylases of the invention. The HIF hydroxylases of the invention, and in particular the human HIF hydroxylases, may also be referred to as EGLN polypeptides.

In a preferred embodiment the HIF hydroxylase of the invention is a prolyl-hydroxylase. Typically the HIF hydroxylase is a human HIF hydroxylase and in particular it is PHD 1, 2 or 3. In a preferred embodiment the various assays, methods, medicaments and other embodiments of the invention employ, or are concerned, with a human HIF hydroxylase and in particular PHD 1, 2 or 3.

A polypeptide of the invention may be in isolated and/or purified form, free or substantially free of material with which it is naturally associated, such as other polypeptides or such as human polypeptides other than that for which the amino acid sequence is encoded by the gene encoding the HIF hydroxylase and in particular the PHD-1, -2 or -3 gene or (for example if produced by expression in a prokaryotic cell) lacking in native glycosylation, e.g. unglycosylated.

It will be understood that the polypeptide may be mixed with carriers or diluents which will not interfere with the intended purpose of the polypeptide and still be regarded as substantially isolated. A polypeptide in substantially purified form will generally comprise the polypeptide in a preparation in which more than 50% e.g. more than 80%, 90%, 95% or 99%, by weight of the polypeptide in the preparation is a polypeptide of the invention. Routine methods can be employed to purify and/or synthesize the proteins according to the invention. Such methods are well understood by persons skilled in the art and, include techniques such as those disclosed in Sambrook et al, Molecular Cloning: A Laboratory Manual, Second Edition, CSH Laboratory Press, 1989, the disclosure of which is included herein in its entirety by way of reference.

The term "variant" refers to a polypeptide which shares at least one property or function with the HE hydroxylases of SEQ ID NOS: 2, 4, 6 or 8 and in particular those of SEQ ID NOS: 2, 4 or 6. A "fragment" of the invention also possesses at least one function or property of the HIF hydroxylase of SEQ ID NO: 2, 4, 6 or 8 and in particular of SEQ ID NOS: 2, 4 or 6. The HIF hydroxylases of the invention are hydroxylases, that is they have the ability to hydroxylate an amino acid residue in a peptide. Preferably, a polypeptide of the invention is capable of hydroxylating one or more prolyl residues of a peptide substrate. In preferred aspects of the invention, a HIF hydroxylase, variant or fragment in accordance with the invention has the ability to hydroxylate one or more residues of HIF-1α, preferably a prolyl residue of HIF and in particular Pro 564 and/or Pro 402 of HIF-1α or a peptide analogue of HIF-1α or fragment thereof incorporating such a prolyl. Preferably, a variant of a HIF hydroxylase in accordance with the present invention has at least 60% sequence identity with the amino acid sequence of SEQ ID NO: 2, 4, 6 or 8 and in particular with that of SEQ ID NO: 2, 4 or 6.

The present invention also includes active portions, fragments, derivatives and functional mimetics of the polypeptides of the invention. An "active portion" of a polypeptide means a peptide which is less than said full length polypeptide, but which retains hydroxylase activity and in particular maintains HIF hydroxylase activity, preferably HIF prolyl hydroxylase activity. Such an active fragment may be included as part of a fusion protein, e.g. including a binding portion for a different i.e. heterologous ligand.

A "fragment" of a polypeptide generally means a stretch of amino acid residues of at least about five contiguous amino acids, often at least about seven contiguous amino acids, typically at least about nine contiguous amino acids, more preferably at least about 13 contiguous amino acids, and, more preferably, at least about 20 to 30 or more contiguous amino acids. Fragments of the HIF hydroxylase sequence may include antigenic determinants or epitopes useful for raising antibodies to a portion of the amino acid sequence. Alanine scans are commonly used to find and refine peptide motifs within polypeptides, this involving the systematic replacement of each residue in turn with the amino acid alanine, followed by an assessment of biological activity. Such scans may therefore be used in the identification of preferred fragments of the invention.

The polypeptides of the present invention generally have hydroxylase activity, preferably prolyl hydroxylase activity. Thus, the invention also relates to such polypeptides, in particular, for use in assays of hydroxylase activity on substrates such as HIF. The polypeptides may also be used for hydroxylation of suitable substrates and in particular prolyl hydroxylation of such substrates. A variant or an active fragment of a HIF hydroxylase of the invention may typically be identified by monitoring for hydroxylase activity as described in more detail below. In preferred embodiments the HIF hydroxylase has prolyl hydroxylase activity such as prolyl-4-hydroxylase activity.

Such HIF hydroxylases may be a eukaryotic polypeptide, preferably a mammalian polypeptide, more preferably a human polypeptide.

A HIF hydroxylase preferably has HIF prolyl hydroxylase (HPH) activity and preferably recognises and/or has specificity for the substrate amino acid sequence motif LXXLXP, in particular LXXLAP, or LXXLRP where X is any amino acid i.e. hydroxylates the proline residue of the LXXLXP or LXXLAP motif of a polypeptide which comprises this sequence.

A HIF hydroxylase preferably contains a β-barrel jelly roll structure consisting of a minimum of eight strands. Typically, the jelly roll structure may have eight strands. FIG. 9 shows an alignment of various HIF hydroxylases with the locations of the eight β-barrel strands of the jelly roll motif indicated. A diagram of the jelly roll structure is shown in FIG. 10.

Preferred HIF hydroxylases comprise the sequence;

HXD[X]$_n$H where X is any amino acid and n is between 1 and 200, 20 and 150 or 30 and 100 amino acids, for example 10, 20, 30, 40, 50, 60, 70, 80, 90 or 100 amino acids.

In especially preferred embodiments, the HXD portion of the motif is located on the second strand of the jelly roll motif of the HIF hydroxylase and the remaining H is on or close to the seventh strand of the motif.

In some enzymes related to the PHD 1, 2 and 3 enzymes isolated; such as clavaminic acid synthase, the HXD motif is replaced by a HXE motif. Thus the invention also encompasses HIF hydroxylases which have in place of a HXD motif a HXE motif. This may be because the HIF hydroxylase normally has such a motif, or alternatively, because the HXD motif originally present has been replaced by a HXE motif. Thus for any of the HXD motifs described herein, the invention also encompasses enzymes with a motif where the Aspartic acid residue has been replaced with a Glutamic acid residue.

A suitable HXD[X]$_n$H motif (SEQ ID NO: 19) may comprise the residues His487, Asp489 and His 548 with reference of the Egl-9 sequence. A suitable HIF hydroxylase may thus comprise or include the sequence;

HXD[X]$_{58}$H (SEQ ID NO: 19)

Amino acid residues described herein are numbered according to the EGL-9 sequence (GI5923812), unless otherwise stated. Sequences of the catalytic regions of EGL-9 and other HIF hydroxylases are shown in FIG. 9. It will be appreciated that because of variations in sequence, the equivalent or corresponding residues in other HIF hydroxylase sequences may have different numbers. Reference herein to a residue numbered according to the EGL-9 sequence is understood to include the equivalent residue in other HIF hydroxylases.

Preferred HIF hydroxylases may comprise one or more of the following residues; Met473, Asp494, Tyr502, Leu517, Pro532, Asp543, Val550, Arg557.

Such a preferred polypeptide may comprise the following amino acid sequence;

M(X)$_{13}$HXD(X)$_4$D(X)$_7$Y(X)$_{14}$L(X)$_{14}$P(X)$_{10}$D(X)$_4$HXV(X)$_6$R (SEQ ID NO: 20)

where X is any amino acid residue.

Especially preferred HIF hydroxylases may additionally comprise one or more of the following residues;
Arg469, Tyr477 Pro478, Gly479, Asn480, Gly481, Tyr584, Val585, Val488, Asn490, Pro491, Gly495, Arg496, Cys497; Thr499, Ile501, Tyr503, Asn505, Trp508, Asp509, Gly514, Gly515, Phe520, Pro521, Glu522, Asp535, Arg536, Leu537, Phe539, Trp541; Ser542, Arg544; Arg545, Asn546, Pro547; Glu549, Pro552, Ala559, Thr561, Val562, Tip563, Tyr564, Asp566, Glu569, Arg570, Ala573, Ala575, Lys576, Lys578.

Such an especially preferred polypeptide may, for example, comprise the following amino acid sequence;

RXXXMXXXYP GNGXXYVXHY DNPXXDGRCX TXIYYXNXXW D(X)$_4$GGXLX XFPE(X)$_9$PX XDRLXFXWSD RRNPHEVXP(X)$_4$ RXAXTVWYXD XXERXXAXAK XK (SEQ ID NO: 21)

where X is any amino acid residue.

In other preferred embodiments one or more of the following variations of the above sequence may be present. Residue 478 may be Asn, residue 485 may be Ile, residue 496 may be Lys, residue 497 may be Val, residue 515 may be Ser, residue 520 may be Tyr, residue 530 may be Ile, Val or Met, residue 536 may be Lys, residue 537 may be Ile, residue 539 may be Ile, residue 546 may be Thr, residue 559 may be Ser, residue 560 may be Ile, Met or Leu, residue 561 may be Cys and/or residue 564 may be Phe.

A suitable HIF hydroxylase may comprise a polypeptide sequence selected from the group consisting of SM20 (NCBI Acc No: NP071334), EGL-9 (GI5923812), CGI 114 (AAF52050), C1 or fl2 (NP071334), EGLN1/PHD2 (gi|457146), EGLN2/PHD1 (gi|457148), EGLN3/PHD3 (gi|4547150), FALKOR (gi|3649965), and FLJ21620 (BAB15101) as shown in Table 1.

A polypeptide of the invention may further comprise an amino acid sequence which shares greater than about 60% sequence identity with one of the above amino acid sequences, preferably greater than about 70%, more preferably greater than about 80%, more preferably greater than about 90%, most preferably greater than about 95%. Suitable sequences have prolyl hydroxylase and in particular HIF prolyl hydroxylase activity.

In one embodiment the invention provides a polypeptide having a least 60% sequence identity with the amino acid sequence encoded by the PHD2 (EGLN1) gene.

Further aspects of the present invention relate to methods for identifying HIF hydroxylases. Such a method may comprise;
screening a database for an open reading frame encoding a polypeptide comprising the sequence;

M(X)$_{13}$HXD(X)$_4$D(X)$_7$Y(X)$_{14}$L(X)$_{14}$P(X)$_{10}$D(X)$_4$HXV(X)$_6$R (SEQ ID NO: 20)

expressing said open reading frame to produce said polypeptide; and,
determining the ability of said polypeptide to hydroxylate a prolyl or other residue of HIF polypeptide as described herein. Crystallographic information may also be used to identify other HIF hydroxylases, for use in subsequent assays of HIF hydroxylase activity.

In an alternative aspect of the present invention, a HIF hydroxylase of the invention may be a variant which does not show the same activity as the HIF hydroxylase, but is one which inhibits a function of the wild type polypeptide. For example, a modified or variant HIF hydroxylase may be one which competes for HIF hydroxylase substrates but which does not lead to prolyl hydroxylation of such substrate, Such variants may be used in the various embodiments of the invention.

Amino Acid Sequence Identity

A polypeptide may comprise an amino acid sequence which shares greater than about 60% sequence identity with a polypeptide sequence described or referenced herein, greater than about 70%, greater that about 80% greater than about 90%, greater than about 95%, or greater than about 98%.

For amino acid "homology", this may be understood to be identity e.g. as determined using the algorithm GAP (as described below).

Amino acid identity is generally defined with reference to the algorithm GAP (Genetics Computer Group, Madison, Wis.). GAP uses the Needleman and Wunsch algorithm to align two complete sequences that maximizes the number of matches and minimizes the number of gaps. Generally, the default parameters are used, with a gap creation penalty=12 and gap extension penalty=4. Use of GAP may be preferred but other algorithms may be used, e.g. BLAST, (which uses the method of Altschul et al. (1990) *J. Mol. Biol.* 215: 405-410), gapped BLAST, PSI-BLAST, (Altshul S. (1997) *Nucleic Acid Res.* 17 3389-33402), PASTA (which uses the method of Pearson and Lipman (1988) *PNAS USA* 85: 2444-2448), or the Smith-Waterman algorithm (Smith and Waterman (1981) *J. Mol. Biol.* 147: 195-197). Generally, the default parameters are used, with a gap creation penalty=12 and gap extension penalty=4.

Sequence comparison may be made over the full-length of the relevant sequence shown herein, or may more preferably be over a contiguous sequence of about or greater than about 20, 25, 30, 33, 40, 50, 67, 133, 167, 200, 233, 267, 300, 333, 400 or more amino acids, compared with the relevant amino acid sequence.

Where default parameters or other features of these programs are subject to revision, it is to be understood that reference to the programs and their parameters are as of the priority date of the instant application.

Substitutions made to polypeptides of the invention may include conserved substitutions, for example according to the following table, where amino acids on the same block in the second column and preferably in the same line in the third column may be substituted for each other:

| ALIPHATIC | Non-polar | G A P |
| | | I L V |
| | Polar-uncharged | C S T M |
| | | N Q |
| | Polar-charged | D E |
| | | K R H |
| AROMATIC | | F W Y |

Alternatively, any amino acid may be replaced by a small aliphatic amino acid, preferably glycine or alanine.

In addition, deletions and insertions (e.g. from 1 to 5 subject to a maximum of 40% of the amino acids) may also be made. Insertions are preferably insertions of small aliphatic amino acids, such as glycine or alanine, although other insertions are not excluded.

Variant polypeptides may also modified in any of the ways described herein for polypeptides of the invention. This includes for example "reverse" C-terminal to N-terminal sequences, synthetic amino acids, glycosylated peptides, phosphorylated peptides, addition of metal ions such as ions of calcium, zinc, iron or manganese modified side chains and labelling. Polypeptides may be provided in the form of molecules which contain multiple copies of the polypeptide (or mixtures of polypeptides). For example, the amino group of the side chain of lysine may be used as an attachment point for the carboxy terminus of an amino acid. Thus two amino acids may be joined to lysine via carbonyl linkages, leading to a branched structure which may in turn be branched one or more times. By way of example, four copies of a polypeptide of the invention may be joined to such a multiple antigen peptide (MAP), such as a MAP of the structure $Pep_4$-$Lys_2$-Lys-X, where Pep is a polypeptide from the HIF hydroxylase or variant thereof (optionally in the form of a heterologous fusion), Lys is lysine and X is a terminal group such as β-alanine which provides for joining of the MAP core to a solid support such as a resin for synthesis of the $Pep_4$-MAP peptide and which may be removed from the support once synthesis is complete.

Other multiple polypeptide structures may be obtained using the MAP cores described in: Lu et al, 1991, Mol Immunol, 28, 623-30; Briand et al, 1992, J Immunol Methods, 156, 255-65; Ahlborg, 1995, J Immunol Methods, 179, 269-75.

Where multimers of the invention are provided, they may comprise different polypeptides of the invention or be multimers of the same polypeptide.

Except where specified to the contrary, the polypeptide sequences described herein are shown in the conventional 1-letter code and in the N-terminal to C-terminal orientation. The amino acid sequence of polypeptides of the invention may also be further modified to include non-naturally-occurring amino acids or to increase the stability of the compound in vivo. When the compounds are produced by synthetic means, such amino acids may be introduced during production. The compound may also be modified following either synthetic or recombinant production.

Polypeptides of the invention may also be made synthetically using D-amino acids. In such cases, the amino acids may be linked in a reverse sequence in the C to N orientation. β-amino acids (or higher homologues) may also be used.

A number of side-chain modifications for amino acids are known in the art and may be made to the side chains of polypeptides of the present invention. Such modifications include for example, modifications of amino groups by reductive alkylation by reaction with an aldehyde followed by reduction with $NaBH_4$, amidination with methylacetimidate or acylation with acetic anhydride.

The guanidino groups of arginine residues may be modified by the formation of heterocyclic condensation products with reagents such as 2,3-butanedione or glyoxal. Sulphydryl groups may be modified by methods such as carboxymethylation, tryptophan residues may be modified by oxidation or alkylation of the indole ring and the imidazole ring of histidine residues may be modified by alkylation.

The carboxy terminus and any other carboxy side chains may be blocked in the form of an ester group, e.g. a $C_{1-6}$alkyl ester.

The above examples of modifications to amino acids are not exhaustive. Those of skill in the art may modify amino acid side chains where desired using chemistry known per se in the art.

Polypeptides may be made synthetically or recombinantly, using techniques which are widely available in the art. Synthetic production generally involves step-wise addition of individual amino acid residues to a reaction vessel in which a polypeptide of a desired sequence is being made.

Polynucleotides

The invention also includes nucleotide sequences that encode for a HIF hydroxylase or a variant or fragment thereof as well as nucleotide sequences which are complementary thereto. In particular, the invention provides nucleotide sequences which encode a human HIF hydroxylase or a fragment or variant of a human HIF hydroxylase as well as nucleotide sequences complementary to any of these sequences. The nucleotide sequence may be RNA or DNA including genomic DNA, synthetic DNA or cDNA. Preferably the nucleotide sequence is a DNA sequence and most preferably, a cDNA sequence. The invention also encompasses PNA (protein nucleic acid) molecules comprising the sequences of the invention. Nucleotide sequence information for human PHD 1, 2 and 3 is provided in SEQ ID NOs: 1, 3 and 5 respectively. Nucleotide sequence information is provided in SEQ ID NO: 7, for the EGL-9 polypeptide of *C. elegans*, Such nucleotides can be isolated from cells or synthesised according to methods well known in the art, as described by way of example in Sambrook et al, 1989.

Typically a polynucleotide of the invention comprises a contiguous sequence of nucleotides which is capable of hybridizing under selective conditions to the coding sequence or the complement of the coding sequence of SEQ ID NO: 1, 3, 5 or 7 and in particular to the coding sequence or the complement of SEQ ID NO: 1, 3 or 5.

A polynucleotide of the invention can hybridize to the coding sequence or the complement of the coding sequence of SEQ ID NO: 1, 3, 5 or 7, and in particular to the coding sequence or the complement of SEQ ID NO: 1, 3 or 5, at a level significantly above background. Background hybridization may occur, for example, because of other cDNAs present in a cDNA library. The signal level generated by the interaction between a polynucleotide of the invention and the coding sequence or complement of the coding sequence of SEQ ID NO: 1, 3, 5 or 7 is typically at least 10 fold, preferably at least 100 fold, as intense as interactions between other polynucleotides and the coding sequence of SEQ ID NO: 1, 3, 5 or 7. The intensity of interaction may be measured, for example, by radiolabelling the probe, e.g. with $^{32}P$. Selective hybridisation may typically be achieved using conditions of medium to high stringency. However, such hybridisation may be carried out under any suitable conditions known in the art (see Sambrook et al, 1989. For example, if high stringency is required suitable conditions include from 0.1 to 0.2×SSC at 60° C. up to 65° C. If lower stringency is required suitable conditions include 2×SSC at 60° C.

The coding sequence of SEQ ID NO: 1, 3, 5 or 7 may be modified by nucleotide substitutions, for example from 1, 2 or 3 to 10, 25, 50 or 100 substitutions. The polynucleotide of SEQ ID NO: 1, 3, 5 or 7 may alternatively or additionally be modified by one or more insertions and/or deletions and/or by an extension at either or both ends. A polynucleotide may include one or more introns, for example may comprise genomic DNA. The modified polynucleotide generally encodes a polypeptide which has HIF hydroxylase activity, typically which has hydroxylase activity and in particular prolyl hydroxylase activity. Alternatively, a polynucleotide encodes a ligand-binding portion of a polypeptide or a polypeptide which modulates HIF hydroxylase activity. Degenerate substitutions may be made and/or substitutions may be made which would result in a conservative amino acid substitution when the modified sequence is translated, for example as shown in the Table above.

A nucleotide sequence which is capable of selectively hybridizing to the complement of the DNA coding sequence of SEQ ID NO: 1, 3, 5 or 7 will generally have at least 60%, at least 70%, at least 80%, at least 88%, at least 90%, at least 95%, at least 98% or at least 99% sequence identity to the coding sequence of SEQ ID NO: 1, 3, 5 or 7 over a region of at least 20, preferably at least 30, for instance at least 40, at least 60, more preferably at least 100 contiguous nucleotides or most preferably over the full length of SEQ ID NO: 1, 3, 5 or 7. Preferably the nucleotide sequence encodes a polypeptide which has the same domain structure as a HIF hydroxylase as described in more detail above.

For example the UWGCG Package provides the BEST-FIT program which can be used to calculate homology (for example used on its default settings) (Devereux et al (1984) *Nucleic Acids Research* 12, p 387-395). The PILEUP and BLAST algorithms can be used to calculate homology or line up sequences (typically on their default settings), for example as described in Altschul (1993) J. Mol. Evol. 36:290-300; Altschul et al (1990) J. Mol. Biol. 215:403-10.

Software for performing BLAST analyses is publicly available through the National Centre for Biotechnology Information (www.nih.gov).

This algorithm involves first identifying high scoring sequence pair (HSPs) by identifying short words of length W in the query sequence that either match or satisfy some positive-valued threshold score T when aligned with a word of the same length in a database sequence. T is referred to as the neighborhood word score threshold (Altschul-et al, 1990). These initial neighborhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) *Proc. Natl. Acad. Sci.* USA 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) *Proc. Natl. Acad. Sci.* USA 90: 5873-5787 and Altschul and Gish (1996) *Methods Enzymol.* 266: 460-480. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

Any combination of the above mentioned degrees of sequence identity and minimum sizes may be used to define polynucleotides of the invention, with the more stringent combinations (i.e. higher sequence identity over longer lengths) being preferred. Thus, for example a polynucleotide which has at least 90% sequence identity over 25, preferably over 30 nucleotides forms one aspect of the invention, as does a polynucleotide which has at least 95% sequence identity over 40 nucleotides.

The nucleotides of the invention may comprise a label for example, they may be radiolabelled or fluorescently labelled. The label may be such that it is only visualised on hybridisation to a complementary nucleic acid. For example, the label may be quenched until hybridisation. The nucleotides of the invention may be immobilised to a support such as a membrane or as a microarray.

The nucleotides according to the invention have utility in production of the proteins according to the invention, which may take place in vitro, in vivo or ex vivo. Accordingly, the invention provides a polypeptide encoded by a polynucleotide of the invention and in particular encoded by SEQ ID NO: 1, 3, 5 or 7. The invention includes a PHD polypeptide encoded by PHD gene, in particular by the PHD 1, 2 or 3 genes. The invention also provides fragments of such polypeptides which have HIF hydroxylase activity and in particular prolyl hydroxylase activity.

The nucleotides may be involved in recombinant protein synthesis or indeed as therapeutic agents in their own right, utilised in gene therapy techniques. Nucleotides complementary to those encoding HIF hydroxylase, or antisense sequences, or interfering RNA may also be used in gene therapy.

The present invention also includes expression vectors that comprise nucleotide sequences encoding the proteins of the invention. Such expression vectors are routinely constructed in the art of molecular biology and may for example involve the use of plasmid DNA and appropriate initiators, promoters, enhancers and other elements, such as for example polyadenylation signals which may be necessary, and which are positioned in the correct orientation, in order to allow for protein expression. Other suitable vectors would be apparent to persons skilled in the art. By way of further example in this regard we refer to Sambrook et al. 1989.

Polynucleotides according to the invention may also be inserted into the vectors described above in an antisense orientation in order to provide for the production of antisense RNA. Antisense RNA or other antisense polynucleotides may also be produced by synthetic means. Such antisense polynucleotides may be used as test compounds in the assays of the invention or may be useful in a method of treatment of the human or animal body by therapy.

Polynucleotides of the invention may also be used to design double stranded RNAs for use in RNA interference. Such RNA comprises short stretches of double stranded RNA having the same sequence as a target mRNA. Such sequences can be used to inhibit translation of the mRNA. Alternatively, small fragments of the gene encoding a HIF hydroxylase may be provided, cloned back to back in a plasmid. Expression leads to production of the desired double stranded RNA, Such short interfering RNA (siRNA) may be used for example to reduce or inhibit expression of a HIF hydroxylase of the invention, in assays or in a method of therapy. The invention also relates to such siRNAs. Such siRNAs may be designed to inhibit groups of HIF hydroxylases of the invention by basing their sequences on regions of conserved sequence in the encoding genes of the hydroxylases. Alternatively, the siRNAs may be made specific to a particular HIF hydroxylase by choosing a sequence unique to the encoding gene of the particular hydroxylase gene to be inhibited.

Preferably, a polynucleotide of the invention in a vector is operably linked to a control sequence which is capable of providing for the expression of the coding sequence by the host cell, i.e. the vector is an expression vector. The term "operably linked" refers to a juxtaposition wherein the components described are in a relationship permitting them to function in their intended manner. A regulatory sequence, such as a promoter, "operably linked" to a coding sequence is positioned in such a way that expression of the coding sequence is achieved under conditions compatible with the regulatory sequence.

The vectors may be for example, plasmid, virus or phage vectors provided with a origin of replication, optionally a promoter for the expression of the said polynucleotide and optionally a regulator of the promoter. The vector may be an artificial chromosome. The vectors may contain one or more selectable marker genes, for example an ampicillin resistance gene in the case of a bacterial plasmid or a resistance gene for a fungal vector. Vectors may be used in vitro, for example for the production of DNA or RNA or used to transfect or transform a host cell, for example, a mammalian host cell. The vectors may also be adapted to be used in vivo, for example in a method of gene therapy.

Promoters and other expression regulation signals may be selected to be compatible with the host cell for which expression is designed. For example, yeast promoters include S. cerevisiae GAL4 and ADH promoters, S. pombe nmt1 and adh promoter. Mammalian promoters include the metallothionein promoter which can be induced in response to heavy metals such as cadmium. Viral promoters such as the SV40 large T antigen promoter or adenovirus promoters may also be used. An IRES promoter may also be used. All these promoters are readily available in the art.

Mammalian promoters, such as β-actin promoters, may be used. Tissue-specific promoters are especially preferred. Inducible promoters are also preferred. Promoters inducible by hypoxic conditions may, for example, be employed. Viral promoters may also be used, for example the Moloney murine leukaemia virus long terminal repeat (MMLV LTR), the roes sarcoma virus (RSV) LTR promoter, the SV40 promoter, the human cytomegalovirus (CMV) IE promoter, adenovirus, HSV promoters (such as the HSV IE promoters), or HPV promoters, particularly the HPV upstream regulatory region (URR). Viral promoters are readily available in the art.

The vector may further include sequences flanking the polynucleotide giving rise to polynucleotides which comprise sequences homologous to eukaryotic genomic sequences, preferably mammalian genomic sequences, or viral genomic sequences. This will allow the introduction of the polynucleotides of the invention into the genome of eukaryotic cells or viruses by homologous recombination. In particular, a plasmid vector comprising the expression cassette flanked by viral sequences can be used to prepare a viral vector suitable for delivering the polynucleotides of the invention to a mammalian cell. Homologous recombination may also be used to disrupt or mutate endogenous sequences in cells encoding HIF hydroxylases. Other examples of suitable viral vectors include herpes simplex viral vectors and retroviruses, including lentiviruses, adenoviruses, adeno-associated viruses and HPV viruses. Gene transfer techniques using these viruses are known to those skilled in the art. Retrovirus vectors for example may be used to stably integrate the polynucleotide giving rise to the polynucleotide into the host genome. Replication-defective adenovirus vectors by contrast remain episomal and therefore allow transient expression.

The invention also includes cells that have been modified to express a HIF hydroxylase of the invention. Such cells include transient, or preferably stable higher eukaryotic cell lines, such as mammalian cells or insect cells, using for example a baculovirus expression system, lower eukaryotic cells, such as yeast or prokaryotic cells such as bacterial cells. Particular examples of cells which may be modified by insertion of vectors encoding for a polypeptide according to the invention include mammalian thymic epithelial cells, fibroblasts, HEK293T, U20S, CHO, HeLa, BHK, 3T3 and COS cells.

A polypeptide of the invention may be expressed in cells of a transgenic non-human animal, typically a mammal, preferably a rodent, more preferably a mouse. The animal may be a larger animal such as a pig or sheep. A transgenic non-human animal expressing a polypeptide of the invention is included within the scope of the invention. Also included are transgenic animals expressing an antisense RNA, siRNA or ribozyme designed to inhibit expressions of a polypeptide of the invention. The transgenic animals of the invention may have a gene encoding an endogenous HIF hydroxylase disrupted or mutated. For example, the endogenous HIF hydroxylase may be rendered inactive and lack hydroxylase activity.

Antibodies

According to another aspect, the present invention also relates to antibodies, specific for a polypeptide of the invention. Such antibodies are for example useful in purification, isolation or screening methods involving immunoprecipitation techniques or, indeed, as therapeutic agents in their own right. Antibodies may be raised against specific epitopes of the polypeptides according to the invention.

Antibodies may be used to impair HIF hydroxylase function. An antibody, or other compound, "specifically binds" to a protein when it binds with preferential or high affinity to the protein for which it is specific but does not substantially bind or binds with only low affinity to other proteins. A variety of protocols for competitive binding or immunoradiometric assays to determine the specific binding capability of an antibody are well known in the art (see for example Maddox et al, J. Exp. Med. 158, 1211-1226, 1993). Such immunoassays typically involve the formation of complexes between the specific protein and its antibody and the measurement of complex formation.

Antibodies of the invention may be antibodies to human polypeptides or fragments thereof. For the purposes of this invention, the term "antibody", unless specified to the contrary, includes fragments which bind a polypeptide of the invention. Such fragments include Fv, F(ab') and F(ab')$_2$ fragments, as well as single chain antibodies. Furthermore, the antibodies and fragment thereof may be chimeric antibodies, CDR-grafted antibodies or humanised antibodies.

Antibodies may be used in a method for detecting polypeptides of the invention in a biological sample, which method comprises:

I providing an antibody of the invention;
II incubating a biological sample with said antibody under conditions which allow for the formation of an antibody-antigen complex; and
III determining whether antibody-antigen complex comprising said antibody is formed.

A sample may be for example a tissue extract, blood, serum and saliva. Antibodies of the invention may be bound to a solid support and/or packaged into kits in a suitable container along with suitable reagents, controls, instructions, etc. Antibodies may be linked to a revealing label and thus may be suitable for use in methods of in vivo HIF hydroxylase imaging.

Antibodies of the invention can be produced by any suitable method. Means for preparing and characterising antibodies are well known in the art, see for example Harlow and Lane (1988) "Antibodies: A Laboratory Manual", Cold Spring Harbor Laboratory Press, Cold Spring Harbor, N.Y.

For example, an antibody may be produced by raising antibody in a host animal against the whole polypeptide or a fragment thereof, for example an antigenic epitope thereof, herein after the "immunogen".

A method for producing a polyclonal antibody comprises immunizing a suitable host animal, for example an experimental animal, with the immunogen and isolating immunoglobulins from the animal's serum. The animal may therefore be inoculated with the immunogen, blood subsequently removed from the animal and the IgG fraction purified.

A method for producing a monoclonal antibody comprises immortalizing cells which produce the desired antibody. Hybridoma cells may be produced by fusing spleen cells from an inoculated experimental animal with tumour cells (Kohler and Milstein (1975) *Nature* 256, 495-497).

An immortalized cell producing the desired antibody may be selected by a conventional procedure. The hybridomas may be grown in culture or injected intraperitoneally for formation of ascites fluid or into the blood stream of an allogenic host or immunocompromised host. Human antibody may be prepared by in vitro immunisation of human lymphocytes, followed by transformation of the lymphocytes with Epstein-Barr virus and in transgenic mice enabling production of human antibodies.

For the production of both monoclonal and polyclonal antibodies, the experimental animal is suitably a goat, rabbit, rat or mouse. If desired, the immunogen may be administered as a conjugate in which the immunogen is coupled, for example via a side chain of one of the amino acid residues, to a suitable carrier. The carrier molecule is typically a physiologically acceptable carrier. The immunogen may, for example, be administered with an adjuvant. The antibody obtained may be isolated and, if desired, purified.

Assays

Our data shows that hydroxylation of HIF-α is mediated by a hydroxylase enzyme which has specificity or selectivity for HIF-α. The enzyme responsible are referred to as HIF hydroxylases and include EGL-9 and 2 and 3. The action of HIF hydroxylases, and in particular human HIF hydroxylases, represent a novel target for the control of HIFα. By blocking HIF hydroxylase activity, this will reduce hydroxylation of HIF-α and thus lead to the accumulation of HIF-α in cells. This in turn will lead to the activation of systemic local defenses against hypoxia or ischaemia that may include the promotion of angiogenesis, erythropoiesis, energy metabolism, inflammation, vasomotor function, and will also affect apoptotic/proliferative responses.

We describe below in more detail a number of different assays that may be carried out to identify modulators of HIF hydroxylase activity and in particular of prolyl hydroxylase activity, or which affect regulation of HIF-α levels in a cell and hence which affect HIF mediated activity. Some of these assays utilise HIF polypeptides and VHL polypeptides, and in particular HIF hydroxylases in accordance with the present invention. Typically, the assays may utilise a human HIF hydroxylase such as PHD 1, 2 or 3 or a fragment or variant of a human HIF hydroxylase. In a preferred embodiment an enzyme with HIF prolyl-hydroxylase activity may be used. These components are described in more detail below. Each of these components, where required may be provided either in purified or unpurified form, for example, as cellular extracts or by purification of the relevant component from such extracts. Alternatively, the relevant component can be expressed using recombinant expression techniques and purified: for use in the assay. Alternatively, the components may be expressed recombinantly in a cell for use in cell based assays.

Typically, a polynucleotide encoding the relevant component is provided within an expression vector. Such expression vectors are routinely constructed in the art and may for example involve the use of plasmid DNA and appropriate initiators, promoters, enhancers and other elements, such as for example polyadenylation signals which may be necessary and which are positioned in the correct orientation in order to allow full protein expression. Suitable vectors would be very readily apparent to those of skill in the art, such as those described in more detail herein with reference to the HIF hydroxylases. Promoter sequences may be inducible or constitutive promoters depending on the selected assay format. The promoter may be tissue specific. Examples of promoters and other flanking sequences for use in the expression vectors are described in more detail herein with reference to the HIF hydroxylases of the invention and in particular to the human HIF hydroxylases of the invention.

HIF Polypeptides and Peptide Analogues

The assays of the present invention may use a substrate of a HIF hydroxylase and in particular a prolyl containing substrate of the enzyme. In particular, such substrates may be used in assays to monitor for the activity of a modulator of HIF hydroxylase activity. The substrate may be a HIF polypeptides or peptide analogue thereof. Typically, a HIF polypeptide will be used as the substrate.

Any suitable substrate in which a residue, preferably a proline residue, is hydroxylated by a HIF hydroxylase of SEQ ID NO: 2, 4, 6 or 8 may be used and in particular one which is hydroxylated by the HIF hydroxylase of SEQ ID NO: 2, 4 or 6. In preferred embodiments of the invention, such a substrate is a HIF polypeptide such as a HIF-1α or HIF-2α subunit protein or fragment of either or peptide analogue of the subunit or fragment. Preferably, the HIF-α peptide conveys an oxygen regulated response. More preferably, the HIF-α peptide is capable of oxygen regulated binding to pVHL. Preferably, such HIF polypeptides, fragments or peptide analogues incorporate a proline residue equivalent to Pro 564 and/or Pro 402 as defined with reference to HIF-1α. The proline equivalent to Pro 564 and/or Pro 402 of HIF-1α may be determined by aligning the HIF variant, fragment or analogue to the sequence of HIF-1α to obtain the best sequence alignment and identifying thereby the proline equivalent to Pro 564 and/or Pro 402 of HIF-1α. In the assays of the invention the hydroxylation of one or both of these pralines may be determined.

A HIF polypeptide may be of eukaryotic origin, in particular a human or other mammalian, HIF-α subunit protein or fragment thereof. Alternatively, the polypeptide may be of *C. elegans* origin. In those assays which monitor for hydroxylation of HIF-α through its interaction with and subsequent destruction by VHL, the HIF polypeptide has the ability to bind to a wild type full length pVHL protein, such that the binding is able, in a normoxic cellular environment, to target the HIF-α subunit for destruction i.e. the polypeptide comprises a pVHL binding domain.

A number of HIFα subunit proteins have been cloned. These include HIF-1α, the sequence of which is available as Genbank accession number U22431, HIF-2α, available as Genbank accession number U81984 and HIF-3α, available as Genbank accession numbers AC007193 and AC079154. These are all human HIF a subunit proteins and all may be used in the invention. HIF-α subunit proteins from other species, including murine HIF-1α (accession numbers AF003695, U59496 and X95580), rat HIF-1α (accession number Y09507), murine HIF-2α (accession numbers 081983 and D89787) and murine HIF-3α (accession number AF060194) may also be used in the invention. Other mammalian, vertebrate, invertebrate or other homologues may be obtained by techniques similar to those described above for obtaining pVHL homologues.

One HIF-α protein of particular interest is the *C. elegans* HIF-α subunit protein. The HIF-α/VHL system of regulation is conserved in *C. elegans*, so that the *C. elegans* system may be used in assays of the present invention.

There are a number of common structural features found in the two HIF-α subunit proteins identified to date. Some of these features are identified in O'Rourke et al (1999, J. Biol. Chem., 274; 2060-2071) and may be involved in the trans-activation functions of the HIF-α subunit proteins. One or more of these common structural features are preferred features of the HIF polypeptides.

Fragments of HIF-1α or peptide analogues preferably include proline residue 402 and/or 564 (U22431), which are hydroxylated by HIF prolyl hydroxylases. Suitable fragments may include or consist of residues 344-698, particularly residues 364-678, more particularly residues 364-638 or 384-638 and still more particularly residues 364-598 or 394-598. Other suitable fragments may include or consist of residues 549-652 and even more particularly the N-terminal region thereof which interacts with the VHL protein. C-terminal fragments may include residues 549 to 582 and in particular residues 556-574. Other suitable fragments comprise or consist of residues 344-417, more preferably 380-417. Such a region, or its equivalent in other HIF-α subunit proteins, is desirably present in the HIFα polypeptides described herein. The substrates used in the assays of the invention may typically comprise residues 549 to 582 of the human HIF-1α sequence.

Variants of the above HIF-α subunits may be used, such as synthetic variants which have at least 45% amino acid identity to a naturally occurring HIF-α subunit (particularly to a human HIF-α subunit such as, for example HIF-1α), preferably at least 50%, 60%, 70%, 80%, 90%, 95% or 98% identity. Such variants may include substitutions or modifications as described above with respect to HIF hydroxylases. Amino acid activity may also be calculated as described above with reference to HIF hydroxylases.

HIF fragments may also include non-peptidyl functionalities and may be optimised for assay purposes such that the level of identity is lowered. Such functionalities may be covalently bound such as sugars or non-covalently bound such as metal ions.

HIFα polypeptides as described herein may be fragments of the HIF-α subunit protein or variants as described above, provided that said fragments retain the ability to interact with a wild-type pVHL, preferably wild-type human pVHL. When using proteinogenic amino acid residues, such fragments are desirably at least 20, preferably at least 40, 50, 75, 100, 200, 250 or 400 amino acids in size. Desirably, such fragments include proline residue 402 and/or 564. Some preferred fragments include the region 556-574 found in human HIF-1α or its equivalent regions in other HIF-α subunit proteins, e.g. 517-542 of HIF-2α. Optionally, the fragments also include one or more domains of the protein responsible for trans-activation. Reference herein to HIF-α polypeptide or HIF-α subunit protein includes the above mentioned mutants and fragments or other HIF-α fragments which are functionally able to bind VHL protein unless the context is explicitly to the contrary.

Cell based assays of the present invention may involve upregulation of an endogenous HIF-α or expression of a HIF-α by recombinant techniques and in particular of HIF-1α.

VHL

Some assays in accordance with the present invention utilise VHL and in particular monitor the interaction between hydroxylated HIF and VHL and the subsequent destruction of HIF-α. The VHL may be any suitable mammalian VHL, particularly human VHL. It may be a *C. elegans* VHL. Human VHL has been cloned and sources of the gene can be readily identified by those of skill in the art. Its sequence is available as Genbank accession numbers AF010238 and L15409. Other mammalian VHLs are also available, such as murine VHL (accession number U12570) and rat (accession numbers U14746 and S80345). Non-mammalian homologues include the VHL-like protein of *C. elegans*, accession number F08G12.4. VHL gene sequences may also be obtained by routine cloning techniques, for example by using all or part of the human VHL gene sequence as a probe to recover and to determine the sequence of the VHL gene in other species. A wide variety of techniques are available for this, for example PCR amplification and cloning of the gene using a suitable source of mRNA (e.g. from an embryo or a liver cell), obtaining a cDNA library from a mammalian, vertebrate, invertebrate or other source, e.g a cDNA library from one of the above-mentioned sources, probing said library with a polynucleotide of the invention under stringent conditions, and recovering a cDNA encoding all or part of the VHL protein of that mammal. Suitable stringent conditions include hybridization on a solid support (filter) overnight incubation at 42° C. in a solution containing 50% formamide, 5×SSC (750 mM NaCl, 75 mM sodium citrate), 50 mM sodium phosphate (pH7.6), 5×Denhardt's solution, 10% dextran sulphate and 20 μg/ml salmon sperm DNA, followed by washing in 0.2×SSC at from about 50° C. to about 60° C.). Where a partial cDNA is obtained, the full length coding sequence may be determined by primer extension techniques.

A further approach is to use the above-identified sequences as query sequences to search databases for homologous gene sequences or partial gene sequences (particularly ESTs). Matches identified may be examined and where an actual or putative VHL sequence is found, the gene recovered by physical cloning using, for example PCR and RACE-PCR based on the sequence of the match.

Although wild-type VHL is preferred, mutants and variants of VHL which still retain the ability to interact directly with the HIF-α subunit may also be used. Examples of VHL mutants are well known in the art and include mutants described by Stebbins et al (Science, 1999, 284; 55-61) which have changes to the Elongin C interacting interface.

Mutants and other variants will generally be based on wild-type mammalian VHLs and have a degree of amino acid identity which is desirably at least 70%, preferably at least 80%, 90%, 95% or even 98% homologous to a wild type mammalian VHL, preferably to human VHL.

It is not necessary to use the entire VHL proteins (including their mutants and other variants) for assays of the invention. Fragments of the VHL may be used provided such fragments retain the ability to interact with the target domain of the HIFα subunit. Optionally, the fragment may include the Elongin C interacting interface domain. Fragments of VHL may be generated in any suitable way known to those of skill in the art. Suitable ways include, but are not limited to, recombinant expression of a fragment of the DNA encoding the VHL. Such fragments may be generated by taking DNA encoding the VHL, identifying suitable restriction enzyme recognition sites either side of the portion to be expressed, and cutting out said portion from the DNA. The portion may then be operably linked to a suitable promoter in a standard commercially available expression system. Another recombinant approach is to amplify the relevant portion of the DNA with suitable PCR primers. Small fragments of the VHL (up to about 20 or 30 amino acids) may also be generated using peptide synthesis methods which are well known in the art. Generally fragments will be at least 40, preferably at least 50, 60, 70, 80 or 100 amino acids in size.

Particularly preferred fragments include those which are based upon the beta domain located within the fragment 63-156 of the 213 amino acid human VHL protein, or the equivalent domain in other variants. In a preferred embodiment, such domains will have at least 70%, preferably 80%, 90%, 95% or even 98% degree of sequence identity to the 64-156 fragment of human VHL. Fragments of this region and its variants may be used. These fragments may be 15-80 amino acids in length, for example from 20 to 80, such as 30-60 amino acids in length. Fragments may include the regions 71-90 or 90-109 of human VHL or their equivalents in the above described variants. Desirably, the wild-type sequence of the beta domain is retained.

One fragment which may be used is that in which up to 53 of the N-terminal residues, e.g. from 1 to n wherein n is an integer of from 2 to 53, have been deleted, the rest of the protein being wild-type.

The ability of suitable fragments to bind to the HIFα subunit (or fragment thereof) may be tested using routine procedures such as those described in the accompanying Examples relating to intact VHL. Reference herein to a VHL protein includes the above mentioned mutants and fragments which are functionally able to bind the HIF α subunit unless the context is explicitly to the contrary.

Hydroxylases

In a number of the assays in accordance with the present invention, hydroxylase enzyme is provided. In preferred embodiments, the hydroxylase enzyme is a HIF hydroxylase in accordance with the present invention. The enzyme is preferably a prolyl hydroxylase. In a particularly preferred embodiment of the invention the HIF hydroxylase used comprises:
 (a) the amino acid sequence of SEQ ID NO: 2, 4, 6 or 8;
 (b) a variant thereof having at least 60% identity to the amino acid sequence of SEQ ID NO: 2, 4, 6 or 8 and having HIF hydroxylase activity; or
 (c) a fragment of either thereof having HIF hydroxylase activity.

Such hydroxylase enzymes, and in particular prolyl-hydroxylases such as for example 4-prolyl hydroxylase, are obtainable from extracts of mammalian cells, including immortalised mammalian cells in culture such as HeLa, RCC or CHO-K1 cells, primary cells, tissues or primary cell lysates (e.g. rabbit reticulocyte or human placental lysates). Cell extracts may be prepared in accordance with standard techniques available in the art by reference to the accompanying examples. Assays may alternatively be carried out as cell based assays in which hydroxylase enzyme is expressed endogenously.

In a preferred embodiment of any one of the assays in accordance with the present invention, the assay utilises a HIF hydroxylase, typically a human HIF hydroxylase, and in particular a PHD hydroxylase of the present invention. Such hydroxylases may be upregulated before or during the course of the assay. Alternatively, the enzyme may be expressed recombinantly, and the HIF hydroxylase of the invention isolated from such recombinant expression systems in purified or unpurified form for use in the assays. Alternatively, cells may be provided which have been transformed or transfected with expression vectors expressing a HIF hydroxylase in accordance with the present invention. Such methods provide assays for substances that inhibit, promote or otherwise modulate the individual activities of HIF hydroxylases in either a specific or a general manner. The methods may also be used to identify substances that inhibit, promote or otherwise modulate the activities of a group of HIF hydroxylases such as, for example, all of PHD 1, 2 and 3 or any two of the three enzymes.

The assays of the invention may use an EGLN polypeptide such as EGLN1 (gi|457146), EGLN2 (gi|457148), EGLN3 (gi|4547150), FLJ21620 (BAB15101) or Clorf12 (NP071334).

In general, the HIF hydroxylases of the invention are iron dependent, that is they typically require ferrous (FeII) ions for activity. Accordingly, the assays of the invention will typically include ferrous compounds, unless the purpose of the assay is to determine the effect of the absence of ferrous ions or it is desired to carry out control reactions where no ferrous ions are present.

Assay Methods

The present invention provides an assay method for identifying an agent which modulates the interaction of a hypoxia inducible factor (HIF) hydroxylase with a substrate of the hydroxylase, the method comprising:
 contacting a HIF hydroxylase and a test substance in the presence of a substrate of the hydroxylase under conditions in which the hydroxylase interacts with the substrate in the absence of the test substance; and
 determining the interaction, or lack of interaction, of the hydroxylase and the substrate. The interaction of the hydroxylase with the substrate may be determined by measuring the hydroxylase activity of the hydroxylase.

The interaction between hydroxylase and substrate refers to physical interaction or to functional interaction. The interaction may therefore be measured by any suitable method, including binding of the hydroxylase to a substrate, the activity of the hydroxylase on the substrate, or any activity related to the action of the hydroxylase on the substrate, such as the levels of co-factors or by-products used or produced in the hydroxylation reaction, or downstream effects mediated through hydroxylation of the substrate.

In another aspect of the present invention, there is provided an assay for an inhibitor of HIF-α destruction or HIF-α transcription inactivation comprising providing HIF-α or a peptide analogue thereof, incubating HIF-α or the peptide analogue with a test substance under conditions which allow for hydroxylation of HIF-α in the absence of the test substance, and monitoring for hydroxylation of HIF-α. Preferably, HIF-α or the peptide analogue thereof includes a prolyl residue such as Pro 564 and/or Pro 402 of HIF-α or an equivalent prolyl in a peptide analogue, and said assay is carried out under conditions which allow for hydroxylation of Pro 564 and/or Pro 402 in the absence of the test substance, and monitoring for hydroxylation of Pro 564 and/or Pro 402.

In a further aspect, there is provided an assay for an inhibitor of VHL-mediated HIF-α destruction, which comprises
 providing a HIF-α, or fragment thereof which includes a VHL-binding portion, together with its cognate prolyl-hydroxylase under conditions suitable for the hydroxylation of a proline residue in the HIF-α VHL-binding domain;
 providing a putative modulator of hydroxylation; and determining whether the amount of hydroxylation of said proline residue has been modulated by said putative modulator. In one embodiment of the invention the cognate prolyl-hydroxylase is a prolyl-4-hydroxylase.

Conversely, in hypoxic conditions such as those commonly found in tumours, the lack of hydroxylation of HIF, and in particular of proline hydroxylation, may lead to the accumulation of HIFα and the concomitant promotion of angiogenesis and other growth promoting events. Alternatively, in ischaemic/hypoxic conditions in which normal levels of HIF activity are present, it may also be desirable to increase existing HIF activity. Thus mechanisms which either upregulate a HIF hydroxylase, increase the activity of a HIF hydroxylase, rescue or bypass the hydroxylase are a target in such cells.

The invention also provides an assay for a promoter of hydroxylation of HIF-α, for example prolyl hydroxylation at Pro 564 and/or Pro 402 which comprises providing HIF-α or a peptide analogue; incubating HIF-α or the peptide analogue under hypoxic conditions or conditions under which hydroxylation of HIF-α does not occur in the absence of the test substance, and monitoring for hydroxylation of HIF-α or the peptide analogue thereof, such as at Pro 564 and/or Pro 402.

Accordingly, there is provided an assay for a promoter of hydroxylation of a proline residue in HIF-α, which comprises;
   providing HIF-α, or fragment thereof which includes a VHL-binding portion, under hypoxic conditions, said HIF-α or fragment thereof containing a proline residue in the VHL-binding domain;
   providing a putative hydroxylation promoting agent; and
   determining whether said agent provides for hydroxylation of said proline.

In the experiments described herein, HIF hydroxylases, and in particular PHI) polypeptides, have been found to hydroxylate HIF-α at one or more proline residues within the pVHL binding domain. This hydroxylation mediates pVHL binding. Accordingly, the present invention provides an assay for a modulator of HIF hydroxylase activity comprising contacting a HIF hydroxylase and a substrate of the hydroxylase, preferably a prolyl-containing substrate, in the presence of a test substance; and, determining the hydroxylase activity of the HIF hydroxylase, and in particular the prolyl hydroxylase thereof.

Such an assay may be used to identify inhibitors of HIF hydroxylase activity and are thus preferably carried out under conditions under which hydroxylation, and in particular prolyl hydroxylation, takes place in the absence of the test substance. As an alternative, the assays may be used to look for promoters of hydroxylase activity, for example, by looking for increased hydroxylation of the proline substrate compared to an assay carried out in the absence of a test substance. Alternatively, the assays may be carried out under conditions in which hydroxylation is reduced or absent, such as under hypoxic conditions and monitoring for the presence of or increased hydroxylation under such conditions.

Such an assay method may by virtue of using a specific HIF hydroxylase polypeptide be specific for inhibitors or promoters of the activity of that polypeptide and may by way of comparison be used to define inhibitors or activators that are specific for that HIF hydroxylase and not active or less active on a different HIF hydroxylase. In particular, such assays may be used to identify inhibitors or activators specific for a particular human HIF hydroxylase such as PHD 1, 2 or 3.

An assay method for obtaining an agent which modulates the activity of a HIF hydroxylase may include:
   contacting an HIF hydroxylase polypeptide and a substrate thereof, such as an HIFα polypeptide in the presence of a test substance; and,
   determining the hydroxylase activity of said HIF hydroxylase, preferably the prolyl hydroxylase activity, or HIF-α hydroxylase activity thereof.

In one embodiment the assay method may be for obtaining an agent which modulates the activity of an EGLN polypeptide and comprise:
   contacting an EGLN polypeptide and a test compound in the presence of an HIF polypeptide under conditions in which the EGLN polypeptide normally catalyses prolyl hydroxylation of said HIF polypeptide; and
   determining the HIF prolyl hydroxylase activity of said EGLN polypeptide.

Such assays may be performed under conditions in which the HIF hydroxylase/ELGN polypeptide normally catalyses hydroxylation and, in particular prolyl hydroxylation of a HIFα polypeptide. Suitable conditions may include pH 6.6 to 8.5 in an appropriate buffer (for example, Tris.HCl or MOPS) in the presence of 2-oxoglutarate, dioxygen and preferably ascorbate and ferrous iron.

Reducing agents such as dithiothreitol or tris(carboxyethyl)phosphine may also be present to optimise activity. Other enzymes such as catalase and protein disulphide isomerase may be used for the optimisation of activity. The enzymes, such as protein disulphide isomerase, may be added in purified or unpurified form. Further components capable of promoting or facilitating the activity of protein disulphide isomerase may also be added.

In an alternative embodiment, the invention provides an assay method for identifying an agent which modulates the interaction of a EGLN polypeptide and a HIF polypeptide comprising:
   contacting an EGLN polypeptide and a test compound in the presence of an HIF polypeptide, under conditions in which the EGLN polypeptide normally interacts with the HIF polypeptide; and
   determining the interaction of said HIF polypeptide and said EGLN polypeptide.

The present invention also provides an assay method for the identification of a HIF hydroxylase and in particular for the identification of a HIF prolyl hydroxylase. The method typically comprising:
   (a) providing a test polypeptide;
   (b) bringing into contact a HIF polypeptide and the test polypeptide under conditions in which the HIF polypeptide is hydroxylated by a HIF hydroxylase; and
   (c) determining whether or not the HIF polypeptide is hydroxylated.

In one embodiment the assay method may, in step (b), bring the HIF polypeptide and test polypeptide into contact under conditions in which the HIF polypeptide is hydroxylated by a PHD (EGLN) polypeptide.

Typically, libraries of test polypeptides may be screened to identify a HIF hydroxylase, for example an expression library from a particular species or tissue may be screened or one produced under a particular set of conditions. Alternatively, candidate HIF hydroxylases identified on the basis of criteria such as sequence homology or a particular protein structure may be assessed and their hydroxylase activity confirmed.

The HIF polypeptide used in the screening may be any of those described herein. It may be a human HIF polypeptide or a homolog from another species such as, for example, ceHIF. It may be from the species the library of test polypeptides is derived from. The hydroxylation of the HIF polypeptide, and in particular the hydroxylation of proline, may be identified by any of the methods discussed herein. For example hydroxylation may be confirmed by using a functional assay based on the effect of the hydroxylation on the HIF polypeptide, such as its decreased stability.

Once a HIF hydroxylase has been identified it may be farther characterised by, for example, assessing whether or not it is inhibited by compounds such as dimethyloxalolyl-glycine (DMOG) a precursor or pro-drug for oxalolylglycine. The effect of the HIF hydroxylase on HIF stability in the organism or tissue the hydroxylase is identified from may be assessed. The identified hydroxylase may be used in the same way as the other hydroxylases of the invention and in particular in the assays and therapeutic applications of the invention.

The present invention also provides an assay method for identifying alternative substrates of a HIF hydoxylase of the invention. Thus polypeptides or polypeptide analogues which can be hydroxylated and in particular have proline residues hydroxylated may be identified. The assay method typically comprises:

(b) contacting a test polypeptide with a HIF hydroxylase of the invention under conditions which HIF would normally be hydroxylated by the hydroxylase;
(c) determining whether the polypeptide is hydroxylated.

Typically, hydroxylation and in particular prolyl hydroxylation of the test substance may be confirmed using any of the methods discussed herein.

The present invention also provides an assay method for identifying a polypeptide or polypeptide analogue capable of specifically interacting with a HIF hydroxylase of the invention and in particular which is capable of specifically binding to the active site of the HIF hydroxylase in a manner which mimics or resembles the binding of the normal substrate of the enzyme. The method typically comprises:

(a) contacting a test polypeptide with a HIF hydroxylase of the invention under conditions which HIF would bind to the hydroxylase;
(b) determining whether the test polypeptide or analogue binds the hydroxylase.

The binding of the test polypeptide to the hydroxylase may be confirmed by any of the techniques discussed herein. In one embodiment binding of the polypeptide to a HIF hydroxylase may identified by looking for co-immunoprecipitation of the test polypeptide with the hydroxylase. The ability of the test polypeptide to inhibit binding of HIF to the hydroxylase may also be used.

The alternative polypeptide substrates and the polypeptides identified as being capable of specifically binding the hydroxylases of the invention may be used in the assay methods of the invention, for example, to identify modulators. Those polypeptides capable of preventing the normal interaction of HIF with a hydroxylase of the invention may also be used therapeutically.

The assays of the invention may also comprise modifying the agent identified. The assays may also comprise formulating the identified agent into a pharmaceutical composition. Typically, such pharmaceutical compositions may be for the treatment of a condition associated with increased or decreased HIF levels or activity.

Methods for Monitoring Modulation

The precise format of any of the screening or assay methods of the present invention may be varied by those of skill in the art using routine skill and knowledge. The skilled person is well aware of the need to additionally employ appropriate controlled experiments. The assays of the present invention may involve monitoring for hydroxylation of a suitable substrate (in particular monitoring for prolyl hydroxylation), monitoring for the utilisation of substrates and co-substrates, monitoring for the production of the expected products between the enzyme and its substrate. Assay methods of the present invention may also involve screening for the direct interaction between components in the system. Alternatively, assays may be carried out which monitor for downstream effects such as binding and subsequent destruction of HIF by VHL, alterations to the levels of HIF in the system and downstream effects mediated by HIF such as HIF mediated transcription using suitable reporter constructs or by monitoring for the upregulation of genes or alterations in the expression patterns of genes know to be regulated directly or indirectly by HIF.

Various methods for determining hydroxylation are known in the art and are described and exemplified herein. Any suitable method may be used for determining activity of the HIF hydroxylase such as by substrate or co-substrate utilization, product appearance such as peptide hydroxylation or down-stream effects mediated by hydroxylated or non-hydroxylated products.

Our finding that the Pro564 residue of HIF-1α is hydroxylated by a prolyl-hydroxylase provides the basis for assay methods designed to screen for inhibitors or promoters of this process. Any suitable method may be used to monitor for hydroxylation of HIF-1α or a HIF polypeptide or analogue thereof. Assays may be carried out to monitor directly for hydroxylation of the relevant proline residue or another position. Alternatively, assays may be carried out to monitor for depletion of co-factors and co-substrates. Alternatively, such assays may monitor the downstream effects of hydroxylation of HIF or indeed inhibition of hydroxylation of HIF, for example, by monitoring the interaction between HIF and VHL levels of HIF protein or HIF mediated transcription. Alternatively, reporter gene constructs driven by HIF regulated promoters may be used. Assays are also provided for the identification of enhancers of the activity of the HIF hydroxylase and in particular of the HIF prolyl hydroxylase activity of these enzymes. The assay may be used to identify an enhancer a human HIF hydroxylases and, in particular, of PHD 1, 2 or 3. Such enhancers may be used to reduce HIFα activity.

In one embodiment, to perform an assay for an inhibitor of VHL-mediated HIF-α destruction a suitable substrate of the HIF hydroxylase is provided. This may be HIF-α or a fragment thereof which includes a VHL binding portion and which included the Pro564 and/or Pro 402 residue is provided. The substrate may not be hydroxylated at the Pro564 and/or Pro 402 position. This may be achieved by providing synthetic polypeptide substrates, or by producing HIF-α polypeptides in bacterial cells, insect cells or mammalian cells or in in vitro transcription and translation systems. Alternatively, assays may be carried out over a selected time course such that the substrate is produced during the course of the assay, initially in un-hydroxylated form.

The substrate, enzyme and potential inhibitor compound may be incubated together under conditions which, in the absence of inhibitor provide for hydroxylation of Pro564 and/or Pro 402, and the effect of the inhibitor may be determined by determining hydroxylation of the substrate. This may be accomplished by any suitable means. Small polypeptide substrates may be recovered and subject to physical analysis, such as mass spectrometry or chromatography, or to functional analysis, such as the ability to bind to VHL (or displace a reporter molecule from VHL) and be targeted for destruction. Such methods are known as such in the art and may be practiced using routine skill and knowledge. Determination may be quantitative or qualitative. In both cases, but particularly in the latter, qualitative determination may be carried out in comparison to a suitable control, e.g. a substrate incubated without the potential inhibitor.

Inhibitor compounds which are identified in this manner may be recovered and formulated as described above for polypeptides of the invention.

Another assay of the invention is for a promoter of hydroxylation of HIF-α subunits. Typically, a HIF-α subunit or portion thereof is prepared as described above, and incubated under hypoxic conditions. By "hypoxic", it is meant less than 5%, preferably less than 3%, more preferably less than 1%, end preferably less than 0.5%, such as less than 0.1% $O_2$. The HIF-α subunit is incubated with a cell extract which includes the HIF hydroxylase as described above, optionally further in the presence of a source of ferrous (FeII) ions and/or ascorbate. A suitable concentration of ferrous ions is in the range of from 1 to 500 µM, such as from 25 to 250 µM and in particular from 50-200 µM. Ferrous ions may be supplied in the form of ferrous chloride, ferrous sulphate, and the like. Ascorbate may be provided in the form of a salt, such as sodium ascorbate, and in a concentration range of from 0.1 to 10 mM, such as from 1 to 5 mM. Another cofactor is α-ketoglutarate, which may also be supplied in the form of a salt at a range of from 0.1 to 5 mM, such as from 1 to 5 mM.

In this embodiment of the invention, the substrate will be incubated in the presence of a potential hydroxylation promoting agent, and the effect of the agent determined, by determining the hydroxylation of the Pro564 and/or Pro 402. As with the assay of the other aspect of the invention described above, determination may be quantitative or qualitative, and in either case determined relative to a suitable control.

The interaction between the polypeptides may be studied in vitro by labelling one with a detectable label and bringing it into contact with the other which has been immobilised on a solid support. Suitable detectable labels include $^{35}S$, which may be incorporated into recombinantly produced peptides and polypeptides. Recombinantly produced peptides and polypeptides may also be expressed as a fusion protein containing an epitope which can be labelled with an antibody.

Fusion proteins may, for example, incorporate six histidine residues at either the N-terminus or C-terminus of the recombinant protein. Such a histidine tag may be used for purification of the protein by using commercially available columns which contain a metal ion, either nickel or cobalt (Clontech, Palo Alto, Calif., USA). These tags also serve for detecting the protein using commercially available monoclonal antibodies directed against the six histidine residues (Clontech, Palo Alto, Calif., USA).

The protein which is immobilized on a solid support may be immobilized using an antibody against that protein bound to a solid support or via other technologies which are known per se. A preferred in vitro interaction may utilise a fusion protein including glutathione-S-transferase (GST). This may be immobilized on glutathione agarose beads. In an in vitro assay format of the type described above, a test compound can be assayed by determining its ability to diminish the amount of labelled peptide or polypeptide which binds to the immobilized GST-fusion polypeptide. This may be determined by fractionating the glutathione-agarose beads by SDS-polyacrylamide gel electrophoresis. Alternatively, the beads may be rinsed to remove unbound protein and the amount of protein which has bound can be determined for example, by counting the amount of label present in a suitable scintillation counter.

Thus, assays in accordance with the present invention may involve monitoring for the interaction between VEIL and HIF. The interaction between HIF and VHL is mediated by hydroxylation of HIF. The VHL-HIF interaction leads to ubiquitylation of HIF. Assays to monitor for test substances which interfere with the interaction between HIF and VHL, and in particular which interfere with hydroxylation of HIF may be monitored by any suitable method using HIF associated regulation. For example, in assay systems making use of recombinant HIF hydroxylase in accordance with the present invention, or in which HIF hydroxylase expression is upregulated within a cell, the effect of test substances can be monitored through monitoring the levels of HIF in the cell. Alternatively, transcription and expression of genes known to be upregulated or down regulated by the presence of HIF could be monitored. In particular, upregulation of HIF regulated genes would demonstrate inhibition of prolyl hydroxylation whereas down regulation would suggest enhancement or promotion of prolyl hydroxylation.

In alternative embodiments, reporter constructs may be provided in which promoters mediated by HIF are provided operably linked to a reporter gene. Any suitable reporter gene could be used, such as for example enzymes which may then be used in colorometric, fluorometric, fluorescence resonance or spectrometric assays.

HIF hydroxylase is a 2OG dependent oxygenase which catalyses the following reaction, in which R is HIFα and ROH singly is hydroxylated HIFα;

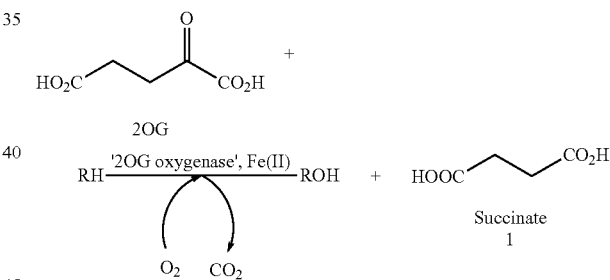

Typically, the hydroxylation is prolyl hydroxylation. The hydroxylase, may catalyse more than one hydroxylation of HIF-α.

In the assay methods described herein, typically the HIF hydroxylase and the substrate of the hydroxylase are contacted in the presence of a co-substrate, such as 2-oxoglutarate (2OG). The hydroxylase activity of the HIF hydroxylase may be determined by determining the turnover of the co-substrate. This may be achieved by determining the presence and/or amount of reaction products, such as hydroxylated substrate or succinic acid. The amount of product may be determined relative to the amount of substrate, Typically, in such embodiments the substrate may be an HIF-α polypeptide and, for example, the product measured may be hydroxylated HIF-α polypeptide.

HIFα prolyl hydroxylase activity may be determined by determining the turnover of said 2OG to succinate and $CO_2$, as described in Myllyharju J. et al EMBO J. 16 (6): 1173-1180 (1991) or as in Cunliffe C. J. et al Biochem. J. 240 617-619 (1986), or other suitable assays for $CO_2$, bicarbonate or succinate production. These methods may be used in the assays of the invention and in particular to assess the HIF-α prolyl hydroxylase activity of the HIF hydroxylase of the invention, including that of human HIF hydroxylases and in particular of PHD or EGLN polypeptides of the invention. Such assays can be modified to high throughput format and the invention encompasses such high throughput assays for hydroxylase activity.

Alternatively, the end-point determination may be based on conversion of HIFα or peptide fragments (including synthetic and recombinant peptides) derived from HIFα into detectable products. Peptides may be modified to facilitate the assays so that they can be rapidly carried out and may be suitable for high throughput screening.

For example, reverse phase HPLC (C-18 octadecylsilane column), as exemplified herein, may be used to separate starting synthetic peptide substrates for HIF hydroxylase from the hydroxylated products, as the latter have a shorter retention time in the column. Modifications of this assay or alternative assays for HIF hydroxylase activity may employ, for example, mass spectrometric, spectroscopic, and/or fluorescence techniques as are well known in the art (Masimirembwa C. et al Combinatorial Chemistry & High Throughput Screening (2001) 4 (3) 245-263, Owicki J. (2000) J. Biomol. Screen. 5 (5) 297-305, Gershkovich A et al (1996) J. Biochem. & Biophys. Meths. 33 (3) 135-162, Kraaft G. et al (1994) Meths. Enzymol. 241 70-86). Fluorescent techniques may employ versions of the substrate modified in such as way as to carry out or optimise spectroscopic or fluorescence assays.

For example, HIFα polypeptide may be immobilised e.g. on a bead or plate, and hydroxylation of the appropriate residue detected using an antibody or other binding molecule which binds the pVHL binding domain of HIFα with a different affinity when a proline residue such as proline 402 or praline 564 is hydroxylated from when the residue is not hydroxylated. Such antibodies may be obtained by means of standard techniques which are well known in the art, e.g. using a hydroxylated HIFα peptide.

Binding of a molecule which discriminates between the hydroxylated and non-hydroxylated form of a HIFα polypeptide may be assessed using any technique available to those skilled in the art, which may involve determination of the presence of a suitable label.

Assays may be used to screen for inhibitors of HIF hydroxylase and in particular for inhibitors of HIF prolyl hydroxylase (HPH) activity in a similar way to that described for the human prolyl hydroxylase involved in collagen biosynthesis (CPH) (Cunliffe et al. Biochemical J. 240 611-619 (1986); Cunliffe C J et al. Biochem. J. 239 311-315 (1986), Franklin T J and Hitchen M Biochem. J. 261: 127-130 (1989) Franklin T J. et al. Biochemical Society Transactions 19 (4): 812-815 (1991)).

HIF prolyl-hydroxylase activity of a HIF hydroxylase polypeptide may be determined by determining the hydroxylation of one or more proline residues of the substrate of the HIF hydroxylase used, which will typically be a HIFα polypeptide. Preferably, the hydroxylation of one or more praline residues within the pVHL binding domain of the HIF-α polypeptide, for example, proline 402 and/or praline 564. For convenience, these proline residues are referred to herein as Pro402 and Pro564 or position 402 and position 564. It will be understood that this terminology is also applied to polypeptides which contain far fewer than 564 residues, and to other HIF-α isoforms where the equivalent proline residue may occur at a slightly different position.

Assay methods of the present invention may also take the form of an in vivo assay. The in vivo assay may be performed in a cell line such as a yeast strain in which the relevant polypeptides or peptides are expressed from one or more vectors introduced into the cell.

C. elegans Assay Systems

Our finding that the HIF-VHL interaction is conserved in C. elegans provides a system to study the interaction in an in vivo environment, and its consequences.

Thus in a further aspect, the invention provides an assay for a modulator of HIF-VHL interaction, said method comprising:

providing a C. elegans which has wild-type HIF and VHL genes in normoxic or hypoxic conditions (wherein hypoxic conditions are as defined above);

exposing said C. elegans to a potential modulator of the HIF-VHL interaction; and determining the extent to which the modulator promotes or decreases the interaction between HIF and VHL in said C. elegans.

The determining may comprise immunoprecipitating one or other of the HIF and VHL components and then determining, e.g. by antibody detection, the amount of the other of the HIF and VHL component which is associated with the immunoprecipitated protein. Radiolabelling of one of the two proteins may allow determination of the amount of VHL or HIF captured. Alternatively, a reporter gene may be linked to a HIF-responsive promoter, and the amount of HIF in the subject C. elegans determined by measuring the activity of a reporter gene product, such as green fluorescent protein, luciferase, chloramphenicol acetyl transferase, beta-galactosidase, and the like.

In alternative aspects of the invention, the source of 2-oxoglutarate dependent dioxygenase and in particular the prolyl-hydroxylase of the invention is a HIF hydroxylase according to the invention. Such polypeptides may be introduced using recombinant systems so as to allow for the assay of inhibitory, augmenting, blocking or other modulating activities that show differential effects among the said HIF hydroxylase.

In Vivo Assays

The assays may be carried out using cell based, organ based or whole animal assays conducted in vivo. Such assays may utilize the endogenous expression of the HIF hydroxylase nucleotides and/or polypeptides. In other forms of the invention, upregulation of specific endogenous HIF hydroxylases may be achieved by stimulators of the expression thereof. Such stimulators may be growth factor such as platelet derived growth factor or angiotensin II, or chemicals such as phorbol esters that are known to upregulate specific HIF hydroxylases. In another form of the invention, nucleotide constructs may be introduced into cells or transgenic animals to increase production of one or more specific HIF hydroxylases. Alternatively nucleotide constructs may be introduced into cells so as reduce or abrogate expression of one or more specific HIF hydroxylases. Appropriate methods that include but are not limited to homologous recombination, antisense expression, ribozyme expression and RNA interference are outlined herein and known by those skilled in the art.

Tissue culture cells, organs, animals and other biological systems, obtained by the aforementioned forms of the invention, may be used to provide a further source of a HIF hydroxylase, or may be used for the assay, or especially comparative assay, of the activity of test substances may inhibit, augment, block or otherwise modulate the activity of specific HIF hydroxylases.

The activity of the HIF hydroxylases may be assayed by any of the aforementioned methods or by cell, tissue, or other assays conducted in vivo that measure the effects of altered activity of the HIF hydroxylases. A preferred form of these assays measures the level of a HIF-α polypeptide or the level of activity of a HIF-α polypeptide that is a substrate for the PHD polypeptide.

The level of a HIF-α peptide may measured by such methods as immunoblotting, immunoprecipitation, or other immunological methods using specific antibodies and methods that are known to those skilled in the art. The amounts and the activity of HIF-α peptides can be related to each other but are not necessarily related to each other. Therefore in a further form of the invention, the activity of a HIF-α peptide that is a target for a HIF hydroxylase is assayed by measurement of transcriptional activity or another property of the said HIF-α polypeptide.

HIF-α polypeptides are known to form complexes with other molecules that include other HIF subunits and co-activator molecules such p300. In this form HIF complexes activate hypoxia response elements that are found in the promoters and/or enhancers of endogenous genes that are regulated by the said HIF complexes. Such hypoxia response elements may also be isolated and operationally linked to reporter genes so as to assay the activity of the HIF complex through detection and/or quantitation of the reporter gene or its product. Therefore in a further form of the invention the activity of a HIF-α polypeptide that is regulated by its cognate HIF hydroxylase will be assayed by measuring the effects of the HIF complex on the expression of an endogenous gene or reporter gene that is functionally linked to a HIF binding hypoxia response element. Examples of endogenous genes that are regulated in this way are to be found in the role of the aryl hydrocarbon nuclear translocator (ARNT) in hypoxic induction of gene expression, see for example, Studies in ARNT-deficient cells. S. M. Wood, J. M. Gleadle, C. W. Pugh, O. Hankinson, P. J. Ratcliffe. Journal of Biological Chemistry 271 (1996) 15117-15123, and Hypoxia inducible expression of tumor-associated carbonic anyhydrases, C. C. Wykoff, N. J. P. Beasley, K. J. Turner, J. Pastorek, A. Sibtain. G. D. Wilson, H. Turley, K. Talks, P. H. Maxwell, C. W. Pugh, P. J. Ratcliffe, A. L. Harris. Cancer Research 60 (2000) 7075-7083. Examples include but are not limited to glucose transporter isoform 1, phosphoglycerate kinase-1, carbon anhydrase isoform 9, vascular endothelial growth factor. Each of said genes contains one or hypoxia response elements that may be isolated and operationally linked as single or multiple copies to a reporter gene for the measurement of activity of a HIF-α polypeptide that varies in accordance with the activity of a HIF hydroxylase.

The activity of genes or gene products that are regulated by a HIF-α polypeptide in accordance with the activity of a HIF hydroxylase affects cellular, organ, and animal physiology in a manner that provide further aspects of the invention. Thus a further embodiment of the invention provides for assays that utilise a specific functional response that is regulated in accordance with the activity of a HIF-α polypeptide in accordance with the activity of a HIF hydroxylase. Such responses include the uptake rate of glucose or glucose analogues that are not metabolized, the ingrowth of blood vessels by angiogenesis, the activity of a carbonic anhydrase enzyme. It is recognised that many other responses that operate at a cellular or systemic level are controlled by the activity of a HIF-α polypeptide in accordance with the activity of a HIF hydroxylase and may be utilized as assays of the said HIF hydroxylase activity in further aspects of the invention.

A HIF-α polypeptide that is a substrate for a HIF hydroxylase may be fused to a further polypeptide so as to cause the activity of the said HIF hydroxylase to regulate the activity of the fusion peptide. Accordingly a further form of the invention provides for the assay of the activity of a fusion polypeptide. In the preferred form such a fusion polypeptide may contain the whole of part of a HIF-α polypeptide, for example human HIF-1α residues 344-698, 344-417, 554-698, 652-826, or 775-826 linked to a heterologous transcription factor and expressed together with its cognate DNA response element. The Gal4 DNA binding domain including the amino acids 1-143 together with the Gal binding upstream activating sequence (UAS) is an example of such a transcription factor and cognate DNA response element whose operation can be assayed by those skilled in the art.

In a preferred embodiment, the assays discussed herein relate to, or utilise, human HIF hydroxylases and in particular PHD 1, 2 or 3. These may also be referred to as EGLN polypeptides.

Test Compounds

Compounds which may be screened using the assay methods described herein may be natural or synthetic chemical compounds used in drug screening programmes. Extracts of plants, microbes or other organisms, which contain several characterised or uncharacterised components may also be used.

Combinatorial library technology (including solid phase synthesis and parallel synthesis methodologies) provides an efficient way of testing a potentially vast number of different substances for ability to modulate an interaction. Such libraries and their use are known in the art, for all manner of natural products, small molecules and peptides, among others. The use of peptide libraries may be preferred in certain circumstances.

Potential inhibitor compounds may be polypeptides, small molecules such as molecules from commercially available combinatorial libraries, or the like. Small molecule compounds which may be used include 2-oxoglutarate analogues, or HIF-α analogues, or those that incorporate features of both 2-oxoglutarate and affect HIF-α, which inhibit the action of the enzyme. We have found in particular that compounds dimethyl-oxalylglycine, N-oxalylglycine and N-oxalyl-2S-alanine and certain thiols all act as inhibitors of the HIF-α hydroxylase. N-oxalyl-2R-alanine, an enantiomer of N-oxalyl-2S-alanine, is also an inhibitor of HIF hydroxylase and may be used in the invention. Thus the invention provides the use of a compound which acts as a hydroxylase inhibitor, and in particular prolyl hydroxylase inhibitor for the manufacture of a medicament for the treatment of a condition in a patient which requires the promotion of cell growth, such as angiogenesis. The invention also provides a method of treatment of a patient suffering from a condition which is treatable by promoting cell growth, which comprises administering to said patient an effective amount of a HIF hydroxylase inhibitor. Such inhibitors include dimethyl-oxalylglycine, N-oxalylglycine and N-oxalyl-2S-alanine, and salts thereof. More generally, such inhibitors include other N-oxalyl-amino acid compounds and salts thereof, wherein the amino acids are either naturally occurring amino acids or synthetic amino acids with a side chain which provides for the compound to act as an inhibitor. Such side chains include hydrocarbyl side chains containing a carbon chain which may be straight or branched, optionally including one or two heteroatoms such as N, O or S, and optionally substituted by a group such as halogen (particularly fluoro, chloro, bromo or iodo), thiol, hydroxy, methoxy, amino, mono- or di-Cl-3 alkyl amino or nitro. Salts include pharmaceutically acceptable salts such as sodium, potassium, magnesium and the like.

Potential promoting agents may be screened from a wide variety of sources, particularly from libraries of small compounds which are commercially available. Oxygen-containing compounds may be included in candidate compounds to be screened, for example 2-oxoglutarate analogues.

CPH Inhibitors

Inhibitors of the 2-OG dependent enzyme collagen prolyl hydroxylase (CPH) are well known in the art and have been previously proposed for use in the treatment of lung fibrosis, skin fibrosis (scleroderma), atherosclerosis and other conditions associated with collagen biosynthesis. Inhibitors of parahydroxyphenylpyruvate oxygenase (a non-haem oxygenase employing ferrous iron as a co-factor) such as triketones are used as herbicides (Lee D. et al (1998) Pestic. Sci. 54(4) 377-384).

The present inventors have now found that certain of these CPH inhibitors also inhibit the biological activity of HIF hydroxylases and in particular the ability of the HIF hydroxylase to catalyse prolyl hydroxylation of HIF (HPH activity).

Another aspect of the present invention therefore provides the use of a CPH inhibitor or modified CPH inhibitor which inhibits the biological activity of a HIF hydroxylase, and in particular its HPH activity, in the manufacture of a medicament for use in the treatment of a condition associated with reduced or suboptimal HIF levels or activity, for example ischaemia, wound healing, auto-, allo-, and xeno-transplantation, systemic high blood pressure, cancer, and inflammatory disorders. In one embodiment a CPH inhibitor which inhibits the biological activity of a human HIF hydroxylase such as a PHD polypeptide (EGLN polypeptide) may be used.

CPH inhibitors which inhibit HIF hydroxylases, and in particular the prolyl hydroxylase activity (HPH activity) of a HIF hydroxylase, may be modified to generate selective inhibitors of HIF hydroxylases and in particular of HPH activity. Further, the discovery allows for the development of collagen prolyl hydroxylase inhibitors that do not inhibit HIF hydroxylases, and in particular HPH, by the use of comparative screening assays.

Another aspect of the present invention therefore provides the use of a modulator of a HIF hydroxylase in the manufacture of a medicament for the treatment of a condition associated with reduced HIF levels or activity as described above and below.

Such an modulator may be a selective inhibitor. A selective inhibitor is an inhibitor which shows a greater level of inhibition of a HIF hydroxylase than on other enzymes including collagen proly hydroxylase. In particular, a selective inhibitor is one which inhibits HPH activity relative to CPH activity as described above.

HPH Modulators

Various methods and uses of modulators which inhibit, potentiate, increase or stimulate hydroxylation of HIF-α by HIF hydroxylase are provided as further aspects of the present invention.

The purpose of disruption, interference with or modulation of the hydroxylation of HIF-1α by a HIF hydroxylase may be to modulate cellular functions such as angiogenesis, erythropoiesis, energy metabolism, inflammation, matrix metabolism vasomotor function, and apoptotic/proliferative responses and pathophysiological responses to ischaemia/hypoxia, all of which are mediated by HIFα, as discussed above and further below.

A test compound which increases, potentiates, stimulates, disrupts, reduces, interferes with or wholly or partially abolishes hydroxylation of HIF-α polypeptide and which may thereby modulate HIF hydroxylation activity, may be identified and/or obtained using the assay methods described herein.

Agents which increase or potentiate hydroxylation, and in particular prolyl hydroxylation of HIF, may be identified and/or obtained under conditions which, in the absence of a positively-testing agent, limit or prevent hydroxylation. Such agents may be used to potentiate, increase, enhance or stimulate the function of a HIF hydroxylase, and may have an effect on cells under hypoxic conditions such as those found in tumours, in which the lack of hydroxylation leads to the accumulation of HIFα and the concomitant promotion of angiogenesis and other growth promoting events.

The term 'agent' includes a compound having one of the formulae I to XXVIII as described herein in particular a compound shown in Table 3.

Methods of determining the presence of, and optionally quantifying the amount of HIF hydroxylase in a test sample may have a diagnostic or prognostic purpose, e.g. in the diagnosis or prognosis of any medical condition discussed herein (e.g. a proliferative disorder such as cancer) or in the evaluation of a therapy to treat such a condition.

In various aspects, the present invention provides an agent or compound identified by a screening method of the invention to be a modulator of HIFα hydroxylation e.g. a substance which inhibits or reduces, increases or potentiates the hydroxylase activity of a HIF hydroxylase.

Following identification of a modulator, the substance may be purified and/or investigated further (e.g. modified) and/or manufactured. A modulator may be used to obtain peptidyl or non-peptidyl mimetics, e.g. by methods well known to those skilled in the art and discussed herein. A modulator may be modified, for example to increase selectively, as described herein. It may be used in a therapeutic context as discussed below.

Agents according to the present invention, which are useful in modulating the hydroxylation of HIF-α and therefore the modulation of HIF's intracellular levels and hence one or more of its cellular functions, may modulate the hydroxylase activity of the HIF hydroxylase. Such agents may specifically inhibit the ability of the HIF hydroxylase, and in particular of a PHD polypeptide, to hydroxylase the appropriate residue of HIF-α. Assays and screens for such agents are provided as described above in accordance with the present invention, along with the agents themselves and their use in modulating the hydroxylation and thereby the function of HIF-α.

An agent able to inhibit hydroxylation of HIF-α by a HIF hydroxylase may include a substance able to affect the catalytic properties of the enzymatically active site of the hydroxylase. An inhibitor of hydroxylation may interact with the HIF hydroxylase within the active prolyl hydroxylase domain, for example within the HXD[X]$_n$H or jelly roll motifs described herein or in the HXE[X]$_n$ H motifs. Residues within this domain are involved in interaction with HIF-α and catalysis of the hydroxylation. An inhibitor may, for example, interact with His358 or ARG 557 of the EGLN2/PHD1 sequence using the EGL9 numbering system or the equivalent residue of other HIF hydroxylases, or may interact with residues in the region between residues 369 and 389 or other residues of the jelly roll motif of the PHD1 sequence or the equivalent residues of other HIF hydroxylases. Residues outside of the domain may also be involved in interacting with HIF-α and agents which interfere with such interaction may also affect the hydroxylation as discussed elsewhere herein. Alternatively or additionally, the inhibitor may bind in such a way as to inhibit dioxygen binding. For example, it is appreciated that dioxygen may approach the iron in the HIF hydroxylase from a different direction to the HIF-α substrate and in particular through a tunnel through the centre of the jelly roll motif. Inhibitors may bind to residues within or at the entrance to this tunnel.

Further aspects of the present invention relate to methods for modulating the amount of HIF polypeptide in a cell. Such a method may comprise contacting the cell with a substance which inhibits the hydroxylase activity of a HIF hydroxylase and in particular its prolyl hydroxylase activity.

A suitable substance is an agent as described herein. A substance which is a selective HIF hydroxylase inhibitor may be used in such a method. A selective HIF hydroxylase inhibitor is an inhibitor which inhibits the biological activity of a HIF hydroxylase but does not inhibit biological activity of a collagen prolyl hydroxylase, as described herein and in particular one which inhibits HPH activity of a HIF hydroxylase but not CPH activity of a collagen prolyl hydroxylase.

Examples of HPH Modulators

Compounds which modulate 2OG oxygenases, in particular collagen 4-prolyl hydroxylase, may be useful as modulators of HIF prolyl hydroxylase, or may be used as 'lead' compounds which may be modified and/or optimised to develop modulators of HIF prolyl hydroxylase, in particular selective modulators.

Some of these compounds generally possess the formula:

(A)

where the group $R^1$ is capable of forming an electrostatic interaction with the side chain of the arginine which together with other residues binds the 5-carboxylate of 2-oxoglutarate during catalysis, A*B is a chain of two atoms which are, independently, carbon, oxygen, nitrogen or sulphur, which chain can be functionalised, y is 0 or 1 and C*D is a chain of two atoms which are, independently, carbon, oxygen, nitrogen, or sulphur, which chain can be functionalised, A, B, C and D being linked to one another by single and/or double and/or triple bonds, such that when y is 0 or 1 at least one of the atoms of which is capable of chelating with a metal group and when y is 1 said chain is attached to $R^2$ which is capable of chelating with a metal group. Generally at least one of A, B, C and D is not carbon. Typical chains include C—N—C—C, C—C—C=O and C—O—C—C. The chain atoms can form part of a ring, such as pyrolidine and tetrahydro-pyran, and unsaturated derivatives thereof including pyridine and pyran or partially hydrogenated pyrans. The rings can be fused. When y=0 C and/or D is attached to, for example, =S, =O, —SH or —OH. Typically R' is an acid group such as carboxylate, —SO$_3$H, —B(OH)$_2$ or —PO$_3$H$_2$. Typical values for $R^2$ include —SH, —OH, —CO$_2$H, —SO$_3$H, —B(OH)$_2$ or —PO$_3$H$_2$, —NHOH, —CONHR$^3$, CONHOR$^3$, —CONR$^3$OH and —CONR$^3$OR$^3$ where $R^3$ is a branched or straight chain alkyl group of 1 to 6 carbon atoms which can be functionalised. Preferred compounds will have typical values for more than one group, for example for all groups.

One class of compounds which have been found to modulate the activity of HIFα hydroxylases and in particular their prolyl hydroxylase activity are oxalo-amino acid derivatives, including oxalo derivatives having one of the following general formulae (I to IV), for example compounds having the formula V, VI or VII;

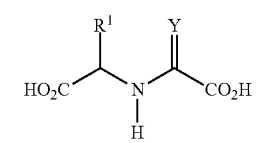

N-oxalo inhibitors for in vitro use

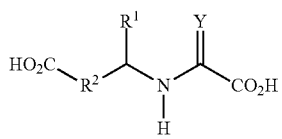

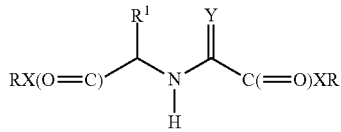

N-oxalo inhibitors for in vivo use

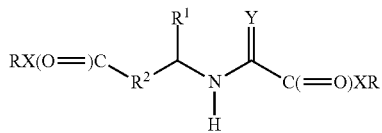

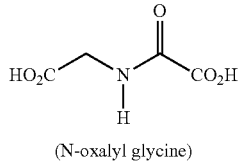

(N-oxalyl glycine)

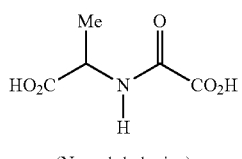

(N-oxalyl alanine)

such as oxalyl-L-alanine (IS70) as well as oxalyl-D-alanine (IS71)

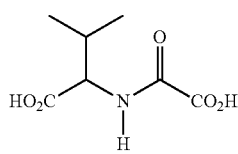

(N-oxalyl valine)

where $R^1$ and R may independently be H, a branched or straight $C_1$ to $C_6$ alkyl chain, especially methyl, which can be functionalised, e.g. as —C$_2$H$_4$CO$_2$C$_2$H$_5$, any natural amino acid side chain such as alanine, valine and glutamic acid, a 4 to 7 membered heterocyclic ring optionally containing 1 or 2 N, S, O or P atoms or a 5 or 6 membered aromatic ring, optionally containing 1 or 2 N, O or S atoms, such as phenyl or naphthyl which may be fused to another ring or a said alkyl chain substituted by a said aromatic ring;

$R^2$ is C1 to C6 alkyl chain which may be functionalised such that $R^2$ is $(CR^1R^1)_n$ where n=1 to 6 and where the R' groups may be the same or different and are as defined above or $R^2$ is absent;

X is NH, NR", where R" is OH, a branched or straight $C_1$ to $C_6$ alkyl chain which can be functionalised, or O i.e. XR is O-alkyl having a branched or straight $C_1$ to $C_6$ alkyl chain, especially MeO, which can be functionalised; and, Y is O or S.

The said alkyl groups and chains are typically functionalised by fluorine, alcohol, thiol, a carboxylic acid, phosphonic or phosphinic acid, sulphonic acid or other chelating group, in the case of the chains typically via an alkyl group.

Formula I is further exemplified by compound IS3 and oxalylglycine (IS2), Formula II is by oxaloylamino-L-alanine, and Formula III by compounds IS1 and dimethyloxaloylglycine (MMOG) in Table 3 as well as the methyl esters of methyloxalyl-L-alanine (IS80) and methyloxalyl-D-alanine (IS81), methyloxalyl-L-alanine (IS68) and methoxalyl-D-alanine (IS69), diethyl N-methoxyoxalyl-L-glutamate (IS12), -oxalyl-L-glutamate (IS13), oxalyl S-alanine (IS70) and oxalyl R-alanine (IS71).

These compounds may obtained by synthesis as described in Cunliffe et al (1992) J. Med. Chem. 35 2652-2658.

The present inventors have found that N-oxalo derivatives of amino acids, which are known to inhibit collagen prolyl-hydroxylase (CPH), inhibit the modification of HIF-α by HIF hydroxylase and in particular by inhibiting their prolyl hydroxylase activity (HPH). This leads to reduced pVHL binding and increased cellular HIF levels.

N-oxaloglycine has been found to be an inhibitor of both CPH and HPH. However, (RS)-N-oxaloalanine is a poor inhibitor of CPH compared to N-oxaloglycine and (S) oxaloalanine is a preferred inhibitor of HIF hydroxylase, and in particular of HPH activity, as described below. (S)-oxalovaline has little or no activity as an HPH inhibitor.

Selectivity for particular HIF hydroxylase may be increased or enhanced by modification of the oxaloglycine backbone. N-Oxalo amino acid derivatives may be converted into methyl or ethyl ester form for use as a 'pro drug' as described in E. Baeder et al. (1994) Biochem. J. 300.525-530 and exemplified in Table 2.

Another class of compounds of interest for use in the modulation of HIF hydroxylases, and in particular of HPH activity, are hydroxamic acid derivatives of the general formulae (VIII-XII):

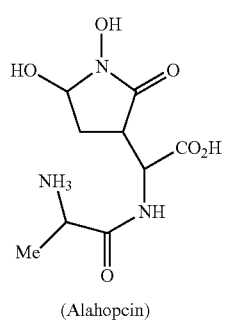

(Alahopcin)

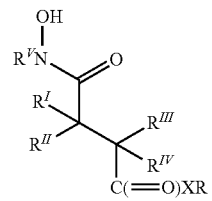

IX

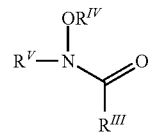

X

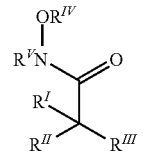

XI

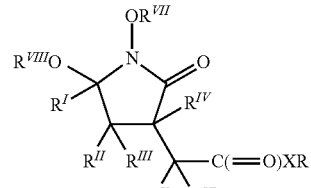

XII

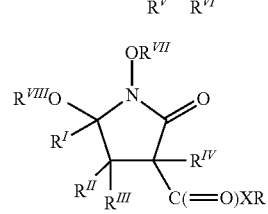

XIII

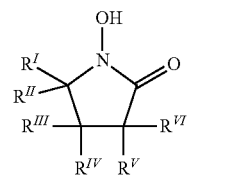

XIIIA where $R^I$ to $R^{VIII}$ may independently be H, OH, a branched or straight $C_1$ to $C_6$ alkyl chain, optionally with 1, 2, 3, 4 or 5 halo substitutions, which can be functionalised, a 4 to 7 membered heterocyclic ring optionally containing 1 or 2 N, S, O or P atoms, or a 5 or 6 membered aromatic ring, optionally containing 1 or 2 N, O or S atoms which may be fused to another ring or a said alkyl chain substituted by a said aromatic ring such that $R^{III}$ can also be $NH_2$ or a salt thereof such as HCl, or $NHR^{IX}$ where $R^{IX}$ is acyl, such as unsubstituted or substituted alkanoyl such as acetyl or phenoxyacetyl; and, XR is OH, $NH_2$ or $NHR^X$, where $R^X$ is OH, a branched or straight $C_1$ to $C_6$ alkyl chain, or O-alkyl having a branched or straight $C_1$ to $C_6$ alkyl chain.

Preferred compounds are those where R is methyl or benzyl and/or $R^{II}$ is hydrogen and/or $R^{III}$ is $NH_2$ or $NHCOCH_2O_6H_5$ Hydroxamic acids may be obtained as described in Walter M. W. et al (1999) Bioorg. Chem. 27 (1): 35-40.

Hydroxamic acids, including cyclic and natural products such as alahopcin (Higashide E, et al (1995) J. Antibiotics 38: 285-295), are known to be inhibitors of CPH and are therefore of interest for the inhibition of HIF hydroxylases and in particular of HPH. Modulators based on these compounds, which are specific for HPH, may be developed using the methods described within.

Compounds of formula X are exemplified by benzohydroxamic acid and compounds of formula XI, which are a sub-class of formula X, are exemplified by compounds NK45, NK46, NK47 and NK84 in Table 3.

Another class of compounds of interest for use in the modulation of HIF hydroxylases, and in particular of HPH activity, are hydroxylated aromatic compounds including catechols, phenanthrolines and hydroxanthroquinones, including hydroxyanthroquinones of the formulae;

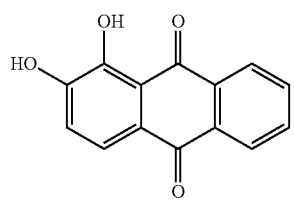

XIV

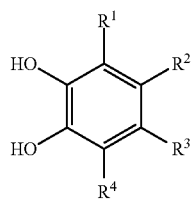

XV

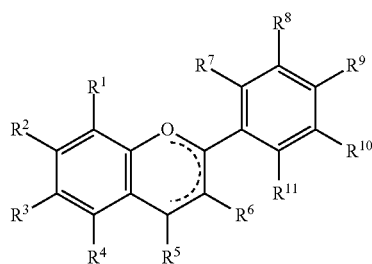

XVA where $R^1$ to $R^{11}$ may independently be H, a branched or straight $C_1$ to $C_6$ alkyl chain, OH, O-alkyl having a branched or straight $C_1$ to $C_6$ alkyl chain optionally containing 1 or 2 N, O or S atoms, COOH, a branched or straight $C_1$ to $C_6$ alkyl ester (alkoxycarbonyl), a 4 to 7 membered heterocyclic ring optionally containing 1 or 2 N, S, O or P atoms or a 5 or 6 membered aromatic ring, optionally containing 1 or more N, O or S atoms, which can be fused to another ring, or a said alkyl chain substituted by a said aromatic ring, and

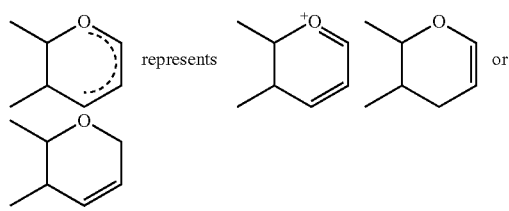 represents 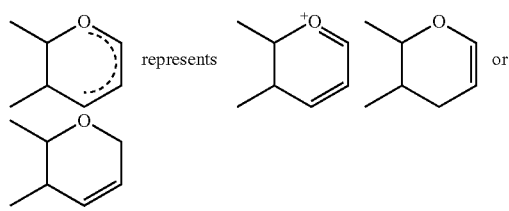 or 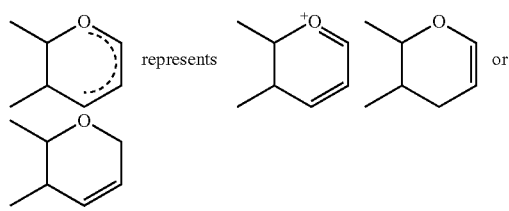

Dihydroxybenzoate (EDB), as shown in Table 3, and 3,4-dihydroxybenzoic acid (protocatechuic acid) are examples of a compound of formula XV.

These compounds of formula XIV are known CPH inhibitors (Franklin et al (2001) Biochem. J. 353: 333-338, Cunliffe et al Biochem J. (1986) 239(2) 311-315, Franklin et al (1989) Biochem, J. 261 (1) 127-130). Modulators based on these compounds which are specific for HPH may be developed using the methods described within. Specific compounds of formula XVA include:

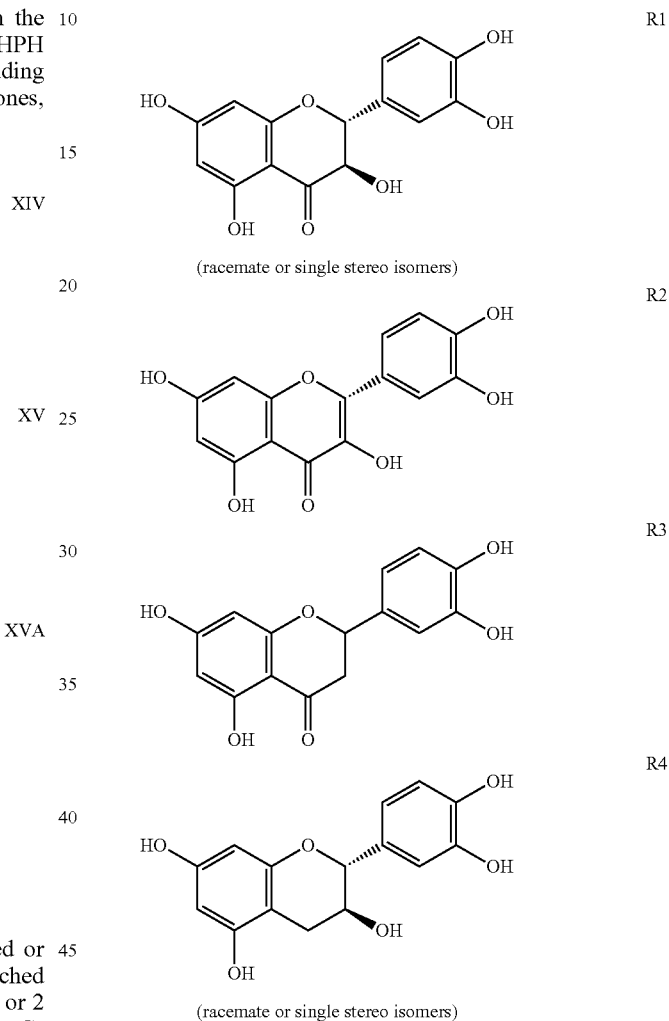

(racemate or single stereo isomers)

Thus typically $R^1$, $R^3$, $R^7$, $R^8$ and $R^{11}$ are hydrogen and $R^2$, $R^4$, $R^9$ and $R^{10}$ are OH. Another class of compounds of interest for use in the modulation of HIF hydroxylases, and in particular of HPH activity are N-containing heterocyclic compounds which have one of the following general formulae:

XVI: 3-hydroxyquinolone-2-carboximide Derivatives

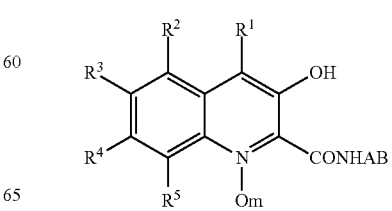

where $R^1$ to $R^5$ may be H, a branched or straight $C_1$ to $C_6$ alkyl chain such as Me, a 4 to 7 membered heterocyclic ring optionally containing 1 or more N, S, O or P atoms, or a 5 or 6 membered aromatic ring, optionally containing 1 or more N, O or S atoms, which can be fused to another ring, or a said alkyl chain substituted by a said aromatic group, A=substituted alkylene, B=$CO_2H$, $NHSO_2CF_3$, tetrazolyl, imidazolyl or 3-hydroxyisoxazolyl, and m is 0 or 1.

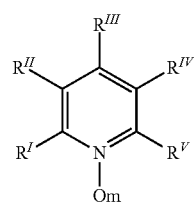

XVII pyridine and pyridine N-oxide derivatives

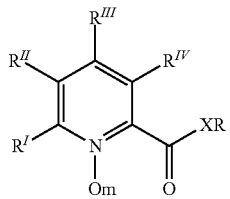

XVIII where $R^I$ to $R^{IV}$ may independently be H, a branched or straight chain alkyl of from 1 to 6 C atoms, a halogen group (i.e. fluoro-, chloro-, bromo- or iodo-), a carboxylate group, a 4 to 7 membered heterocyclic ring optionally containing 1 or more N, S, O or P atoms, a 5 or 6 membered aromatic ring, optionally containing 1 or more N, O or S atoms which can be fused to another ring or a said alkyl chain substituted by a said aromatic ring, or a C(=O)XR group as defined below, X is O, NH, NR, where R is H, OH, a branched or straight chain alkyl of from 1 to 6 C atoms which can be functionalised, alkoxy containing a branched or straight chain alkyl of from 1 to 6 C atoms which can be functionalised, a 4 to 7 membered heterocyclic ring optionally containing 1 or 2 N, S, O or P atoms, a 5 or 6 membered aromatic ring, optionally containing 1 or 2 N, O or S atoms which can be fused to another ring, such that RX is typically straight or branched $C_1$ to $C_6$ alkoxy, and m is 0 or 1.

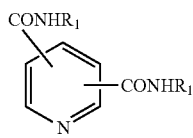

XIX where $R^1$ is as defined in EP0114031: i.e. $C_1$ to $C_4$ alkyl chain, such as $C_2H_4$, which may be substituted with an alkoxy group with a $C_1$ to $C_4$ alkyl chain such as methyl and the $CONHR_1$ groups are typically in the 2 and 4 positions. Thus R' is typically methoxyethyl.

Compounds of formula XVII and XVIII are exemplified by 2,5-(C8), 2,4-(C9), 2,3-(C10) and 3,4-(C11)-pyridine dicarboxylic acids, and compounds of the formula XIX are exemplified by the compounds IS4, IS5, IS6, IS7, IS8 and IS9 in Table 3.

Another suitable N containing heterocycle may have the formula;

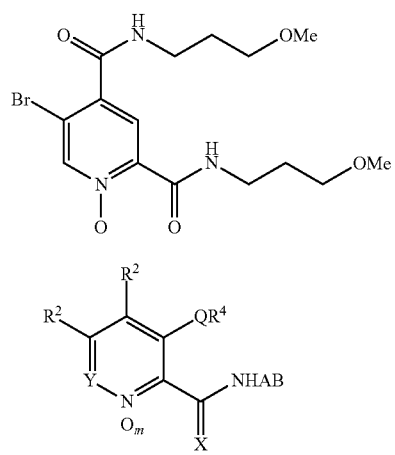

XX

XXI

Pyridylcarbonyl glycines and derivatives where X=O, Y=N or $CR_3$, m=0 or 1, A=substituted alkylene, B=$CO_2H$, $NHSO_2CF_3$, tetrazolyl, imidazolyl or 3-hydroxyisoxazolyl, R1, R2 and R3 may independently be H, OH, halo, cyano, $CF_3$, $NO_2$, $CO_2H$, alkyl, cycloalkyl, cycloalkoxy, aryl, aralkynyl, alkynylcarbonyl, alkylcarbonyloxy, carbamoyl, alkynyloxyalkyl, alkenyloxy, alkoxyalkoxy, alkynyl, retinyloxycarbonyl, alkenyloxycarbonyloxy, where $R^1$ and $R^2$ or $R^2$ and $R^3$=$(CH_2)_o$ in which 1-2 $CH_2$ groups of the saturated or C:C unsaturated chain may be replaced by O, S, SO, $SO_2$ or imino, o=3-5, R4=H.

XXII: 3-alkoxypridine-2-carboxamide derivatives

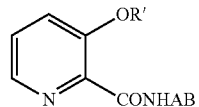

where A, B and $R^4$ as defined in WO97/41103: A=(substituted alkylene), B=(modified) carboxy, tetrazolyl, imidazolyl, 3-hydroxyisoxazolyl, R4=H, OH, halo, cyano, $CF_3$, $NO_2$, $CO_2H$, alkyl (e.g. branched or straight chain C1-C6 alkyl), cycloalkyl, cycloalkylalkyl, cycloalkylalkoxy, cycloalkoxyalkyl, aryl, aralkyl, aralkoxy, hydroxyalkyl, alkenyl, alkynyl, alkynyloxyalkyl, alkoxycarbonyl, alkylcarbonyloxy, arylcarbonyloxy, cinnamoyl, alkenylcarbonyl, arylcarbamoyl or aralkoxycarbonyloxy.

Various-containing heterocycles and derivatives are known to be inhibitors of CPH. Their mechanism of action is believed to be via bidentate chelation of the aromatic nitrogen (or its N-oxide) and a carbonyl group located at the 2-position on the heterocyclic ring. Suitable compounds are described in Bickel et al Hepatology 28(2) 404-411, DE-A-1974628, EP-A-0846685, WO-A-9741103, EP07865871, DE-A-19504226, EP-A-0673932, EP-A-0673931 and EP-A-0673930.

Analogues of these compounds, appropriately derivatised for pharmaceutical use, may be made selective for HIF hydroxylases, and in particular for HPH activity, using the methods described herein.

2,4-diethylpyridine dicarboxylate is a known CPH inhibitor (Friedman L. et al (2000) PNAS 97 (9) 4736-4741) which was found not to inhibit HPH. This provides indication that selective HIF hydroxylase inhibitors, and in particular selective HPH inhibitors, are possible.

Another class of compounds of interest for use in the modulation of HIF hydroxylases, and in particular of HPH activity, have the general formulae (XXV-XXVIII, XXVIIIA and XXVIIIB):

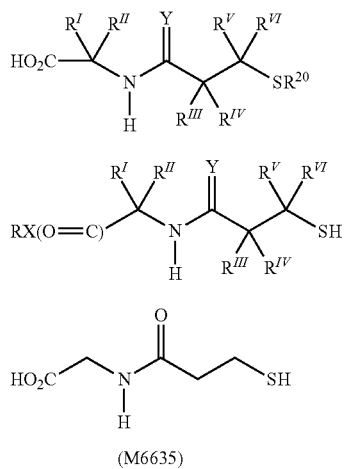

XXV

XXVI

XXVII (M6635)

where R, $R^I$ to $R^{VI}$ may independently be H, a branched or straight $C_1$ to $C_6$ alkyl chain, a 4 to 7 membered heterocyclic ring optionally containing 1 or 2 N, S, O or P atoms, a 5 or 6 membered aromatic ring, optionally containing 1 or 2 N, O or S atoms, which can be fused to another ring, or a said alkyl chain substituted by a said aromatic ring, preferably H or methyl, $R^{20}$ is hydrogen or acyl typically aromatic acyl such as benzoyl.

X is NH, NR", where R" is OH, Me, alkyl, OMe, Oalkyl with a $C_1$ to $C_6$ alkyl chain, and
Y is O or S.

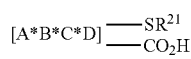 XXVIII such as

XXVIIIA:

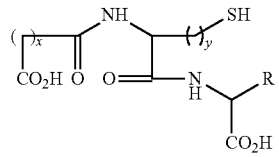

where A*B*C*D* are as defined for formula (A), $R^{21}$ is hydrogen or acyl, typically aromatic acyl such as benzoyl, R is as defined for formula III, n is from 1 to 5, x is from 1 to 5 and y is from 1 to 5, such that the resulting methylene chains can be functionalised by one or more groups as defined for R or by $NH_2$, such as glutathione (gamma-glutamyl-cysteinyl-glycine) (C16) and cysteinyl glycine (CO166).

These compounds may be obtained from commercial sources (for example, Sigma Chemical Co.) or prepared using standard methodology.

N-(Mercaptopropionyl)glycine and glutathione have been found to be inhibitors of HPH. This provides indication that appropriately functionalised thiols may be inhibitors of 2OG dependent oxygenases. N-(Mercaptopropionyl)glycine was not an inhibitor of clavaminate synthase from *Streptomyces clavligerus* under standard assay conditions, demonstrating that this family of compounds can be selective for different 2OG oxygenases. Modification of N-(mercaptopropionyl)glycine may improve selectivity for HPH. These compounds may be made into useful pharmaceutical agents by conversion into their ester 'pro drug' forms. These are commonly methyl or ethyl esters although others are possible.

N-(Mercaptopropionyl)glycine and glutathione are structurally related to L-δ(α-aminoadipoyl)-L-cysteinyl-D-valine (ACV) which is the substrate of isoepenicillin-N-synthase (IPNS). IPNS is an oxidase which is closely related to the 2OG dependent oxygenases by sequence and structure, although it does not use a 2OG co-substrate. Glutathione is important in maintaining the correct redox potential inside cells and the observation that it is an inhibitor of HPH may have physiological relevance.

Compounds of Formula XXVIII include N-(3-mercaptopropanoyl)-L-alanine (IS37) and the corresponding D isomer (IS38) as well as N-(3-benzoylthiopropionoyl)-L-alanine (IS20) and the corresponding D isomer (IS21). Other compounds include:

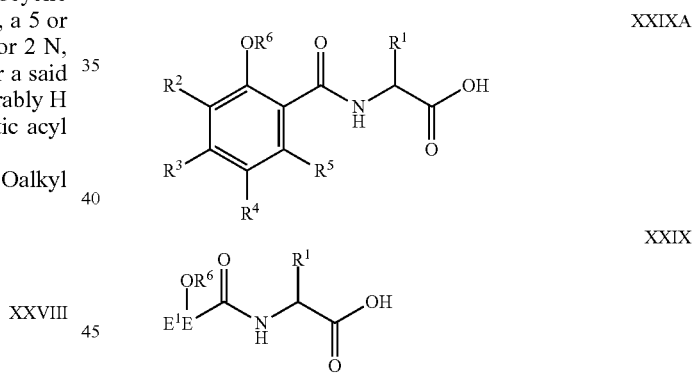

XXIXA

XXIX where $R^1$ is H, a branched or straight $C_1$ to $C_6$ alkyl chain which can be functionalised, any natural amino acid side chain for example of glutamic acid, a 4 to 7 membered heterocyclic ring optionally containing 1 or 2 N, S, O or P atoms or a 5 or 6 membered aromatic ring, optionally containing 1 or 2 N, O or S atoms which may be fused to another ring or a said alkyl chain substituted by a said aromatic ring and each of $R^2$ to $R^6$, which may be the same or different, is as defined for $R^1$ or is $NH_2$ or $OR^7$ where $R^7$ is as defined for R' and E represents a monocyclic ring system such as thiophene or pyran and E' is absent or forms with E a bicyclic ring system such as naphthalene or indole, E' typically being benzene. The ring or rings can be functionalised at any of their carbon atoms with a group as defined for R'. Typical compounds include 2-hydroxy-hippuric acid, N(2-hydroxy-benzoyl)-glycine (C14) and N-benzoyl-glutamic acid (C15).

Where appropriate the acids can be in the form of salts, eg. sodium salts.

Peptide fragments derived from the sequence of a HIF hydroxylase or an HIF-α polypeptide form another class of compounds which may have modulating activity. Nucleic acid encoding such peptides, vectors and host cells containing such nucleic acid, and methods of expressing nucleic acid encoding such peptides are further aspects of the present invention. In a preferred embodiment such fragments are fragments of human HIF hydroxylases and in particular of any of PHD 1, 2 or 3.

A suitable modulator may be an analogue of HIFα, the prime substrate for HIF prolyl hydroxylation by HIF hydroxylase, and may act, for example, as a competitive inhibitor of HIFα, or through another mechanism, such as by irreversibly modifying the HIF hydroxylase. Uncoupled oxidation of the co-substrate 2OG may still occur in the event of competitive inhibition of HIF-α.

A suitable fragment of an HIFα polypeptide may comprise a proline residue which is hydroxylated by a HIF hydroxylase in the full-length polypeptide, and which is, itself, capable of being hydroxylated by a HIF hydroxylase, for example a fragment containing a proline residue which corresponds to proline residue 402 or 564 of the human HIF-1α sequence. Smaller fragments, and analogues and variants of these fragments may similarly be employed, e.g. as identified using techniques such as deletion analysis or alanine scanning.

Knowledge of the HIFα sequence, in particular the identity of the residues which are hydroxylated, therefore allows an inhibitor to be designed with a proline analogue in the position of hydroxylation to inhibit the hydroxylation reaction.

In particular, a modulator, such as an inhibitor, may include a peptide fragment of HIFα or analogue thereof in which the praline residue which undergoes hydroxylation, e.g. proline 564, is replaced by a proline analogue which is not a HIF hydroxylase substrate, such as 5-oxaproline, 3,4-dehydroproline and 4-thiaproline (Wu et al (1999) J. Am. Chem. Soc. 121(3)587-588, DE-A-3818850). The proline inhibitor analogues may be modified such that they also bind to the 2-oxoglutarate binding residues of the hydroxylase.

Examples of proline analogues are;

XXIII:

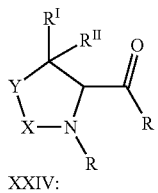

XXIV:

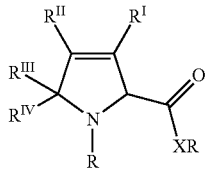

where one of Y or X=O (oxaprolines) and the other is —CR'R"— or Y=S (4-thiaprolines) where one of X and Y is C=O or —SO$_2$ or —P(=O)O(H) and the other is CR'R"—,
and R is a peptide or peptide analogue and R, R$^I$, R$^{II}$ are H, a branched or straight C$_1$ to C$_6$ alkyl chain, a 4 to 7 membered heterocyclic ring optionally containing 1 or more F, N, S, O or P atoms, 5 or 6 membered aromatic ring, optionally containing 1 or more N, O or S atoms, which can be fused to another ring.

Peptides or peptide analogues suitable for use in accordance with the present invention tend to be short, and may be about 40 amino acids in length or less, preferably about 35 amino acids in length or less, more preferably about 30 amino acids in length, or less, more preferably about 25 amino acids or less, more preferably about 20 amino acids or less, more preferably about 15 amino acids or less, more preferably about 10 amino acids or less, or 9, 8, 7, 6, 5 or less in length. Peptides according to the present invention may be about 10-40 amino acids in length, about 5-10, about 10-15, about 10-20, about 10-30, about 20-30, or about 30-40 amino acids in length. Peptides which are HIFα fragments generally include one or more of the relevant proline residues.

A peptide modulator which is a derivative of a peptide for which the specific sequence is disclosed herein may be in certain embodiments the same length or shorter than the specific peptide. In other embodiments the peptide sequence or a variant thereof may be included in a larger peptide, as discussed above, which may or may not include an additional portion of HIF hydroxylase or HIF-1 polypeptide. 1, 2, 3, 4 or 5 or more additional amino acids, adjacent to the relevant specific peptide fragment of the HIF hydroxylase or HIF-1 polypeptide, or heterologous thereto may be included at one end or both ends of the peptide.

Peptides may be modified, for example, for use as pharmaceuticals, for example by replacing amide bonds and/or using D rather than Lα-amino acids or β-amino acids or by using conformational restraints.

Examples of potential HIF hydroxylase inhibitors, and in particular of HPH activity, of the classes described above are shown in Table 3.

In the formulae described herein, a branched or straight C$_1$ to C$_6$ alkyl chain may be a methyl, ethyl, propyl, butyl, iso-butyl, sec-butyl, tert-butyl, pentyl, neopentyl tert-pentyl or a primary, secondary or tertiary hexyl group. Preferably the alkyl group is methyl or ethyl while the preferred heterocyclic rings are pyrolidine or tetrahydropyrane and the aromatic rings are benzene, naphthalene or pyridine.

Without being limited to any particular mechanism, analysis of the structure of IPNS complexed to Fe(II), and ACV, together with the structural relationship between N-(mercaptopropionyl) glycine, 2OG, and N-oxaloglycine, provides indication that the former inhibits HIF hydroxylase and in particular HPH activity via a complex in its thiol binds to the Fe(II) and the carboxylate to the same residues as the S-carboxylate of 2OG.

HPH Selectivity

A number of distinct HIF hydroxylases with HIF prolyl hydroxylase activity exist in humans and it may be also be advantageous to modulate these selectively, as single targets, or in selected groups as well as an entire family. Agents which modulate HIF hydroxylase activity and in particular HIF prolyl hydroxylase activity are therefore preferably specific i.e. they have an increased or enhanced effect on a HIF hydroxylase relative to other 2OG dependent oxygenases as defined below, in particular collagen prolyl hydroxylases (CPH). Such agents may be specific for a particular human HIF hydroxylases and in particular PHD 1, 2 or 3.

Assay methods as described herein may therefore further comprise contacting the test compound with one or more 2OG dependent oxygenases under conditions in which said 2OG dependent oxygenases are normally active and determining activity of said oxygenases.

A difference in activity in the presence relative to the absence of test compound is indicative of the test compound modulating the activity of the one or more 2OG dependent oxygenases.

A test compound which provides increased or enhanced modulation of a HIF hydroxylase, relative to the one or more 2OG dependent oxygenases shows selectivity or specificity for the HIF hydroxylase.

2OG dependent oxygenases may include for example, clavaminte synthase, deacetoxycephalosporin C synthase, collagen-prolyl-4-hydroxylase, collagen prolyl-3-hydroxylase, lysyl hydroxylase, aspartyl hydroxylase, phytanoyl coenzyme A hydroxylase or gamma-butyrobetaine hydroxylase. 2OG dependent oxygenases may be mammalian, preferably human polypeptides.

The structures of various 2-OG oxygenase enzymes have been reported; oxygenase clavaminic acid synthase (Zhang Z. et al (2000) Nature Structural Biol. 7 127-133), deacetoxycephalosporin C synthase (Lloyd et al (1999) J. Mol. Biol. 287 943-960), cephalosporin synthase (Valegard K. et al (1998) Nature 394 805-809), isopenicillin N-synthase (Roach P. (1995) Nature 375 700-704) and 2OG dependent oxygenases (Schofield, C. & Zhang, Z. (1999) Curr. Opin. Struct. Biol. 9 722-731).

The assays of the invention may also be used to identify agents which are: selective for HIF hydroxylases, and in particular HPH activity, but not for other 2OG dependent oxygenases; agents which are selective for HIF hydroxylase, and in particular HIF prolyl hydroxylase activity, compared to other hydroxylases and prolyl hydroxylases; and agents which are specific for a particular HIF hydroxylase. The assays may be used to identify agents selective for a particular human HIF hydroxylase, such as for example specific for an enzyme with the amino acid sequence of SEQ ID NO: 2, or SEQ ID NO; 4 or SEQ ID NO: 6.

The invention provides for the use of such selective inhibitors of HIF hydroxylases in the manufacture of a medicament for the treatment of a condition associated with reduced HIF levels of activity.

In alternative aspects of the present invention, the assays can be used to establish whether agents which have been identified as inhibitors or activators of other 2OG dependent oxygenases are specific for such oxygenases, or at least do not affect HIF hydroxylase and in particular HIF prolyl hydroxylase activity of the polypeptides of the present invention. In particular, the assays may be used to establish that such agents do not affect human HIF hydroxylases. Thus, the assays may be carried out using agents which have been identified as inhibitors of a 2OG dependent oxygenase, such as collagen prolyl hydroxylase to identify whether such an agent is specific for collagen prolyl hydroxylase and is not active or shows reduced activity against HIF hydroxylases and in particular their prolyl hydroxylase activity.

Assay Formats

A screening or assay method may include purifying and/or isolating a test compound, agent, or substance of interest from a mixture or extract, i.e. reducing the content of at least one component of the mixture or extract, e.g. a component with which the test substance is naturally associated. The screening or assay method may include determining the ability of one or more fractions of a test mixture or extract to modulate the hydroxylase and in particular the prolyl activity of the HIF hydroxylase, and typically these activities in relation to HIF-α.

The purification and/or isolation may employ any method known to those skilled in the art. An agent or compound obtained and/or identified using an assay method described herein may be modified, for example to increase selectivity for a HIF hydroxylase relative to other 2OG dependent oxygenases such as CPH or to increase selectivity for a particular HIF hydroxylase relative to other HIF hydroxylases.

The approach of modifying a class of compounds containing specific functional groups to be selective for particular enzymes is well-known, for example the inhibition of specific serine proteases by differently modified trifluoroketones, chloromethylketones, beta lactams, or other generic serine protease inhibitors (Walker B. & Lynas J. (2001) Cell. Mol. Life Sci. 58(4) 596-624, Rai R. (2001) et al Curr. Med. Chem. 8 (2) 101-119, Marquis R. (2000) Ann. Rep. Med. Chem. 35 309-320, Lebon, F. & Ledecq, M. (2000) Curr. Med. Chem. 7 (4) 455-477).

Selectivity for a particular HIF hydroxylase can be achieved by performing assays as described herein with a plurality of different HIF hydroxylases. The preferential or selective modulation of the HIF hydroxylase activity, and in particular the prolyl hydroxylase activity, of one or more HIF hydroxylases relative to the other HIF hydroxylase by a test compound may thereby be determined. Similarly, selectivity for the PHD family of HIF hydroxylases can be achieved by performing assays as described herein with a plurality of different 2-oxoglutarate dependent oxygenases i.e. a panel of related enzymes. The preferential or selective modulation of the HIF prolyl hydroxylase activity of one or more PHD polypeptides relative to the activity of other 2-oxoglutarate dependent oxygenases by a test compound may thereby be determined.

Structural information, including primary sequence data and 3D information such as crystallographic data, may also be used to identify structural differences between HIF hydroxylases and other 2-oxoglutarate dependent oxygenases. These differences may be used to design compounds which selectively or preferentially modulate HIF hydroxylases as described herein relative to other 2-oxoglutarate dependent oxygenases.

Structural Analysis and Rational Drug Design

Secondary structural analysis predicts that the HIF hydroxylases fold to produce a common jelly roll structure that positions a non-haem iron co-ordinating $HXD[X]_nH$ motif at the catalytic site.

Kinetic and time resolved crystallographic studies of the catalytic mechanism among members of this class of oxygenase have indicated ordered binding of Iron (II), 2-oxoglutarate, and prime substrate (Zhang et al., (2000) supra; Zhou et al (1998) J. Am. Chem. Soc. 120 13539-13540).

Binding of the latter 'primes' the enzyme for reversible binding of dioxygen, probably by displacing a water molecule from the iron. Weak binding at the iron centre is associated with a cofactor requirement for iron (II). The activity of the recombinant enzyme requires iron, and is directly inhibited by cobaltous ions by substitution at the catalytic center. A mutation (EGLN2/PHD1; H358A) that is predicted to abrogate iron binding, but not otherwise alter the 3-dimensional structure was observed to completely ablate enzyme activity, Structural analysis and sequence studies show that SM20 comprises an iron atom at its active site in complex with residues His313 and Asp315 (Acc No: af229245 or gi11320937). Related enzymes clavaminate synthase (CAS) and deacetoxycephalosporin C synthase (DAOCS) also show iron coordination at the active site as shown in FIG. 8.

An inhibitor may form a mono-, di-, or tri-dentate complex with the coordinate iron atom to inhibit the activity of the enzyme. Examples of such inhibitors include the hydroxamates and hydroxyanthroquinones described herein. The coordination of an inhibitor to the iron atom may be determined by spectroscopic analysis or crystallography.

As noted above, an agent may be peptidyl, e.g. a peptide which includes a sequence as recited above, or may be a functional analogue of such a peptide.

As used herein, the expression "functional analogue" relates to peptide variants or organic compounds having the same functional activity as the peptide in question, which may interfere with the hydroxylation and in particular the prolyl hydroxylation of HIFα by a HIF hydroxylase. Examples of such analogues include chemical compounds which are modelled to resemble the three dimensional structure of the substrate of the HIF hydroxylase (HIFα) in the contact area or in the pVHL binding domain, and in particular the arrangement of the key amino acid residues, including proline 564.

In a further aspect, the present invention provides the use of a HIFα polypeptide, in particular a peptide fragment which undergoes hydroxylation by a HIF hydroxylase, in a method of designing a peptide or non-peptidyl mimetic, which mimetic is able to interact with the HIF hydroxylase active site and modulate the hydroxylation of a proline residue i.e. proline 402 or 564 of HIFα, by the HIF hydroxylase.

Accordingly, the present invention provides a method of designing a mimetic, for example of a HIFα polypeptide, which modulates the hydroxylation of a proline residue by a HIF hydroxylase, said method comprising:

(i) analysing a substance to determine the amino acid residues essential and important for biological activity to define a pharmacophore; and, (ii) modelling the pharmacophore to design and/or screen candidate mimetics which modulate the hydroxylation as described.

Suitable modelling techniques are known in the art. This includes the study of the bonding between a HIF hydroxylase and HIF-α and the design of compounds which contain corresponding functional groups arranged in such a manner that they could reproduce that bonding.

The iron atom at the HIF hydroxylase active site is normally hexacoordinate (but can be pentacoordinate during catalysis). The amino acid sequence provides three ligands so there are three positions vacant for binding to inhibitors. Inhibitor molecules may therefore be designed to coordinate with the iron atom at these three positions.

The designing of mimetics to a known pharmaceutically active compound is a known approach to the development of pharmaceuticals based on a "lead" compound, for example a compound as described herein. This might be desirable where the active compound is difficult or expensive to synthesise or where it is unsuitable for a particular method of administration, for instance, HIF-α or HIF hydroxylase and in particular peptides derived from them may not be well suited as active agents for oral compositions as they tend to be quickly degraded by proteases in the alimentary canal.

There are several steps commonly taken in the design of a mimetic from a compound having a given target property. Firstly, the particular parts of the compound that are critical and/or important in determining the target property are determined. In the case of a peptide, this can be done by systematically varying the amino acid residues in the peptide, e.g. by substituting each residue in turn. These parts or residues constituting the active region of the compound are known as its "pharmacophore".

Once the pharmacophore has been found, its structure is modelled according to its physical properties, e.g. stereochemistry, bonding, size and/or charge, using data from a range of sources, e.g. spectroscopic techniques, X-ray diffraction data and NMR. Computational analysis, similarity mapping (which models the charge and/or volume of a pharmacophore, rather than the bonding between atoms) and other techniques can be used in this modelling process.

In a variant of the above approach, the three-dimensional structure of a ligand and its binding partner are modelled. This can be especially useful where the ligand and/or binding partner change conformation on binding, allowing the model to take account of this in the design of the mimetic.

Polypeptide Inhibitors of the Invention

The invention also provides a polypeptide of SEQ ID NO: 9 DLDLEMLAP*YIPMDDDFQL wherein P* is 4-hydroxy proline. Such peptides may be provided in an isolated form. The invention also provides variants of SEQ ID NO:9, as defined above. Variants will retain the ability to antagonize the interaction of a HEF-α subunit with VHL. This means that the presence of the variant in a cell will lead to an increase in HIF-α subunit protein compared to the amount of HIF-α subunit protein present in the absence of the polypeptide.

Particular examples of such substitutions include the following:

```
                                SEQ ID NO: 10
         DLDLEMLAP*YISMDDDFQL;

SEQ ID NO: 11
         DLDLEMLLP*YIPMDDDFQL;

SEQ ID NO: 12
         DLDLEMLVP*YIPMDDDFQL;

SEQ ID NO: 13
         DLDLEMIAP*YIPMDDDFQL;

SEQ ID NO: 14
         DLDLEMIAP*YIPMEDDFQL;,
         and

SEQ ID NO: 15
         DLDLEMLVP*YISMDDDFQL.
```

The invention also provides an isolated polypeptide which is a variant of SEQ ID NO: 9, wherein such variants comprise from 1 to 4 amino acid substitutions of any amino acid apart from P*, said variant retaining the ability to antagonize the interaction of a HIF-α subunit with VHL, A particular polypeptide of the latter type is:

```
                                    (SEQ ID NO: 16)
   PFSTQDTDLDLEMLAPYIPMDDDFQLRSFDQLSP;
``` or variants thereof as defined for SEQ ID NO:9 above; and polypeptides consisting of from 35 to 50 amino acids which contain SEQ ID NO:16.

Fragments of these polypeptides which retain the P* residue, and which are at least 6, preferably at least 10, such as at least 12 or at least 15 amino acids in length are also a further aspect of the invention, and are also referred to herein as polypeptides of the invention. Preferably these fragments retain the motif LXP*, e.g. LAP*, and more preferably the fragments retain the motif LXXLAP*, e.g. LXXLAP* (SEQ ID NO: 17). "X" means any amino acid. In particular, such a polypeptide has or includes the sequence LAP*YIP (SEQ ID NO: 49). Thus the invention also relates to a peptide comprising or having the sequence LAP*YEP (SEQ ID NO: 49) and having the ability to antagonize the interaction between HIF and VHL. Such peptides may be formulated or used as described for peptides of SEQ ID NO:9.

We have also found that a second proline residue in HIF-1α is subject to hydroxylation. Our findings indicate that residue 402 which shares a common motif of "LXXLAP" with the site of hydroxylation at position 564. Our findings indicate that this site. Polypeptides of at least 8, e.g. at least 10, at least 12, at least 15 or at least 18 amino acids, up to no more than 50, such as no more than 35 or no more than 20 amino acids, based upon the sequences of this region also form a further aspect of the invention. Such polypeptides include those in which proline at 402 is hydroxylated. Substitutions, modifications, purification, isolation and/or synthesis may be carried out as described for HIF hydroxylases described above.

The hydroxylated peptides in accordance with the present invention can be used in assays to monitor for agents which inhibit the interaction between VHL and HIF. In accordance with this aspect of the invention, a hydroxylated polypeptide as described above is incubated with VHL or a HIF binding region thereof in the presence of a test substance and the interaction between the hydroxylated polypeptide and the VHL polypeptide is monitored. The polypeptides may also be used as displacement probes in high throughput assays for inhibitors.

These polypeptides of the present invention may be prepared as a pharmaceutical preparation. Such preparations will comprise the polypeptide together with suitable carriers, diluents and excipients. Typically, they will comprise the polypeptide together with a pharmaceutically acceptable polypeptide. Such formulations form a further aspect of the present invention.

Formulations may be prepared suitable for any desired route of administration, including oral, buccal, topical, intramuscular, intravenous, subcutaneous and the like.

Formulations for topical administration to the skin may include ingredients which enhance the permeability of the skin to the polypeptides. Such formulations may be in the form of ointments, creams, transdermal patches and the like.

Formulations for administration by injection (i.m., i.v., subcutaneous and the like) will include sterile carriers such as physiological saline, optionally together with agents which preserve or stabilise the polypeptide. Albumin may be a suitable agent.

Formulations of polypeptides in particular may be used in methods of treatment ischaemic conditions, such as organ ischaemia, such as is manifest in coronary, cerebrovascular and peripheral vascular insufficiency. Any ischaemia is a therapeutic target. The therapy may be applied in two ways; following declared tissue damage, e.g. myocardial infarction (in order to limit tissue damage), or prophylactically to prevent ischaemia, e.g. promotion of coronary collaterals in the treatment of angina. Additionally, vasomotor control is subject to regulation by HIF. Activation of HIF might affect systemic vascular resistance and hence systemic blood pressure.

Polypeptides may also be used in combination with promoters of angiogenesis. These include vascular endothelial growth factor and other angiogenic growth factors such as basic fibroblast growth factors and thymidine phosphorylase and pro-angiogenic and might be used in combination therapy. Other compounds which might conceivably be used in combination are 2-deoxy ribose and prostaglandin E.

In administering polypeptides of the invention to a subject, the doses will be determined at the discretion of the physician, taking into account the needs of the patient and condition to be treated. Generally, doses will be provided to achieve concentrations at a desired site of action that are from 0.1 μM to 1 mM, for example in the 1-10 μM range.

Therapeutic Applications

A compound, substance or agent which is found to have the ability to affect the hydroxylase activity of a HIF hydroxylase, and in particular its prolyl hydroxylase activity, has therapeutic and other potential in a number of contexts, as discussed. For therapeutic treatment, such a compound may be used in combination with any other active substance, e.g. for anti-tumour therapy another anti-tumour compound or therapy, such as radiotherapy or chemotherapy.

An agent identified using one or more primary screens (e.g. in a cell-free system) as having ability to modulate the HIFα hydroxylation activity of a HIF hydroxylase may be assessed further using one or more secondary screens. A secondary screen may involve testing for an increase or decrease in the amount of HIF-α or HIF activity, for example as manifest by the level of a HIF target gene or process present in a cell in the presence of the agent relative to the absence of the agent.

A HIF hydroxylase or a HIF polypeptide may be used in therapies which include treatment with full length polypeptides or fragments thereof, or otherwise modified polypeptides (e.g. to enhance stability or ensure targeting, including in conjunction with other active agents such as antibodies.

Generally, an agent, compound or substance which is a modulator according to the present invention is provided in an isolated and/or purified form, i.e. substantially pure. This may include being in a composition where it represents at least about 90% active ingredient, more preferably at least about 95%, more preferably at least about 98%. Any such composition may, however, include inert carrier materials or other pharmaceutically and physiologically acceptable excipients, such as those required for correct delivery, release and/or stabilisation of the active agent. As noted below, a composition according to the present invention may include in addition to an modulator compound as disclosed, one or more other molecules of therapeutic use, such as an anti-tumour agent.

Products Obtained by Assays of the Invention

The invention further provides compounds obtained by assay methods of the present invention, and compositions comprising said compounds, such as pharmaceutical compositions wherein the compound is in a mixture with a pharmaceutically acceptable carrier or diluent. The carrier may be liquid, e.g. saline, ethanol, glycerol and mixtures thereof, or solid, e.g. in the form of a tablet, or in a semi-solid form such as a gel formulated as a depot formulation or in a transdermally administerable vehicle, such as a transdermal patch.

The invention farther provides a method of treatment which includes administering to a patient an agent which interferes with the hydroxylation of the target residue of an HIFα polypeptide by a HIF hydroxylase. Such agents may include inhibitors of hydroxylase activity, typically of prolyl hydroxylase activity and in particular these activities in relation to HIF. Examples of inhibitors of HIF prolyl hydroxylase activity include, for example compounds of structures I to XXVIII as described herein. Exemplary purposes of such treatment are discussed elsewhere herein.

The invention further provides various therapeutic methods and uses of one or more substances selected from (i) a HIF hydroxylase which is able to bind to HIF-1; (ii) a modulator identified by a screening method of the present invention; (iii) a mimetic of any of the above substances which can bind to HIF-1 or a HIF hydroxylase, or the polypeptide inhibitors of the invention.

The therapeutic/prophylactic purpose of such a method or use may be the modulation of the level of HIFα in a cell by modulation, e.g. disruption or interference, of the hydroxylation of HIFα, which may occur for example at proline 402, 564 or other proline residue. Hydroxylation of HIFα promotes pVHL binding which leads to ubiquitin dependent proteolysis of HIFα as described above.

The therapeutic/prophylactic purpose may be related to the treatment of a condition associated with reduced or suboptimal or increased HIF levels or activity, or conditions in which have normal HIF levels, but where an modulation in HIF levels such as an increase or decrease in HIF levels is desirable such as: (i) ischaemic conditions, for example organ ischaemia, including coronary, cerebrovascular and peripheral vascular insufficiency. The therapy may be applied in two ways; following declared tissue damage, e.g. myocardial infarction (in order to limit tissue damage), or prophylactically to prevent ischaemia, e.g. promotion of coronary collaterals in the treatment of angina.
(ii) wound healing and organ regeneration
(iii) auto-, allo-, and xeno-transplantation.
(iv) systemic blood pressure
(v) cancer; HIFα is commonly up-regulated in tumour cells and has major effects on tumour growth and angiogenesis.
(vi) inflammatory disorders.
(vii) pulmonary arterial blood pressure, neurodegenerative disease.

Pharmaceutical Compositions

In various further aspects, the present invention thus provides a pharmaceutical composition, medicament, drug or other composition for such a purpose, the composition comprising one or more agents, compounds or substances as described herein, including HIF hydroxylase inhibitors and in particular inhibitors of their HIF prolyl hydroxylase (HPH) activity such as compounds of formulae I to XXVIII, the use of such an composition in a method of medical treatment, a method comprising administration of such a composition to a patient, e.g. for treatment (which may include preventative treatment) of a medical condition as described above, use of such an agent compound or substance in the manufacture of a composition, medicament or drug for administration for any such purpose, e.g. for treatment of a condition as described herein, and a method of making a pharmaceutical composition comprising admixing such an agent, compound or substance with a pharmaceutically acceptable excipient, vehicle or carrier, and optionally other ingredients.

In one embodiment the method for providing a pharmaceutical composition may typically comprise:
  (a) identifying an agent by an assay method of the invention; and
  (b) formulating the agent thus identified with a pharmaceutically acceptable excipient.

The pharmaceutical compositions of the invention may comprise an agent, polypeptide, polynucleotide, vector or antibody according to the invention and a pharmaceutically acceptable excipient.

The agent may be used as sole active agent or in combination with one another or with any other active substance, e.g. for anti-tumour therapy another anti-tumour compound or therapy, such as radiotherapy or chemotherapy.

Whatever the agent used in a method of medical treatment of the present invention, administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors.

An agent or composition may be administered alone or in combination with other treatments, either simultaneously or sequentially dependent upon the condition to be treated, e.g. as described above.

Pharmaceutical compositions according to the present invention, and for use in accordance with the present invention, may include, in addition to active ingredient, a pharmaceutically acceptable excipient, carrier, buffer, stabiliser or other materials well known to those skilled in the art. In particular they may include a pharmaceutically acceptable excipient. Such materials should be non-toxic and should not interfere with the efficacy of the active ingredient. The precise nature of the carrier or other material will depend on the route of administration, which may be oral, or by injection, e.g. cutaneous, subcutaneous or intravenous.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Liposomes, particularly cationic liposomes, may be used in carrier formulations. Examples of techniques and protocols mentioned above can be found in Remington's Pharmaceutical Sciences, 16th edition, Osol, A. (ed), 1980.

The substance or composition may be administered in a localised manner to a particular site or may be delivered in a manner in which it targets particular cells or tissues, for example using intra-arterial stent based delivery.

Targeting therapies may be used to deliver the active substance more specifically to certain types of cell, by the use of targeting systems such as antibody or cell specific ligands. Targeting may be desirable for a variety of reasons, for example if the agent is unacceptably toxic, or if it would otherwise require too high a dosage, or if it would not otherwise be able to enter the target cells.

In a further embodiment the invention provides for the use of an agent of the invention in the manufacture of a medicament for the treatment of a condition associated with increased or decreased HIF levels or activity. The condition may, for example, be selected from the group consisting of ischaemia, wound healing, auto-, allo-, and xeno-transplantation, systemic high blood pressure, cancer, and inflammatory disorders.

Gene Therapy

The HIF hydroxylases of the present invention can be used to promote or enhance hydroxylation of HIF-α in target cells. Such promotion of hydroxylation may therefor facilitate ubiquitilation and subsequent destruction of HIF-α and thus reduce accumulation of HIF-α in cells. This will be of assistance in reducing angeogenesis and effect other apoptotic and proliferative responses in target cells. Thus, in accordance with this aspect of the invention a nucleic acid encoding a HIF hydroxylase may be provided to target cells in need thereof.

Where the substances are peptides or polypeptides, they may be produced in the target cells by expression from an encoding nucleic acid introduced into the cells, e.g. from a viral vector. The vector may be targeted to the specific cells to be treated, or it may contain regulatory elements which are switched on more or less selectively by the target cells.

Nucleic acid encoding a substance e.g. a peptide able to modulate, e.g. interfere with, prolyl hydroxylation of HIF-α by a HIF hydroxylase, may be used in methods of gene therapy, for instance in treatment of individuals, e.g. with the aim of preventing or curing (wholly or partially) a disorder.

Nucleic acid encoding a HIF hydroxylase as described herein may also be used in the anti-sense regulation of the HIF hydroxylase activity and in particular, of the HIF prolyl hydroxylase activity within a cell.

Down-regulation of expression of a gene encoding a HIF hydroxylase may be achieved using anti-sense technology, or RNA interference.

In using anti-sense genes or partial gene sequences to down-regulate gene expression, a nucleotide sequence is placed under the control of a promoter in a "reverse orientation" such that transcription yields RNA which is complementary to normal mRNA transcribed from the "sense" strand of the target gene. See, for example, Smith et al, (1988) Nature 334, 724-726. Antisense technology is also reviewed in Flavell, (1994) PNAS USA 91, 3490-3496.

The complete sequence corresponding to the reverse orientation of the coding sequence need not be used. For example, fragments of sufficient length may be used. It is a routine matter for the person skilled in the art to screen fragments of various sizes and from various parts of the coding sequence to optimise the level of anti-sense inhibition. It may be advantageous to include the initiating methionine ATG codon, and perhaps one or more nucleotides upstream of the initiating codon. A further possibility is to target a conserved sequence of a gene, e.g. a sequence that is characteristic of one or more genes, such as a regulatory sequence.

The sequence employed may be 500 nucleotides or less, possibly about 400 nucleotides, about 300 nucleotides, about 200 nucleotides, or about 100 nucleotides. It may be possible to use oligonucleotides of much shorter lengths, 14-23 nucleotides, although longer fragments, and generally even longer than 500 nucleotides are preferable where possible.

Anti-sense oligonucleotides may be designed to hybridise to the complementary sequence of nucleic acid, pre-mRNA or mature mRNA, interfering with the production of a HIF hydroxylase encoded by a given DNA sequence (e.g. either native polypeptide or a mutant form thereof), so that its expression is reduce or prevented altogether. Anti-sense techniques may be used to target a coding sequence, a control sequence of a gene, e.g. in the 5' flanking sequence, whereby the anti-sense oligonucleotides can interfere with control sequences. Anti-sense oligonucleotides may be DNA or RNA and may be of around 14-23 nucleotides, particularly around 15-18 nucleotides, in length. The construction of antisense sequences and their use is described in Peyman and Ulman, Chemical Reviews, 90:543-584, (1990), and Crooke, Ann. Rev. Pharmacol. Toxicol., 32:329-376, (1992).

It may be preferable that there is complete sequence identity in the sequence used for down-regulation of expression of a target sequence, and the target sequence, though total complementarity or similarity of sequence is not essential. One or more nucleotides may differ in the sequence used from the target gene. Thus, a sequence employed in a down-regulation of gene expression in accordance with the present invention may be a wild-type sequence (e.g. gene) selected from those available, or a mutant, derivative, variant or allele, by way of insertion, addition, deletion or substitution of one or more nucleotides, of such a sequence.

The sequence need not include an open reading frame or specify an RNA that would be translatable. It may be preferred for there to be sufficient homology for the respective sense RNA molecules to hybridise. There may be down regulation of gene expression even where there is about 5%, 10%, 15% or 20% or more mismatch between the sequence used and the target gene.

Other approaches to specific down-regulation of genes which may be used to modulate HIF hydroxylase expression are well known, including the use of ribozymes designed to cleave specific nucleic acid sequences. Ribozymes are nucleic acid molecules, actually RNA, which specifically cleave single-stranded RNA, such as mRNA, at defined sequences, and their specificity can be engineered. Hammerhead ribozymes may be preferred because they recognise base sequences of about 11-18 bases in length, and so have greater specificity than ribozymes of the Tetrahymena type which recognise sequences of about 4 bases in length, though the latter type of ribozymes are useful in certain circumstances. References on the use of ribozymes include Marschall, et al. Cellular and Molecular Neurobiology, 1994. 14(5): 523; Hasselhoff, Nature 334: 585 (1988) and Cech, J. Amer. Med. Assn., 260: 3030 (1988).

Vectors such as viral vectors have been used in the prior art to introduce nucleic acid into a wide variety of different target cells. Typically the vectors are exposed to the target cells so that transfection can take place in a sufficient proportion of the cells to provide a useful therapeutic or prophylactic effect from the expression of the desired peptide. The transfected nucleic acid may be permanently incorporated into the genome of each of the targeted cells, providing long lasting effect, or alternatively the treatment may have to be repeated periodically.

A variety of vectors, both viral vectors and plasmid vectors, are known in the art, see U.S. Pat. No. 5,252,479 and WO93/07282. In particular, a number of viruses have been used as gene transfer vectors, including papovaviruses, such as SV40, vaccinia virus, herpesviruses, including HSV and EBV, and retroviruses. Many gene therapy protocols in the prior art have used disabled murine retroviruses.

As an alternative to the use of viral vectors in gene therapy other known methods of introducing nucleic acid into cells includes mechanical techniques such as microinjection, transfer mediated by liposomes and receptor-mediated DNA transfer.

Receptor-mediated gene transfer, in which the nucleic acid is linked to a protein ligand via polylysine, with the ligand being specific for a receptor present on the surface of the target cells, is an example of a technique for specifically targeting nucleic acid to particular cells.

In various further aspects, the present invention thus provides a pharmaceutical composition, medicament, drug or other composition for use in a method of treating a medical condition described above, the composition comprising an isolated nucleic acid molecule as described herein, the use of such an composition in a method of medical treatment, a method comprising administration of such a composition to a patient, e.g. for treatment (which may include preventative treatment) of a medical condition as described above, use of such an agent compound or substance in the manufacture of a composition, medicament or drug for administration for any such purpose, e.g. for treatment of a condition as described herein, and a method of making a pharmaceutical composition comprising admixing such an agent, compound or substance with a pharmaceutically acceptable excipient, vehicle or carrier, and optionally other ingredients.

A peptide or other substance having an ability to modulate or interfere with the prolyl hydroxylation of the residue of HIF-α by a polypeptide, or a nucleic acid molecule which encodes a peptide having that ability, may be provided in a kit, e.g. sealed in a suitable container which protects its contents from the external environment. Such a kit may include instructions for use.

Use of Polypeptides

Another aspect of the present invention provides the use of a HIF hydroxylase as described herein or a fragment thereof for the hydroxylation, and in particular the prolyl hydroxylation, of an HIF polypeptide, or a proline-containing substrate of HIF hydroxylation.

Another aspect of the present invention provides a method of producing a HIF hydroxylase comprising:
(a) causing expression from nucleic acid which encodes a HIF hydroxylase in a suitable expression system to produce the polypeptide recombinantly;
(b) determining the prolyl hydroxylation of an HIFα polypeptide by said recombinantly produced polypeptide. The polypeptide expressed by the method may be a PHD (EGLN) polypeptide.

Suitable expression systems are well-known in the art. HIF hydroxylases may be expressed in a prokaryote, such as *E. coli*, lower eukaryote such as *S. cerevisiae* or a higher eukaryotic cell, such as a mammalian cell e.g. a CHO or COS cell.

Prolyl hydroxylation of an HIFα polypeptide, in particular within the pVHL binding domain, such as residue 402 or 564, may be determined as described herein.

Another aspect of the present invention provides an assay method for identifying/obtaining a HIF hydroxylase, and in particular a HIFα prolyl hydroxylase, comprising,
(a) providing a test polypeptide,
(b) bringing into contact an HIFα polypeptide and the test polypeptide under conditions in which the HIFα polypeptide is hydroxylated by a HIF hydroxylase; and
(c) determining hydroxylation and in particular the prolyl hydroxylation of the HIFα polypeptide.

A HIF hydroxylase polypeptide according to the present invention can also be used to identify additional substrates of HIF hydroxylases. For example, peptides which have either previously been demonstrated to be hydroxylated by other hydroxylases, or other peptides may be brought into contact with a HIF hydroxylase according to the present invention and monitoring for hydroxylation of such peptides. Any suitable conditions may be selected including the provision of agents and co-factors known to enhance hydroxylation by the hydroxylases of the present invention. In a preferred aspect, prolyl containing substrates are contacted with a HIF hydroxylase of the present invention, and hydroxylation of the prolyl residue is monitored. Hydroxylation of the substrate may be monitored by any suitable method including monitoring levels of co-factors or by products of hydroxylation.

The invention also provides a method of modulating the amount of HIF polypeptide in a cell comprising contacting the cell with a substance which inhibits the 4-prolyl hydroxylase activity of a HIF hydroxylase such as, for example, an EGLN polypeptide. The substance may, for example, be an agent of the invention. In a preferred embodiment, the substance inhibits the biological activity of HIF hydroxylase, such as, for example an EGLN polypeptide, but does not inhibit biological activity of a collagen prolyl hydroxylase.

Various further aspects and embodiments of the present invention will be apparent to those skilled in the art in view of the present disclosure.

Certain aspects and embodiments of the invention will now be illustrated by way of example and with reference to the figures described below.

BRIEF DESCRIPTION OF THE DRAWINGS

FIGS. 1A-1B. Analysis of the minimal pVHL binding domain of HIF-1α. FIG. 1A. Left panel; sequence alignment of the minimal pVHL binding domain from HIF-1α and HIF-2α, with HIF-α genes from other organisms. FIG. 1B. Summary of the ability of synthetic polypeptides to block the HIF-1α/pVHL interaction before and after exposure to reticulocyte lysate supplement with Fe(II). Treated and untreated polypeptides were added to a mixture of HIF-1α and pVHL.HA IVTTs that was then assayed for interaction by anti-HA immunoprecipitation. Substituted residues are underlined. Y* denotes phosphotyrosine.

FIG. 2. Amino acid sequences of human HIF-1α and *C. elegans* HIF. Identical amino acids are boxed in black. The PAS domains are indicated. The VHL minimal binding region defined in studies of human HIF-1α is indicated.

FIG. 3A Line up of the indicated amino acids of the indicated HIF alpha chains showing conservation of the LxxLAP motif in all three domains demonstrated to be involved in VHL dependent ubiquitylation.

FIG. 6 shows the effect of dimethyl oxalyl glycine on HIF activity in Hep3B 30 and U20S cell lines.

FIG. 9 shows sequence alignments of the predicted jelly roll cores of HIF-PHs. Sequences shown are *C. elegans* EGL-9 (462-580), Human EGLN1 (288-403), Human EGLN2 (462-580), Human EGLN3 (111-225), rat SM20 (226-341), Also shown is the *Streptomyces* sp. Prolyl-3-hydroxylase (P3OH). The residues of the 2-His-1-Asp motif are indicated by arrows, as is the arginine proposed to bind the 5-carboxylate of 2-oxoglutarate (Mukherji et al (2001) Chem. Comm. 11 972-973).

FIG. 13A Proposed model for peptide effects on HIFα-VHL interaction. Degradation is prevented by the NODD and CODD polypeptides competing for prolyl hydroxylation and/or VHL binding, thereby blocking subsequent ubiquitination. FIG. 13B Transfections of the N-terminal or C-terminal ODD (HIF-1α aa343-417 or aa549-82) led to increased HRE-dependent luciferase activity comparable to hypoxic levels. In contrast, no induction was seen following transfections with corresponding sequences bearing P402A or P564G mutations. RLU: Relative Light Units. FIG. 13C Use of a CHO cell line, lacking HIFα chains (KA-13), or its stable HIF-1α transfectant (KH-1) shows dependence of the observed HRE response on HIF-1α expression. FIG. 13D and FIG. 13E, Amino acids 390-410 for the NODD and amino acids 556-72 for the CODD were the shortest active domains defined. FIG. 13F, Sequence alignment of human and mouse HIF-1α NODD (SEQ ID NOS 50 and 51, respectfully) and CODD domains (SEQ ID NOS 39 and 52, respectfully). Figure discloses motif sequence as SEQ ID NO: 53.

EXAMPLES

Figure 3B:
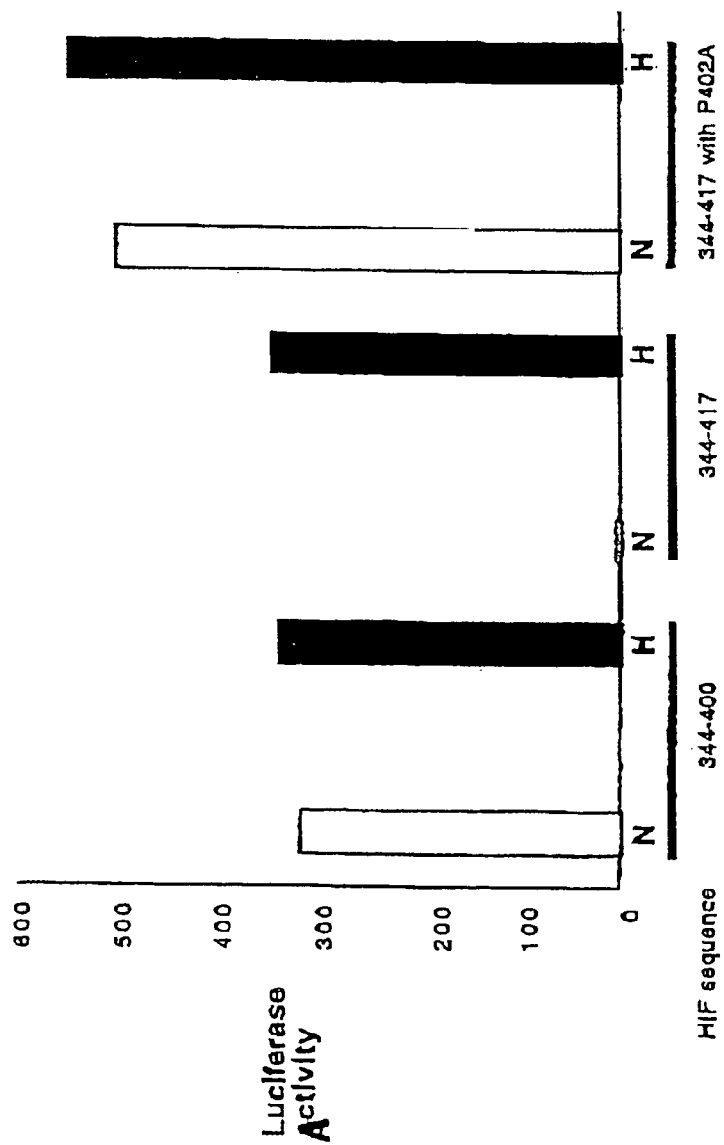
FIG. 3B U2OS cells were transiently co-transfected with plasmids encoding the indicated Gal-Hif-1 alpha-VP16 sequences in combination with pUAS-tk-luc (a Gal 4 upstream activating sequence dependent luciferase reporter gene plasmid). Luciferase activities were determined in extracts made from transfected cells maintained for 48 hours, either entirely in normoxia (white bars) or with hypoxic stimulation for the last 16 hours. (black bars). Low normoxic activity (explicable by rapid destruction of the fusion protein) is seen when the Gal-Hif-VP 16 fusion protein contains wild type Hif-1 alpha amino acids 344-417 but not when the sequence bears the P402A mutation or is truncated to amino acid 400.

Example 1. Oxygen Regulated Modification by Enzymatic Prolyl Hydroxylation Targets HIF-q to the Von Hippel-Lindau Ubiauitvlation Complex In this example it is shown that the interaction between pVHL and a specific domain of the HIF-1α subunit is regulated by enzymatic hydroxylation of a proline residue (HIF-1α P564) in a manner that is dependent on oxygen and iron. An absolute requirement of the enzyme for dioxygen as a co-substrate and iron as a cofactor suggests a direct mechanism of cellular oxygen sensing.

In previous studies of the HIF-α/pVHL interaction we found that treatment of cells with cobaltous ions and iron chelators prevented the HIF-α/pVHL association suggesting that the oxygen sensing mechanism might impinge directly on this protein interaction (8). Surprisingly, these studies indicated that the HIF-α/pVHL complex could be retrieved intact from hypoxic cells. Given the rapidity of pVHL dependent proteolysis of HIF-α in oxygenated cells, we considered that re-oxygenation of cell extracts during cell lysis might have promoted the observed HIF-α/pVHL interaction in vitro. To test this we repeated pVHL co-immunoprecipitation experiments in extracts of $^{35}$S-methionine/ cysteine labelled cells exposed to hypoxia and harvested in a hypoxia work station using deoxygenated buffers, or exposed to hypoxia and harvested conventionally (18).

Experiments were performed on stably transfected renal carcinoma cells expressing hemagglutinin (HA) tagged VHL (RCC4/VHL.HA)(11). RCC4 cells, which lack pVHL, were used as a control. RCC4/VHL.HA cells were labelled with $^{35}$S-amino acids in the presence of the proteasomal inhibitor MG132, either in normoxia or hypoxia for 4 hrs. Cells were lysed on ice, either in the hypoxic workstation or on the bench. RCC4 cells were also similarly labelled and lysed and both labelling and lysis were carried out under normoxic conditions. pVHL and associated proteins were captured with anti-HA antibody. As reported previously (8), anti-HA immunoprecipitates captured HIF-α subunits (HIF-1α and HIF-2α) efficiently from the proteasomally blocked normoxic cells. However, when hypoxic RCC4/VHL.HA cells were lysed under hypoxic conditions, HIF-α subunits were not co-precipitated with pVHL, despite abundance in the lysate as demonstrated by a HIF-1α immunoblot. This contrasted with the result using conventional buffers, which had not been deoxygenated, where HIF-α subunits were captured very efficiently. Capture of pVHL and elongins B&C was found to be similar in all RCC4/VHL.HA samples.

Taken together with previously published data, these results indicate that the classical features of regulation by oxygen and iron availability (and interference by cobaltous ions) are reflected in the HIF-α/pVHL interaction in vivo, and that promotion of the interaction mediated by oxygen can occur rapidly during the preparation of a cell extract.

1.1: Oxygen Sensitivity of the HIF-α/pVHL Interaction $^{35}$S-Methionine labelled HIF-lα subunits and pVHL.HA were produced separately by IVTT (in vitro transcription and translation) in reticulocyte lysates. IVTTs were performed under different conditions, mixed, and assayed for interaction by anti-HA co-immunoprecipitation. These in vitro assays allowed analysis of the HIFα/pVHL interaction using the recombinant proteins.

Labelled HIF-1α and pVHL.HA were generated separately in reticulocyte lysates (IVTT), in the presence or absence of Co (II), desferrioxamine, or Fe(II). Lysates were mixed in various combinations, and interactions assayed by anti-HA immunoprecipitation. We found that supplementary Fe(II) (ferrous chloride, 100 μM) in the HIF-1α IVTT greatly enhanced capture by pVHL.HA, whereas addition of Co(II) (cobaltous chloride, 100 μM) or desferrioxamine, 100 μM (DFO) to the HIF-1α IVTT greatly diminished capture. In contrast, pVHL IVTTs performed under these different conditions were all equally effective in supporting the HIF-1α interaction.

Further experiments were carried out to determine the effect of producing the IVTTs under hypoxic conditions. Labelled HIF-1α was generated in IVTT reactions in the presence or absence of Fe(II) either under ambient conditions or in a hypoxic workstation. Samples were then diluted in buffer in the hypoxic workstation and purified recombinant GST-VHL-elonginC-elonginB was added. VHL and associated proteins were captured using glutathione-agarose. The results showed that when HIF-1α IVTTs were prepared under hypoxic conditions, hypoxia reduced their ability to interact with pVHL, irrespective of whether the latter was produced either as a normoxic or hypoxic IVTT, or as a bacterially expressed complex of pVHL and elongins B and C.

Next, we used reticulocyte IVTTs of Gal4/VP16 fusion proteins bearing specific HIF subsequences to show that the regulated interaction with pVHL was supported even by a minimal pVHL binding HIF-1α subsequence comprising residues 556-574. Fusions bearing amino acid residues 556-574, 549-574, 556-582 or 549-582 of HIF-1α were expressed in reticulocyte lysates with or without added Fe(II). The fusion proteins included the HIF-1α sequence between a Gal4 DNA binding domain and VP16 transactivation domain. As a control a fusion containing no HIF-1α sequences was also assessed. Aliquots were assessed for co-immunoprecipitation with pVHL.HA by anti-HA immunoprecipitation. All of the fusions bearing HIF-1α subsequences displayed iron-dependent recognition by pVHL including the fusion comprising the shortest region of HIF-1α subsequence tested comprising residues 556-574. The control fusion, lacking HIF-1α sequences, did not recognise pVHL either in the presence or absence of iron.

To better understand these findings we surveyed the ability of a series of recombinant pVHL and HIF-1α products produced in different prokaryotic and eukaryotic expression systems (20) to interact. All pVHL products could interact with HIF-1α that was derived from mammalian expression systems. In contrast, HIF-1α could interact only if produced in vivo in tissue culture cells, or in reticulocyte IVTT, and not if produced in bacteria, wheat germ lysates, or insect cells. Together, these results indicate that a factor in mammalian cell extracts was necessary to promote the interaction with specific HIF-1α sequences and that this factor operated in an iron and oxygen dependent manner.

1.2: Modifying Activity which Promotes Interaction of HIF and VHL

To analyse this further we immunopurified a Gal/HIF-1α/VP16 fusion protein expressing HIF-1α residues 549-582, from IVTT reactions prepared in the presence of DFO, using anti-Gal antibodies. The unlabelled HIF-1α substrate was immunopurified on beads, washed, and aliquots incubated under different test conditions in buffer or cell extract. After further washing, the beads were assayed for ability to interact with 35-S labelled pVHL IVTT (21) which was then visualised by fluorography. Increased ability to capture pVHL was seen after exposure of the HIF fusion protein to cell extract in the presence of Fe(II) but not after exposure to Fe(II) without cell extract. The increased ability to capture pVHL after exposure to cell extract and Fe(II) was also found to be oxygen dependent. In analogous experiments it was found that the modifying activity was present in extracts prepared from a variety of mammalian cells, (Hela, RCC, CHO-K1 and rabbit reticulocyte lysate), but that insect cell lysates were essentially inactive on the mammalian HIF fusion protein. The Fe(II) dependent activity of the cell extract was reduced by cooling and was abrogated by pre-heating at 60'C for 10 minutes. The modifying activity did not pass through a 5 kDa ultrafilter. Titration of Fe(II) supplementation indicated full activation at 5 μM. Pre-incubation of the cell extract with hexokinase (50 U/ml) and glucose (50 mM) to deplete ATP did not alter activity, though this treatment abrogated the ability of the cell extracts to phosphorylate a control target. Pretreatment of extracts with clotrimazole (10 μM), methyl-viologen (1 mM), or NADase (20 mU/ml), did not significantly affect activity.

Experiments were also performed using PK epitope tagged HIF-1α (PK.HIF) expressed in insect cells as a HIF substrate. Both RCC4 cell extract, and reticulocyte lysate, in the presence of Fe(II) promoted the ability of HIF to capture wild type but not mutant (Pro86His) pVHL. Thus human HIF-1α produced in insect cells required treatment with mammalian extract to promote interaction with wild type but not mutant pVHL (22). Addition of NaCl to the RCC4 cell extract (to 1M final concentration) abrogated the modifying activity, whereas incubation of the PK-HIF in NaCl (1M) after exposure to the cell extract did not alter its subsequent ability to capture pVHL. Likewise treatment of the HIF fusion protein after modification by exposure to extract, with phosphatase or DFO did not prevent pVHL capture. Overall this suggested an enzyme-mediated modification of HIF-1α that was not phosphorylation.

1.3: Study of the HIF-1α Recognition.

FIG. 1A shows alignment of the known or putative pVHL binding domains amongst HIF-α homologues. The effects of selected point mutations in human HIF-1α on the ability to interact with pVHL were also tested. Wild type (WT) and modified full length HIF-1α molecules bearing the mutations D556N, D558N, D560Q, P564G, Y565A, P567G, M568R, D569N and D570N were generated in reticulocyte lysate and examined for interaction with VHL.HA by anti-HA immunoprecipitation. Among the tested substitutions, mutation of conserved proline, Pro564Gly totally abrogated interaction and Tyr565Ala reduced the interaction, whereas other mutations had little effect or even enhanced interaction.

Further studies were performed using synthetic polypeptides as inhibitors of the HIF-1α/pVHL interaction (23). When added to an interaction mix of pVHL.HA and HIF-1α IVTT's the 34 residue sequence encompassing amino acids 549-582 was unable to block interaction. However, blocking activity was strikingly induced by exposure to cell extract supplemented with Fe(II) (FIG. 1B). Induction of blocking activity showed precisely the same characteristics as had been determined for promotion of interaction between pVHL and recombinant HIF proteins. Results for a series of polypeptides derived from this domain are summarized in FIG. 1B and implicate a similar minimal interaction domain. One of the polypeptides shown to have blocking activity following exposure to Fe(II) supplemented cell extract was 19:WT. This polypeptide comprises HIF-1α polypeptide residues 556 to 574 and its ability to block binding following exposure to a variety of direct oxidation conditions was assessed. Exposure of polypeptide to Fe(II) (100 μM) with hydrogen peroxide (1 mM), NADH oxidase (1 U/μl) with NADH (1 mM), NADH-FMN oxidoreductase (7 mU/μl) with NADH (1 mM) or metachlorobenzoic acid (1 mM) did not promote the blocking activity whereas exposure to cell extract plus iron did.

In summary, no polypeptide could block the interaction without prior enzymatic modification, blocking activity could not be induced by a variety of direct oxidation systems, phosphorylation of Tyr565 had no effect on the ability of extract, to promote blocking activity, and the mutant sequence Pro564Gly did not block the HIF-1α/pVHL interaction, even after exposure to extract.

Mass spectrometric analyses (24) (MALDI-Tof) of extract-treated synthetic polypeptide, and recombinant HIF (expressed in insect cells and subsequently treated with mammalian extracts to promote pVHL binding ability) implied several oxidations as evidenced by +16 Da mass shifts in ions derived from this sequence. Further analyses by MS/MS (ESI-QTof) indicated oxidation affecting Pro564 and the nearby methionine residues. Since the methionine residues are either non-conserved or could be mutated without effect, and direct oxidation methods known to oxidize methionine efficiently could not mimic the enzymatic activity, we postulated that the enzymatic oxidation that promoted interaction of this HIF-1α sequence with pVHL was the oxidation of Pro564.

1.4 Hydroxyproline Incorporation into a Synthetic Polypeptide.

We synthesized a polypeptide (HIF-1α residues 556-574), containing a trans-4-hydroxy-S-proline residue at position 564 (19:Pro564Hyp), since the trans-4-hydroxylation is the commonest enzymatic proline oxidation (25). A peptide blocking assay was carried out using the 19:Pro564Hyp modified polypeptide and, as a control, the unmodified polypeptide without the trans-4-hydroxylation (19:WT). The 19:WT polypeptide was either incubated with cell extract before the binding assay or was untreated. The 19:Pro564Hyp polypeptide was added to a mixture of HIF-1α and pVHL-HA IVTTs at a concentration of 1, 0.25, 0.05 or 0.01 μM and the cell extract treated or untreated 19:WT polypeptide at a concentration of 0.5 μM. Interaction of HIF-1α with pVHL was then assayed by anti-HA immunoprecipitation. The hydroxyproline substituted polypeptide (19:Pro564Hyp) was highly effective at inhibiting the HIF-1α/pVHL interaction without the need for modification by cell extract. The 19:WT control unsubstituted equivalent polypeptide showed the expected requirement for cell extract in order to inhibit interaction. Control reactions carried out with no blocking polypeptide showed the expected binding of HIF-1α to pVHL-HA. A pVHL capture assay was then carried out using biotinylated synthetic polypeptides. The same polypeptides, 19:Pro564Hyp and 19:WT were assessed for the ability to capture wild type or mutant (Pro86His) pVHL. 19:WT control polypeptide captured pVHL only after incubation with cell extract, whereas 19:Pro564Hyp captured wild type pVHL without pre-treatment. In both cases capture was specific for wild type, as opposed to mutant, pVHL.

In summary, in striking contrast with previously tested polypeptides, 19:Pro564Hyp blocked the HIF-1α/pVHL interaction without the need for exposure to cell extract. Moreover, a biotinylated version of 19:Pro564Hyp specifically captured wild type but not mutant pVHL, and its ability to capture pVHL was not increased further by incubation with cell extract (26). In comparison, the equivalent unmodified synthetic polypeptide 19:WT could not interact without prior incubation with cell extract.

These results reveal that the enzymatic activity promoting interaction of HIF-1α with pVHL is a prolyl-4-hydroxylase, which we term HIF-α prolyl-hydroxylase (HIF-PH). All previously described prolyl-4-hydroxylases are members of the superfamily of 2-oxoglutarate-dependent, and related, dioxygenases (27). Consistent with the data presented above none of these enzymes have an absolute requirement for ATP or NAD(P) but they do have an absolute requirement for Fe(II) as a co-factor and dioxygen as a co-substrate (27). Structural studies within the class have defined a non-haem iron centre co-ordinated by an HXD/E . . . H motif (28). Interestingly, and consistent with our findings, the Fe(11) is not firmly bound and can be readily removed by chelating agents, and enzyme inhibition occurs following substitution of Fe(II) with Co(II) or Ni(II)(25).

1.5: Effect of Ascorbate Supplementation and Various Inhibitors on HIF-PH Activity.

The capture of labelled pVHL by different HIF substrates was monitored after exposure to various test conditions.

The effect of ascorbate on pVHL capture by a Gal/HIF-1α549-582/VP16 fusion protein substrate was monitored and ascorbate (2 mM) was found to enhance the modifying activity of cell extract, but have no effect in the absence of cell extract. Ascorbate therefore enhances the activity of HIF-PH.

We went on to test a series of 2-oxoglutarate analogues which act as competitive inhibitors of this class of enzyme (29) for ability to inhibit HIF-PH as assessed by the ability of cell extracts to modify either HIF polypeptide (19:WT) or a HIF fusion protein (Gal/HIF-1α549-582/VP16) so as to promote pVHL capture. Concordant results were obtained with both sources of HIF sequence. In one such experiment the effect of N-oxalylglycine on pVHL capture by a biotinylated HIF polypeptides as substrate was monitored. The WT:19 and 19:Pro564Hyp polypeptides described above were used as substrates. N-Oxalylglycine (0.2-1 mM) was found to completely inhibit the modifying activity of cell extract on 19:WT. Inhibition by N-Oxalylglycine was overcome by addition of 5 mM 2-oxoglutarate. As previously, 19:Pro564Hyp captured pVHL efficiently without modification by cell extract, and this was not influenced by exposure to N-oxalylglycine. Similar inhibition, also competed by 2-oxoglutarate, was observed with N-oxalyl-2S-alanine but not the enantiomer N-oxalyl-2R-alanine, demonstrating that the effect was not due to simple Fe(II) chelation in solution. We also used a 2-oxoglutarate dependent dioxygenase, phytanoyl-CoA α-hydroxylase (30), together with a readily available unnatural substrate (isovaleryl CoA) (31) to deplete the cell extract of 2-oxoglutarate produced by the citric acid cycle; as predicted, this prevented the subsequent modification of HIF polypeptide. The effect of dimethyl-oxalylglycine on HIF-1α expression was also studied. HIF-1α immunoblot analysis of extracts of Hep3B and U2OS cells exposed to dimethyl-oxalylgylcine (0, 0.1 or 1.0 mM)

for 6 hours was carried out. HIF-1α was seen to be strongly induced under normoxic culture conditions.

Prolyl-4-hydroxylases have been identified in many organisms. In mammalian cells these form $\alpha_2\beta_2$ tetramers in which the β-subunit is identical with the multifunctional protein disulfide isomerase (27). These enzymes function in collagen modification in the endoplasmic reticulum, and are reported to have a strict substrate specificity for prolyl residues in collagen repeat sequences, typically (Pro-Pro-Gly)$_n$(27). When tested as substrate for recombinant [α1 or α2] human prolyl-4-hydroxylase, the HIF polypeptide showed no activity (32). Taken together these findings lead us to postulate that HIF-PH is a novel prolyl-4-hydroxylase which marks HIF promoting recognition by the pVHL ubiquitination ligase system. Since such enzymes utilise molecular oxygen as a co-substrate this predicts a mechanism for direct sensing of oxygen. To test this we examined the effect of hypoxia in the presence of supplements of other co-factors, on HIF-PH activity as assessed by ability to modify the Gal/HIF-1α549-582/VP16 fusion protein so as to promote pVHL capture. HIF substrate was incubated with cell extract (supplemented with 2 mM ascorbate and 10 μM Fe(II)) for 1, 2, 5 or 10 mins at 30° C. under ambient conditions or in the hypoxic workstation. The reaction was stopped by washing with DFO, and the HIF substrate assayed for ability to interact with pVHL. A time-dependent increase in capture was seen in normoxia and a marked suppression of activity by hypoxia.

1.6: Summary of Example 1.

Our findings therefore demonstrate a novel method of protein modification that regulates interaction with pVHL ubiquitylation complexes and indicate that enzymatic prolyl hydroxylation may act directly as a sensor of molecular oxygen. The known properties of 2-oxoglutarate dependent oxygenases readily explain the classical features of mimicry of hypoxia by iron chelators or cobaltous ions. Two explanations have been advanced previously for these findings. First, it has been proposed that cobaltous ions might substitute for ferrous ions at an oxygen sensing iron centre (15). Since most iron centres (e.g. haem and the large majority of iron sulphur clusters) do not exchange in this way it was proposed that such a protein must be turning over rapidly. Second, it has been postulated that cobaltous ions and iron chelators might act by interfering with Fenton chemistry and signalling through reactive oxygen species (17, 33). For instance non-enzymatic 'metal catalysed oxidation' systems that oxidatively modify specific amino acids by local Fenton chemistry can also be inhibited by iron chelators and non-iron transition metal ions (34) providing an alternative hypothesis for effects of these substances on the HIF system. Clearly the labile iron centres associated with prolyl-4-hydroxylases can accommodate the original iron centre substitution hypothesis without the need to propose rapid turnover of the sensor. In contrast we were repeatedly unable to promote specific interactions of HIF-α sequences with pVHL by a variety of non-enzymatic oxidation systems and our evidence clearly indicates an enzymatic mechanism of proline hydroxylation. Our findings do not exclude direct oxidation processes or other oxygen sensing systems impinging on HIF at other sites, on other molecules involved in HIF signal transduction, or indeed on components of the enzymatic prolyl hydroxylation complex. Though our evidence indicates that HIF-PH is distinct from the [α1 and α2] prolyl-4 hydroxylases associated with collagen modification, it is interesting that these enzymes employ protein disulfide isomerase as a β subunit, thus providing a potential link to sulfhydryl redox chemistry. Also of interest, P4HA1 has recently been shown to be HIF responsive (35), suggesting that similar hypoxic induction of HIF-PH activity could down-regulate HIF in prolonged hypoxia, contributing to accommodation of the HIF response.

The pVHL multi-protein complex belongs to the SCF class of ubiquitin ligases, with pVHL acting as the F-box like substrate recognition component (36, 37). To date, characterised examples of recognition by F-box proteins have been regulated by phosphorylation of the target sequence. Furthermore, HIF-α is a phosphoprotein, and phosphorylation has been implicated in HIF regulation (38, 39). While our findings do not exclude the possibility that HIF-α phosphorylation could influence pVHL recognition, they demonstrate that the key event in recognition of the minimal interaction domain studied here is enzymatic hydroxylation of Pro564. This defines a novel mechanism of regulating substrate recognition for the F-box class of ubiquitin ligases. Furthermore, it is of interest that evolutionarily conserved proline residues are observed at a number of other sites in HIF-α subunits, and that other internal regions of HIF-1α can convey oxygen-dependent destruction (6). In other studies we have defined a second subdomain within the N-terminal portion of the HIF-1α oxygen dependent degradation domain that supports pVHL dependent ubiquitylation and contains a functionally critical proline residue. Furthermore, we have established the existence of a functionally conserved pVHL/HIF system in *C. elegans* (see below) and demonstrated the critical importance of a conserved proline residue in the ceVHL/ceHIF interaction (indicated in FIG. 1A).

Overall this suggests that similar marking modifications may occur elsewhere in HIF-α molecules and could contribute to the oxygen sensitive properties of other domains. Whether proline hydroxylation occurs in other molecules on residues that form part of so-called "PEST" domains that are associated with rapid turnover is also clearly now of interest (40). Equally, if the prolyl modification is relatively specific to pVHL-mediated ubiquitylation then the new findings may help define other substrates that are important in pVHL tumor suppressor function.

REFERENCES & NOTES FOR EXAMPLE 1

1. G. L. Semenza, *Genes Dev* 14, 1983-91. (2000).
2. N. V. Iyer, et al., *Genes Dev.* 12, 149-162 (1997).
3. E. Maltepe, J. V. Schmidt, D. Baunoch, C. A. Bradfield, M. C. Simon, *Nature* 386, 403-407 (1997).
4. G. L. Wang, B.-H. Jiang, E. A. Rue, G. L. Semenza, *Proc. Natl. Acad. Sci. USA* 92, 5510-5514 (1995).
5. S. Salceda, J. Caro, *J. Biol. Chem.* 272, 22642-22647 (1997).
6. L. E. Huang, J. Gu, M. Schau, H. F. Bunn, *Proc. Natl. Acad. Sci. USA* 95, 7987-7992 (1998).
7. M. S. Wiesener, et al., *Blood* 92, 2260-2268 (1998).
8. P. H. Maxwell, et al., *Nature* 399, 271-275 (1999).
9. K. Iwai, et al., *Proc. Natl. Acad. Sci. USA* 96, 12436-12441 (1999).
10. J. Lisztwan, G. Imbert, C. Wirbelauer, M. Gstaiger, W. Krek, *Genes Dev* 13, 1822-33 (1999).
11. M. E. Cockman, et al., *J Biol Chem* (2000).
12. M. Ohh, et al., *Nat Cell Biol* 2, 423-7. (2000).
13. T. Kamura, et al., *Proc Natl Acad Sci USA* 97, 10430-5. (2000).
14. K. Tanimoto, Y. Makino, T. Pereira, L. Poellinger, *Embo J* 19, 4298-309. (2000).
15. M. A. Goldberg, S. P. Dunning, H. F. Bunn, *Science* 242, 1412-1415 (1988).

16. G. L. Wang, G. L. Semenza, *Blood* 82, 3610-3615 (1993).
17. G. L. Semenza, *Cell* 98, 281-284 (1999).
18. Hypoxia (<0.1% oxygen) was obtained in a workstation with $O_2$, $CO_2$ and temperature control (Ruskinn Technologies, Leeds, UK). For hypoxic harvest, buffers were preincubated in the chamber overnight. RCC4-VHL.HA, labelling conditions and co-immunoprecipitation assays have been described previously (11); in the current study 12.5 μM MG132 was used for proteasomal inhibition. For standard harvest, the cells were removed from the chamber after hypoxic exposure, prior to cell lysis. Co-immunoprecipitation assays on all lysates were performed at 4° C. under ambient oxygen conditions. Parallel experiments established that adding desferrioxamine (100 μM) to the lysis and immunoprecipitation buffers did not alter the protein species co-precipitated with pVHL.
19. pcDNA3.VHL.HA and pcDNA3.HIF-1α.PK were used to program TNT reticulocyte lysate (Promega). When programming in hypoxia, reaction mix was preincubated in the workstation for 10 minutes before addition of the DNA template. An aliquot was removed from the workstation for transcription/translation under ambient oxygenation. Interaction assays were as described previously (11).
20. Protein expression systems used were wheatgerm lysate (Promega) programmed with pcDNA3 based vectors, insect cell expression using recombinant baculovirus (pFastBac1, (GibcoBRL) encoding PK.HIF-1α (344-698) and PK.HIF-1α (1-826)) bacterial expression as glutathione-S-transferase (GST-VBC complex) and maltose binding protein fusions (pMAL-HIF-1α (344-698)). For insect cell expression, S19 cells (GibcoBRL) were infected 60 hours prior to harvest.
21. pGal/HIF-1α549-582/VP16 was used to program reticulocyte lysate in the presence of unlabelled methionine. The fusion protein product was immunopurified with beads pre-coated with anti-Gal4 antibody RK5C1 (Santa Cruz). After washing with NETN buffer, experimental exposures were to hypotonic extraction buffer HEB: 20 mM Tris pH7.5, 5 mM KCl, 1.5 mM MgCl2, 1 mM DTT) or cell lysate prepared in HEB. Incubations were for 60 minutes at 22° C. unless otherwise stated, following which the beads were washed with NETN containing DFO, and incubated for 2 hours at 4° C. in NETN+DFO with 5 μl rabbit reticulocyte lysate programmed with pcDNA3.VHL.HA.
22. Baculoviral PK.HIF-1α (1-826) or PK.HIF-1α (344-698) were immunoprecipitated with anti-PK antibody (Serotec). Bead bound immunoprecipitates were washed, then incubated with test cell lysates, following which the immunoprecipitates were washed again with NTEN containing DFO, incubated with pVHL, and assayed for interaction.
23. For polypeptide inhibition assays, polypeptides were added to NETN buffer containing a mixture of HIF-1α and pVHL.HA. Final concentration of polypeptide was 1 μM unless otherwise stated. Pre-incubation of polypeptide in cell extract or other conditions was for 60 minutes at 30° C.
24. Samples for mass spectroscopic analyses were either biotinylated synthetic polypeptides 19:WT (residues 556-574), or 34:WT (residues 549-582), or PK-tagged HIF-1α retrieved from insect cell lysates. After modification by mammalian cell lysates the material was purified either by streptavidin/biotin capture (synthetic polypeptides) or anti-PK immunoprecipitation and SDS-PAGE. Proteolytic digestion was performed either on the beads or in-gel with trypsin and V8 protease at pH7.8, or V8 protease at pH4.5. Samples were lyophilised, and dissolved in aqueous 0.1% TFA. Polypeptides were concentrated, desalted on a 300 μm ID/5 mm length C18 PepMap column (LC Packings, San Francisco, Calif., USA) and eluted with 80% acetonitrile. The HPLC (CapLC, Waters, Milford, Mass., USA) was coupled via a Nano-LC inlet to a Q-Tof mass spectrometer (Micromass, Manchester, UK) equipped with a nanoelectrospray Z-spray source. The eluted polypeptide mixture was analysed by tandem mass spectrometric sequencing with an automated MS-to-MS/MS switching protocol. Online determination of precursor-ion masses was performed over the m/z range from 300 to 1200 atomic mass units in the positive charge detection mode with a cone voltage of 30 V. The collision induced dissociation for polypeptide sequencing by MS/MS was performed with argon gas at 20-40 eV and a 3 Da quadrupole resolution.
25. K. I. Kivirikko, R. Myllyla, in *The Enzymology of Post-translational Modification of Proteins* R. B. Freeman, H. C. Hawkins, Eds. (Academic Press, London, 1980) pp. 53-104.
26. For pVHL capture assays using biotinylated polypeptides, the polypeptide was interacted with VHL.HA for 30 minutes at 4° C., and precipitated with streptavidin beads. Pre-incubation with cell extract or buffer under test conditions was for 30 minutes at 30° C.
27. K. I. Kivirikko, J. Myllyharju, *Matrix Biol* 16, 357-68. (1998).
28. C. J. Schofield, Z. Zhang, *Curr Opin Struct Biol* 9, 722-31. (1999).
29. C. J. Cunliffe, T. J. Franklin, N. J. Hales, G. B. Hill, *J Med Chem* 35, 2652-8. (1992).
30. G. A. Jansen, et al., *J Lipid Res* 40, 2244-54. (1999).
31. M. Mukherji, M. D. Lloyd et al. unpublished observations.
32. Prolyl 4-hydroxylase activity was assayed by a method based on the hydroxylation-coupled decarboxylation of 2-oxo[1-$^{14}$C]glutarate (Kivirikko, K. I., Myllylä, R.: Post-translational enzymes in the biosynthesis of collagen: intracellular enzymes. Methods Enzymol., 82, 245-304, 1982) using recombinant human type I and II prolyl 4-hydroxylases expressed in insect cells (26). 0.5 or 1.0 mg of polypeptide was used in each reaction. The assay was performed by Dr. Johanna Myllyharju at the Collagen Research Unit, Department of Medical Biochemistry, University of Oulu, Finland.
33. W. Ehleben, T. Porwol, J. Fandrey, W. Kummer, H. Acker, *Kidney Int.* 51, 483-491 (1997).
34. E. R. Stadtman, *Annu. Rev. Biochem.* 62, 797-821 (1993).
35. Y. Takahashi, S. Takahashi, Y. Shiga, T. Yoshimi, T. Miura, *J Biol Chem* 275, 14139-46. (2000).
36. D. Skowyra, K. L. Craig, M. Tyers, S. J. Elledge, J. W. Harper, *Cell* 91, 209-219 (1997).
37. E. E. Patton, A. R. Willems, M. Tyers, *Trends Genet.* 14, 236-243 (1998).
38. D. E. Richard, E. Berra, E. Gothie, D. Roux, J; Pouysségur, *J. Biol. Chem.* 274, 32631-32637 (1999).
39. P. W. Conrad, T. L. Freeman, D. Beitner-Johnson, D. E. Millhorn, *J. Biol. Chem.* 274, 33709-33713 (1999).
40. M. Rechsteiner, S. W. Rogers, *Trends Biol. Sci.* 21, 267-271 (1996).

Example 2. Identification of Hypoxia Inducible Factor and Von Hippel-Lindau Tumour Suppressor Homologues in C. elegans In this Example we define a HIF homologue in c. elegans and demonstrate that both the transcriptional response to hypoxia, and an important mode of regulation through interaction with the von Hippel-Lindau tumour suppressor are conserved.

2.1 Identification of a Homologue.

Figure 2:
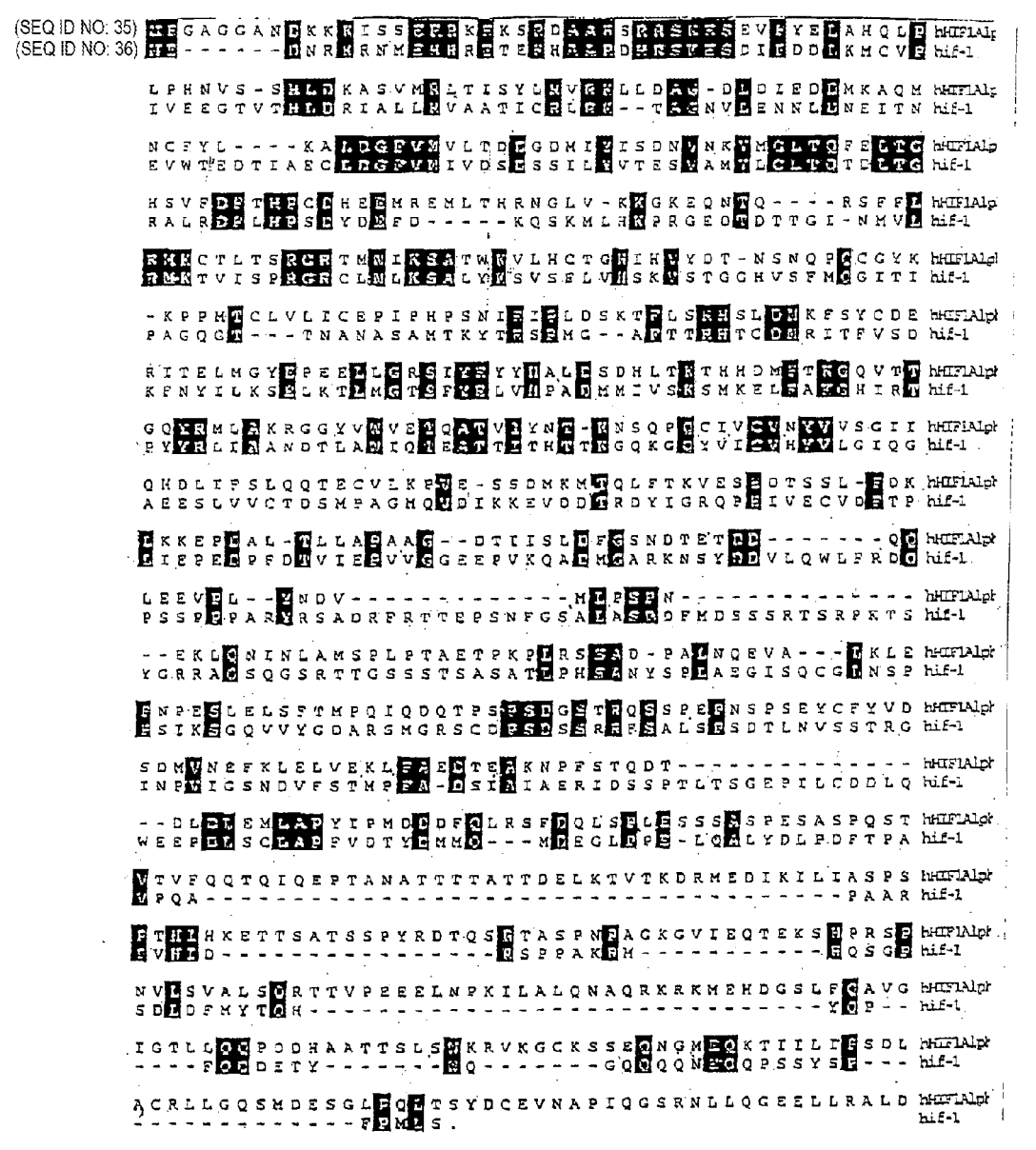

We sought homologues to HIF-α subunits in the c. elegans EST database using an tBLASTn inquiry with the human sequence. Prior to completion of the c. elegans sequencing program an EST was found with significant homology to HIF-α in the basic-helix-loop-helix region, and we assembled a contig of ESTs covering the putative homologue. Complete determination of the c. elegans sequence revealed a further six predicted PAS proteins but no closer matches to mammalian HIF-α. The EST contig we had identified corresponds to a predicted open reading frame (ORF) on chromosome V (F38A6.3) that is identical except for a 104 amino acid amino terminal extension in the latter. Extensive searching of the EST database has not revealed any cDNAs that map to this putative 5' extension. No PCR products corresponding to the extension could be identified and RACE-PCR products did contain a putative trans spliced leader sequence. These findings argue against the predicted N-terminal extension and support the presence of a 719 amino acid protein encoded by 9 exons. FIG. 2 shows an alignment of the human and c. elegans sequences.

2.2: Regulation of HIF in c. elegans.

To characterize the putative c. elegans HIF homologue (ceHIF), we constructed a riboprobe encompassing nucleotides 1366 to 1496 of the predicted open reading frame, and raised antisera to a bacterially expression recombinant protein containing amino acids 360 to 497 of the putative protein. The antisera recognised a single species of the appropriate mobility in Cos7 cells transfected with an expression vector expressing the full length cDNA. Total RNA and protein extracts were prepared from populations of worms exposed to normobaric hypoxia by incubation in bell jars flushed with premixed gases of specified oxygen content balanced with nitrogen. Immunoblotting of worm extracts showed a striking induction of ceHIF under hypoxia.

Immunoblots of ceHIF levels in extracts of c. elegans were carried out to monitor regulation by hypoxia and iron chelation. Firstly, the oxygen dependence of protein induction was analysed. Worms were grown on plates in bell jars flushed with air (N), or with oxygen/balance nitrogen having an oxygen concentration of 5%, 1%, 0.5% or 0.1% for 18 hrs. A graded increase in protein level was seen as the oxygen level was reduced below 5% with the highest level of induction at 0.5 and 0.1% oxygen concentration. The time course of protein induction was then studied. Worms were grown in bell jars flushed with a 0.1% oxygen/balance nitrogen mixture for 0, 4, 8, 16 or 24 hrs before preparation of extracts. The results showed strong induction within 4 hours which was sustained over a 24 hour period. The time course of protein decay on re-oxygenation was then assessed. Worms were grown in bell jars flushed with air (N) or a 0.1% oxygen/balance nitrogen mixture. Extracts were made either immediately, or after 4 and 8 minutes of re-oxygenation. Decay of ceHIF protein was very rapid on re-oxygenation. Protein levels were clearly reduced after 4 minutes and undetectable after 8 minutes of re-oxygenation of the culture. A time course RNAse protection assay showing cehif mRNA levels in worms exposed to 0.1% oxygen/balance nitrogen for 0, 4, 8, 16 and 24 hrs was carried out. No induction of ceHIF mRNA by hypoxia was seen. Thus ceHIF expression was strongly induced by hypoxia at the protein level, but not at the mRNA level, in a manner very similar to that described for mammalian HIF-α subunits. In mammalian cells HIF-α protein is also strongly induced by iron chelating agents as well as hypoxia, a characteristic that has suggested that an interaction of iron and oxygen is central to the underlying mechanism of oxygen sensing. Induction by iron chelation was also studied in C. elegans. Worms were cultured in liquid media in the presence or absence of the penetrant bidentate iron chelator 2', 2' dipyrridyl (200 μM) for 6 or 16 hrs. A striking Induction of ceHIF by iron chelation was observed at both 6 and 16 hours and the level of induction was equivalent to that observed in severe hypoxia. ceHIF was not induced in the absence of iron chelation.

2.3 Conserved Role for VHL.

Regulation of mammalian HIF-α subunit protein levels occurs though a one or more systems of ubiquitin mediated, oxygen regulated proteolysis. To date the most clearly defined of these involves the von Hippel-Lindau tumour suppressor protein (pVHL), which physically interacts with specific HIF-α residues, acting as the recognition component of an E3 ubiquitin ligase. In VHL defective renal carcinoma cells HIF-α subunits are constitutively stabilised leading to greatly increased steady-state levels in normoxia. Recently a putative pVHL homolgue in c. elegans has been proposed on the basis of database analysis and a sequence alignment showing 23% amino acid identity. The analysis of HIF regulation in c. elegans performed here shows a conserved role for pVHL.

To determine whether pVHL function in HIF regulation might also be conserved we first tested for interaction. 35-S labelled ceHIF and HA tagged pVHL were synthesised by IVTT in rabbit reticulocyte lysate, the ceHIF and/or tagged pVHL were then added to EBC buffer with or without worm extract, prior to immunoprecipitation with an anti-HA antibody. Co-immunoprecipitation of ceHIF with pVHL was observed, but only when the recombinant ceHIF IVTT was preincubated with worm extract. Interestingly, though mammalian HIF-α produced in reticulocyte lysates will interact with pVHL, we have found that this is dependent on a factor in the reticulocyte lysate that can be substituted by other mammalian cell extracts, but not the c. elegans extract. Though the human and c. elegans systems appear homologous, this suggests the existence of a species specific modifying factor that promotes the HIF/pVHL interaction. Mammalian pVHL recognises HIF-α through a subsequence within a transferrable oxygen dependent degradation domain (ODDD) that shows short regions of conservation with ceHIF. To test the functional importance of this we mutated a conserved proline residue that is critical for the mammalian interaction and replaced it with glycine. Whilst wild type ceHIF could interact with tagged pVHL, the ceHIF Pro621-Gly mutant form was unable to interact with pVHL mirroring the findings with mammalian HIF.

To pursue the functional importance of the interaction between ceVHL and ceHIF, we next employed a viable homozygous deletion mutant worm lacking ceVHL, and assayed worm extracts for ceHIF by immunoblotting. In normoxic ceVHL worms ceHIF levels were strikingly upregulated and were essentially unregulated by oxygen, being similar in hyperoxia (80% O2), air, and hypoxia (0.1% O2). Thus a critical function for pVHL in the response to oxygen appears also to be conserved. Surprisingly, ceVHL deficient worms are phenotypically relatively normal, with only slightly slower growth rates and mildly reduced reproductive capacity compared to wild type.

This tight conservation of the HIF/pVHL system indicates that c. elegans provides a new model for analysis of the oxygen sensing and signalling pathways that regulate HIF, and for the analysis of downstream effects on patterns of gene expression. As a first step in exploring this potential we assessed ceHIF induction by hypoxia in a mutant worms selected to test candidate molecules in the sensing/signalling pathway. A number of studies support the involvement of oxygen radicals though the source and mode of interaction with the HIF/pVHL complex is unclear. Other studies have suggested the involvement of particular growth factor signalling pathways in HIF regulation, but the relation of these findings to the oxygen sensitive signal is uncertain. In one line of investigation it has been found that insulin and insulin-like growth factors can activate HIF in normoxic cells, that the tumour suppressor PTEN acts as a negative regulator of HIF, and that the downstream target of PTEN, Akt shows oxygen dependent phosphorylation, suggesting the involvement of an insulin receptor/PI3-kinase pathway in HIF regulation. This pathway is conserved in c. elegans, and interestingly has been implicated in ROS metabolism. We therefore tested several mutants to determine their effect on the interaction of ceHIF with VHL.

The level of ceHIF in wild type and a series of mutant worms was determined by immunoblotting. Worms were grown on plates in bell jars flushed with normoxic (21% oxygen) or hypoxic (0.1% oxygen) gas mixtures for 6 hrs. As expected the vhl mutant worms were found to have high levels of ceHIF protein regardless of oxygen tension. The mutants daf-18 (encoding a PTEN homologue), daf-2 (encoding an insulin receptor homologue) and age-1 (encoding a PI3-kinase homolgue), in contrast with the vhl mutant worms, all showed regulation of ceHIF by oxygen that was similar to wild type. The other mutants screened for effects on ceHIF were selected on the basis of known effects on ROS metabolism, or altered phenotypic sensitivity to oxidant stress included several mutants affecting mitochondrial proteins (mev-1, clk-1, gas-1), a ctl-1 mutant that affects cytosolic catalase activity and others (mev-2, mev-3) where the product is not yet characterized and again regulation was similar to wild type suggesting that this a distinct oxygen sensing system that in c. elegans is not tightly linked to general systems of oxidant defense.

In view of the data presented here demonstrating a critical role for enzymatic hydroxylation of prolyl residues within HIF in its normoxic recognition by pVHL and subsequent ubiquitylation and destruction by the proteasome in the mammalian system we also tested worms bearing mutations in known prolyl hydroxylases (dpy-18 and phy-2), and genes containing sequence motifs compatible with a function as a prolyl hydroxylase (egl-9—located at F22E12.4). The effect of prolyl hydroxylase mutants on HIF activity was studied by blotting. Extracts were made from wild type and mutant worms grown in normoxic (21% oxygen) and hypoxic (0.1% oxygen) conditions. Immunoblots for ceHIF were performed after separation on SDS/PAGE. The band representing ceHIF was identified. No detectable ceHIF was seen in an extract from normoxic wild type worms. In contrast in normoxic extracts from egl-9 deficient worms ceHIF is easily detected (allele MT 1201; allele MT 1216 grown at 25 degrees C.), at levels comparable with those seen in extracts from these strains grown in hypoxic conditions. As the egl-9 deficient worms have high normoxic levels of ceHIF, this suggests that this gene product is involved in the normal degradation of ceHIF. The dpy-18 and phy-2 deficient worms showed normal ceHIF levels.

We also used dimethyloxalylglycine (a cell permeant alpha ketoglutarate analogue known to block this family of dioxygenases) and demonstrated an increased abundance of ceHIF in normoxia in the present of the inhibitor. In these experiments extracts were made from wild type worms grown in normoxic (21% oxygen) conditions in the presence and absence of dimethyloxalylglycine (1 mM). Immunoblots for ceHIF were performed after separation on SDS/PAGE. The band representing ceHIF was identified and it could clearly be seen that inhibitor treatment clearly results in a substantial increase in the amount of immunodetectable ceHIF in normoxia.

2.4: Expression of HIF Target Genes.

We wished to test directly for effects of the HIF/pVHL system on patterns of gene expression in c. elegans. First we tested for hypoxia inducible expression amongst a set of c. elegans homologues of mammalian genes that are known HIF targets, and compared the upregulation of mRNA upon hypoxic exposure of wild type worms with that observed in the vhl mutant worm. The results obtained are shown in Tables A and B below.

Table A summarises results for a subset of genes selected for analysis on the basis of putative homology to mammalian HIF target genes and tested for regulation by hypoxia and VHL in c. elegans. Table B summarises results for a subset of genes confirmed as regulated by vhl by RNAse protection after identification in comparative array screening of wild type and vhl mutant worms, and subsequently tested for regulation by hypoxia. The full gene array dataset from which these genes were identified are available at genome-www4.standford.edu.

TABLE A

| Sequence Name | Gene Description | Regulated by Hypoxia | Regulated by VHL |
|---|---|---|---|
| F13D12.2 | Lactate de hydrogenase | + | + |
| F54D8.4 | Putative carbonic anhydrase | − | − |
| T28F2.3 | Putative carbonic anhydrase | − | − |
| R01E6.3 | Putative carbonic anhydrase, strong similarity to human CA2 | + | + |
| R173.1 | Putative carbonic anhydrase | − | − |
| K05G3.3 | Putative carbonic anhydrase, strong similarity to human CA7 | − | − |
| B0412.2 | daf-7/member of the TGFβ superfamily | − | − |
| C14F5.1 | nip 3/bcl-2 | − | − |
| B0432.5 | Putative tyrosine hydroxylase | − | − |

TABLE B

| Sequence Name | Gene Description | Regulated by Hypoxia | Regulated by VHL |
|---|---|---|---|
| F22B5.4 | Protein of unknown function | + | + |
| F35G2.4 | Prolyl 4-hydroxylase alpha subunit | + | + |
| C55B7.4 | Member of the acyl-CoA dehydrogenase protein family | + | + |
| K09E4.4 | Strong similarity to human alpha T-acetylglucosaminidase | − | − |
| T05B4.2 | Member of the nuclear hormone receptor/Zinc finger protein family | + | + |
| H14N18.4 | Member of the gamma-glutamyltransferase (tentative) protein family | − | − |
| C16C10.3 | Piwi related protein | + | + |

Clear induction by hypoxia was observed for mRNA encoding lactate dehydrogenase-A and an isoform of carbonic anhydrase, and in each case the mRNA was strikingly upregulated in vhl worms.

Second we tested for induction by hypoxia among a subset of pVHL dependent differentially expressed gene defined by array screening. Of eight genes demonstrated by RNAse to be upregulated in vhl worms five were strongly inducible by hypoxia in wild type worms.

Oxygen homeostasis is a fundamental physiological problem in all organisms that can live in an aerobic environment, and genetic studies in bacteria and yeast have defined specific sensing systems that regulate gene expression in accordance with oxygen availability. However efforts to link these systems to responses in mammalian cells have so far been unsuccessful, and database analysis has not reveal a HIF homologue in the s. cerevisiae genome or sequenced prokaryotic genomes. The current work therefore provides the clearest analysis to date of homology with a primitive organism that has been developed for genetic analysis. Given recent advances in large scale analysis of gene expression gene function in c. elegans the findings provide important new opportunities to understand cellular responses to oxygen availability.

In mammalian cells transcriptional activation of HIF is believed to be a multi-step process involving separate regulatory steps in nuclear localization, DNA binding, and co-activator recruitment as well as different systems of ubiquitin mediated proteolysis. Somewhat surprisingly, in VHL defective renal carcinoma cell lines HIF-α subunits are constitutively stabilised and hypoxia inducible mRNAs are constitutively upregulated in normoxic cells, indicating that at least in this cell background pVHL has a dominant non-redundant function in the regulation of the HIF transcriptional response. Both ceHIF protein and its transcriptional target mRNAs also showed striking up-regulation in normoxic vhl mutant worms. Importantly this indicates that a critical non-redundant function of VHL in regulation of HIF extends outside the cell background of VHL associated tumours, and most likely operates generally in higher eukaryotes.

In mammalian systems the HIF/pVHL system has important functions in the regulation of oxygen delivery through effects on angiogenesis, vasomotor control and erythropoiesis. Conservation, in c. elegans indicates that the HIF/pVHL system of oxygen regulated gene expression antedates the development of these complex oxygen delivery systems and that the system must have a critical function in other responses to oxygen availability. The effects observed already on the expression of metabolic enzymes may provide clues to such functions. However though the viability of both vhl mutant and hif mutant worms in the laboratory suggests that the critical functions that have directed the evolution of this system are likely to be observed under other, presumably more stressful, conditions.

2.5: Methods

Identification of c. elegans hif cDNA. C. elegans EST database searches were performed using the tBLASTn program and the human HIF-1α sequence as a probe. The putative c. elegans hif cDNA was assembled from 4 overlapping cDNA clones, yk510h7, yk4a2, yk383g1, and yk272d11 (kindly provided by Yuji Kohara, National Institute of Genetics, Mishima, Japan), and inserted into the polylinker of pcDNA1AMP (invitrogen) to create pcDNA1cehif using standard methods.

Antibody Generation and Immunoblotting.

DNA encoding amino acids 360 to 497 of ceHIF was inserted into pGEX-4t-1 and the corresponding GST/ceHIF fusion protein was expressed in E. coli. The protein was purified using glutathione agarose and used to raise antisera in rabbits. Antisera were tested for reactivity using extracts of Cos7 cells transfected with pcDNA1cehif, and purified by ammonium sulphate precipitation. Worm extracts used in immunoblotting were prepared from washed worms by homogenisation in 4 volumes extraction buffer (150 mM NaCl, 1 mM EDTA, 50 mM Tris pH 7.5, 1% NP-40 1% sodium deoxycholate) using an Ultraturax T20 homogeniser.

Riboprobes and RNAse Protection

Riboprobe templates were generated from total c. elegans RNA using RT-PCR. Details of the primers, and sequences are provided in supplementary information. RNAse protection assays were performed as described in (ref) using 10-50 mg total RNA prepared from a mixed population of worms using Tri-Reagent (Sigma).

Protein Expression and Interaction Assays.

35S labelled proteins were generated in reticulocyte lysates (Promega) programmed with plasmids encoding wild type ceHIF (pcDNA1cehif), mutant ceHIF (pcDNA1cehif.P621G) or c-terminal HA tagged ceVHL (pcDNA3ceVHL-HA). pCDNA1cehif.PxxxG was generated from pcDNA1cehif using a site directed mutagenesis system (Stratagene) and the following forward and reverse primers:

```
                                            (SEQ ID NO: 46)
5' GATTTATCGTGCTTGGCAGGATTCGTTGACACTTATG (forward)

(SEQ ID NO: 47)
5' GTGTCAACGAATCCTGCCAAGCACGATAAATCAGGC (reverse).
``` pcDNA3ceVHL.HA was obtained by RT-PCR amplification of nucleotides 1 to 525 of the predicted ORF of sequence F08G12.4 from c. elegans RNA, and exchange for human VHL sequence in pcDNA3-VHL.HA. For interaction assays 1 µl of each programmed lysate was mixed in EBC buffer at 4° C. for 1 hr before anti-HA immunoprecipitation as described in Cockman et al. Pretreatment of ceHIF with worm extract was for 30 min at 25° C. with 10 µl of extract derived by hypotonic extraction of a worm homogenate in 20 mM Tris pH7.5, 5 mMKCl, 1.5 MgCl2, 1 mMDTT.

Worm Strains and Experimental Conditions

C. elegans strains were cultured as described by Brenner [Brenner, 1974 #1]. Exposure to hypoxia was in bell jars gassed with humidified air or certificated nitrogen/oxygen mixes (British Oxygen Company). Exposure to iron chelators worms was by growth in a liquid medium as described previously [Lewis, 1997 #2] with or without 200 µM 2,2 Dipyridyl. Wild type worms were Bristol strain (N2). ok161 was generated by Dr. Robert Barstead, Oklahoma Medical Foundation, using ultraviolet and psoralen mediated utagenesis. PCR using oligonucleotides from the flanking genomic sequence was used to select worms bearing a deletion at the F08G12.4 (vhl) locus. Confounding mutations in ok161 were removed by backcross selection using visible markers that flank the VHL locus (dpy-6 unc-9).

Example 3: The VHL E3 Ligase Complex Interacts with Two Independent Regions of HIF-1α

In this Example we show that two independent regions of the HIF-1α ODDD are targeted for ubiquitylation by VHL E3 in a manner dependent upon proline hydroxylation. However these two VHL E3 target sites differ in their overall sequence, their ability to bind VHL directly and their requirement for other cellular factors. These data reinforce the critical role for pVHL in regulation, but implicate a more complex model for pVHL/HIF-α interactions.

Immunoprecipitation and band shift assays show that VHL and subunits are physically associated in a wide range of cell types, consistent with a general role for VHL in oxygen-dependent regulation of HIF-α subunits. At the same time biochemical studies show that VHL exists as a multiprotein complex with elongins B and C, CUL-2 and RBX1. This complex is homologous to the SCF (Skp-1-Cdc53/Cullin-F-box) class of E3 ubiquitin ligases. Like SCF E3, the VHL complex has inherent ubiquitin ligase activity. VHL itself is thought to play a role analogous to the F-box substrate recognition component. HIF-α subunits are therefore clear candidate substrates for VHL E3 and have since been shown to be ubiquitylated in a VHL-dependent manner in vitro.

Example 1 above demonstrates that degradation of HIF-1α mediated by the VHL binding site occurs through oxygen-dependent hydroxylation at proline 564. It is currently unclear whether oxygen-dependent degradation of HIF-α subunits is solely VHL-dependent. In renal cell carcinoma lines and in CHO cells VHL appears to be the critical mediator. However only one VHL binding site has been identified in HIF-1α and regions outside this site can confer oxygen-dependent regulation in vivo. To investigate the mechanisms underlying this we have employed in vitro ubiquitylation assays which provide evidence of functional interaction with the VHL E3 ligase. We find that two independent regions of the HIF-1α ODDD are targeted for ubiquitylation by VHL E3 in a manner dependent upon proline hydroxylation. However these two VHL E3 target sites differ in their overall sequence, their ability to bind VHL directly and their requirement for other cellular factors. These data reinforce the critical role for pVHL in HIF-α regulation, but implicate a more complex model for pVHL/HIF-α interactions.

Materials and Methods

Plasmid Constructs—

$His_6$-E1-tagged mouse E1 cDNA in pRSET was a kind gift of T. Hunt. pcDNA3-VHLHA has been previously described Cockman et al. pGAL 344-417VP16 has been previously described (O'Rourke). Plasmids bearing mutations were generated using a site-directed mutagenesis kit (QuickChange; Stratagene) and mutagenic oligonucleotides designed according to the manufacturer's recommendations. All PCRs were performed using pfu DNA polymerase (Stratagene).

Cell Culture and Transient Transfections—

7860, U2OS and RCC4 cells were maintained in Dulbecco's modified Eagle's medium supplemented with 10% fetal calf serum, glutamine (2 mM), penicillin (50 IU/ml) and streptomycin sulfate (50 µg/ml). Ka13 cells (Wood et al) were grown in Ham's F12 medium with the same supplements.

Cell Extract Preparation and Western Blotting—

Cytoplasmic extract for ubiquitylation assays was prepared as previously described (Cockman et al). S100 extract was obtained by an additional ultracentrifugation step at 100,000 g at 4° C. for 4 h. Extracts for Western blotting were prepared by resuspending cell pellets in 7M urea, 10% glycerol, 1% SDS, 10 mM Tris pH6.8, containing 50 µM phenylmethylsulfonyl fluoride and leupeptin, pepstatin and aprotinin all at 0.1 µg/ml, followed by disruption using a hand-held homogenizer (Ultra-Turrax T8 with 5G dispersing tool; Janke & Kunkel GmbH). Following SDS-PAGE. proteins were transferred onto Immobilon-P membrane (Millipore) and processed for western blotting using the indicated antibody.

Antibodies—

Anti-HA antibody (12CA5) was from Roche Molecular Biochemicals, anti-GAL4 (DBD) (RK5C1) agarose conjugate from Santa Cruz Biotechnology and anti-HIF-1α clone 54) antibody from Transduction Laboratories.

Ubiquitylation Enzymes and Assays—

The E1 activating enzyme used in ubiquitylation assays was either obtained from Affiniti Research (Exeter, UK) or purified from BL21 (DE3) E. coli transfected with plasmid expressing $His_6$-tagged mouse E1. $His_6$-E1 was purified by $Ni^{2+}$-agarose affinity chromatography. After dialysis against phosphate buffered saline, glycerol was added to 10% (vol/vol) and 25 ng/µl aliquots stored at −80° C. Human CDC34 recombinant E2 enzyme was from Affiniti Research (Exeter, UK). VHL E3 was obtained by anti-HA immunoprecipitation from stably transfected 7860-VHLHA cell lysates (Iliopoulos et al). GAL-HIF-1α substrate was prepared by anti-GAL immunoprecipitation from [$^{35}$S] methionine-labeled TnT rabbit reticulocyte (Promega) translates. Each 40 µl ubiquitylation reaction consisted of 4 µl of 5 mg/ml ubiquitin, 4 µl of 10×ATP regenerating system (20 mM Tris pH7.5, 10 mM ATP, 10 mM magnesium acetate, 300 mM creatine phosphate, 0.5 mg/ml creatine phosphokinase), 2 µl, E1, 3 µl E2, 6 µl VHL E3 immunopurified on protein G sepharose, 6 µl GAL-HIF-1α substrate immunopurified on agarose beads. Reactions were incubated at 30° C. for 2 h with occasional mixing, stopped by the addition of SDS sample buffer and analysed by SDS-PAGE and autoradiography. Cytoplasmic extract-based ubiquitylation assays have been previously described (Cockman).

In Vitro Interaction Assays—

TnT rabbit reticulocyte (Promega) translates (4 µl [$^{35}$S] methionine-labeled) were mixed either in 70 µl hypotonic extraction buffer (20 mM Tris ph7.5; 5 mMKCl; 1.5 mMMgCl2; 1 mM DTT) or RCC4 cytoplasmic extract at 30 degrees C. for 1 hour. Samples were then cooled and incubated with 400 µl extract from 786-0 cells stably transfected with pcDNA3 VHL.HA for 90 minutes on ice prior to immunoprecipitation with excess anti-HA antibodies and protein G beads. Input samples of the GAL-HIF-1 alpha fusion proteins and retrieved immunoprecipitates were analysed by SDS/PAGE and autoradiography.

Luciferase and Beta-Galactosidase Assays—

Luciferase activities in cell extracts were determined using a commercially available luciferase assay system (Promega) and a TD-20e luminometer (Turner Designs). Relative beta-galactosidase activity in extracts were measured using o-nitrophenyl-beta-D-galactopyranoside (0.67 mg/ml) as substrate in a 0.1 M phosphate buffer (pH 7.0) containing 10 mM KCl, 1 mM $MgSO_4$ and 30 mM beta-mercaptoethanol incubated at 30° C. for 15-45 min. The $A_{420}$ was determined after stopping the reaction by the addition of 0.4M sodium carbonate (final concentration).

Cell Extract Preparation and Western Blotting—

Cytoplasmic extract for ubiquitylation assays was prepared as previously described (Cockman et al). S100 extract was obtained by an additional ultracentrifugation step at 100,000 g at 4° C. for 4 h. Extracts for Western blotting were prepared by resuspending cell pellets in 7M urea, 10% glycerol, 1% SDS, 10 mM Tris pH6.8, containing 50 µM phenylmethylsulfonyl fluoride and leupeptin, pepstatin and aprotinin all at 0.1 µg/ml, followed by disruption using a hand-held homogenizer (Ultra-Turrax T8 with 5G dispersing tool; Janke & Kunkel GmbH). Following SDS-PAGE.

proteins were transferred onto Immobilon-P membrane (Millipore) and processed for Western blotting using the indicated antibody.

3.1 the VHL E3 Ligase can Interact Functionally with Two Distinct Regions of the HIF-1α ODDD In Vitro.

In order to understand more about the interactions of pVHL with HIF-1α we analysed VHL-dependent ubiquitylation of the HIF-1α ODDD in an in vitro assay using cytoplasmic extracts as a source of ubiquitylation enzymes. 35S-methionine labelled GAL-HIF-1 alpha fusion proteins containing the amino acids 344 to 698, 344 to 553, 554 to 698 or 504 to 554 of HIF-1α were generated by IVTT and subjected to in vitro ubiquitylation in cytoplasmic extracts from RCC4 cells, which lack pVHL (RCC4), or RCC4 cells stably transfected with pcDNA3 VHL.HA (RCC4/VHL) in the presence or absence of exogenous ubiquitin. PVHL dependent ubiquitylation, resulting in a strong signal of decreased mobility at the top of the lane, was clearly observed when the substrate contained HIF-1 alpha amino acids 344-698, 344-553 and 554-698, but not amino acids 504-554. HIF-α residues 344-553 and 554-698 are both capable of oxygen-dependent regulation in vivo (O'Rouke et al) and when analysed in vitro here both regions exhibit VHL-dependent ubiquitylation. This indicates that the VHL E3 ligase can interact functionally with at least two sites in HIF-1α.

3.2 Requirements for Functional Interactions.

To investigate this further, it was necessary to develop a ubiquitylation assay using purified components. 35S-methionine labelled GAL-HIF-1α amino acids 344-698 fusion protein was generated by IVTT, immunopurified with anti-Gal antibody conjugated agarose and subjected to in vitro ubiquitylation with purified components. This resulted in the production of high molecular weight GAL344-698-related species in a ubiquitin and ATP-dependent manner. These high molecular weight species correspond to ubiquitylated forms of GAL344-698 as their production is E1-, E2- and VHLE3-dependent.

In vitro ubiquitylation was then performed on a variety of GAL-HIF-1α fusions. 35S-methionine labelled immunopurified GAL-HIF-1α fusions comprising amino acid residues 344 to 698, 344 to 553, 554 to 698 or 652 to 826 of HIF-1α were used as substrates using reaction mixtures containing E1, E2, VHL E3 ligase, ubiquitin and ATP or reaction mixtures where ubiquitin or VHL E3 ligase were omitted to act as controls. VHL E3 ligase dependent ubiquitylation was clearly seen when the substrate contained HIF-1α amino acids 344-698, 344-553 or 554-698 but not for substrates containing residues 652-826 of HIF-1α. The fusion containing residues 652-826 of HIF-1α acted as a control as residues 652-826 of HIF-1α show no oxygen-dependent regulation at the protein level in vivo (O'Rouke) and do not interact with pVHL in vitro (Cockman et al). As the GAL 344-553 and GAL 554-698 substrates were both found to be targets for the VHL E3 but GAL652-826 are not, the results obtained using the purified component assay concurs with the cytoplasmic extract assay in identifying HIF-1α residues 344-553 and 554-698 as independent VHL E3 targets in vitro.

3.3 Cytoplasmic Extract Enhances Functional Interaction of the VHL E3 Ligase with the 5' Target Site in HIF-1α.

It was noted however that VHL-dependent ubiquitylation of the GAL 344-553 substrate differed greatly between the two assays. In the cytoplasmic extract assay GAL 344-553 is a much better substrate for VHL-dependent ubiquitylation than GAL 554-698, but in the purified component assay the position is reversed with GAL 344-553 an extremely weak substrate. We wondered whether cytoplasmic extract was important for recognition of the 344-553 region by VHL E3. To test this 35S-methionine labelled GAL 344-553 substrate was generated by IVTT, incubated in buffer, cytoplasmic extract or nuclear extract prior to in vitro ubiquitylation in the purified component assay in the presence or absence of the VHL E3 ligase. Treatment with cytoplasmic extract dramatically enhanced the VHL dependent ubiquitylation of the substrate. Thus, whilst the buffer-treated substrate remains an extremely weak target for VHL E3, pre-treatment with cytoplasmic extract has a dramatic effect, converting the GAL 344-553 substrate into a strong target for VHL-dependent ubiquitylation. Accompanying this effect a marked mobility shift of the GAL 344-553 substrate was seen due to phosphorylation in the cytoplasmic extract.

Phosphorylation is known to play an important role in regulating recognition of substrates by the SCF E3 ligase. HIF-1α is known to be a phosphoprotein, although an oxygen-dependent phosphorylation event has not been identified. A potential link between HIF-1α phosphorylation and ubiquitylation was therefore of interest. Pre-incubation of the GAL 344-553 substrate with nuclear extract also resulted in a phosphorylation-induced mobility shift, but this was not accompanied by increased VHL-dependent ubiquitylation.

To clarify the role of phosphorylation in the cytoplasmic extract effect, hexokinase treatment was used. 35S-methionine labelled GAL-HIF-1 alpha amino acids 344-553 fusion protein substrate was generated by IVTT, incubated in buffer, cytoplasmic extract, cytoplasmic extract that had been depleted of ATP by pre-incubation with hexokinase or cytoplasmic extract which had been heat denatured. Enhanced VHL dependent substrate ubiquitylation was found to persist in the absence of ATP (and consequent absence of phosphorylation) but not following heat denaturation. As the ATP-depleted extract can no longer support GAL 344-553 phosphorylation but is still capable of supporting enhanced VEIL-dependent ubiquitylation, phosphorylation of GAL 344-553 is therefore not the key event mediating interaction with VHL E3. As heat-treated cytoplasmic extract was unable to support enhanced VHL-dependent ubiquitylation this suggests that a protein factor may be involved either in binding to, or modifying the GAL 344-553 substrate.

The demonstration in Example 1 above that interaction of VHL with the VHL binding site in HIF-1α is promoted by cytoplasmic extract and iron led us to test the effect of cytoplasmic extract on ubiquitylation of the GAL 554-698 substrate and to test the effect of iron on ubiquitylation of GAL 344-417. 35S-methionine labelled GAL-HIF-1α fusions comprising amino acids 344-417 or 554-698 of HIF-1α substrates were generated by IVTT, incubated in buffer, cytoplasmic extract, cytoplasmic extract supplemented with 100 µM iron chloride prior to in vitro ubiquitylation in the purified component assay in the presence or absence of the VHL E3 ligase. Iron was found to enhance the ubiquitylation of Gal-HIF-1α 344-417 fusions in the presence of cytoplasmic extract. Cytoplasmic extract enhanced the ubiquitylation of Gal-HIF-1 alpha 554-698 although the effect was less pronounced than that of GAL344-417. These data suggested that the two independent VHL E3 ligase target sites may be regulated by a similar mechanism.

3.4 Mapping of 380-417 as a Minimal Domain Targeted by Cytoplasmic Extract and VHL E3.

To begin to understand the mechanism it was necessary to define a minimal functional domain. Residues 344-553 correspond to exons 9-11 of HIF-1α and so an exon-based deletional strategy was used. 35S-methionine labelled GAL- HIF-1 alpha amino acids 344-553 fusion protein substrate was generated by IVTT, incubated in buffer or cytoplasmic extract prior to in vitro ubiquitylation in the purified component assay in the presence or absence of the VHL E3 ligase. The GAL 344-503 fusion (corresponding to exons 9 and 10 of HIF-1α) still displayed enhanced VHL-dependent ubiquitylation following cytoplasmic extract pre-treatment. Exons 9 and 10 were then assayed individually by generating fusions carrying GAL-HIF-1α amino acid residues 344 to 503, 344 to 417 or 418 to 503. The only fusion which was not ubiquitylated was that carrying residues 418 to 503. Thus both ubiquitylation and the cytoplasmic extract effect were found to localise to exon 9, represented by GAL 344-417. VHL dependent extract enhanced ubiquitylation therefore clearly depends on HIF-1α amino acids 344-417.

The corresponding exon in HIF-2α was then assayed. The substrates used were Gal-HIF-2α fusion comprising amino acids 344-417 or 345-416. Residues 345-416 of HIF-2α were also found to be a target for VHL-dependent ubiquitylation and also exhibited enhanced ubiquitylation following cytoplasmic extract pre-treatment. The function of this region is therefore conserved between HIF-1α and HIF-2α and sequence comparisons will help to identify critical residues.

Deletional analysis was further extended to screen the HIF-1α 344-417 region. Gal-HIF-1α fusions comprising amino acids 344 to 417, 344 to 400, 344 to 379, 360 to 417 or 380 to 417 of HIF-1α were individually assessed as above. Deletions made at the C-terminus completely ablated VHL-dependent ubiquitylation (GAL 344-400 and GAL 344-379), whereas deletions made at the N-terminus retained activity. The minimal functional domain defined by this analysis was HIF-1α residues 380-417. Although the output ubiquitylation signal was reduced, GAL 380-417 was still a target for VHL-dependent ubiquitylation and still displayed enhanced ubiquitylation following cytoplasmic extract pre-treatment.

3.5 Identification of a Potential Functional Motif Conserved Between the 5' and 3' VHL E3 Target Sites.

The HIF-1α 380-417 sequence was analysed in an attempt to identify residues critical to the functional effect. The HIF-1α sequence was aligned with the corresponding region of HIF-2α and the VHL-binding site. Within the VHL-binding site, hydroxylation at praline 564 is identified in Example 1 above as a key regulatory event. Interestingly, a potential conserved motif encompassing this proline can be identified between the two VHL E3 ligase target sites (FIG. 3A). Mutations of this potential motif were assayed in the context of GAL 344-417. 35S-methionine labelled GAL-HIF-1 alpha amino acids 344-417 wild type and mutant substrates (comprising the mutation P402A or the double mutation LL397, 400A) were generated by IVTT, incubated in buffer or cytoplasmic extract prior to in vitro ubiquitylation in the presence or absence of the VHL E3 ligase. The double mutation of leucines 397 and 400 to alanine (LL 397,400 AA) was found to ablate VHL-dependent ubiquitylation. The point mutation of proline 402 to alanine (P 402 A) also ablated VHL-dependent ubiquitylation.

Mutations of the 344-417 region were then tested for their effects on oxygen-dependent regulation in vivo. The HIF-1α 344-417 region is known to confer oxygen-dependent regulation on a GAL-VP16 fusion (O'Rouke). The C-terminal deletion (344-400) and the P 402 A mutation were tested in this context and both were found to abolish oxygen-dependent regulation in vivo (FIG. 3B).

3.6 Identification of Critical Point Mutations.

Figure 4:
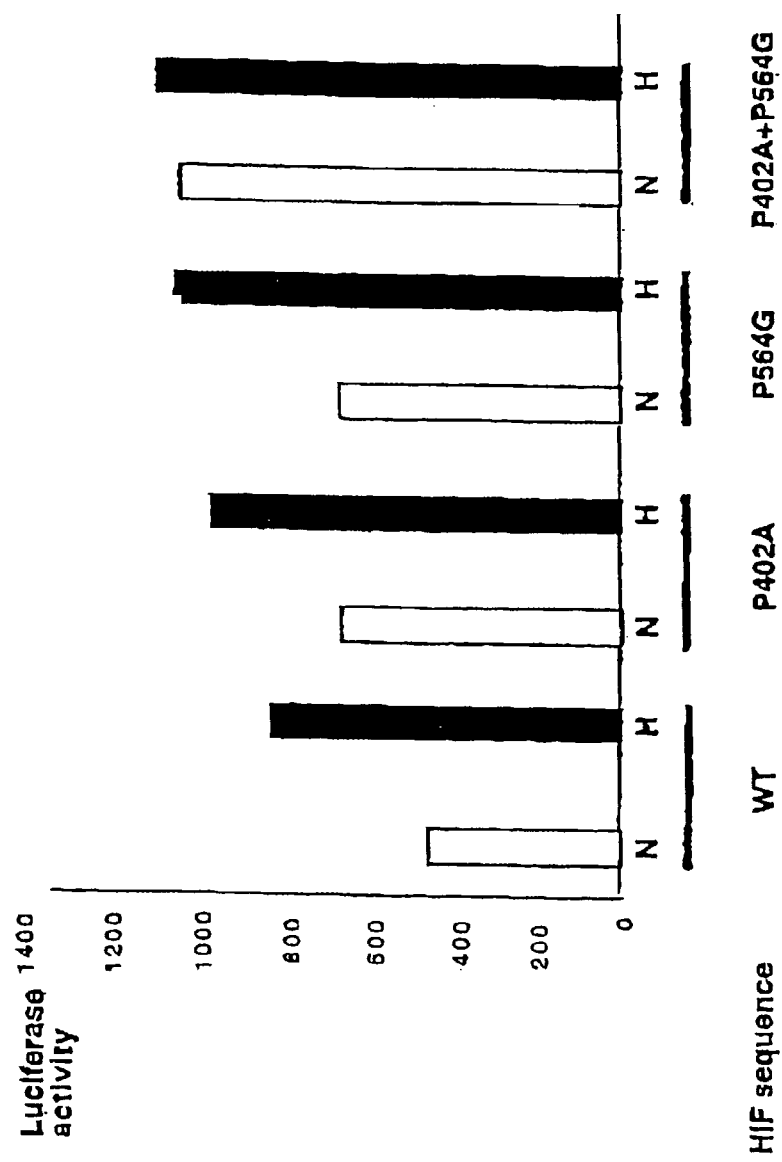
FIG. 4 The CHO mutant cell line Ka13 (deficient in Hif alpha subunit activity) was co-transfected with pcDNA3 expression plasmids encoding wild type full length Hif-1 alpha (HIF-1), full length Hif-1 alpha bearing the P402A mutation. (P402A), full length Hif-1 alpha bearing the P564G mutation (P564G) or full length Hif-1 alpha bearing the double mutation (P402A+P564G) in combination with a hypoxia response element dependent luciferase reporter gene construct. Luciferase activities were determined in extracts made from transfected cells maintained for 48 hours, either entirely in normoxia (white bars) or with hypoxic stimulation for the last 16 hours (black bars). The individual mutations showed slightly enhanced normoxic activity compared with the wild type sequence but the combined mutant showed constitutive activity in normoxia with no further induction by hypoxia.

Identification of critical point mutations allows these two VHL E3 target sites to be assayed within the full-length HIF-1α molecule. The P 402 A mutation was introduced to ablate activity of the 5' VHL E3 target site and the P 564 G mutation to ablate activity of the 3' VHL E3 target site. 35S-methionine labelled full length HIF-1α wild type and mutant substrates were generated by IVTT and subjected to in vitro ubiquitylation in cytoplasmic extracts from RCC4 cells, which lack pVHL (RCC4), or RCC4 cells stably transfected with pcDNA3 VHL.HA (RCC4/VHL) in the presence or absence of exogenous ubiquitin. The double mutant P402A+P564G was found to show no VHL dependent ubiquitylation, but isolated mutations of the critical prolines at each individual VHL E3 target site did not ablate ubiquitylation. Thus when these mutations are introduced individually the mutant HIF-1α proteins still remain targets for VHL-dependent ubiquitylation (presumably because each retains an active VHL E3 target site). HIF-1α therefore appears to contain two, and only two target sites for VHL-dependent ubiquitylation. To assay importance in vivo, the single and double VHL E3 target site mutants were transfected into the HIF-1α deficient cell line KA13 (Wood et al) and tested for their ability to mediate oxygen-dependent trancriptional regulation (FIG. 4). The transfected wild-type HIF-1α protein displayed oxygen-dependent regulation. However the P 402 A, and P 564G point mutants were transcriptionally active under normoxic conditions and showed very little upregulation in hypoxia (FIG. 4). The P 402 A+P 564G double mutant was essentially constitutive under normoxic conditions (FIG. 4).

3.7 the 5' and 3' VHL E3 Target Sites Differ in their Functional Requirements.

The ability of pVHL to interact directly with both the 5' and 3' E3 target sites was tested in vitro. The 35S-methionine labelled GAL-HIF-1α fusion proteins GAL 344-553 P402A, GAL 344-553, GAL 652-826, GAL 554-698 were made by IVTT, incubated in buffer or cell extract from RCC4 cells lacking pVHL at 30 degrees C. for 1 hour. Samples were then cooled and incubated with extract from 786-0 cells stably transfected with pcDNA3 VHL.HA for 90 minutes on ice prior to immunoprecipation with anti-HA antibodies and protein G beads. Input samples of the GAL-HIF-1 alpha fusion proteins and retrieved immunoprecipitates were analysed by SDS/PAGE and autoradiography. The 3' VHL E3 target site is already known to bind VHL in an in vitro interaction assay (Cockman et al) and the results obtained confirmed this. In contrast the 5'VHL E3 target site (represented by GAL 344-553) does not appear to bind pVHL in this assay. Either the interaction of pVHL with the 5' E3 target site is transient and too weak to be detected, or the interaction is not direct. After treatment of the Gal-Hif-1 alpha fusion proteins with cytoplasmic extract both the 5' and 3' VHL E3 target sites can be captured by the anti-HA immunoprecipitation. Interaction is not seen when the Gal-Hif-1 alpha fusion protein contains the P402A mutation known to disrupt function of the 5' site.

In a previous domain analysis of HIF-1α the 5' VHL E3 target site was not detected (Ohh et al). We wondered whether this was due to the use of S100 extract, VHL-dependent ubiquitylation of both the 5' and 3' E3 target sites was compared using the standard cytoplasmic extract or S100. 35S-methionine labelled GAL-HIF-1 alpha amino acids 344-553 fusion protein and GAL-HIF-1 alpha amino acids 554-698 fusion protein substrates were generated by IVTT. Ubiquitylation was performed in fresh cytoplasmic extract, cytoplasmic extract which had been left at 4 degrees C. for 4 hours or the S100 supernatant of cytoplasmic extract from RCC4 cells, which lack pVHL or RCC4 cells stably transfected with pcDNA3 VHL.HA. The S100 extracts clearly enabled VHL dependent ubiquitylation of GAL-HIF-1 alpha amino acids 554-698 fusion protein but not GAL-HIF-1 alpha amino acids 344-553 fusion protein. A factor specifically required for recognition of the 5' VHL E3 target site is either lost or inactivated during S100 preparation.

3.8 the 5' VHL E3 Target Site is Also Regulated by Praline Hydroxylation.

It has been shown above that the 3' VHL E3 target site responds to oxygen level via hydroxylation at proline residue 564. This praline residue forms part of a potential motif conserved between the 5' and 3' target sites. Mutation of the corresponding proline residue (P402A) in the 5' target site also results in functional inactivation. It was possible therefore that proline residue 402 was also a target for regulatory hydroxylation, To test this we asked whether polypeptides corresponding to the 3' VHL E3 target site could interfere with the cytoplasmic extract-dependent modification of the 5' VHL E3 target site. 35S-methionine labelled GAL-HIF-1 alpha amino acids 344-553 fusion protein substrate was generated by IVTT and incubated in vitro in buffer or cytoplasmic extracts from RCC4 cells in the presence of wild-type 19mer peptide representing HIF-1 alpha amino acids 556-574 (12.5 µM); a polypeptide where the critical proline is mutated to glycine (P564G); or a polypeptide where the proline is modified to a hydroxy-proline (P—OH). The products of this reaction were then used as substrates in an in vitro ubiquitylation assay in the presence or absence of VHL E3 ligase. The 19mer wild-type polypeptide (P) was found to completely ablate the cytoplasmic extract effect. In contrast a polypeptide in which the critical praline is mutated to glycine (P-G) was found to have no effect. The 3' VHL E3 target site polypeptide can therefore compete the cytoplasmic extract-dependent modification at the 5' site in a manner dependent upon integrity of proline 564. Pre-hydroxylation of proline 564 rendered the polypeptide unable to compete for modification at the 5'VHL E3 target site presumably because it is no longer a substrate for the enzymatic modification which is occurring at the 5' VHL P3 target site. Thus proline hydroxylation appears to be involved in regulating VHL-dependent ubiquitylation at both the 5' and 3' E3 target sites.

3.9 Discussion.

Through the use of in vitro ubiquitylation assays we have identified 2 independent regions of HIF-1α targeted by the VHL E3 ligase. Both target sites are located within the ODDD and are functional in vivo. Identification of the two VHL E3 target sites is consistent with published data which implied the existence of more than one oxygen-dependent degradation domain within HIF-1α. Residues 532-585 of HIF-1α encompassing the 3' VHL E3 target site has previously been shown to be a target for VHL-dependent ubiquitylation. Identification of a second VHL P3 target site provides further evidence of the critical role played by VHL in HIF-1-mediated oxygen-sensing.

Although HIF-1α possesses two target sites for VHL E3, they appear to be functionally different. The 3' VHL E3 target site corresponds to the previously identified VHL-binding site. This region of HIF-1α appears to be targeted directly by VHL acting as the recognition component of the VHL E3 ligase. In contrast we have no evidence that the 5° VHL E3 site can bind VHL directly although it can interact with the complete VHL E3 ligase complex. This may be because the interaction of VHL with the 5' site is indirect or weak compared to the 3' site and difficult to detect by the in vitro binding assay used. Both target sites contain a potential consensus motif "LXXLAP" but differ in the sequences surrounding the motif. Since the sites also differ functionally (i.e. in their ability to interact with VHL and their ability to be ubiquitylated by VHL E3 in S100 extract), this indicates that determinants other than the conserved core residues are important. It is important to understand the key determinants both for oxygen-dependent proline hydroxylation and for subsequent interaction with VHL E3. Particularly since database searches identify "LXXLAP" motifs in a wide variety of cellular proteins.

Although the two sites have functional differences, they both seem to be regulated by the same enzymatic modification. Hydroxylation at proline 564 is the key modification controlling activity of the 3' VHL E3 site. The corresponding proline in the 5' VHL E3 site is also critical for function and polypeptide competition experiments implicate regulatory hydroxylation. Direct evidence of this will come from mass spectrometric analysis. Also of interest is whether the same enzyme is responsible for oxygen-dependent proline hydroxylation at both sites. Sequence differences in the target sites may allow recruitment of different enzymes which in turn may allow graded or cell-type specific differences in the oxygen response. S100 extract was found to be incapable of supporting VHL-dependent ubiquitylation at the 5' site. This may be due to removal of a 5' site-specific enzyme. Alternatively it may be due to removal of a bridging protein proposed to act between the 5' VHL E3 target site and VHL E3, The bridging protein may be an unknown protein or an already identified component of the VHL E3 ligase.

REFERENCES

Cockman, M. E., et al., *Hypoxia inducible factor-alpha binding and ubiquitylation by the von Hippel-Lindau tumor suppressor protein.* J Biol Chem, 2000. 275: p. 25733-41.
2. Brenner, S., *The genetics of caenorhabditis elegans.* Genetics, 1974. 77: p. 71-94.
3. Wood, S. M., et al., *Selection and analysis of a mutant cell line defective in the hypoxia-inducible factor-1alpha-subunit (HIF-1alpha).* Journal of Biological Chemistry, 1998. 273: p. 8360-8368.
4. Huang, L. E., et al., *Regulation of hypoxia-inducible factor 1α is mediated by an oxygen-dependent domain via the ubiquitin-proteasome pathway.* Proceedings of the National Academy of Sciences, USA, 1998. 95: p. 7987-7992.
5. Iliopoulos, O., et al., *Negative regulation of hypoxia-inducible genes by the von Hippel-Lindau protein.* Proceedings of the National Academy of Sciences, USA, 1996, 93: p. 10595-10599.
6. Ohh, M., et al., *Ubiquitination of hypoxia-inducible factor requires direct binding to the beta-domain of the von Hippel-Lindau protein.* Nat Cell Biol, 2000. 2(7): p. 423-427.
7. O'Rourke, J. F., et al., *Oxygen-regulated and transactivating domains in endothelial PAS protein 1: comparison with hypoxia inducible factor-1 alpha.* Journal of Biological Chemistry, 1999. 274: p. 2060-2071.
8. Lewis, J. A. and Fleming J. T. *Basic culture methods* (1995) *In Methods in Cell Biology*, Vol 48 (ed. H. F. Epstein and D. C. Shakes) p. 3 Academic Press, San Diego, Calif.

Experimental for Example 4

Materials and Methods

C. elegans Culture, Strains and Extract Preparation.

Worms were cultured using standard methods. Exposure to hypoxia was in bell jars gassed with humidified air or certificated nitrogen I oxygen mixes (British Oxygen Company). Exposure to 2,2 dipyridyl (200 µm), or dimethyloxalylglycine (1 mM) was performed during growth in a liquid medium. Wild type worms were Bristol strain (N2). Mutant strains were obtained from the Caenorhabditis Genetics Centre and are as indicated in table 5. A deletion mutant in the vhl-1 gene (ok1610) was generated using trimethylpsoralen. The vhl-1 strain CB5603 was constructed by backcrossing ok161 twice against wildtype (N2), then constructing a triple mutant with markers on either side of vhl-1 (genotype: dpy-6 (e2062) vhl-1 (ok161) unc-9 (8101), and then removing these markers by further crosses against N2.

Worm extracts were prepared by homogenisation (Ultra-turax T20, 1KA Labortechnlk) in 4 volumes extraction buffer (100 mM NaCl, 1 mm EDTA, 50 mM Tris pH7.5, 1% NP-40, 1% sodium deoxycholate) for immunoblotting or in 2 volumes of hypotonic extraction buffer, HEB (20 mM Tris pH7.5 5 mM KCl, $MgCl_2$ 1 mM DTT) for modification reactions.

Mammalian Cells and Extract Preparation

HeLa and RCC4 cells were cultured in DMEM. Cell extracts were prepared in HEB.

Antibodies for Immunoblotting and Immunoprecipitation.

For detection of native C. elegans HIF-1 and VHL-1 proteins, antisera were produced in rabbits immunised with either a glutathione-S-transferase fusion protein expressing amino acids 360-467 of HIF-1, or a maltose binding protein fusion linked to full length (1-174) VHL-1. Recombinant proteins were expressed in E. coli. Antisera were tested for reactivity using extracts of appropriately transfected Cos7 cells, and purified by ammonium sulphate precipitation. Mouse anti-HA antibody was 12CAS (Roche), and mouse anti-Gal4 antibody was RK5C1 (Santa Cruz).

Riboprobes and RNAse Protection.

Details of riboprobe templates are provided in table 4. RNAse protection assays were performed as described (Wiesener et al., (1998) Blood 92 2260-2268) using total RNA prepared from a mixed population of worms using Tri-Reagent (Sigma), or total RNA prepared from HeLa cells using RNAzolB (Biogenesis).

Plasmid C. elegans cDNAs.

The hif-1 cDNA was assembled from 4 overlapping cDNA clones, yk510h7, yk4a2, yk383g1 and yk272d11 (Yuji Kohara, National Institute of Genetics, Japan), and inserted into pcDNA1AMP (Invitrogen). The vhl-1 cDNA and the cDNA encoding the predicted ORF of T20B3.7 were obtained by RT-PCR of worm RNA and inserted into pcDNA3 (with linkers that encoded an N-terminal HA tag), and pSP72 (Promega) respectively. The egl-9 cDNA was subcloned into pcDNA1 from yk130h5 (Yuji Kohara). Phy-1 and phy-2 cDNAs were subcloned in pCR-Script (Winter and Page, (2000) Mol. Cell. Biol. 20 4084-4093) Gal4/HIF-1 fusion proteins were generated by PCR and inserted into pcDNA3Gal (O'Rourke et al., (1999) J. Biol. Chem. 274 2060-2071).

For insect cell expression, sequences encoding Gal4/HIF-1 (289-790) and EGL-9 (1-723) were subcloned into pFastBac1 (Gibco BRL). For bacterial expression, sequences encoding Gal4/HIF-1 (590-790) and EGL-9 (359-723) were subcloned into pET-28a (Novagen), and pMAL-p2X (NEB) respectively.

Mammalian cDNAs

The cDNAs encoding the human polypeptides designated EGLN-2 (PHD1), EGLN1 (PHD2), and EGLN3 (PHD3) were obtained by PCR amplification and/or restriction endonuclease digestion from publicly available cDNA banks (The I.M.A.G.E consortium, end NEDO human cDNA sequencing project) or a human colonic cDNA library. Products were ligated into pcDNA3 for expression in reticulocyte lysate IVTTs, or into pMAL-c2X for expression in E. coli as maltose binding protein fusions. pPDS15 (Lipscomb et. al. (1999) J. Neurochem. 73 429-432) was used for expression of rat SM-20 in reticulocyte lysate IVTT; sequences encoding amino acids 60-355 were subcloned into pTYB11 (NEB) for expression in E. coli.

For bacterial expression, human HIF-1α sequences encoding amino acids 344-503 or 530-698 were subcloned into pET28a.

Mutations were generated using a site directed mutagenesis system (Stratagene). All plasmid sequences were verified by DNA sequencing.

Protein Expression.

$^{35}$S-labelled or unlabelled proteins were generated in TNT reticulocyte lysate or wheat germ lysate (Promega). Protein expression in insect cells was performed using the Bac-to-BacI/Sf9 system (Gibco BRIE.). Bacterially expressed proteins were produced in E. coli strain BL21 (DE3). Proteins were used in lysates or purified using amylase resin, DEAE-Sepharose, nickel affinity chromatography, or anti-Gal antibodies, as appropriate.

Interaction Assays

Assays for interaction between recombinant VHL and HIF polypeptides conformed to the following experimental design. Recombinant VHL and HIF polypeptides were produced separately in vitro. The HIF polypeptide was then pre-incubated with extract or a recombinant enzyme as described below, then mixed with VHL and incubated in EBC buffer (50 mM Tris pH 7.5, 150 mM NaCl, 0.5% v/v Igepal, 0.5 mM EDTA) at 4° C. for 1 hour, before immunoprecipitation with anti HA antibodies (for HA tagged VHL) or anti Gal antibodies (for Gal4HIF fusions) and analysis by PAGE (Jaakkola et al. (2001) supra).

Figure 5:
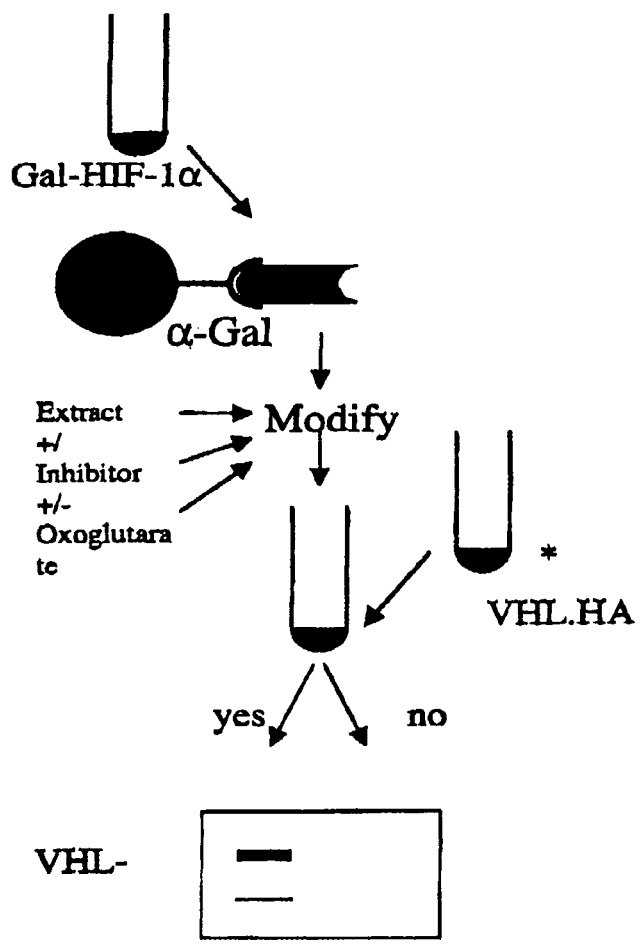
FIG. 5 shows a schematic of the on-bead modification assay used to assay for HIF prolyl hydroxylase activity.

A schematic of the on bead modification assay is shown in FIG. 5.

Preincubation of C. elegans HIF-1 with worm extract or recombinant EGL-9 was for 30 min at 25° C. Preincubation of mammalian HIF-α polypeptides with cell extract or recombinant enzymes was at 37° C. for 10-30 min unless otherwise stated. For assays of recombinant enzymes, 2-oxoglutarate (2 mM), iron (100 µM), and ascorbate (2 mM) were added to the reaction buffer unless otherwise indicated. Reactions performed in hypoxia were in the stated atmospheric oxygen concentration (balance nitrogen) obtained using a controlled environment Invivo$_2$ 400 hypoxia work-station (Ruskinn Technologies) and buffers pre-equilibrated with the appropriate atmosphere. Reactions (50 µl) were performed in open Eppendorf tubes with mixing and stopped by the addition of 20 volumes desferrioxamine (100 µM}.

For peptide blocking experiments peptides (final conc. 1 µM) were pre-incubated with VHL-1 for 15 min before addition to the interaction.

For VHL capture assays using synthetic biotinylated HIF1-α peptides, peptide was preincubated as indicated for 30 min at 37° C., then bound to strepavidin beads, washed, mixed with recombinant VHL or extract, re-captured using beads, and bound VHL analysed by PAGE.

For HIF-1α capture assays using 786-0/VHL cell extract, HIF-1α polypeptides were produced by IVTT, pre-incubated with enzyme, then interacted with cell extract under conditions (10 mM Tris pH7.5, 0.25M NaCl, 0.5% NP40, at 4° C.) that do not permit modification of HIF1-α (Masson et al. (2001) EMBO), then immunoprecipitated with anti-HA and analysed by PAGE.

Details of the capture assay protocol are provided below.

HPLC Analyses

Hydroxylation of the HIF-1α peptide B19Pro (residues 556-574) was analysed by reverse phase HPLC using a Phenomenex Hypersil 5 μ C18(octadecylsilane) 250× 4.6 mm column and a 5% to 95% acetonitrile gradient in 0.1% TFA at 1 ml/min as the mobile phase. A Gilson HPLC system using 306 pumps and 115 UV detector controlled by Gilson 715 software was used. Standards were unmodified B19Pro and a synthetic peptide (B19Hyp) bearing a hydroxyproline substitution at Pro564.

Assays were performed with 2.5 mM ascorbate, 1.25 mM DTT, 50 μM αKG, 1.25 mM Fe(II), 25 μM peptide, 0.66 mg/ml catalase, 1.75 mg/ml EGLN2pMAL, in 50 mM Tris/HCl, 1.5 mM $MgCl_2$ 5 mM KCl. All cofactors were mixed simultaneously by the addition of enzyme to separate drops and incubation was at 37° C. for 30 mins. Assays stopped with methanol (70 μl) and frozen on dry-ice before centrifugation and injection.

For analysis of hydroxyproline, peptides or proteins were subject to acid hydrolysis, derivatisation with phenylisothiocyanate and HPLC using standard methods.

Decarboxylation assays were performed using 1-[$^{14}$C]-2-oxoglutarate purified polypeptide substrates at approximately 25 μM, and a purified EGLN2 (PHD1) fusion as described in Mukherji et al. (2001) supra.

On Bead Modification

Gal/549-582/VP16 In vitro transcription translation (IVTT) was prepared using 20 μl Promega TnT Quick Coupled Retic lysate (Promega, Madison, USA) 1 μl DNA (1 μg/ul), 2 μl 1 mM desferrioxamine (DFO) and 2 μl cold methionine (supplied with IVTT kit). For a positive control, the 2 μl DFO was replaced with 2 μl 1 mM $FeCl_2$ (freshly made). The IVTT reaction was incubated at 30° C. for 90 min Beads were prepared using 20 μl gal beads (Santa Cruz no. sc-S10 AC), 5 μl IVTT, & 100 μl EBC+100 μM DFO and incubated in an End-Over-End rotator for 30-60 min. The beads were then spun at 2,000 rpm for 1 minute, the supernatant removed and the beads washed in 1 ml of EBC (no EDTA or DFO). This was repeated three times.

The beads were then re-suspended in 1000 μl HEB (hypotonic extraction buffer: 20 mM Tris pH7.5, 5 mM KCl, 1.5 mM $MgCl_2$, 1 mM dithiothreitol) for each reaction. 100 μl of the re-suspended beads were transferred into fresh microfuge tubes containing 500 μl of HEB+DTT, The tubes were spun at 2000 rpm for 1 minute and the supernatant removed. Beads were then incubated at room temperature for ten minutes in an end-over-end rotator with a lysate sample under modification conditions as described below then spun at 2000 rpm for 1 minute.

Supernatant was removed and the beads washed three times in 500 μl EBC (50 mM Tris pH 7.5, 150 mM NaCl, 0.5% v/v Igepal, 0.5 mM EDTA)+DFO (In the case of incubation with neat retic lysate, removal of supernatant was facilitated by addition of 500 μl of EBC+DFO prior to the first spin), The supernatant was then removed from the final wash and the beads used for pull down assays.

VHL Capture Assays

VHL capture or 'pull-down' assays on the Gal/549-582/VP16 beads modified as described above were performed on ice. VHL-HA (T2.1) IVTT performed by mixing 20 μl Promega TnT Quick Coupled Retie lysate (Promega) with 3 μl $H_2O$, 1 μl DNA (1 μg/μl) and 1 μl (0.37 MBq) $^{35}$S-methionine (Amersharn Redivue no. AG1094) and incubating at 30° C. for 90 minutes. VHL-HA IVTT was then diluted in 100 μl of EBC+100 μM DFO, for each set of beads to be assayed. To the modified, washed gal/ODD/PI6 beads, 100 μl of the VHL IVTT (T2.1) were added in EBC buffer+100 μM DFO.

The reaction was incubated in an end-over-end rotator for 2 hours in cold room, then spun at 2.000 rpm for 1 minute and the supernatant removed (radioactive liquid waste). The beads were washed with 500 μl of EBC buffer and 1001.1M DFO and spun again at 2.000 rpm for 1 minute. The wash steps were repeated a total of 5 times. The supernatant was removed from the final wash and eluted in 15 μl of 2×SDS sample buffer.

Samples were stored at −0.20° C. and examined by SDS-PAGE.

DNA and Protein Manipulation

DNA manipulation and cloning and protein expression and analysis by SDS-Polyacrylamide Gel Electrophoresis (SDS-PAGE) were performed according to standard techniques which are well known to those of skill in the art and described in detail in Molecular Cloning: a Laboratory Manual: 2nd edition, Sambrook et al., 1989, Cold Spring Harbor Laboratory Press and Current Protocols in Molecular Biology, Ausubel et al. eds., John Wiley & Sons, 1992.

4.1: Identification and Characterization of a HIF-1α Homologue in *C. elegans*

A tBLASTn inquiry with the HIF-α human sequence was used to identify HIF-α subunit homologues in the *C. elegans* EST database. An EST contig was identified which was identical to an open reading frame (ORF: F38A6.3). This ORF was predicted following determination of the *C. elegans* genome sequence, with the exception of a 104 amino acid amino terminal extension in the latter. No further ESTs or PCR products corresponding to the extension were identified and RACE-PCR products contained a putative trans spliced leader sequence. These findings predict that F38A8.3 encodes a 119 amino acid polypeptide that lacks the proposed amino terminal extension.

To characterize the regulation of the putative HIF-α homologue (HIF-1), we raised antisera to a recombinant polypeptide and immunoblotted worm extracts. Extracts were prepared from worms exposed to hypoxia, or the cell penetrating iron chelator 2, 2° dipyridyl.

Immunoblotting showed a striking induction of HIF-1 by both stimuli. Induction by hypoxia was progressively below 5% oxygen and maximal at the lowest tested concentrations of 0.5% and 0.1% oxygen. In 0.1% oxygen, HIF-1 protein level was strongly induced within 4 hrs, and sustained over 24 hrs, but disappeared within minutes following re-oxygenation. In contrast, hif-1 mRNA levels were unchanged by hypoxia. Thus, these experiments confirmed up-regulation of HIF-1 by hypoxia, and suggested a mode of regulation at the protein level similar to that described for mammalian HIF-α subunits.

4.2 Critical Function of a pVHL Homologue VHL-1 in the Regulation of HIF-1 in *C. elegans*.

We compared HIF-1 expression in wild type and a series of mutant worms that were selected because of potential relevance to previously proposed models for oxygen sensing and signal transduction processes in the mammalian HIF system (Chandel et al., (2000) J. Biol. Chem. (Aug) 1-37; Ehleben et al. (1997) Kidney Int. 51 483-491; Zundel et al. (2000) Genes & Dev. 14 391-396) for review see (Semenza, (1999) Cell 98 281-284). These included mutants in the PTEN/insulin receptor/PI-3-kinase pathway (daf-18, daf-1, age-1), a mutant in a putative homologue of VHL (vhl-1), mutants affecting mitochondrial proteins (mev-1, clk-1, gas-1), a mutant that affects cytosolic catalase activity ctl-1, and others selected for resistance or sensitivity to oxidant stresses but where the mutant gene is not yet characterized (mev-2, mev-3).

With the exception of vhl-1 all mutant worms showed preserved regulation of HIF-1 protein levels. In contrast, the vhl-1 worms showed high levels of HIF-1 in normoxia that were essentially unregulated by oxygen. These results confirmed that proposed homology for vhl-1 (Woodward et al. (2000) Genomics 65 253-265), and indicated a conserved role for C. elegans VHL-1 protein in the response to hypoxia.

4.3 Interaction of HIF-1 with VHL-1 is Regulated by Prolyl Hydroxylation.

To address the mechanism of regulation of HIF-1 by VHL-1, interaction between the two proteins was tested. $^{35}$S-methionine labelled hemagglutinin (HA) tagged VHL-1 (HA.VHL-1), and HIF-1 were produced separately in vitro in coupled transcription translation reactions (IVTT) in reticulocyte lysate. IVTTs were then mixed and assayed for interaction by anti-HA immunoprecipitation. When produced this way, the proteins did not interact. However, when recombinant HIF-1 was pre-incubated with worm extract, a clear interaction was observed.

A series of N-terminal truncations of HIF-1 linked to a Gal4 DNA binding domain was constructed. The Gal/HIF-1 fusion proteins were expressed in reticulocyte lysates, pre-incubated with worm extracts and then tested for interaction with HA.VHL-1. These experiments demonstrated that whilst N terminal truncations up to and including Gal4/HIF-1 (590-719) were captured efficiently by HA.VHL-1, Gal4/HIF-1 (641-719) was not, implicating HIF-1 amino acids 590-641 in the interaction.

Inspection of this region revealed homology to pVHL-binding domains in human HIF-1α that have recently been shown to contain sites of prolyl hydroxylation (Ivan et al., (2001) Science 292 464-468; Jaakkola et al. Science (2001) 292 468-472). We therefore mutated the homologous prolyl residue in C. elegans HIF-1 (P621 to G) and found that this mutation ablated interaction with HA.VHL-1.

The demonstration of a critical conserved prolyl residue in C. elegans HIF-1, together with the need for pre-incubation with worm extract provided indication that the mechanism regulating the HIF-1/VHL-1 interaction through enzymatic prolyl hydroxylation might also be conserved in C. elegans. To verify this, N-oxalyl-2S-alanine, a 2-oxoglutarate analogue that inhibits this class of enzymes (Cunliffe et al. (1992) supra) was added to the worm extract during pre-incubation with HIF-1. This strongly inhibited activity in a manner that was competed by excess 2-oxoglutarate, as inhibition was antagonized by 5 mM 2-OG.

To test whether hydroxylation of the critical P621 residue in C. elegans HIF-1 could indeed promote binding to VH1-1, we synthesised N-terminal biotinylated peptides corresponding to residues 607-634 of C. elegans HIF-1 that contained either a proline (B28Pro) or a (2S, 4R)-trans-hydroxyproline residue (B28Hyp) at position 621. We found that B28Hyp but not B28Pro blocked capture of pretreated HIF-1 by HA.VHL-1, when added to the interaction mix.

Furthermore. B28Hyp but not B28Pro captured immunodetectable native VHL-1 when mixed with extracts from wild type but not vhl-1 mutant worms. Finally, to test the importance of prolyl hydroxylation in regulating C. elegans HIF-1 in vivo we exposed worms to the cell-penetrating prolyl hydroxylase inhibitor, dimethyloxalylglycine. This strongly induced HIF-1 in normoxic worms. These results demonstrated that conservation of the HIF/pVHL system in C. elegans extends to the mode of regulation by prolyl hydroxylation.

4.4 the C. elegans egl-9 Gene Product is a Prototype HIF-PH.

The best characterised prolyl hydroxylases are the procollagen-modifying enzymes (Kivirikko and Myllyharju, (1998) Matrix Biol. 16 357-368). However, worms containing inactivating mutations in each of two isoforms of the catalytic subunits, dpy-1B (also termed phy-1) and phy-2 (Friedman et al., 2000 supra: Winter and Page, 2000 supra) showed not mal HIF-1 regulation, consistent with HIF-PH being distinct from the collagen modifying enzymes.

We searched C. elegans and mammalian databases for additional HIF-PH candidate genes that were well conserved between these species and possessed a common β-barrel jelly roll motif.

Of particular interest was a family of genes related to the C. elegans gene egl-9, a gene of previously unknown function that was first identified on the basis of an egg-laying abnormal (egl) phenotype (Trent et al., (1983) Genetics 104 619-647).

Sequence analyses coupled with secondary structure predictions in the light of crystallographic data (Valegard et al. (1998) supra: Zhang et al, (2000) Nature Structural Biology 7 127-133) predicted that these genes would encode a family of enzymes conserved in C. elegans and mammals. The predictions suggested that the enzymes would contain not only the jelly roll motif, but also conserved iron and 2-oxoglutarate binding residues in the same relationship that they occur in crystallographically characterised enzymes e.g. the HXD . . . H iron binding motif on the second and seventh strands of the jelly roll motif.

Mutants worms containing defective egl-9 alleles were therefore assessed for regulation of HIF-1 by immunoblotting. Three strains bearing inactivating mutant alleles of egl-9, (sa307, sa330, and n571) (Darby et al., (1999) PNAS 96 15202-15207; Trent et al. (1983) Genetics 104 619-647) all showed striking constitutive up-regulation of HIF-1 in normoxia and loss of induction by hypoxia. Moreover, a further temperature sensitive egl-9 mutant, n586 showed enhanced normoxic HIF-1 level at the non-permissive temperature.

To determine the effect of EGL-9 on the HIF-1 transcriptional response, we measured mRNA levels of a range of hypoxia inducible transcripts and found striking up-regulation in egl-9 worms. A strongly inducible mRNA of unknown function (F22B6.4) was also identified. These findings demonstrated a critical function for EGL-9 in the regulation of HIF-1 and provided further indication that EGL-9 functions as a HIF.PH that targets HIF-1 to VHL-1.

We produced recombinant EGL-9 and assessed its ability to catalyse the post-translational modification of HIF-1. HIF-1 was captured efficiently by HA.VHL-1 after incubation with EGL-9 programmed reticulocyte or wheat germ lysates, but not unprogrammed lysate.

In contrast, IVTTs expressing recombinant C. elegans PHY-1, PHY-2 and the gene product of the predicted ORF T20B3.7 that also has significant homology to known prolyl hydroxylases, had no activity in these assays.

To test whether EGL-9 could act directly on HIF-1, further preparations were made by baculoviral expression in insect cells and by expression as maltose binding protein (Map) fusion proteins in *E. coli*. Since full length MBP/EGL-9 protein was insoluble when expressed in *E. coli* we prepared an N-terminal truncation containing residues 359-723 (MBP/ΔN.EGL-9) that preserved the predicted catalytic domain and had HIF.1 modifying activity when expressed as an IVTT. *C. elegans* HIF-1 substrates were made as N-terminal Gal4 fusion proteins in either insect cells or *E. coli* and purified by anti-Gal immunoprecipitation. These substrates were incubated with lysates of insects cell expressing full length EGL-9 or purified MBP/ΔN.EGL.9, and tested for ability to capture VHL-1.

Both forms of recombinant EGL-9 efficiently promoted modification of HIF.1 as indicated by HA.VHL-1 capture. Moreover analysis of this activity demonstrated 2-oxoglutarate, iron, and oxygen dependence, and direct inhibition by cobaltous ions.

To demonstrate that activity in the HA.VHL-1 capture assays, corresponded to hydroxylation of the critical HIF-1 residue P621, we assayed modified HIF-1 polypeptides for 4-hydroxyproline content by HPLC. To provide larger quantities of protein for this analysis, we co-transformed *E. coli* with wild type or the P621 to G mutant form of a $His_6$/Gal4/HIF-1 (590-719) (HGH) fusion protein and either MBP/ΔN.EGL-9 or MBP. $His_6$/Gal4/HIF-1 substrates were retrieved by nickel affinity chromatography and aliquots assayed for ability to capture 35S-methionine labelled HA.VHL-1 using anti-Gal immunoprecipitation, or subjected to acid hydrolysis and HPLC analysis for the presence of phenylisothiocyanate derivatised 4-hydroxyproline.

Figure 12:
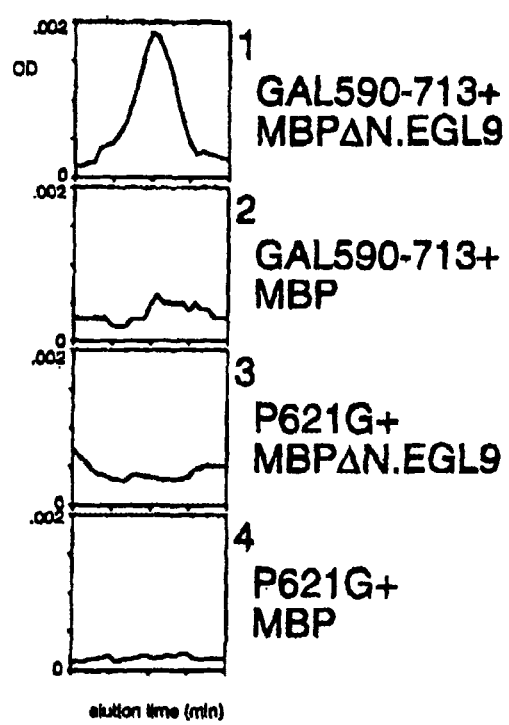
FIG. 12 shows an HPLC analysis of the hydroxylation of proline 621 of HIF-1 by EGL 9. *E. coli* were co-transformed with a plasmid expressing either $His_6GalHIF-1$ (590-713) or a mutant (P621G) derivative and plasmids expressing MBP/ Δ.EGL-9 or MBP alone. Retrieved His6GalHIF-1 was analysed by HPLC for 4-hydroxyproline as shown.
Figure 13A:
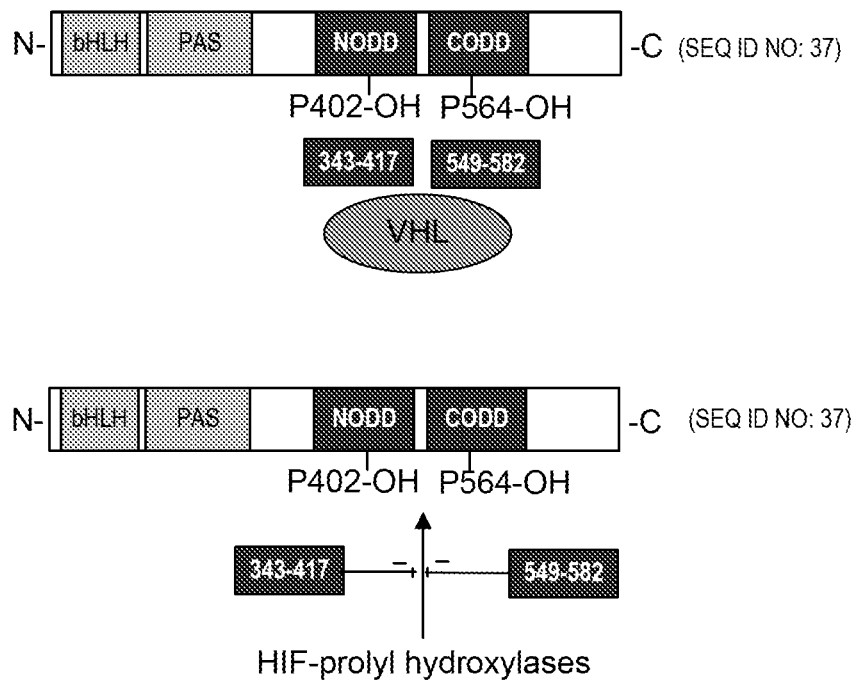
FIGS. 13A-13F shows NODD and CODD expression plasmids enhance HRE reporter gene activity.
Figure 13B:
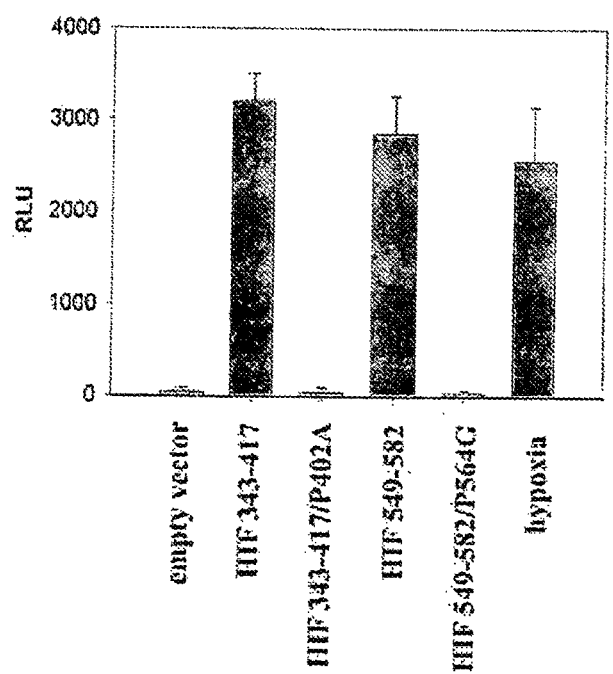
Figure 13C:
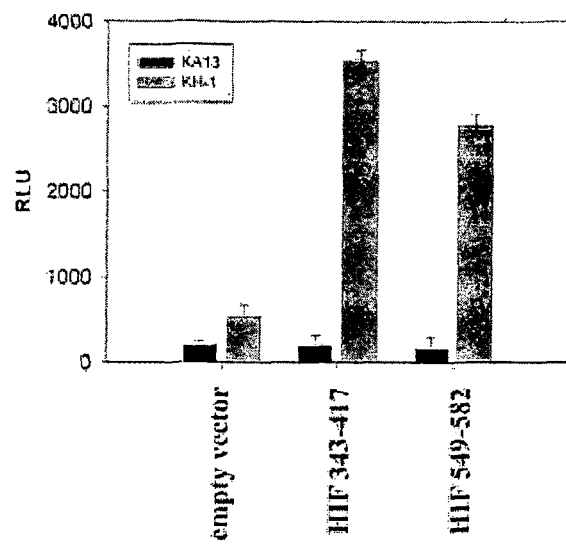
Figure 13D:
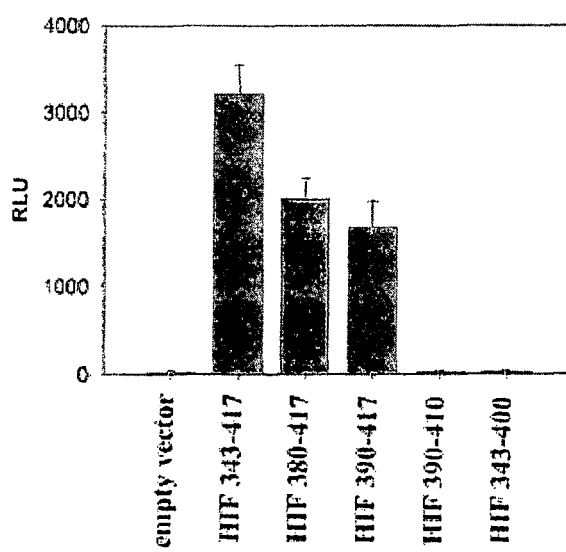
Figures 13E, 13F:
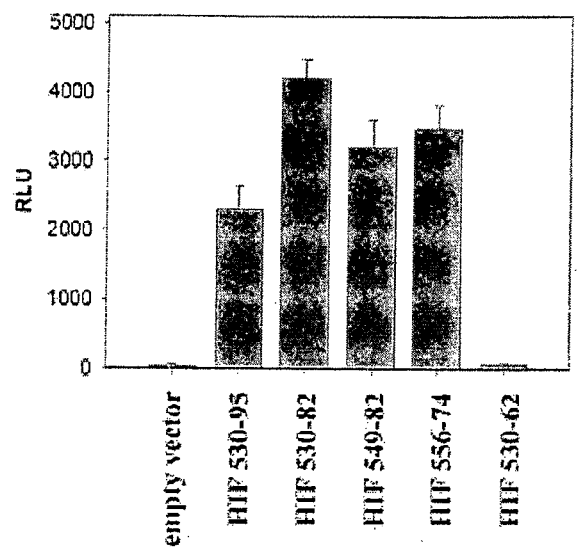

In concordance with the HA.VHL-1 capture assay results, 4-hydroxyproline was produced in the wild type but not the mutant $HiS_6$/Gal4/HIF-1 substrate following exposure to active enzyme (FIG. 12) These results therefore demonstrated the activity of EGL-9 as a prolyl hydroxylase that targets HIF-1 to VHL-1 in *C. elegans*.

4.5 Identification of a Series of Mammalian HIF-PH Isoforms.

Sequence similarity between EGL-9 and a rat gene product termed SM-20 (Wax et al., (1994) J. Biol. Chem. 269 13041-13047) has been noted previously though no functional connection was recognised (Darby et at. (1999) supra). Our sequence-structure search identified a larger series of homologies and predicted three closely related genes in each of the human and rodent genomes that bore striking homology to egl-9, in particular over the core putative catalytic domain.

FIG. 9 illustrates sequence alignment of EGL-9 (acc. no. AAD56365) SM.20 (acc. no, AAA 19321) and the predicted human proteins defined by acc. nos.) XP_040482, AAG33965, and NP_071356 (EGLN1-3), corresponding to Unigene clusters Hs.324277, Hs.6523, and Hs. 18878.

The human protein products have been termed EGLN1, 2, and 3 or 'Prolyl Hydroxylase Domain containing' (PHD) 2, 1 and 3 respectively. Note that the gene termed EGLN3 or PHD3 has previously been identified as human homologue of rat SM-20 (Dupuy et al. (2000) Genomics 69 348-354).

To test the role of these gene products in regulating the interaction between human HIFα sub-units and the VHL E3 ligase complex, we first produced the proteins by reticulocyte IVTT. Since unprogrammed lysate has a low level of HIF-PH activity (Jaakkola. et. al., 2001 supra) we tested for enhanced ability of the programmed lysates to promote the HIFα/VHL E3 interaction. After incubation with relevant enzyme, HIF-α substrates were mixed with extracts from 786-0/VHL cells that stably express HA tagged human pVHL, and tested for interaction by anti-HA immunoprecipitation.

With full length wild type HIF-1α, striking activity was observed with rat SM-20 and all three human gene products, but not a mutant EGLN1 bearing an H358A substitution at the predicted catalytic site, and not a different human 2-oxoglutarate dependent oxygenase (phytanoyl coenzyme A hydroxylase (Mukherji et al. 2001) that was tested as a negative control. Similar results were obtained with HIF-2α.

Examination of HIF.1α mutants bearing missense substitutions at the critical prolyl residues in the: HIF-1α ODDD (Masson et al 2001) showed that that enzymes were differentially efficient at promoting interaction via the C-terminal (P564) and N-terminal. (P402) prolyl hydroxylation sites. Whereas interaction through the C-terminal site could be promoted by all enzymes, VHL E3 capture was less efficient when only the N-terminal site (P402) was intact, and was only promoted by EGLN2 (PHD1) and EGLN1 (PHD2). No activity at all was observed with a double HIF-1α mutant, P402A P564G, that ablates both hydroxylation sites.

In keeping with these results, all enzymes strongly promoted interaction of pVHL with isolated HIF-1α sequences {residues 549-582) from the C-terminal site. Further analysis demonstrated that this activity was strongly inhibited by iron chelation, cobaltous ions, and the 2-oxogluarate analogue N-oxalylglycine.

To confirm direct action on HIF-α sequences, we prepared purified EGLN2 as an MBP fusion protein in *E. coli* and assayed activity using either purified His-tagged HIF-1α polypeptides containing the N-terminal (344-503) or C-terminal (530-698) hydroxylation sites, or a synthetic peptide consisting of the minimal HIF-1α C-terminal substrate (B19Pro, residues 556-574). These experiments demonstrated activity by pVHL capture assays, HPLC/MS detection of the hydroxylated peptide product or derivatised 4-hydroxyproline, and by 2-oxoglutarate decarboxylation assays.

To verify expression of all three isoforms, we performed RNase protection analysis using riboprobes specific for each transcript. Since recently published work has indicated that the rate of HIF degradation in normoxia is enhanced by prior exposure of cells to a period of hypoxia (Berra et al. (2001) FEBS Letters 491 85-90) it has been predicted that HIF-PH would itself be induced by the transcriptional response to hypoxia.

RNase protection demonstrated that all three HIF-PH mRNAs are expressed in HeLa cells and that, in this cell line, transcripts for EGLN1 (PHD2) and EGLN3 (PHD3) but not EGLN2 (PHD1) are induced by hypoxia. In keeping with this, semi-quantitative analysis of lysates prepared from HeLa cells that had been grown in normoxia or exposed to hypoxia for 16 hours then assayed for HIF-PH activity in vitro using the pVHL capture assay, demonstrated induction of total HIF-PH activity that was blocked by actinomycin D.

Finally, we used pVHL capture assays to measure the activity in vitro of recombinant EGLN2 on a HIF-1α 549-582 substrate at graded levels of hypoxia in a controlled hypoxia work-station. We first measured the effect of graded hypoxia on the HIF modifying activity of extracts of vhl-defective RCC4 cells that contain a relatively high level of total HIF-PH activity. A progressive reduction in activity was observed with graded hypoxia. Similar assays were then performed using EGLN2 produced in reticulocyte lysate by IVTT, or purified MBP/PHD-1 obtained by expression in *E. coli*. Closely similar progressive reductions in the activity of each preparation were observed with graded hypoxia. Thus, the oxygen dependent activity of recombinant PHD-1 from either source parallels that observed in crude cell extracts, and mirrors the progressive increases in HIF-1α protein and DNA binding that are observed when cells are exposed to graded hypoxia in culture (Jiang et al., (1996) Am. J. Physiol. 271 C1172-C1180).

4.6 HIF Prolyl Hydroxylase Activity

Full length rat SM20, a truncated form of rat SM 20 lacking the amino terminal 59 amino acids and the human homologue EGLN-2 were shown to modify HIF amino acids 549-582 in a manner which facilitates interaction with the VHL protein. This is known to depend on hydroxylation of proline 564.

Wheat germ lysate was programmed with pcDNA3 based plasmids containing no insert, an insert encoding the full open reading frame of rat SM20, a truncated form of rat SM20 lacking the amino terminal 59 amino acids or the human homologue known as EGLN2 in the absence of exogenous iron or with the addition of 100 μM ferrous chloride. The nucleotide sequence corresponding to these putative proteins were generated by PCR and their identity was confirmed by sequencing. The protein products generated conformed with their predicted molecular weights.

Protein containing HIF-1 sequence (amino acids 549-582) was generated in a reticulocyte in vitro transcription translation reaction in the presence of 100 micromolar desferrioxamine, retrieved and then exposed to wheat germ translates containing the putative enzymes as described above. These proteins contain the critical proline (564) which can be modified by hydroxylation and which enables recognition by von Hippel Lindau tumour suppressor protein (pVHL).

The modification of the HIF-1 sequence was assayed by the binding of the HIF-1 to radiolabelled pVHL, generated by in vitro transcription and translation of a pcDNA3 vector containing the human wild type pVHL open reading frame in a rabbit reticulocyte lysate in the presence of $^{35}$S-methionine.

SDS PAGE analysis indicated that the plasmids encoding the genes EGLN-2, full length and truncated rat SM20 produced, in the presence of $Fe^{2+}$, a clear modification of HIF-1 which allowed capture of labeled pVHL.

No pVHL binding was observed in the absence of $Fe^{2+}$ for SM20, or EGLN-2 and only a low level of binding was observed for truncated SM20.

4.7 Mutation of EGLN2

Modification and pVHL binding assays were performed as described above. Rabbit reticulocyte lysate was programmed with pcDNA3 based plasmids containing no insert, an insert encoding the full open reading frame of the human homologue known as EGLN-2, a mutant form of EGLN-2 with a Histidine to Alanine substitution at amino acid residue 358 or a naturally occurring splice variant lacking amino acids 369-389.

pVHL binding was observed only with the full length wild type PHD-3 polypeptide. The full length wild type enzyme was able to modify HIF-1 sequence whilst neither the mutant form nor the deleted splice variant was able to do so. This demonstrates that His358 and the region between residues 369 and 389 are necessary for HIF hydroxylase activity.

4.8 Effects of HIF and pVHL Mutations

Modification and pVHL binding assays were performed as described above. Wheat germ lysate was programmed with pcDNA3 based plasmids containing no insert, an insert encoding the full open reading frame of the human homologue known as EGLN-2, or an insert encoding the full open reading frame of the human homologue known as PHD-3 or EGLN-3.

HIF substrates for modification were wild type or contained mutation of proline 564 to glycine. The pVHL target for capture was wild type or contained the mutation of tyrosine 98 to histidine.

Binding of labeled pVHL was observed in assays using wild type HIF and pVHL. No binding was observed in assays using mutant HIF or pVHL.

Both EGLN2 and EGLN3 were therefore able to modify wild type but not mutant HIF in a manner allowing capture of wild type but not mutant pVHL.

4.9 Oxygen Dependence of Modification of HIF by Recombinant Enzymes

Modification and pVHL binding assays were performed as described above except that enzymes were generated by expression in COS cells or rabbit reticulocyte lysate.

Plasmids used to generate enzymes were as follows; pcDNA3 (without insert); pcDNA3 containing sequence encoding rat SM20 lacking the first 59 amino acids; pcDNA3 containing sequence encoding EGLN2 (PHD 1). Modification of HIF substrate by enzymes was performed in either normoxia (21% $O_2$) or anoxia (2% $O_2$) conditions using a hypoxia workstation.

Given the regulation of HIF-1 by oxygen and the known substrate requirement of 2-oxoglutarate dependent dioxygenases for oxygen, the oxygen dependence of the HIF modifying activity was examined.

In anoxia, EGLN2 (PHD1) or rat SM20 (lacking the amino terminal 59 amino acids) were unable to modify HIF for pVHL binding, in contrast to the clear modification at 21% $O_2$. This demonstrates oxygen dependence and a means of oxygen sensing in the regulation of HIF-1.

4.10 Effects of Oxalylglycine and 2-Oxoglutarate on EGLN2 and EGLN3 In Vitro

Modification and pVHL binding assays were performed as described above. Rabbit reticulocyte lysate was programmed with pcDNA3 based plasmids containing no insert, an insert encoding the full open reading frame of the human homologue of C. elegans Egl-9 known as EGLN-2, or an insert encoding the full open reading frame of the human homologue known as EGLN-3. Modification was performed in the absence of additives, in the presence of oxalylglycine, oxalylglycine plus 2-oxoglutarate, 200 μM desferrioxamine or 200 μM cobaltous chloride.

Enzyme activity was observed to be diminished by oxalylglycine, desferrioxamine and cobaltous ions. The inhibitory effect of oxalylglycine was partially competed by addition of excess 2-oxoglutarate. The family of 2-oxoglutarate dependent dioxygenases demonstrate a requirement for oxygen, iron and 2-oxoglutarate. The ability of these gene products to modify HIF-1 to a VHL binding form was examined in differing conditions of iron availability, 2-oxoglutarate availability and in the presence of a 2-oxoglutarate inhibitor. These results demonstrated an iron and 2-oxoglutarate dependence of activity in reticulocyte lysate.

4.11 Effects of Dimethyl Oxalyl Glycine on HIF Activity In Vivo.

Hep3b and U2OS cells were co-transfected with a mixture of three plasmids; pUAS.tk.luc, encoding a GAL 4 responsive luciferase gene, pgal-hif775-826, a mammalian expression plasmid leading to expression of a fusion between a 147 amino acid DNA binding domain of GAL 4 and the carboxy terminal transactivator of human HIF-1 alpha, and pCMV-.beta-gal, encoding a constitutively expressed beta-galactosidase gene as a transfection control.

48 hours following transfection, cells were incubated in normoxia or 2% hypoxia overnight in the presence or absence of dimethyl oxalyl glycine as indicated. Cell lysates were assayed for luciferase and beta galactosidase activity and the relative luciferase activity in each sample determined.

In both cell lines, the presence of the HIF prolyl hydroxylase inhibitor resulted in enhanced activity of the carboxy terminal transactivator in both normoxia and hypoxia compared to the untreated samples (FIG. 6). This result shows a potentiating action of this inhibitor on a domain of HIF which is not normally considered to be dependent on proteolytic destruction for its activity.

Potentiation of the action of the carboxy terminal transactivator coupled with inhibition of destruction via the oxygen dependent degradation domains enhances the overall inhibitor mediated increase in HIF activity.

Addition of dimethyloxalylglycine to Hep3B and U2OS cells in tissue culture (0.1 mM, 1 mM) was also observed to increase intracellular levels of HIF-1 in Western Blot experiments.

Effects of forced expression of EGLN2 (PHD 1) or a naturally occurring splice variant lacking amino acids 369-389 (PHD4) on HIF Activity Hep3b cells were co-transfected with a mixture of three plasmids; pHRE.luc, encoding a HIF responsive luciferase gene, pcDNA3 or pcDNA3.HIF, mammalian expression plasmids leading to expression of no product or full length human HIF-1 alpha, and pCMV.beta-gal, encoding a constitutively expressed betagalactosidase gene as a transfection control.

48 hours following transfection, cells were incubated in normoxia or 2% hypoxia overnight, Cell lysates were assayed for luciferase and beta galactosidase activity and the relative luciferase activity in each sample determined.

Figure 7:
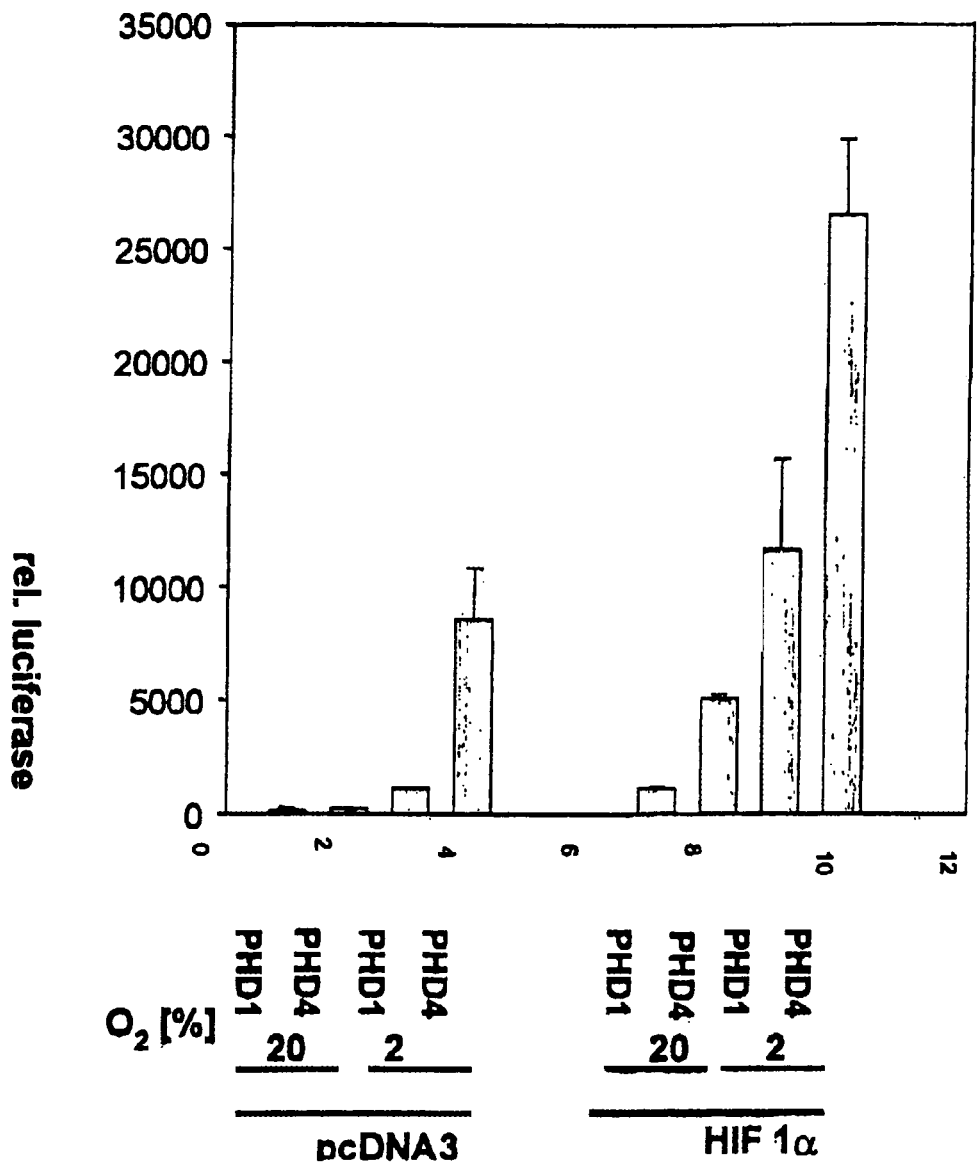
FIG. 7 shows the effects of forced expression of EGLN2 (PHD 1) or a naturally occurring splice variant lacking amino acids 369-389 (PHD4) on the action of HIF in cells incubated in atmospheres containing 20% or 2% oxygen.
Figure 8:
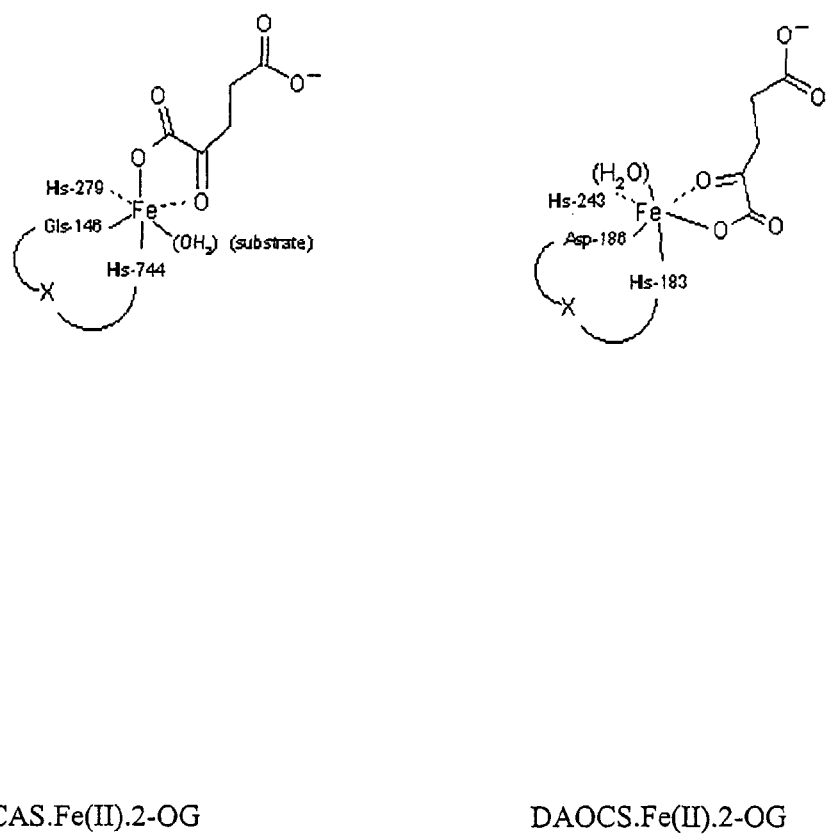
FIG. 8 shows views derived from the active sites of clavaminate synthase and deacetoxycephalosporin C synthase.
Figure 10:
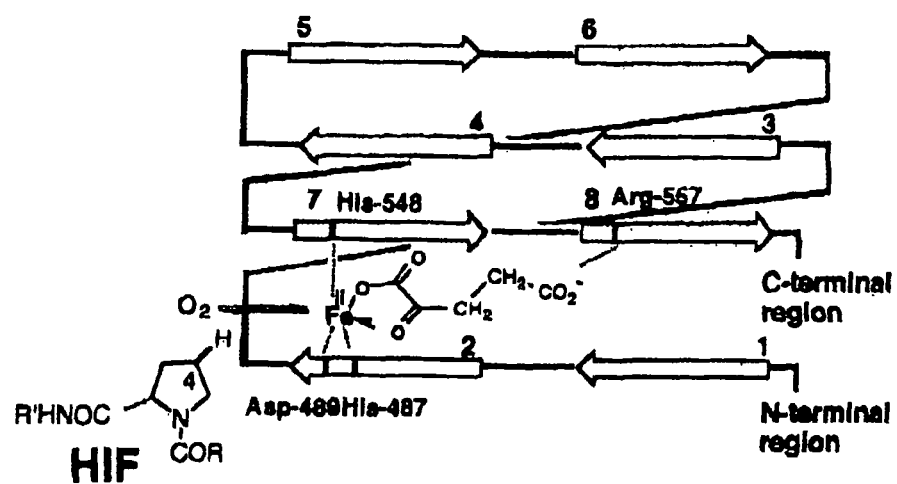
FIG. 10 shows a topographical diagram of the conserved jelly roll core (strands 1 to 8) of 2-oxoglutarate dependent, showing the approximate location of the conserved 2-histidine-1 carboxylate iron binding ligands and 2 oxoglutarate binding basic residue (Arg 557) used to identify candidate HIF-PHs. Numbering refers to the positions in the EGL-9 sequence.
Figure 11:
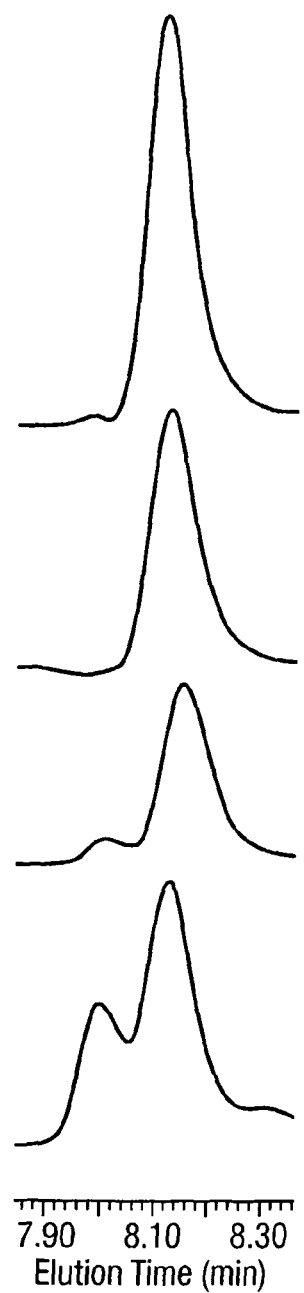
FIG. 11 shows an HPLC elution profile of absorbance at 218 nm of the hydroxylation of a synthetic peptide by purified PHD 1. Synthetic HIF-1α (B 19Pro) peptide was treated with MBP/PHD1 in the presence or absence of 2-oxoglutarate and the products analysed by HPLC as described. Top curve shows results of incubation in the absence of iron(II), upper middle curve shows incubation in the absence of αKG, lower middle shows incubation with all cofactors present. Positions of peaks corresponding to hydroxylated and unhydroxylated B19Pro standards are shown in the bottom panel. Appearance of hydroxlated peptide coincides with the ability to interact with p VHL.

In all circumstances, relative luciferase activity was lower when co-expression included the full length EGLN2 (PHD1) rather than the deleted, non-functional version (PHD4)(FIG. 7), providing indication that expression of full length EGLN2 reduces functional HIF by enhancing the generation of the rapidly destroyed hydroxylated HIF protein.

The effect was even more prominent in circumstances where the level of HIF-1α would be expected to be higher (e.g. when co-expressed from a plasmid or partially stabilised by modest hypoxia). This demonstrates that expression of these gene products is able to enhance HIF-1 degradation in vivo.

4.12 Effect of Inhibitors of HIF Prolyl Hydroxylase Activity

Modification and pVHL binding assays were performed as described above (and by reverse phase HPLC) to determine the effect of inhibitors on the ability of cell extract to modify Gal-Hif549-582-VPI6, thereby allowing capture of radiolabelled recombinant pVHL.

Binding of pVHL was determined using SDS-PAGE and autoradiography.

In the absence of treatment with cell extract, no binding of pVHL was observed, showing the Gal-Hif549-582-VPI6 was unmodified.

Treatment with cell extract in the absence of inhibitor showed strong binding of pVHL. Treatment with cell extract in the presence of oxalyl glycine (NK 87) showed reduced binding of pVHL, showing that oxalyl glycine inhibits the HIF prolyl hydroxylase. Treatment with cell extract supplemented with additional 2-oxoglutarate produced strong pVHL binding. Treatment with cell extract in the presence of NK87 and additional 2-oxoglutarate also produced strong binding, indicating that HK87 competes with the oxoglutarate co-substrate.

Treatment with cell extract in the presence of 1 mM NMPG produces strong binding of pVHL. However, treatment in the presence of 5 mM NMPG reduced the amount of pVHL binding.

As a positive control, pVHL was captured when Gal-HIF-VP16 substrate was synthesised in rabbit reticulocyte lysate in the presence of additional ferrous chloride. Other potential inhibitors as shown in Table 3 were screened for the ability to inhibit HIF hydroxylase activity as described above.

Of the compounds screened in this assay, reduced pVHL binding indicative of inhibition of HIF hydroxylation was observed for Is1, Is3, Is8, benzohydroxamic acid, ethyl dihydroxybenzoate, and NK45.

The present application relates to the characterization of a HIF-1/VHL prolyl hydroxylase system and the identification of a new functional group of 2-oxoglutarate dependent oxygenase that function as HIF prolyl hydroxylases (HIF-PHs). The critical role of these enzymes in the regulation of HIF is emphasised by analysis of vhl-1 and egl-9 mutant worms, which show essentially complete loss of regulation of HIF-1 by oxygen. The availability of recombinant HIF-PHs permits further investigation of the HIF/VHL system and an important challenge will be to determine the extent to which the complex demands of physiological oxygen homeostasis are met by the biochemical properties of these enzymes.

Identification of the HIF system in nematode worms that obtain oxygen directly by diffusion reveals that this system of gene regulation must have evolved before the development of complex systemic oxygen delivery systems, presumably to regulate; responses to oxygen availability at the cellular level.

In mammals, the HIF system regulates not only cellular responses to oxygen, but also a range of systemic functions such as the control of oxygen delivery through effects on angiogenesis, vasomotor control, and erythropoiesis. These complex requirements have argued against the concept of a single oxygen sensor. However, the existence in mammalian cells of (at least) three isoforms of HIF.PH, and (at least) two isoforms of HIF-α, each with more than one site of prolyl hydroxylation (Masson et al., 2001 supra), may provide the potential for different physiological responses to oxygen availability to be generated through combinatorial interactions amongst these molecules.

The characterisation of the HIF PH enzymes described herein has various therapeutic applications, in particular as targets in the development of pharmacological agents which modulate HIF-α levels in a cell.

Example 5

In this Example it is shown that HIF-1α protein and the endogenous HIF target gene encoding carbonic anhydrase 9 (CA-9) are induced by exposure of cells to the PHD inhibitor, dimethyl oxalylglycine. In previous studies we have demonstrated that N-oxalylglycine is an inhibitor of PHD activity in vitro, but seems to be incapable of entering intact cells. The esterified form, dimethyloxalylglycine, has therefore been used to deliver the compound to tissue culture cells.

Hep3B and U2OS cells were exposed to either 0.1 mM or 1 mM dimethyloxalylglycine for 6 hours, harvested and assayed by immunoblotting (Western blotting) for changes in the level of HIF-1α and CA-9 expression. Controls, where no inhibitor was added, were also performed. Clear upregulation of both HIF-1α and the HIF target gene product CA-9 are observed in the presence of dimethyloxalylglycine. Upregulation of HIF-1α increased with increasing concentration of dimethyloxalylglycine, whilst the level of CA-9 expression was similar after exposure to both 0.1 and 1 mM of dimethyloxalylglycine.

Example 6

In this example it is shown that enhanced new vessel growth can be stimulated in a murine subcutaneous sponge angiogenesis assay by injection of the HIF prolyl hydroxylase inhibitor, dimethyl oxalylglycine.

In previous studies we have demonstrated that N-oxalylglycine is an inhibitor of PHD activity in vitro but seems to be incapable of entering intact cells. Application of an esterified form, dimethyloxalylglycine, to tissue culture cells results in stabilisation of HIF alpha chains (Example 1) and activation of transcription of endogenous HIF target genes (Example 5).

Implantation of a polyurethane sponge subcutaneously in a mouse provides an inflammatory stimulus to angiogenesis and is a well established model for assessing the pro- and anti-angiogenic effects of compounds. To test the effects of dimethyl oxalylglycine in vivo, sterile 8 mm sponge discs were inserted under the dorsal skin of C57 Black mice on Day 0. Test solutions were injected through the skin into the sponges of mice once per day on days 1, 2, 4 and 5. Individual mice received 100 microliters aliquots of either sterile dimethyloxalylglycine (0.1 mM, 1 mM or 10 mM) or carrier solution. Animals were sacrificed on day 7 and the sponges removed. The sponges were fixed in 3.7% formaldehyde, paraffin embedded and stained immunohistochemically for von Willebrand factor to identify blood vessels.

Considerably more blood vessels were observed in sponges injected with dimethyloxalylglycine (1 mM) than those receiving solvent alone.

Example 7: The Effect of PK-Tagged PHD1 Expression on HIF-1-α Induction by Hypoxia In this Example it is shown that a recombinant PHD (PHD1) may be overexpressed in a tissue culture cell line in such a manner as to affect the metabolism of a HIF polypeptide.

U2OS cells were stably transfected with a binary system encoding a tetracycline operator fused to an activator, and a plasmid encoding C-terminal PK epitope tagged PHD1 under control of a tetracycline response element. The transfected cells were incubated with 21%, 3% or 0% oxygen in either the presence or absence of doxycycline for 16 hours. Immunoblots were then performed on cell lysates to quantify levels of HIF-1α and also to check for expression of PHD via the PK tag.

Exposure of cells to doxycycline for 16 hours induced expression of PK tagged PHD1. The induced expression of PHD1 substantially reduced expression of HIF-1α in modest hypoxia (3% oxygen) and also reduced expression to a lesser extent under total hypoxia (0% oxygen). Thus in this Example, the expression of endogenous HIF-1 is shown to be strikingly dependent on the activity of the specifically induced PHD1 isoform under the conditions of assay.

Example 8

(S)-2-(Methoxyoxalyl-amino)-pentanedioic acid diethylester (IS12)

or: Diethyl N-methoxyoxalyl-(L)-glutamate (IS12)

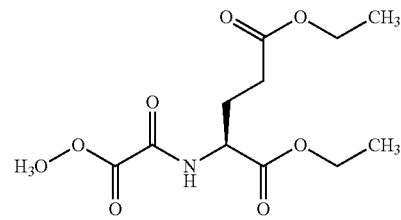 [SMILES: CCOC(=O)CC[C@H](NC(=O)C(=O)OO)C(=O)OCC]

To a stirred solution of 10 mmol (2.40 g) of diethyl (L)-glutamate hydrochloride in 10 ml of toluene, 10 mmol (1.23 g, 0.93 ml) of methyl oxalyl chloride was added and heated until no further HCl gas evolved (4-6 hr). The solvent was evaporated yielding 2.86 g (9.9 mmol, 99%) of IS12 as a yellowish oil, $[\alpha]_D^{25}$ −28.3°(c 1 in methanol); $\nu_{max}$ (NaCl)/cm$^{-1}$ 1738, 1705 (C=O); $\delta_H$ (200 MHz; CDCl$_3$) 1.22, 1.26 (6H, 2 t, $^3J_{HH}$ 7.3, OCH$_2$CH$_3$), 1.95-2.47 (3H, m, CHCH$_2$CH$_2$), 3.88 (3H, s, OCH$_3$), 4.10, 4.20 (4H, 2 quart, $^3J_{HH}$ 7.3, OCH$_2$CH$_3$), 4.60 (1H, ddd, $^3J_{HH}$ 8.1, $^3J_{HH}$ 8.1, $^3J_{HH}$ 4.8, CH), 7.76 (1H, d, $^3J_{HH}$ 8.1, NH); $\delta_C$(50 MHz; CDCl$_3$) 14.1 (OCH$_2$CH$_3$), 27.0, 30.1 (CH$_2$CH$_2$), 52.1, 53.6 (CH, OCH$_3$), 60.8, 62.0 (OCH$_2$CH$_3$), 156.1, 160.4, 170.5, 172.4 (C=O); m/z (AP+) 290 (MH$^+$, 68%).

Example 9

(S)-2-(Oxalyl-amino)pentanedioic Acid (1S13)

or: N-Oxalyl-(L)-glutamate (IS13)

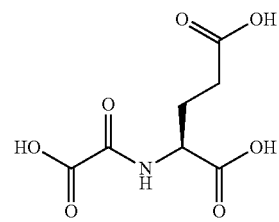 [SMILES: O=C(O)CC[C@H](NC(=O)C(=O)O)C(=O)O]

3 mmol (0.87 g) of IS12 was heated with 5.0 ml of 2 N aqueous sodium hydroxide solution ensuring 1.1 equivalents of sodium hydroxide for the sum of the ester functions to be cleaved in the compound. The reaction was percolated through a column of 'Amberlite IR 120H' ion exchange resin (previously washed with water to about pH 4) and eluated with water until pH raised to 4 again. The water evaporated in vacuo and the residue dried in vacuum. This yielded 0.65 g (2.9 mmol, 97%) of IS13 as a yellowish hygroscopic solid, mp ca. 60° C.; $[\alpha]_D^{25}$ −2.2 (c 1 in methanol) $\nu_{max}$ (NaCl, MeOH)/cm$^{-1}$ 1697 (C=O); $\delta_H$ (200 MHz; D$_2$O) 1.77-2.35 (3H, m, CHCH$_2$CH$_2$), 4.30 (1H, dd, $^3J_{HH}$ 9.1, $^3J_{HH}$ 5.0, C$_H$); $\delta_C$ (50 MHz; D$_2$O) 25.8, 30.3 (CH$_2$CH$_2$), 52.6, (CH), 161.4, 162.9, 174.5, 177.3 (C=O); m/z (AP−) 218 (M-H$^+$, 5%), 168 (M-H$^+$-oxalyl, 85%).

Example 10

(S)-2-(Methoxyoxalyl-amino)-propionic Acid (IS68)

or: Methyloxalyl-L-alanine (IS68)

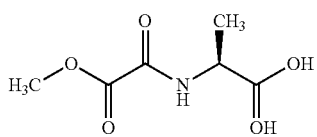

This compound was prepared as in Example 8 using 10 mmol (0.89 g) of (L)-alanine and 10 mmol (1.23 g, 0.93 ml) of methyl oxalyl chloride yielding 1.96 g crude yellow oil. The crude product was chromatographed over silica gel (ethyl acetate eluent) resulting in 1.42 g of IS68 as a yellowish oil, which still contained traces of impurities. A pure sample was obtained from recrystallization from a mixture of ethyl acetate and diethyl ether (0.39 g, 2.2 mmol, 22%), mp 129-130° C.; 1.1° (c 1 in MeOH); $v_{max}$ (NaCl, MeOH)/cm$^{-1}$ 1744, 1693 (C=O); $\delta_H$ (200 MHz; DMSO-d$_6$) 1.35 (3H, d, $^3J_{HH}$ 7.3, CHCH$_3$), 3.43 (1H, br, COOH), 3.81 (3H, s, OCH$_3$), 4.28 (1H, pseudo-quint, $^3J_{HH}$ 7.4, CH), 9.16 (1H, d, $^3J_{HH}$ 7.5, NH); $\delta_C$ (50 MHz; DMSO-d$_6$) 17.3 (CHCH$_3$), 48.8 (CH), 53.7 (OCH$_3$), 157.6, 161.8, 173.8 (C=O).

Example 11

(R)-2-(Methoxyoxalyl-amino)-propionic Acid (IS69)

or: Methyloxalyl-D-alanine (IS69)

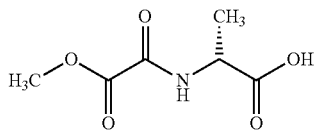

This compound was prepared as for IS68 but with (L)-alanine substituted by (D)-alanine yielding 0.36 g (2.1 mmol, 21%) of IS69 as a colourless solid, mp 131-132° C.; $[\alpha]_D^{25}$ +1.9° (c 1 in MeOH). Analytical data except optical rotation corresponded to those of IS68.

Example 12

(S)-2-(3-Mercapto-propionylamino)-propionic Acid (IS37)

or: N-(3-Mercaptopropanoyl)-(L)-alanine (IS37)

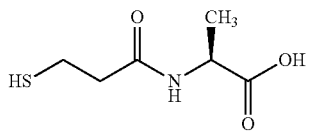

Prepare according to literature procedure: M. A. Ondetti, D. W. Cushman, U.S. Pat. No. 4,053,651, 1977, E. R. Squibb & Sons (Chem. Abstr., Volume 88, 136977). No analytical details but melting point were given in the literature work. A solution of 4 mmol (1.13 g) of IS20 in 2 ml of water was treated with 1.6 ml of conc. aqueous ammonia solution for one hour at room temperature, while a colourless precipitate formed. The mixture was diluted with water and the solids filtered off. The filtrate was washed with ethyl acetate, the aqueous phase was acidified with conc. hydrochloric acid and extracted with ethyl acetate. The combined organics were washed with water, dried over magnesium sulfate and evaporated in vacuo resulting in 0.49 g of crude IS37. Recrystallization from a mixture of ethyl acetate and n-hexane yielded 0.32 g (1.8 mmol, 45%) of IS37 as a colourless solid, mp 78-79° C.; $[\alpha]_D^{25}$ 39.4 (c 1 in methanol); $v_{max}$ (NaCl, MeOH)/cm$^{-1}$ 1728, 1638 (C=O); $\delta_H$ (200 MHz; DMSO-d$_6$) 1.28 (3H, d, $^3J_{HH}$ 7.3, CH$_3$), 2.31 (1H, t, $^3J_{HH}$ 7.9, SH), 2.40-2.48, 2.60-2.73 (4H, 2 m, CH$_2$CH$_2$), 4.22 (1H, quint, $^3J_{HH}$ 7.3, CH), 8.26 (1H, d, $^3J_{HH}$ 7.3, NH), 12.56 (1H, br s, COOH); $\delta_C$ (50 MHz; DMSO-d$_6$) 18.0 (CH$_3$), 20.8 (CH$_2$CH$_2$, second signal covered by DMSO, recording in CDCl$_3$ revealed it at 40.0), 48.3, (CH), 171.0, 175.1 (C=O); m/z (AP-) 176 (M-H$^+$, 100%).

Example 13

(R)-2-(3-Mercapto-propionylamino)-propionic Acid (IS38)

or: N-(3-Mercaptopropanoyl)-(D)-alanine (IS38)

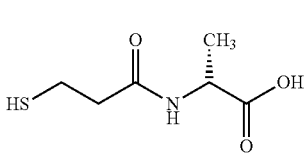

The title compound was prepared as for IS37 but with IS20 substituted by IS21 yielding 0.18 g (1.0 mmol, 25%) of IS38 as a colourless solid, mp 64° C.; $[\alpha]_D^{25}$ +39.5 (c 1 in methanol). Analytical data except optical rotation correspond to those of IS37.

Example 14

(S)-2-(3-Benzoylsulfanyl-propionylamino)propionic Acid (IS20)

or: N-(3-Benzoylthiopropanoyl)-(L)-alanine (IS20)

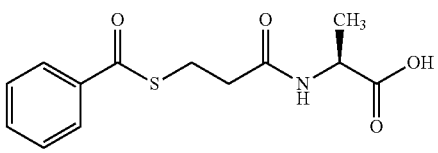 [SMILES: C[C@H](NC(=O)CCSC(=O)c1ccccc1)C(=O)O]

Prepared according to literature procedure: M. A. Ondetti, D. W. Cushman, U.S. Pat. No. 4,053,651, 1977, E. R. Squibb & Sons (Chem. Abstr., Volume 88, 136977). No analytical details but melting point were given in the literature work.

In 16.7 ml of 1 N aqueous sodium hydroxide solution, 16.7 mmol (1.48 g) of (L)-alanine were dissolved. After adding another 9 ml of 2 N sodium hydroxide solution at ice temperature, 16.7 mmol (2.85 g) of 3-bromopropionic acid were added and the reaction was stirred for 3.5 h at room temperature. A mixture of 18.1 mmol (2.50 g) of thiobenzoic acid and 11.6 mmol (1.6 g) of potassium carbonate in 16.7 ml of water and 5 ml of THF was than added to the reaction, which was then stirred overnight. The resultant mixture was acidified with conc. hydrochloric acid, stirred for 30 min. and extracted with ethyl acetate. The combined organics were dried and the solvents evaporated in vacuo. The remaining thick (5.15 g) yellow oil was crystallized from ether yielding 1.83 g (6.5 mmol, 39%) of IS20 as a colourless powder, mp 98-99° C.; $[\alpha]_D^{25}$ −19.1 (c 1 in methanol); $\nu_{max}$ (NaCl, MeOH)/cm$^{-1}$ 1730, 1660 (C=O); $\delta_H$ (200 MHz; CDCl$_3$) 1.44 (3H, d, $^3J_{HH}$ 7.1, CH$_3$), 2.66, 3.32 (4H, 2 d, $^3J_{HH}$ 7.1, CH$_2$CH$_2$), 4.61 (1H, quint, $^3J_{HH}$ 7.1, CH), 6.77 (1H, d, $^3J_{HH}$ 7.1, NH), 7.37-7.61, 7.89-7.96 (5H, 2 m, ar), 10.08 (1H, br s, COM); $\delta_C$(50 MHz; CDCl$_3$) 18.0 (CH$_3$), 24.6, 36.1 (CH$_2$CH$_2$), 48.3, (CH), 127.2, 128.7, 133.6, 136.7 (ar), 171.5, 176.0, 192.4 (C=O); m/z (AP−) 280 (M-H$^+$, 10%).

Example 15

(R)-2-(3-Benzoylsulfanyl-propionylamino)-propionic acid (IS21)

or: N-(3-Benzoylthiopropanoyl)-(D)-alanine (IS21)

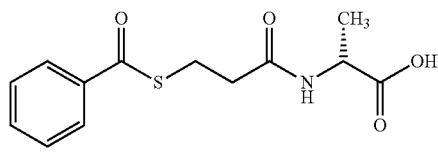

This compound was prepared as for IS20 but with (L)-alanine substituting for (D)-alanine yielding 1.78 g (6.3 mmol, 38%) of IS20 as a colourless powder, mp 98-99° C.; $[\alpha]_D^{25}$ +19.1 (c 1 in methanol). Analytical data except optical rotation corresponded to those of IS20.

Example 16—Peptide Blockade of HIF-α Degradation Modulates Cellular Metabolism and Angiogenesis 16.1 Introduction Ischaemia is a major cause of morbidity and mortality and effective molecular therapies are being intensively sought [1,2]. The transcription factor hypoxia-inducible factor-1 (HIF) is a master regulator of the hypoxic response, controlling genes involved in diverse processes that balance metabolic supply and demand within tissues [3,4,5]. Modulation of HIF activity therefore provides an attractive approach for the treatment of ischaemic disease. Furthermore, HIF driven angiogenesis produces more mature and less leaky vessels than those generated by individual growth factors [6,7,8].

Regulation of HIF is mediated at multiple levels via its α chain [9,10,11,12,13]. It has been reported that PR39, a macrophage derived peptide, results in HIF accumulation and angiogenesis [14]. Analysis of the HIFα oxygen-dependent degradation domains (ODD) by transient transfection studies [11,12,15,16,17,18] suggested a possible specific, alternative approach to HIF stabilisation. We have used peptides containing the sites of regulated prolyl hydroxylation identified as necessary in the previous Examples for proteasomal destruction in the presence of oxygen mediated by the von Hippel-Lindau E3 (VHL E3) ubiquitin ligase complex [19,20,21,22]. Despite the multiple steps involved in HIF activation we demonstrate unequivocally that peptides from two regions of the ODD not only stabilise HIFα but produce a transcriptional response that modulates normoxic angiogenesis and metabolism in vivo, suggesting that the peptides affect mechanisms that are common to all activation steps. These results indicate that these polypeptides, or molecules based on them, provide a possible therapeutic approach for ischaemic tissues.

16.2 Overexpression of CODD and NODD Polypeptides can Induce HRE-Dependent Reporter Gene Expression Since normoxic HIFα degradation is saturable [17] and depends on sub-regions within the ODD we tested whether peptides encoding the HIF-1α amino terminal ODD (NODD) and carboxy terminal ODD (CODD) [21] could affect HIF activity as measured by hypoxia response element (HRE)-dependent reporter gene expression. The proposed model by which the NODD and CODD peptides inhibit HIF activity is shown in FIG. 13. Briefly, Degradation is prevented by the NODD and CODD polypeptides competing for prolyl hydroxylation and/or VHL binding, thereby blocking subsequent ubiquitination. We constructed plasmids encoding NODD (HIF-1-α aa 343-417) or CODD (HIF-1-α aa 549-582) linked to nuclear localisation sequences and a c-myc epitope tag. These plasmids were transiently co-transfected into U2OS and Hep3B cells with an HRE-dependent luciferase reporter plasmid. Under normoxic conditions expression of either ODD derived polypeptide increased relative luciferase activity after 24 hours to levels comparable to those induced in the absence of peptide by hypoxia (results shown in FIG. 13). Transfection of the NODD and CODD expression plasmids had no effect on luciferase activity from reporter plasmids lacking functional HRE's, demonstrating that the effect was mediated via the HRE (results not shown). To confirm that polypeptide action was being mediated via the endogenous HIF pathway we repeated this experiment in a mutant Chinese hamster ovary cell line lacking HIFα chains (Ka13), and a HIF-1α complemented transfectant (KH-1) [23]. Transfection of the NODD and CODD plasmids led to enhanced luciferase activity in KH-1 but not in Ka13 cells (results shown in FIG. 13).

We tested shorter fragments of NODD and CODD peptides, defining amino acids 390-417 and amino acids 556-74 as minimal domains capable of HRE-dependent luciferase activation. (results shown in FIG. 13). A sequence alignment of these minimal domains with the equivalent regions from mouse HIF-1-α is shown in FIG. 13.

HIFα chain degradation depends on recognition by the VHL E3 ubiquitin ligase following oxygen-dependent enzymatic hydroxylation of prolyl residues at positions 402 and 564 [19,20,21]. Using mutated expression plasmids (P402A or P564G) we demonstrated complete ablation of HRE-dependent induction of luciferase activity (results shown in FIG. 13), showing the critical role of these residues for polypeptide function. This suggested that expression of the NODD and CODD fusion proteins interfered with degradation of endogenous HIFα chains, most likely by interfering with VHL recognition or prolyl hydroxylation in normoxic cells, and hence provides a potential route to the therapeutic manipulation of the HIF system.

16.3 Stable NODD and CODD Polypeptide Expression Results in Endogenous HIF-1α Accumulation To explore further the therapeutic potential of NODD and CODD polypeptides to activate endogenous HIF we stably transfected U2OS cells with doxycycline-inducible NODD (doxNODD) and CODD constructs (doxCODD) encoding identical sequences to those used for transient transfections.

Cells stably transfected with NODD or CODD controlled by the tetracycline-inducible system were exposed to doxycycline. Cell extracts were prepared 0, 16, 24 and 48 hours after exposure to doxycycline. The extracts of doxNODD (HIF-1α aa343-417), doxCODD (HIF-1α aa549-82) and control cells (empty vector) were then immunoblotted for HIF-1α protein. Increased HIF-1α signals were detected from 16-48 hours following doxycycline administration in doxNODD and doxCODD cells but not in empty vector cells. Levels of HIF-1α induced by hypoxia were also measured for comparison. The endogenous HIF-1α induction was doxycycline dose (0.2-3.2 µg/ml) and time dependent, peaking after 48 hours. Maximal levels were about 20% and about 70% of HIF-1α levels seen following hypoxic or DFO treatment of the doxNODD and doxCODD cells respectively. Doxycycline did not induce HIF-1α protein in cells transfected with empty vector despite its weak ability to chelate iron.

Immunofluorescence microscopy allowed visualisation of both the c-myc tag of the expressed fusion proteins and endogenous HIF-1α. In doxycycline activated doxCODD cells both were located in nuclei. HIF-1α expression varied considerably from cell to cell. In cells which had not been exposed to doxycycline strong staining was only seen from the endogenous HIF-1-α.

Combined treatment of doxCODD cells with doxycycline and optimal DFO (75 µm) or hypoxic stimuli (1% $O_2$) did not lead to further increases in HIF-1α signals on immunoblots confirming that the peptides had no additional action when endogenous HIFα chains were fully induced by physiological stimuli.

To test directly whether the polypeptides prevented cellular HIF-1α targeting by the VHL-ubiquitin-proteasome system we showed that ubiquitination of exogenous $^{35}$S-methionine labelled HIF-1α was markedly reduced in the presence of doxCODD extracts compared with control cell extracts lacking the peptide transfected with empty vector.

HIF and HIF-dependent target gene expression has been suggested to be subject to a number of negative feedback controls. To investigate the consequences of continuous activation of the system we exposed doxCODD cells to doxycycline for two, four, six or eight days. HIF-1α protein levels were significantly elevated on days 2 and 4 but decreased thereafter. Switching off the system by removing doxycycline from the medium for 48 hours prior to re-exposure resulted in re-induction of elevated HIF-1α protein levels, indicating that the suppressive effects were reversible. This phenomenon will need to be considered in using the HIF system to modulate complex physiological downstream effects for example through the administration of modulators of the invention at spaced intervals or alternatively by inducing the constructs of the invention at spaced intervals.

16.4 NODD and CODD Fusion Proteins Induce Target Gene mRNA and Protein Levels Results thus far presented indicate that under normoxic conditions NODD and CODD polypeptide expression results in stabilisation of endogenous HIF-1α chains and consequent activation of transiently transfected artificial HRE-dependent promoters. Expression of natural HIF target genes in chromosomal DNA may be constrained by other factors. We therefore investigated peptide modulation of endogenous genes known to be HIF targets.

Carbonic anhydrase IX (CAIX) is transcriptionally up-regulated under hypoxic conditions [24]. We used a ribonuclease protection assay to measure CAIX mRNA at intervals following doxycycline treatment in doxCODD and empty vector transfected cells. Levels of mRNA were measured at 0, 24 and 48 hours following treatment. SnRNA (small nuclear RNA) was also probed to ensure equivalent loading. Doxycycline markedly induced mRNA levels in doxCODD cells after 24 and 48 hours to levels similar to those obtained by hypoxic incubation. Cells transfected with empty vector showed no induction of CAIX. Immunoblots demonstrated an associated increase of CAIX protein, paralleling detection of the CODD peptide, visualised by immunoblotting using the c-myc tag. To test the generality of this effect we performed comparable experiments on glucose transporter-1 (Glut-1) mRNA expression, obtaining similar results. When doxycycline was repeatedly added to cell culture medium Glut-1 mRNA, detected by ribonuclease protection, measured after 0, 2, 4, 6 and 8 days Glut-1 mRNA levels increased for the first 4 days and then declined in parallel with the HIF-1α protein levels as observed above, Maximal Glut-1 mRNA levels were comparable to those induced following exposure to 75 µM desferrioxamine.

To test for the physiological relevance of increased Glut-1 expression we conducted glucose uptake experiments. $^3$H-glucose uptake was measured. An enhanced uptake of $^3$H-glucose was measured in doxCODD cells compared with empty vector transfected cells after 24 hours induction with doxycycline. In contrast, basal levels in cells untreated with doxycycline and hypoxically induced levels (hypoxia) of $^3$H-glucose uptake were comparable between cell lines. (*: $P<0.01$; Error bars represent the SEM of 3 replicates.) Thus, in contrast to control cells, expression of the CODD polypeptides mimicked the effect of hypoxia by inducing glucose uptake in stably transfected cells.

16.5 tat-NODD and tat-CODD Fusion Proteins Enter Cultured Cells and Induce HIF-1α Under Normoxic Conditions Experiments presented above show that oxygen-dependent gene expression can be modulated in normoxia by plasmid based expression of NODD and CODD polypeptides. To extend this approach we chose to study the effects of transducing comparable peptides into cells. The transduction domain of HIV tat-protein delivers fused proteins across cell membranes in a transporter independent mechanism [25] [26]. We fused the NODD and CODD peptides to the tat-sequence in combination with HA and HIS tags to facilitate detection and nickel affinity purification. We did not include exogenous nuclear localisation sequences because the tat sequence itself is sufficient for nuclear entry [27].

We performed VHL E3 interaction assays [21] with tat-NODD and tat-CODD, demonstrating their ability to undergo the necessary modifications for interaction with VHL. $^{35}$S-Methionine labelled IVTT products of tat-ODD expression vectors were tested for their ability to bind to VHL E3 ligase. Concordant with the ubiquitination assays discussed above NODD (HIF-1α 343-417) and CODD (HIF-1α 549-582) polypeptides, but not their corresponding proline mutants (HIF-1α 343-417/P402A and HIF-1α 549-582/P564G), bound to VHL E3 ubiquitin ligase after modification by cell extracts. The $^{35}$S-methionine labelled recombinant polypeptides therefore interacted with VHL, supporting the results of the ubiquitination experiments discussed above. The interaction was enhanced by the presence of cell extracts which promote hydroxylation of the prolines at positions 402 and 564 [19]. In contrast, no binding occurred using peptides in which prolines were mutated.

We next tested, by immunoblotting, if these tat-fusion proteins could traverse cell membranes and induce HIF-1α. Two hours following addition of tat-NODD or tat-CODD fusion proteins to cell cultures intact peptide was detectable in whole cell protein extracts by immunoblotting for the HA tag. The HA tag of tat-NODD (tat-343-417) and tat-CODD (tat-549-582) polypeptides were detected in cell extracts, following repetitive polypeptide administration indicating their uptake by the cells. HIF-1α protein was induced by the tat-NODD and the tat-CODD polypeptides (0.5 μM), but not by the corresponding proline mutants. Maximal levels were comparable to those induced following exposure to 75 μM desferrioxamine (DFO). In experiments with repetitive polypeptide administration, endogenous HIF-1α was detectable in normoxia 20 hours after initial exposure of the cells to fusion proteins. In controls, using the corresponding mutant peptides lacking the prolines, we detected no HIF-1α signals. It has been reported that denaturation enhances uptake of tat-fused proteins [25]. Denatured tat-NODD and tat-CODD peptides were still able to enter cells, but were inactive in mediating HIF-1α upregulation, perhaps because they were no longer capable of being hydroxylated.

16.6 Endothelial Activation and In Vivo Angiogenesis Assays

Artificial activation of the HIF signalling pathway using the methods of the invention should induce angiogenesis and will therefore be of potential therapeutic use in ischaemic disease. We tested the effect of polypeptide induced HIF stabilisation in an in vitro angiogenesis assay, co-culturing human microvascular endothelial cells (HMEC-1) with empty vector transfected or doxCODD cells. In view of the possibility of sustained activation inducing a negative feedback loop we opted to test the effects of intermittent induction. In doxCODD, but not in empty vector transfected cells, intermittent exposure to doxycycline over a period of 5 days led to assembly of co-cultured endothelial cells into complex tubular structures visualised by immunostaining for von Willebrand factor but not in control cells. As a positive control epidermal Growth Factor (EGF; 5 ng/ml), which is known to induce growth of HMEC-1, was used. To extend these observations into an in vivo model we assayed the effects of injecting tat-fusion proteins into polyurethane sponges implanted subcutaneously in mice. Intermittent injections on days 1, 2, 4 and 5 led to a markedly accelerated angiogenic response assayed on day 7 when compared with sponges injected with proline mutant fusion proteins, excluding a contribution from the tat component [28]. Immunohistochemistry for von Willebrand factor revealed increased vessel density in sponges explanted after 7 days following treatment with tat-CODD, but not with mutant peptide (tat-CODD/P564G). Staining for VEGF and Glut-1 was enhanced in tat-NODD or tat-CODD treated animals compared to controls. Cells surrounding the sponge showed particularly intense staining. The vessel endothelium within sponges was surrounded by cells expressing smooth muscle actin.

16.7 Summary

Hypoxia-inducible factor-1 (HIF) is a transcription factor known to regulate pro-angiogenic genes and modulate metabolism in response to hypoxic stress. Modulation of HIF activity therefore provides an attractive theoretical route to ameliorating ischaemic disease. Under normoxic conditions HIFα chains are ubiquitylated and destroyed by the proteasome following enzymatic hydroxylation of critical prolyl residues. Here we demonstrate use of polypeptides bearing these prolyl residues to stabilise endogenous HIF, thereby up-regulating HIF target genes. Peptide expression in cell cultures affects physiologically important functions such as glucose transport and leads to tubule formation by co-cultured endothelial cells. Subcutaneous injection of polypeptides results in a markedly accelerated local angiogenic response and induction of glucose transporter-1 gene expression. These results demonstrate the feasibility of utilising these polypeptides to enhance normoxic HIF activity, opening new therapeutic avenues for ischaemic diseases.

In this Example we have described the use of polypeptides which stabilise the hypoxia-regulated transcription factor HIF-1α. We provide evidence that complex physiological systems like glucose uptake and angiogenesis can be induced strongly, even under normoxic conditions.

Related molecular approaches to treating ischaemic disease include use of single growth factors [2] or gene therapy with HIF based sequences lacking the degradation domains [6,29]. The approach used here has advantages over the former in that it co-opts the entire physiological response resulting in metabolic adaptation as well as angiogenesis and provides an alternative to gene therapy that should be easier to apply.

Influences of HIF on cancer growth and apoptosis [30,31] lead to concerns that long-term HIF activation might have deleterious effects, including pro-neoplastic actions. However, these processes probably require additional events beyond HIF activation and are Likely to have a much longer time course than that required for therapeutic angiogenesis. Furthermore, the peptides used here are inherently unstable and act locally, allowing circumscribed dosing schedules that avoid continued and general exposure.

The NODD and CODD polypeptides were effective alone and in combination. Mechanisms of polypeptide action within cells include competition for HIF prolyl hydroxylase activity or VHL binding capacity. Three lines of evidence suggest the latter is more probable. Firstly, we have demonstrated that these NODD and CODD fusion proteins bind to VHL, presumably following their own hydroxylation. Secondly, the action of either peptide is sufficient to stabilise HIFα even though it contains both prolyl residues, which can be targeted by different hydroxylase isoforms [22]. Thirdly, concentrations of synthetic peptide necessary to quench HIF prolyl hydroxylase activity in cell extracts are unlikely to be produced in cells.

Comparison of the NODD and CODD sequences coupled with structural studies clarifying the nature of their interactions with VHL and different prolyl hydroxylase isoforms will allow further refinements to these agents. Use of other protein transduction domains and/or tissue specific targeting sequences, including tripeptides such as GFE for lung or RDV for retina, will lead to new formulations with lower risks of side effects [32,33].

The polypeptides reported here are exciting reagents, allowing controlled activation of the HIF pathway in normoxia. Animal models of ischaemia may be used to demonstrate the net therapeutic benefits of the peptides followed by clinical trials.

16.8 Methods

Plasmids, Transient and Stable Transfections

Plasmid Constructs:

For reporter gene assays DNA fragments encoding HIF-1α amino acids 343-417, 380-417, 390-417, 390-410, 343-400, 530-95, 530-82, 549-82, 556-74 and 530-62 were generated by PCR using oligonucleotides containing 5' SacII or 3' AscI sites and inserted into a pCMV/myc/nuc (Invitrogen) derivative bearing these sites in frame with the NLS and epitope tag. Site directed mutagenesis (QuikChange, Stratagene) was used to mutate the constructs containing HIF-1α aa343-417 or aa549-82 at aa402 [cca to gca] or aa564 [cca to ggc] converting prolines to alanine or glycine respectively. To generate tet-operator dependent plasmids the open reading frames from the aa343-417 and aa549-82 constructs were subcloned into pUHD 10 [34]. Fragments coding for HIF-1α aa343-417 and aa530-82 (with and without P402A and P564G mutants) were subcloned into ptat-HA [25]. All constructs were confirmed by DNA sequencing.

Reporter Gene Assays:

Cells were co-transfected with an HRE containing reporter gene, pCMV/myc/nuc constructs and a constitutively expressed beta-galactosidase gene using Fugene6 (RocheMolecular) [35]. Transfectants were maintained in normoxia for 24 hours or in hypoxia for the final 16 hours. Luciferase activities in cell extracts were determined using a commercial kit (Promega) and a TD-20e luminometer (Turner Designs). Beta-galactosidase activity was measured spectrophotometrically using o-nitrophenyl-beta-D-galactopyranoside as substrate.

Stably transfected cell lines were generated by transfecting U2OS cells bearing the reverse tetracycline responsive transactivator [34] and the tetKRAB silencer construct [36] with pUHD/HIF plasmids. Following selection in G418 (1 mg/ml) individual colonies were picked. DoxNODD (F21) and doxCODD (myc19) clones expressed pUHD/HIF-1aa343-417/3NLS/c-myc and pUHD/HIF-1α aa549-82/3NLS/c-myc respectively.

mRNA and Protein Detection

RNA Analysis:

Total RNA extracted using RNAzol B (Biotec Laboratories) was analysed by ribonuclease protection using $^{32}$P-GTP labelled Glut-1, CAIX and snRNA (as internal control) riboprobes using templates previously described [10][24].

Immunoblotting:

Cell extracts were prepared in buffer (8M urea, 10% glycerol, 1% SDS, 5 mM DTT, 10 mM Tris/pH 6.8), separated by SDS-PAGE and transferred to Immobilon-P membrane (Millipore). Primary antibodies against HIF-1α, c-myc tag and HA tag were from Transduction Laboratories, Innogenex and Roche Molecular respectively.

Ubiquitination and Interaction Assays

Empty vector and doxCODD cells grown to confluence were induced with doxycycline (0.8 µg/ml) for 48 hours and ubiquitination assays performed using cytoplasmic extracts as described previously [37].

For VHL E3 interaction assays $^{35}$S-methionine labelled HIF-1a substrates were prepared by transcription/translation using TnT7 rabbit reticulocyte lysate (Promega). 100 µM DFO was added to the reaction to suppress prolyl hydroxylase activity of the reticulocyte lysate. Substrate modification was achieved by incubation of HIF-1α translate with RCC4 cell lysate in the presence of ferrous chloride (100 µM). Interaction with VHL E3 was analysed as described previously [21].

Glucose Uptake

Empty vector and doxCODD cells were grown to confluence, exposed to 1%, 21% oxygen or 0.8 µg/ml doxycycline for 16 h, washed with glucose-free DMEM and incubated for 10 min with 1 µCi/ml 2-deoxy-D$^3$H-glucose (Amersham, UK), before lysis in 0.5% NP-40, 0.25 M NaCl, 10 mM HEPES/pH 7.6. Glucose uptake was determined by liquid scintillation counting [35].

tat-Protein Synthesis and Purification

HIF-1α-tat-fusion proteins were purified by sonication of transformed BL21pLysS (Novagen) in lysis buffer (0.5% Tween-20, 50 mM NaH$_2$PO$_4$, 300 mM NaCl, 5 mM imidazole) after 4 hours induction with 1 mM IPTG. Lysates were spun down at $10^3$ g before loading on a Ni-NTA column (Qiagen). Proteins were eluted with 100 mM imidazole and desalted on a PD 10 column (Amersham)[25] in 10 mM Tris/pH 7.0 or in 10 mM Tris/pH 8.0, 30 mM KCl. Aliquots were snap frozen in liquid nitrogen. Tat-proteins (0.5 µM final concentration) were given to cultures in DMEM/1% FCS at the beginning and 8 hours after starting the experiments before harvesting the cells after 24 hours.

Angiogenesis Assays

Tubule Formation Assay:

doxCODD or empty vector cells were co-cultivated with human microvascular endothelial cells (HMEC-1) in a ratio of 2:1 in DMEM 10% doxycycline free FCS (Clontech), 2 mM Glutamine and 100 U/ml Penicillin/100 µg/ml Streptomycin. Stimulation with doxycycline (0.8 µg/ml) or epidermal growth factor (5 ng/ml) (Sigma) or control medium was renewed every second day. On day 5 cells were fixed with 70% ethanol, pre-blocked with 1% BSA/PBS. Endothelial cells were detected using antibodies to von Willebrand factor (vWF) (Dako).

Murine Sponge Model:

Sterile polyurethane sponges (8 mm diameter) were inserted subcutaneously under the dorsal skin of anaesthetized black C57 female mice on day 0. On the $1^{st}$, $2^{nd}$, $4^{th}$ and $5^{th}$ days 100 µl of tat-fusion proteins (1 µM) in Tris buffer (10 mM, pH 7.0) were injected into the sponges. On day 7 mice were sacrificed and sponges were excised with surrounding tissue and fixed in 3.5% paraformaldehyde.

Immunohistochemistry:

Paraffin embedded sponges were cut into 6 µm sections, dewaxed with xylene, rehydrated and stained with vWF (Dako), Glut-1 (Alpha Labs), VEGF (Santa Cruz) and smooth muscle cell actin (DAKO) antibodies. Antigen retrieval, blocking of sections, secondary, HRP labelled antibodies and chromogenic reactions were performed according to the manufacturers' recommendations (DAKO Envision System and Vector Labs ABC Vectastain).

REFERENCES

1. Marti, H. H. & Risau, W. Angiogenesis in ischemic disease. *Thromb Haemost* 82 Suppl 1, 44-52. (1999).
2. Ferrara, N. & Alitalo, K. Clinical applications of angiogenic growth factors and their inhibitors. *Nat Med* 5, 1359-64. (1999).
3. Semenza, G. L. Hypoxia-inducible factor 1: master regulator of O2 homeostasis. *Curr Opin Genet Dev* 8, 588-94. (1998).
4. Ratcliffe, P. J., O'Rourke, J. F., Maxwell, P. H. & Pugh, C. W. Oxygen sensing, hypoxia-inducible factor-1 and the regulation of mammalian gene expression. *J Exp Biol* 201, 1153-62. (1998):
5. Semenza, G. L. Surviving ischemia: adaptive responses mediated by hypoxia-inducible factor 1. *J Clin Invest* 106, 809-12. (2000).
6. Elson, D. A. et al. Induction of hypervascularity without leakage or inflammation in transgenic mice overexpressing hypoxia-inducible factor-1 alpha. *Genes Dev* 15, 2520-32 (2001).
7. Yancopoulos, G. D. et al. Vascular-specific growth factors and blood vessel formation. *Nature* 407, 242-8. (2000).
8. Carmeliet, P. & Jain, R. K. Angiogenesis in cancer and other diseases. *Nature* 407, 249-57. (2000).
9. Kallio, P. J. et al. Signal transduction in hypoxic cells: inducible nuclear translocation and recruitment of the CBP/p300 coactivator by the hypoxia-inducible factor-1alpha. *Embo J* 17, 6573-86. (1998).
10. Maxwell, P. H. et al. The tumour suppressor protein VHL targets hypoxia-inducible factors for oxygen-dependent proteolysis. *Nature* 399, 271-5. (1999).
11, Salceda, S. & Caro, J. Hypoxia-inducible factor 1alpha (HIF-1alpha) protein is rapidly degraded by the ubiquitin-proteasome system under normoxic conditions. Its stabilization by hypoxia depends on redox-induced changes. *J Biol Chem* 272, 22642-7. (1997).
12. Huang, L. E., Gu, J., Schau, M. & Bunn, H. F. Regulation of hypoxia-inducible factor 1alpha is mediated by an O2-dependent degradation domain via the ubiquitin-proteasome pathway. *Proc Natl Acad Sci USA* 95, 7987-92. (1998).
13. Arany, Z. et al. An essential role for p300/CBP in the cellular response to hypoxia. *PNAS* 93, 12969-73. (1996).
14, Li, J. et al. PR39, a peptide regulator of angiogenesis. *Nat Med* 6, 49-55. (2000).
15. Srinivas, V., Zhang, L. P., Zhu, X. H. & Caro, J. Characterization of an oxygen/redox-dependent degradation domain of hypoxia-inducible factor alpha (HIF-alpha) proteins. *Biochem Biophys Res Commun* 260, 557-61. (1999).
16. Yu, F., White, S. B., Zhao, Q. & Lee, F. S. Dynamic, site-specific interaction of hypoxia-inducible factor-1alpha with the von Hippel-Lindau tumor suppressor protein, *Cancer Res* 61, 4136-42 (2001),
17. O'Rourke, J. F., Tian, Y. M., Ratcliffe, P. J. & Pugh, C. W. Oxygen-regulated and transactivating domains in endothelial PAS protein 1: comparison with hypoxia-inducible factor-1alpha. *J Biol Chem* 274, 2060-71. (1999).
18. Pugh, C. W., O'Rourke, J. F., Nagao, M., Gleadle, J. M. & Ratcliffe, P. J. Activation of hypoxia-inducible factor-1; definition of regulatory domains within the alpha subunit. *J Biol Chem* 272, 11205-14. (1997).
19. Jaakkola, P. et al. Targeting of HIF-alpha to the von Hippel-Lindau ubiquitylation complex by O2-regulated prolyl hydroxylation. *Science* 292, 468-72. (2001).
20, Ivan, M. et al. HIFalpha targeted for VHL-mediated destruction by proline hydroxylation: implications for O2 sensing. *Science* 292, 464-8. (2001).
21. Masson, N., William, C., Maxwell, P. H., Pugh, C. W. & Ratcliffe, P. J. Independent function of two destruction domains in hypoxia-inducible factor-alpha chains activated by prolyl hydroxylation. *Embo J* 20, 5197-206 (2001).
22. Epstein, A. C. et al. C. elegans EGL-9 and Mammalian Homologs Define a Family of Dioxygenases that Regulate HIF by Prolyl. Hydroxylation. *Cell* 107, 43-54 (2001).
23. Wood, S. M. et al. Selection and analysis of a mutant cell line defective in the hypoxia-inducible factor-1 alpha-subunit (HIF-1alpha). Characterization of hif-1alpha-dependent and -independent hypoxia-inducible gene expression. *J Biol Chem* 273, 8360-8. (1998).
24. Wykoff, C. C. et al. Hypoxia-inducible expression of tumor-associated carbonic anhydrases. *Cancer Res* 60, 7075-83. (2000).
25. Nagahara, H. et al. Transduction of full-length TAT fusion proteins into mammalian cells: TAT-p27Kip1 induces cell migration. *Nat Med* 4, 1449-52. (1998).
26. Schwarze, S. R. & Dowdy, S. F. In vivo protein transduction: intracellular delivery of biologically active proteins, compounds and DNA. *Trends Pharmacol Sci* 21, 45-8. (2000).
27. Truant, R. & Cullen, B. R. The arginine-rich domains present in human immunodeficiency virus type 1 Tat and Rev function as direct importin beta-dependent nuclear localization signals. *Mol Cell Biol* 19, 1210-7 (1999).
28. Albini, A. et al. The angiogenesis induced by HIV-1 tat protein is mediated by the Flk-1/KDR receptor on vascular endothelial cells. *Nat Med* 2, 1371-5 (1996).
29. Vincent, K. A. et al. Angiogenesis is induced in a rabbit model of hindlimb ischemia by naked DNA encoding an HIF-1alpha/VP16 hybrid transcription factor. *Circulation* 102, 2255-61. (2000).
30. Maxwell, P. H., Pugh, C. W. & Ratcliffe, P. J. Activation of the HIF pathway in cancer. *Curr Opin Genet Dev* 11, 293-9. (2001).
31. Carmeliet, P. et al. Role of HIF-1alpha in hypoxia-mediated apoptosis, cell proliferation and tumour angiogenesis. *Nature* 394, 485-90. (1998).
32. Ho, A., Schwarze, S. R., Mermelstein, S. J., Waksman, G. & Dowdy, S. F. Synthetic protein transduction domains: enhanced transduction potential in vitro and in vivo. *Cancer Res* 61, 474-7. (2001).
33. Rajotte, D. et al. Molecular heterogeneity of the vascular endothelium revealed by in vivo phage display. *J Clin Invest* 102, 430-7 (1998).
34. Gossen, M. et al. Transcriptional activation by tetracyclines in mammalian cells. *Science* 268, 1766-9. (1995).
35. Vaux, E. C. et al. Selection of Mutant CHO Cells with Constitutive Activation of the HIF System and Inactivation of the von Hippel-Lindau Tumor Suppressor. *J Biol Chem* 276, 44323-30 (2001).
36. Deuschle, U., Meyer, W. K. & Thiesen, H. J. Tetracycline-reversible silencing of eukaryotic promoters. *Mol Cell Biol* 15, 1907-14. (1995).
37. Cockman, M. E. et al. Hypoxia inducible factor-alpha binding and ubiquitylation by the von Hippel-Lindau tumor suppressor protein. *J Biol Chem* 275, 25733-41. (2000).

Example 17

Effect of Iron Chelation on N-Oxalylglycine Inhibitory Activity and Direct Comparison of the Inhibitory Activity of a Pair of Enantiomers.

To determine whether N-oxalylglycine inhibits HIF-1α modification via iron chelation we performed capture assays using a Gal/HIF-1α/VP16 fusion protein expressing HIF-1α residues 549-582 in the presence of varying concentrations of inhibitor and iron.

Figure 14A:
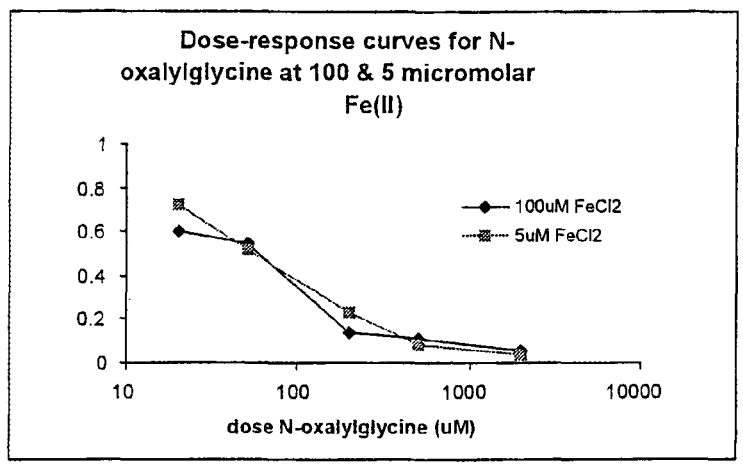
FIGS. 14A-14B show dose-response curves for oxalyglycine as well as oxalyl R and S-alanine.

The unlabelled HIF-1α substrate was immunopurified on beads, washed, and aliquots incubated in the presence of RCC4 cell extract with 0, 20, 50, 200, 500 or 2000 μM N-oxalylglycine and either 5 or 100 μM $FeCl_2$. After washing, the beads were assayed for their ability to interact with 35-S labelled pVHL IVTT, which was then visualised by fluorography. The results obtained are shown in FIG. 14A. The amount of pVHL captured is expressed as relative counts per band. Inhibition of pVHL capture by N-oxalylglycine increased with the concentration of inhibitor and was the same regardless of iron concentration. As iron supplementation has little or no effect on inhibition this shows that the inhibition of HIF-1α modification by N-oxalylglycine is not mediated by iron chelation but by an alternative mechanism.

The inhibitory effect of the pair of enantiomers, N-oxalyl-2S-alanine and N-oxalyl-2R-alanine, on HIF-1α modification was also studied. This was done using the same pVHL capture assay described above again using the Gal/549-582/

Figure 14B:
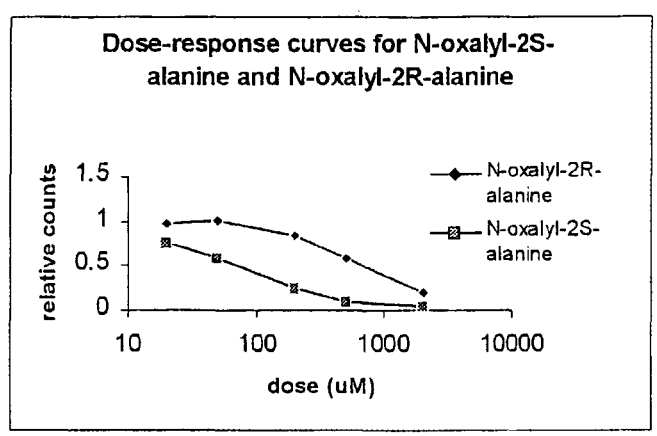
Figure 15:
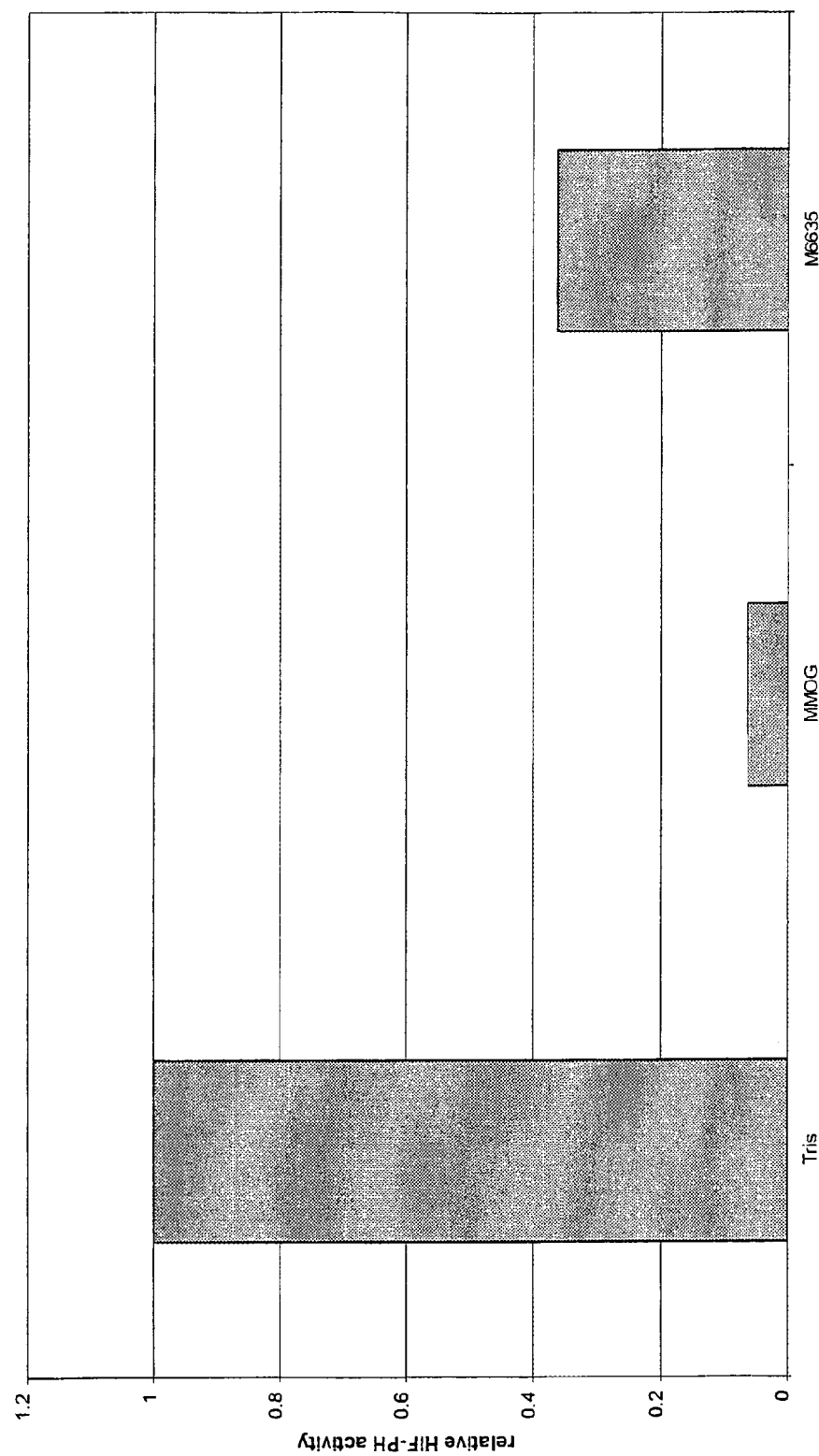
FIGS. 15 to 20 show the relative HIP-PH activity for a variety of inhibitors.
Figure 16:
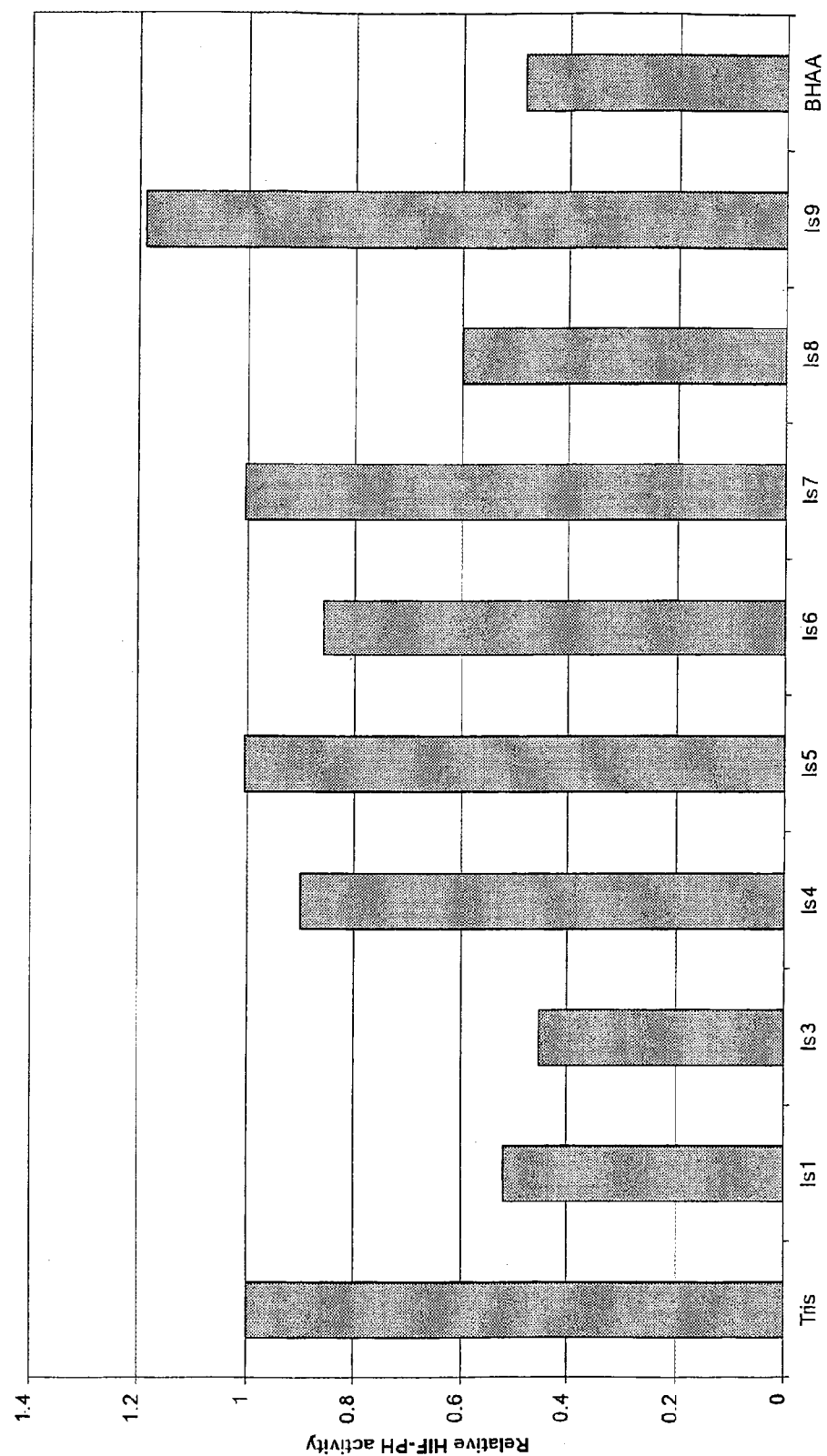
Figure 17:
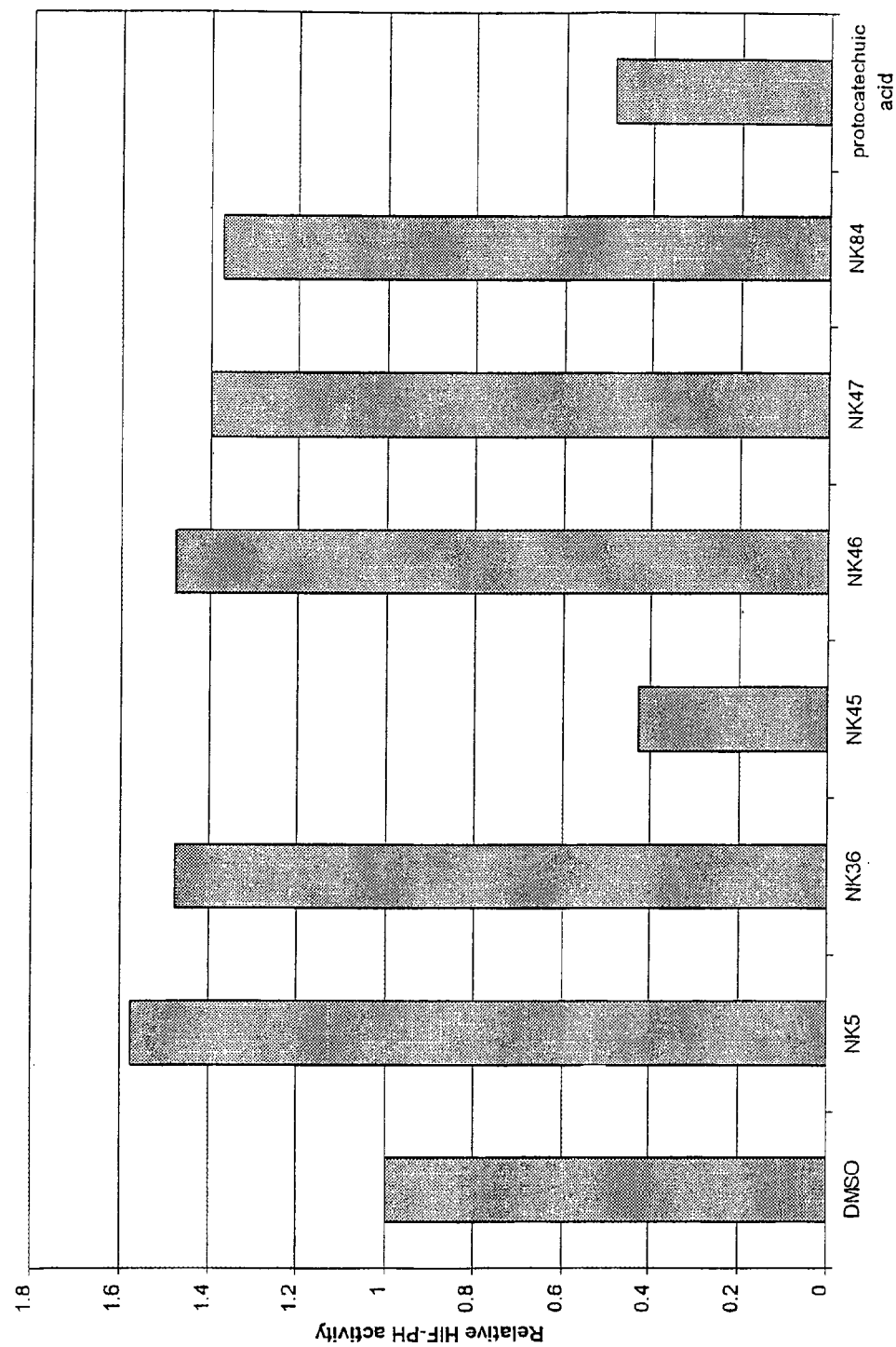
Figure 18:
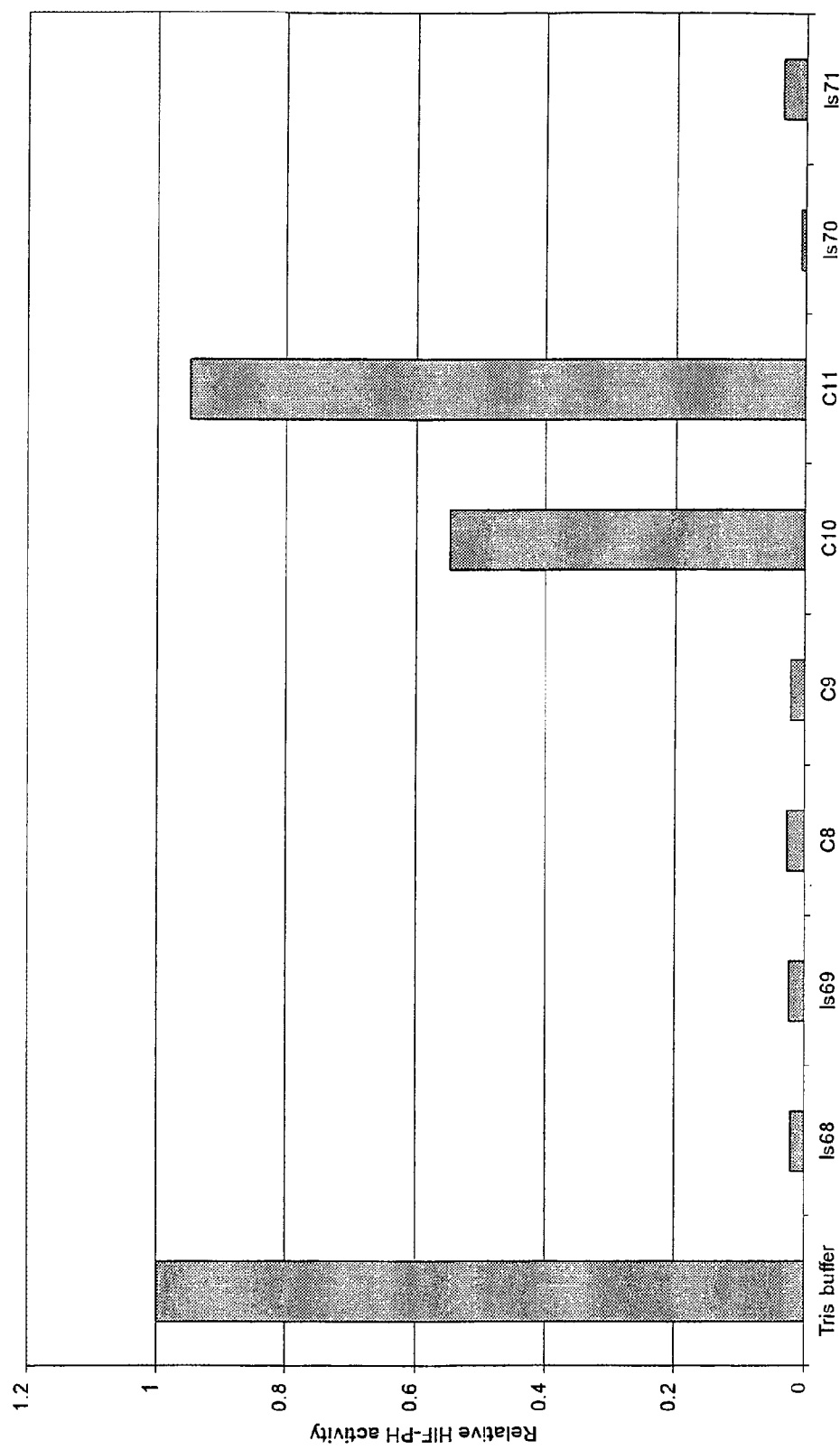
Figure 19:
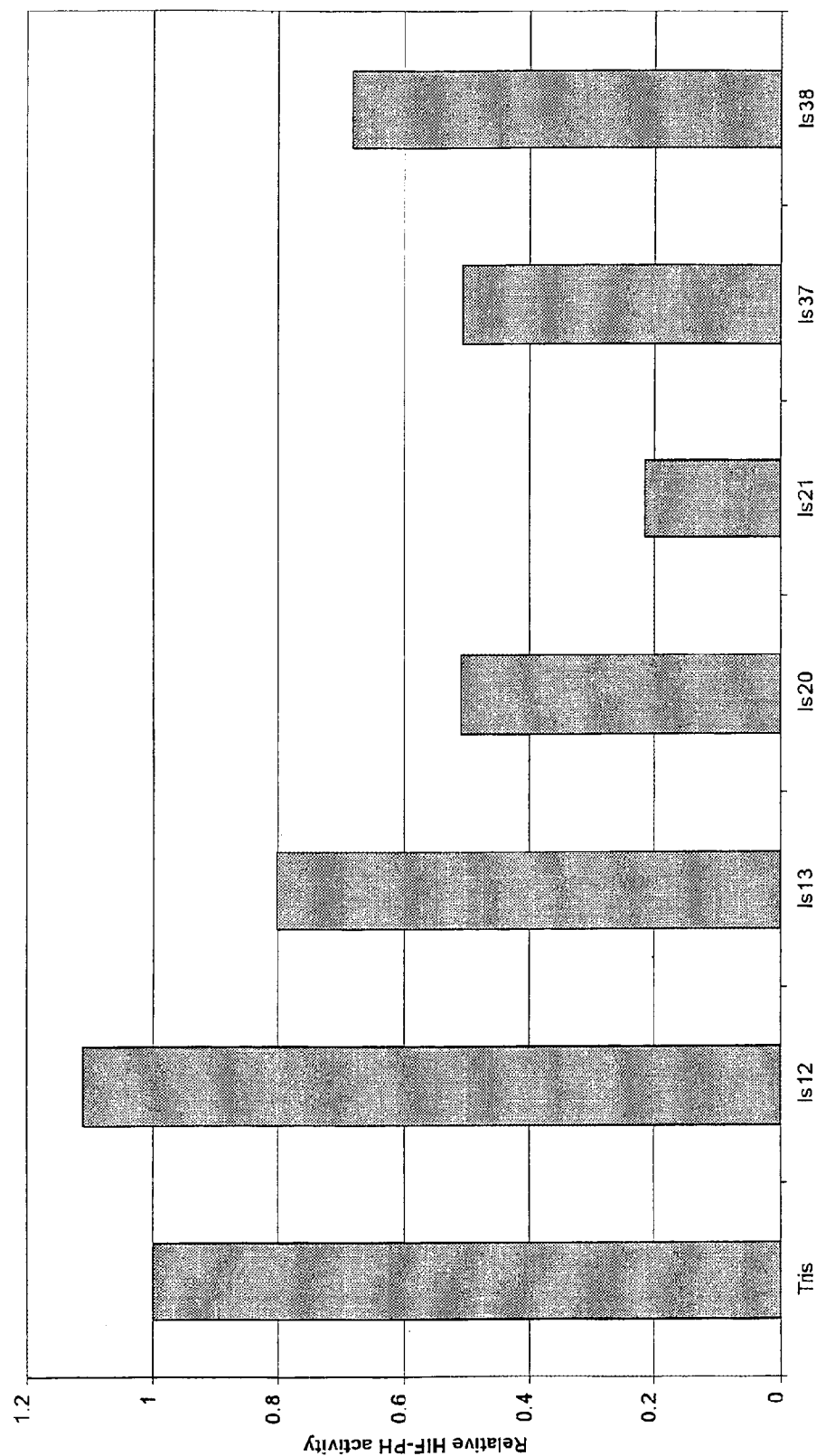
Figure 20:
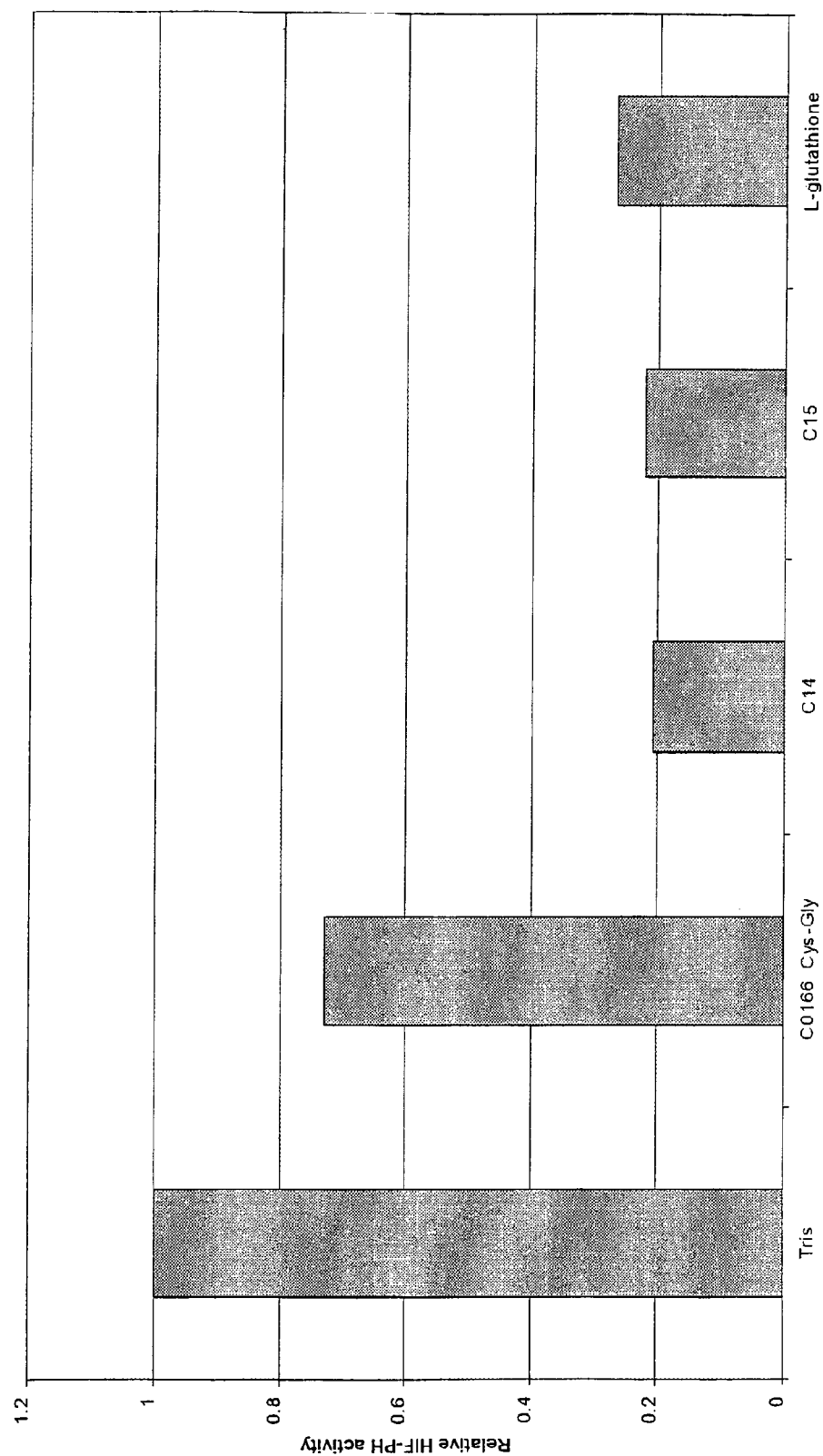

VP16 fusion protein as a substrate. The effect of 0, 20, 50, 200, 500 and 2000 μM concentrations of each enantiomer on pVHL capture was then assessed. The results obtained are shown in FIG. 14B. Again, the amount of labelled pVHL captured is expressed as relative counts per band. The results show that there is approximately one log difference in the ability of the enantiomers to inhibit modification of the HIF substrate and hence pVHL capture. N-oxalyl-2S-alanine enantiomer had the higher inhibitory activity of the two enantiomers.

Example 18

In vitro screening of potential inhibitors of HIF modification was performed using a capture assay. A Gal/HIF-1α/VP16 fusion protein expressing HIF-1α residues 549-582 was prepared by IVTT and used as a substrate in the assay. The unlabelled substrate was immunopurified on beads, washed, and aliquots incubated in the presence of RCC4 cell extract, with 100 μM FeCl$_2$ and 2 mM of the potential inhibitor. The inhibitors were either dissolved in DMSO or Tris as indicated. Controls, where no inhibitor but the equivalent amount of DMSO or Tris was added, were also performed. After washing, the beads were assayed for their ability to interact with 35-S labelled pVHL IVTT. Hydroxylation of the fusion protein by HIF hydroxylase present in the cell extract leads to the ability to capture the labelled pVHL and the amount of labelled protein bound to the fusion protein can then be measured to determine relative HIF hydroxylase activity. FIGS. 15-20 show HIF hydroxylase activity in the presence of a particular inhibitor relative to that seen in the absence of the inhibitor (the DMSO/Tris control).

TABLE 1

| Name | Species | Nucleotide Accession | Protein Accession(s) |
| --- | --- | --- | --- |
| Egl-9 | C. elegans | AF178536 | GI5923812 |
| | | GI5923811 | |
| CG1114 | D. melanogaster | AE003603 | AAF52050 |
| C1orf12 | H. sapiens | AF229245 | NP071334 |
| PHD2 | | AJ310543 | |
| | | gi14547145 | Gi14547146 |
| | M. musculus | AJ310546 | |
| PHD1 | H. sapiens | BC01723 | NP071334 |
| | | AJ310543 | |
| | | gi14547147 | Gi14547148 |
| FALKOR | M. musculus | AF340231 | Gi13649965 |
| | | gi13649964 | |
| FLJ21620 | H. sapiens | AK025273 | BAB15101 |
| | | | Colo7838 |
| PHD3 | H. sapiens | AJ310545 | Gi14547150 |
| | | gi14547149 | |
| | M. musculus | AJ310548 | Gi14547243 |
| | | gi14547242 | |

TABLE 2

| In-vitro inhibitor | Disruption of HIF-VHL interaction | In-vivo esterified equivalent | Induction of HIF in tissue culture |
| --- | --- | --- | --- |
| NK80 | No | | |
| NK81 | Yes | Methylmethoxalyl-D/L-alanine | No |
| NK82 | No | Methylmethoxalyl-L/D-alanine | No |
| NK87 | Yes | Methylmethoxalyl glycine | Yes |
| 2, 4 pyridine dicarboxylic acid | Yes | 2, 4 diethylpyridine dicarboxylate | No |

TABLE 2-continued

| In-vitro inhibitor | Disruption of HIF-VHL interaction | In-vivo esterified equivalent | Induction of HIF in tissue culture |
| --- | --- | --- | --- |
| 2, 5 pyridine dicarboxylic acid | Not tested | 2, 5 diethylpyridine dicarboxylate | No |
| 2, 6 pyridine dicarboxylic acid | Not tested | 2, 6 diethylpyridine dicarboxylate | No |

NK80 is

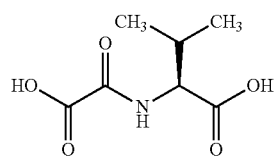

di Na Salt (free acid is IS70)

NK81 is oxalyl L-alanine-

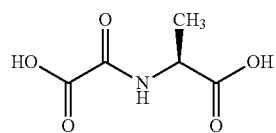

di Na Salt (free acid is IS70)

NK82 is oxalyl D-alanine-

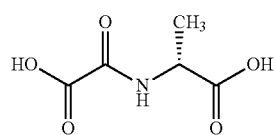

di Na Salt (free acid is IS71)

NK87 is oxalylglycine

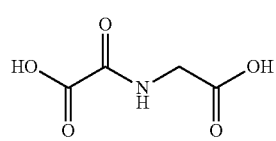

di Na Salt (IS2)

TABLE 3

IS 1

TABLE 3-continued
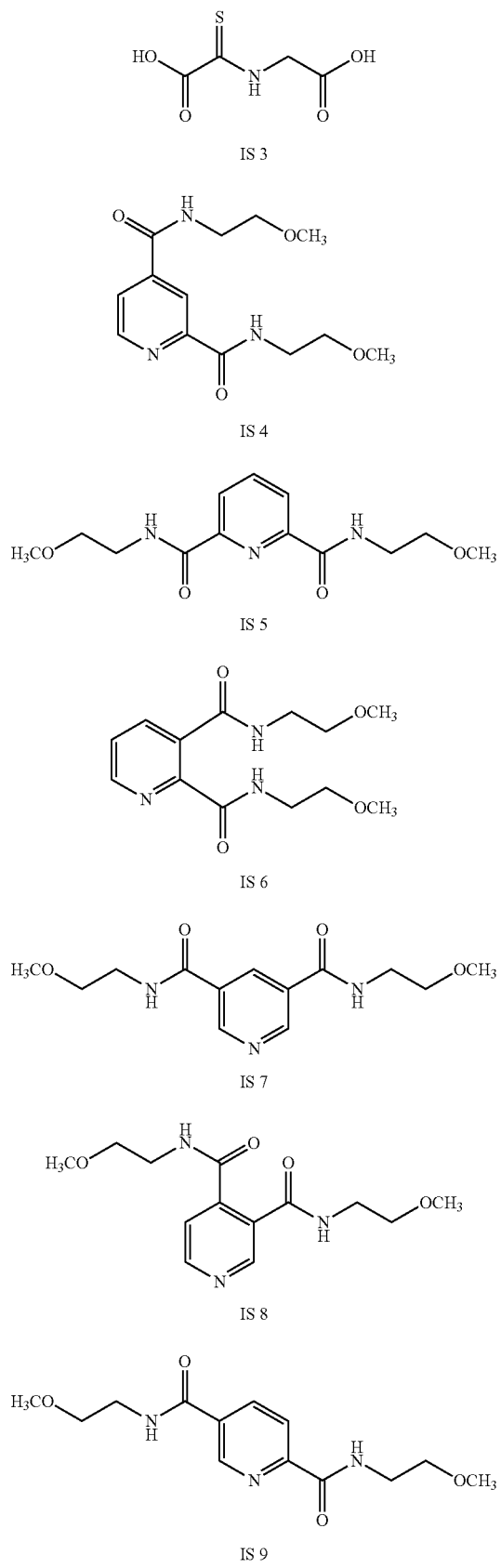
TABLE 3-continued
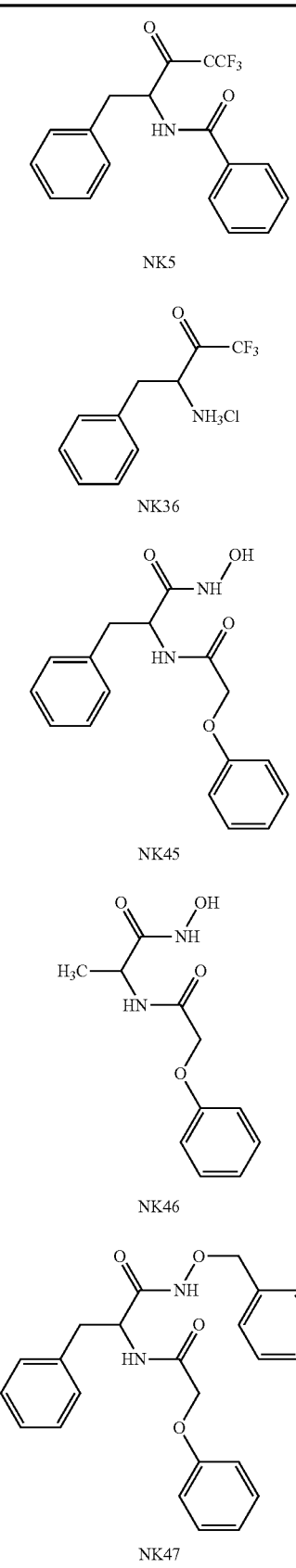

TABLE 3-continued

| Structure | Name |
|---|---|
| | NK84 |
| | EDB |
| | Benzohydoxamic acid (BHAA) |
| | N-oxaloylamino-L-alanine |
| | Dimethyloxaloylglycine (MMOG) |
| | Protocatechuic acid |
| | IS68 |
| | IS69 |
| | IS70 |
| | IS71 |
| | C8 |
| | C9 |
| | C10 |
| | C11 |
| | C14 |
| | C15 |

TABLE 3-continued

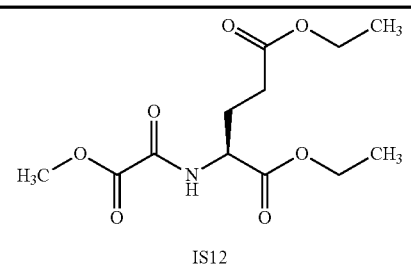

IS12

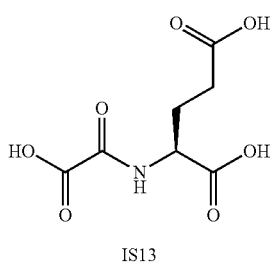

IS13

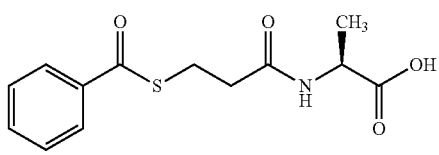

IS20

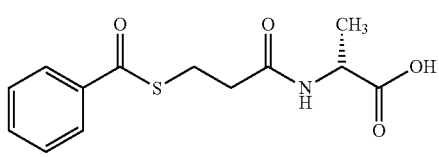

IS21

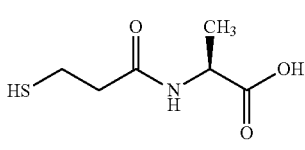

IS37

TABLE 3-continued

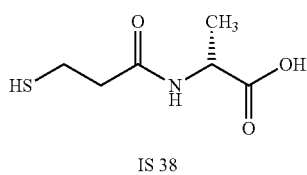

IS 38

TABLE 4

| Designation | Accession No. | Protected Fragment |
| --- | --- | --- |
| EGLN1/PHD2 | BC 001723 | 1136-1481 |
| EGLN2/PHD1 | AF 229245 | 4050-4213 |
| EGLN3/PHD3 | AK 025273 | 817-1046 |
| F22B5.4(*C.elegans*) | | 210-359 |
| HIF-1(*C.elegans*) | | 1366-1496 |

TABLE 5

| Gene | Strain | Allele |
| --- | --- | --- |
| daf-18 | CB1375 | e1375 |
| daf-2 | CB1370 | e1370 |
| age-1 | TJ1052 | hx546 |
| mev-1 | TK22 | knl |
| clk-1 | CB4876 | e2519 |
| gas-1 | CW152 | fc21 |
| ctl-1 | TU2463 | u800 |
| mev-2 | TK93 | kn2 |
| 2mev-3 | TK66 | kn10 |
| dpy-18 | CB364 | e364 |
| phy-2 | JK2757 | ok177 |
| egl-9 | MT1201 | n571 |
| egl-9 | MT1216 | n586 |
| egl-9 | JT307 | sa307 |
| egl-9 | JT330 | sa330 |
| vhl-1 | CB5603 | ok161 |

The invention claimed is:

1. An antibody or a fragment thereof capable of specifically binding a polypeptide comprising:
   (a) the amino acid sequence of SEQ ID NO:2 having HIF (hypoxia-inducible factor) hydroxylase activity; or
   (b) a variant thereof having at least 80% identity to the amino acid sequence of SEQ ID NO:2 and having HIF hydroxylase activity.

2. The antibody or fragment of claim 1 comprising a variant thereof having at least 90% identity to the amino acid sequence of SEQ ID NO:2 and having hydroxylase activity.

3. The antibody or fragment of claim 2 comprising a variant thereof having at least 95% identity to the amino acid sequence of SEQ ID NO:2 and having hydroxylase activity.

4. An antibody or a fragment thereof capable of specifically binding a polypeptide comprising:
   (a) the amino acid sequence of SEQ ID NO:6 having HIF hydroxylase activity; or
   (b) a variant thereof having at least 80% identity to the amino acid sequence of SEQ ID NO:6 and having HIF hydroxylase activity.

5. The antibody or fragment of claim 4 comprising a variant thereof having at least 90% identity to the amino acid sequence of SEQ ID NO:6 and having hydroxylase activity.

6. The antibody or fragment of claim 5 comprising a variant thereof having at least 95% identity to the amino acid sequence of SEQ ID NO:6 and having hydroxylase activity.

* * * * *